United States Patent
Niewöhner et al.

(10) Patent No.: US 6,838,459 B1
(45) Date of Patent: *Jan. 4, 2005

(54) 7-ALKYL-AND CYCLOALKYL-SUBSTITUTED IMIDAZOTRIAZINONES

(75) Inventors: Ulrich Niewöhner, Wermelskirchen (DE); Mazen Es-Sayed, Langenfeld (DE); Helmut Haning, Milford, CT (US); Thomas Schenke, Bergisch Gladbach (DE); Gunter Schmidt, Wuppertal (DE); Karl-Heinz Schlemmer, Wuppertal (DE); Erwin Bischoff, Wuppertal (DE); Klaus Dembowsky, Boston, MA (US); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 35 days.

This patent is subject to a terminal disclaimer.

(21) Appl. No.: 10/251,939

(22) Filed: Sep. 20, 2002

Related U.S. Application Data

(63) Continuation of application No. 09/720,051, filed as application No. PCT/EP99/04032 on Jun. 11, 1999, now Pat. No. 6,476,029.

(30) Foreign Application Priority Data

Jun. 20, 1998 (DE) ............................. 198 27 640

(51) Int. Cl.$^7$ ............................. A61K 31/53; A61P 9/10; A61P 9/08; A61P 7/12; C07D 487/04
(52) U.S. Cl. ........................................ 514/243; 544/284
(58) Field of Search ........................... 544/184; 514/243

(56) References Cited

U.S. PATENT DOCUMENTS 6,476,029 B1 * 11/2002 Niewohner et al. ......... 514/243

* cited by examiner

*Primary Examiner*—Venkataraman Balasubramanian
(74) *Attorney, Agent, or Firm*—Susan M. Pellegrino

(57) ABSTRACT

The present invention relates to 7-alkyl- and cycloalkyl-substituted imidazotriazinones, to processes for their preparation and to their use as medicaments, in particular as inhibitors of cGMP-metabolizing phosphodiesterases.

1 Claim, No Drawings

7-ALKYL-AND CYCLOALKYL-SUBSTITUTED IMIDAZOTRIAZINONES

This application is a continuation of U.S. patent application Ser. No. 09/720,051 filed Mar. 23, 2001, is now U.S. Pat. No. 6,476,029, in which is a 371 of PTC/EP99/04032 filed Jun. 11, 1999.

The present invention relates to 7-alkyl- and cycloalkyl-substituted imidazotriazinones, to processes for their preparation and to their use as medicaments, in particular as inhibitors of cGMP-metabolizing phosphodiesterases.

The published specification DE-28 11 780 describes imidazotriazines as bronchodilators having spasmolytic activity and inhibitory activity against phosphodiesterases which metabolize cyclic adenosine monophosphate (cAMP-PDEs, nomenclature according to Beavo: PDE-III and PDE-IV). An inhibitory action against phosphodiesterases which metabolize cyclic guanosine monophosphate (cGMP-PDEs, nomenclature according to Beavo and Reifsnyder (Trends in Pharmacol. Sci. 11, 150–155, 1990) PDE-I, PDE-II and PDE-V) has not been described. Compounds having a sulphonamide group in the aryl radical in the 2 position are not claimed. Furthermore, FR 22 13 058, CH-59 46 71, DE-22 55 172, DE-23 64 076 and EP-000 9384 describe imidazotriazinones which do not have a substituted aryl radical in the 2 position and are likewise said to be bronchodilators having cAMP-PDE-inhibitory action.

The compounds according to the invention are potent inhibitors either of one or of more of the phosphodiesterases which metabolize cyclic guanosine 3',5'-monophosphate (cGMP-PDEs). According to the nomenclature of Beavo and Reifsnyder (Trends in Pharmacol. Sci. 11, 150–155, 1990) these are the phosphodiesterase isoenzymes PDE-I, PDE-II and PDE-V.

An increase in the cGMP concentration can lead to beneficial antiaggregatory, antithrombotic, antiprolific, antivasospastic, vasodilative, natriuretic and diuretic effects. It can influence the short- or long-term modulation of muscular and cardiac inotropy, of the pulse and of cardiac conduction (J. C. Stoclet, T. Keravis, N. Komas and C. Lugnier, Exp. Opin. Invest. Drugs (1995), 4 (11), 1081–1100).

The present invention, accordingly, provides 7-alkyl- and cycloalkyl-substituted imidazotriazinones of the general formula (I)

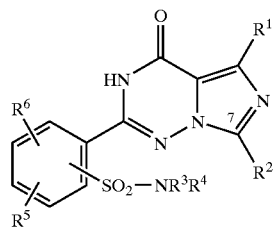

(I)

in which
$R^1$ represents straight-chain or branched alkyl having up to 4 carbon atoms,
$R^2$ represent straight-chain [lacuna] having at least 5 carbon atoms or branched alkyl having at least 3 carbon atoms, or
represents cycloalkyl having 3 to 10 carbon atoms,
$R^3$ and $R^4$ are identical or different and represent hydrogen, or
represent straight-chain or branched alkenyl having up to 8 carbon atoms, or represent a straight-chain or branched alkyl chain having up to 10 carbon atoms which is optionally interrupted by an oxygen atom and which is optionally mono- to trisubstituted by identical or different substituents from the group consisting of trifluoromethyl, trifluoromethoxy, hydroxyl, halogen carboxyl, benzyloxycarbonyl, straight-chain or branched alkoxy, alkoxycarbonyl and alkylthio having in each case up to 6 carbon atoms and/or by radicals of the formulae —$SO_3H$, —$(A)_a$—$NR^7R^8$, —O—CO—$NR^7R^{8'}$, —$S(O)_b$—$R^9$, HN=SO—$R^{9'}$, —$P(O)(OR^{10})(OR^{11})$,

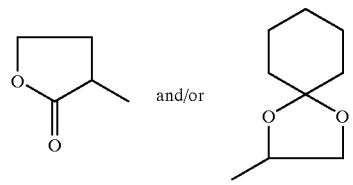

and/or in which
a and b are identical or different and represent a number 0 or 1,
A represents a radical CO or $SO_2$,
$R^7$, $R^{7'}$, $R^8$ and $R^{8'}$ are identical or different and represent hydrogen, or
represent cycloalkyl having 3 to 8 carbon atoms, aryl having 6 to 10 carbon atoms, a 5- to 6-membered unsaturated, partially unsaturated or saturated, optionally benzo-fused heterocycle having up to 3 heteroatoms from the group consisting of S, N and/or O, where the ring systems listed above are optionally mono- to trisubstituted by identical or different substituents from the group consisting of hydroxyl, nitro, trifluoromethyl, trifluoromethoxy, carboxyl, halogen, straight-chain or branched alkoxy and alkoxycarbonyl having in each case up to 6 carbon atoms or by a group of the formula —$(SO_2)_c$—$NR^{12}R^{13}$,
in which
c represents a number 0 or 1,
$R^{12}$ and $R^{13}$ are identical or different and represent hydrogen or straight-chain or branched alkyl having up to 5 carbon atoms,
or
$R^7$, $R^{7'}$, $R^8$ and $R^{8'}$ represent straight-chain or branched alkoxy having up to 6 carbon atoms, or
represent straight-chain or branched alkyl having up to 8 carbon atoms which is optionally mono- or polysubstituted by identical or different substituents from the group consisting of hydroxyl, halogen, aryl having from 6 to 10 carbon atoms, straight-chain or branched alkoxy and alkoxycarbonyl having in each case up to 6 carbon atoms or by a group of the formula —$(CO)_d$—$NR^{14}R^{15}$,
in which
$R^{14}$ and $R^{15}$ are identical or different and represent hydrogen or straight-chain or branched alkyl having up to 4 carbon atoms,
and
d represents a number 0 or 1,
or
$R^7$ and $R^8$ and/or $R^{7'}$ and $R^{8'}$ together with the nitrogen atom form a 5- to 7-membered saturated heterocycle which may optionally contain a further heteroatom from the group consisting of S and O or a radical of the formula —NR$^{16}$,
in which
R$^{16}$ represents hydrogen, aryl having 6 to 10 carbon atoms, or straight-chain or branched alkyl having up to 6 carbon atoms, which is optionally substituted by hydroxyl,
R$^9$ and R$^{9'}$ are identical or different and represent aryl having 6 to 10 carbon atoms or benzyl, or represent straight-chain or branched alkyl having up to 4 carbon atoms,
R$^{10}$ to and R$^{11}$ are identical or different and represent hydrogen or straight-chain or branched alkyl having up to 4 carbon atoms,
and/or the alkyl chain listed above under R$^3$/R$^4$ is optionally substituted by cycloalkyl having 3 to 8 carbon atoms, aryl having 6 to 10 carbon atoms or by a 5- to 7-membered partially unsaturated saturated or unsaturated, optionally benzo-fused heterocycle which may contain up to 4 ring heteroatoms from the group consisting of S, N, O or a radical of the formula —NR$^{17}$, where the alkyl chain may optionally also be attached via a ring nitrogen atom.
in which
R$^{17}$ represents hydrogen, hydroxyl, formyl, trifluoromethyl, straight-chain or branched acyl or alkoxy having in each case up to 4 carbon atoms,
or represents straight-chain or branched alkyl having up to 6 carbon atoms which is optionally mono- to polysubstituted by identical or different substituents from the group consisting of hydroxyl and straight-chain or branched alkoxy having up to 6 carbon atoms,
and where aryl and the heterocycle are optionally mono- to trisubstituted by identical or different substituents from the group consisting of nitro, halogen, —SO$_3$H, straight-chain or branched monohydroxy-substituted alkyl, alkylthio or alkoxy having in each case up to 6 carbon atoms, hydroxyl, trifluorormethyl, trifluoromethoxy and/or by a radical of the formula —(SO$_2$)$_e$—R$^{18}$R$^{19}$,
in which
e represents a number 0 or 1,
R$^{18}$ and R$^{19}$ are identical or different and represent hydrogen, phenyl, benzyl or straight-chain or branched alkyl or acyl having in each case up to 6 carbon atoms,
and/or
R$^3$ or R$^4$ represent radicals of the formulae —NR$^{20}$R$^{21}$ or —(O)—E—NR$^{22}$R$^{23}$,
in which
R$^{20}$ and R$^{21}$ have the meaning of R$^{18}$ and R$^{19}$ given above and are identical to or different from this meaning, or
together with the nitrogen atom form a 5- or 6-membered saturated heterocycle having a further ring heterocycle from the group consisting of S and O or a radical —NR$^{24}$,
in which
R$^{24}$ has the meaning of R$^{16}$ given above and is identical to or different from this meaning,
E is a straight-chain alkylene group having up to 5 carbon atoms, R$^{22}$ and R$^{23}$ have the meaning of R$^{18}$ and R$^{19}$ given above and are identical to or different from this meaning,
and/or
R$^3$ or R$^4$ represent radicals of the formulae

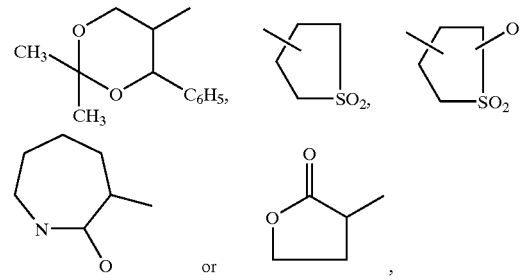

or represent cycloalkyl having 3 to 8 carbon atoms, aryl having 6 to 10 carbon atoms or represent a 5- to 7-membered partially unsaturated, saturated and unsaturated, optionally benzo-fused heterocycle which may contain up to 4 heteroatoms from the group consisting of S, N, O or a radical of the formula —NR$^{25}$ which may optionally also be attached via a ring nitrogen atom,
in which
R$^{23}$ has the meaning of R$^{16}$ given above and is identical to or different from this meaning, or
represents carboxyl, formyl or straight-chain or branched acyl having up to 5 carbon atoms,
and where cycloalkyl, aryl and/or the heterocycle are optionally mono- to trisubstituted by identical or different substituents from the group consisting of halogen, trifluoromethyl, trifluoromethoxy, carboxyl, straight-chain or branched acyl or alkoxycarbonyl having in each case up to 6 carbon atoms, nitro and/or by groups of the formulae —SO$_3$H, —OR$^{26}$, (SO$_2$)$_f$NR$^{27}$R$^{28}$, —P(O)(OR$^{29}$)(OR$^{30}$),
in which
R$^{26}$ represents a radical of the formula

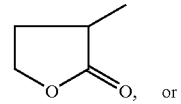

represents cycloalkyl having 3 to 7 carbon atoms, or
hydrogen or straight-chain or branched alkyl having up to 5 carbon atoms which is optionally substituted by cycloalkyl having 3 to 7 carbon atoms, straight-chain or branched alkoxy or alkoxycarbonyl having in each case up to 6 carbon atoms, hydroxyl, carboxyl or phenyl, which for its part may be mono- to trisubstituted by identical or different substituents from the group consisting of straight-chain or branched alkoxy having up to 4 carbon atoms, hydroxyl and halogen,
f is a number 0 or 1,
R$^{27}$ and R$^{28}$ have the meaning of R$^{18}$ and R$^{19}$ given above and are identical to or different from this meaning or represent a radical of the formula —CO—NH$_2$,
R$^{29}$ and R$^{30}$ have the meaning of R$^{10}$ and R$^{11}$ given above and are identical to or different from this meaning, and/or cycloalkyl, aryl and/or the heterocycle are optionally substituted by straight-chain or branched alkyl having up to 6 carbon atoms which is optionally substituted by hydroxyl, carboxyl, by a 5- to 7-membered heterocycle having up to 3 heteroatoms from the group consisting of S, N and/or O or by groups of the formulae —$SO_2$—$R^{31}$, $P(O)(OR^{32})(OR^{33})$ or —$NR^{34}R^{35}$, in which $R^{31}$ is hydrogen or has the meaning of $R^9$ given above and is identical to or different from this meaning, $R^{32}$ and $R^{33}$ have the meaning of $R^{10}$ and $R^{11}$ given above and are identical to or different from this meaning, $R^{34}$ and $R^{35}$ are identical or different and represent hydrogen or straight-chain or branched alkyl having up to 6 carbon atoms which is optionally substituted by hydroxyl or straight-chain or branched alkoxy having up to 4 carbon atoms, or $R^{34}$ and $R^{35}$ together with the nitrogen atom form a 5- to 6-membered saturated heterocycle which may contain a further heteroatom from the group consisting of S and O or a radical of the formula —$NR^{36}$.

in which $R^{36}$ has the meaning of $R^{16}$ given above and is identical to or different from this meaning, or $R^3$ and $R^4$ together with the nitrogen atom form a 5- to 7-membered unsaturated or saturated or partially unsaturated, optionally benzo-fused heterocycle which may optionally contain up to 3 heteroatoms from the group consisting of S, N, O or a radical of the formula —$NR^{37}$, in which $R^{37}$ represents hydrogen, hydroxyl, formyl, trifluoromethyl, straight-chain or branched acyl, alkoxy or alkoxycarbonyl having in each case up to 4 carbon atoms, or represents cycloalkyl having 3 to 8 carbon atoms, or represents straight-chain or branched alkyl having up to 6 carbon atoms which is optionally mono- to trisubstituted by identical or different substituents from the group consisting of hydroxyl, trifluoromethyl, pyridyl, carboxyl, straight-chain or branched alkoxy and alkoxycarbonyl having in each case up to 6 carbon atoms, or $R^{37}$ represents a radical of the formula —$(CO)_g$—G, in which g represents a number 0 or 1, G represents aryl having 6 to 10 carbon atoms or a 5- to 6-membered aromatic heterocycle having up to 4 heteroatoms from the group consisting of S, N and/or O, where the ring systems listed above are optionally mono- to trisubstituted by identical or different substituents from the group consisting of halogen, straight-chain or branched alkoxy, alkyl or alkylthio having in each case up to 6 carbon atoms, hydroxyl and trifluoromethyl, and the heterocycle mentioned under $R^3$ and $R^4$, formed via the nitrogen, is optionally mono- to trisubstituted, optionally also geminally, by identical or different substituents from the group consisting of hydroxyl, formyl, carboxyl, straight-chain or branched acyl and alkoxycarbonyl having in each case up to 6 carbon atoms and groups of the formulae —$P(O)(OR^{38})(OR^{39})$ and —$(CO)_g$—$NR^{40}R^{41}$, in which $R^{38}$ and $R^{39}$ have the meaning of $R^{10}$ and $R^{11}$ given above and are identical to or different from this meaning, g represents a number 0 or 1, and $R^{40}$ and $R^{41}$ are identical or different and have the meaning of $R^{18}$ and $R^{19}$ given above, and/or the heterocycle mentioned under $R^3$ and $R^4$, formed via the nitrogen, is optionally substituted by straight-chain or branched alkyl having up to 6 carbon atoms which is optionally mono- to trisubstituted by identical or different substituents from the group consisting of hydroxyl, halogen, carboxyl, cycloalkyl or cycloalkyloxy having in each case 3 to 8 carbon atoms, straight-chain or branched alkoxy and alkoxycarbonyl having in each case up to 6 carbon atoms or by a radical of the formula —$SO_3H$, —$NR^{42}R^{43}$ or $P(O)OR^{44}R^{45}$, in which $R^{42}$ and $R^{43}$ are identical or different and represent hydrogen, phenyl, carboxyl, benzyl or straight-chain or branched alkyl or alkoxy having in each case up to 6 carbon atoms, $R^{44}$ and $R^{45}$ are identical or different and have the meaning of $R^{10}$ and $R^{11}$ given above, and/or the alkyl is optionally substituted by benzyloxy or aryl having 6 to 10 carbon atoms, which for its part may be mono- to trisubstituted by identical or different substituents from the group consisting of halogen, hydroxyl, straight-chain or branched alkoxy or alkylthio having in each case up to 6 carbon atoms, or by a group of the formula —$NR^{42'}R^{43'}$, in which $R^{42'}$ and $R^{43'}$ have the meaning of $R^{42}$ and $R^{43}$ given above and are identical to or different from this meaning, and/or the heterocycle mentioned under $R^3$ and $R^4$, formed via a nitrogen atom, is optionally substituted by aryl having 6 to 10 carbon atoms or by a 5- to 7-membered saturated, partially unsaturated or unsaturated heterocycle having up to 3 ring heteroatoms from the group consisting of S, N and/or O, optionally also attached via an N function, where the ring systems for their part may be substituted by halogen, hydroxyl or by straight-chain or branched alkyl, alkylthio or alkoxy having in each case up to 6 carbon atoms, or $R^3$ and $R^4$ together with the nitrogen atom form radicals of the formulae

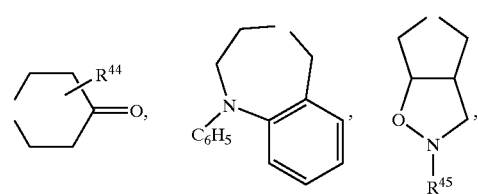

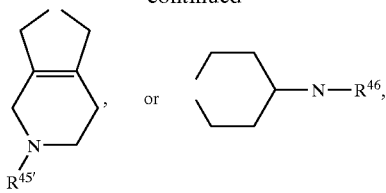

in which
R$^{44}$ represents hydrogen or straight-chain or branched alkyl or alkoxycarbonyl having in each case up to 6 carbon atoms,
R$^{45}$ and R$^{45'}$ are identical or different and represent hydrogen or straight-chain or branched alkyl having up to 3 carbon atoms,
R$^{46}$ represents hydroxyl or straight-chain or branched alkoxy having up to 6 carbon atoms,
R$^5$ and R$^6$ are identical or different and represent hydrogen, straight-chain or branched alkyl having up to 6 carbon atoms, hydroxy or represents straight-chain or branched alkoxy having up to 6 carbon atoms,
and their salts and isomeric forms.

The compounds according to the invention may exist in stereoisomeric forms which are either like image and mirror image (enantiomers), or which are not like image and mirror image (diastereomers). The invention relates both to the enantiomers or diastereomers and to their respective mixtures. The racemic forms can, just like the diastereomers, be separated in a known manner into the stereoisomerically uniform constituents.

The substances according to the invention may also be present as salts. In the context of the invention, preference is given to physiologically acceptable salts.

Physiologically acceptable salts can be salts of the compounds according to the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

In the context of the invention and depending on the various substituents, optionally benzo-fused heterocycle generally represents an aromatic, saturated, partially unsaturated or unsaturated 5- to 7-membered or 5- to 6-membered heterocycle which may contain up to 4 heteroatoms from the group consisting of S, N and O. Examples which may be mentioned are: azepine, diazepine, indolyl, isoquinolyl, quinolyl, benzo[b]thiophene, benzo[b]furanyl, pyridyl, thienyl, tetrahydrofuranyl, tetrahydropyranyl, furyl, pyrrolyl, thiazolyl, triazolyl, tetrazolyl, isoxazolyl, imidazolyl, morpholinyl, thiomorpholinyl, pyrrolidinyl, piperazinyl, N-methylpiperazinyl or piperidinyl. Preference is given to quinolyl, faryl, pyridyl, thienyl, piperidinyl, pyrrolidinyl, piperazinyl, azepine, diazepine, thiazolyl, triazolyl, tetrazolyl, tetrahydrofuranyl, tetrahydropyranyl, morphholinyl and thiomorpholinyl. Preference is given to compounds of the general formula (I) according to the invention
in which
R$^1$ represents straight-chain or branched alkyl having up to 3 carbon atoms,
R$^2$ represents straight-chain [lacuna] having 5 to 15 carbon atoms or branched alkyl having 3 to 15 carbon atoms, or
represents cyclopropyl, cyclobutyl, cyclopentyl, cyclohexyl, cycloheptyl or cyclooctyl,
R$^3$ and R$^4$ are identical or different and represent hydrogen, or
represent straight-chain or branched alkenyl having up to 4 carbon atoms, or
represent a straight-chain or branched alkyl chain having up to 6 carbon atoms which is optionally interrupted by an oxygen atom and which is optionally mono- to trisubstituted by identical or different substituents from the group consisting of hydroxyl, carboxyl, straight-chain or branched alkoxy, alkoxycarbonyl and alkylthio having in each case up to 4 carbon atoms and/or by radicals of the formulae —SO$_3$H, —(A)$_a$—NR$^7$R$^8$, —O—CO—NR$^7$R$^8'$, —S(O)$_b$—R$^9$, HN=SO-R$^{9'}$, —P(O)(OR$^{10}$)(OR$^{11}$),

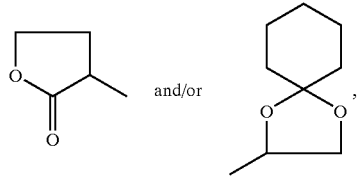

in which
a and b are identical or different and represent a number 0 or 1,
A represents a radical CO or SO$_2$,
R$^7$, R$^{7'}$, R$^8$ and R$^{8'}$ are identical or different and represent hydrogen, or
represent phenyl, naphthyl, or pyridyl, where the ring systems listed above are optionally mono- to disubstituted by identical or different substituents from the group consisting of hydroxyl, nitro, trifluoromethyl, trifluoromethoxy, carboxyl, halogen, straight-chain or branched alkoxy and alkoxycarbonyl having in each case up to 4 carbon atoms, or
represent straight-chain or branched alkoxy having up to 4 carbon atoms, or
represent straight-chain or branched alkyl having up to 6 carbon atoms which is optionally mono- or polysubstituted by identical or different substituents from the group consisting of hydroxyl, fluorine, chlorine, bromine, phenyl, straight-chain or branched alkoxy and alkoxycarbonyl having in each case up to 4 carbon atoms or by a group of the formula —(CO)$_d$—NR$^{14}$R$^{15}$,
in which
R$^{14}$ and R$^{15}$ are identical or different and represent hydrogen or straight-chain or branched alkyl having up to 3 carbon atoms, and
d represents a number 0 or 1, or R$^7$ and R$^8$ and/or R$^{7'}$ and R$^{8'}$ together with the nitrogen atom form a pyrrolidinyl, piperidinyl or morpholinyl ring or a radical of the formula

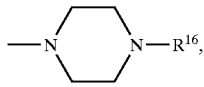

in which
R$^{16}$ represents hydrogen, phenyl, naphthyl or straight-chain or branched alkyl having up to 4 carbon atoms, which is optionally substituted by hydroxyl,
R$^9$ and R$^{9'}$ are identical or different and represent phenyl or benzyl, or represent straight-chain or branched alkyl having up to 3 carbon atoms,
R$^{10}$ and R$^{11}$ are identical or different and represent hydrogen or straight-chain or branched alkyl having up to 3 carbon atoms,
and/or the alkyl chain mentioned above under R$^3$/R$^4$ is optionally substituted by phenyl, naphthyl, morpholinyl, pyridyl, tetrahydropyranyl, tetrahydrofuranyl or thienyl, where the radical may optionally also be attached to the alkyl chain via a ring nitrogen atom, and where aryl and the heterocycle are optionally mono- to disubstituted by identical or different substituents from the group consisting of nitro, fluorine, chlorine, bromine, —SO$_3$H, straight-chain or branched monohydroxy-substituted alkyl, alkylthio or alkoxy having in each case up to 4 carbon atoms, hydroxyl, trifluoromethyl, trifluoromethoxy and/or by a radical of the formula —(SO$_2$)$_e$—NR$^{18}$R$^{19}$,
in which
e represents a number 0 or 1,
R$^{18}$ and R$^{19}$ are identical or different and represent hydrogen, phenyl, benzyl or straight-chain or branched alkyl or acyl having in each case up to 4 carbon atoms, and/or
R$^3$ and R$^4$ represent radicals of the formulae —NR$^{20}$R$^{21}$ or —(O)—E—NR$^{22}$R$^{23}$,
in which
R$^{20}$ and R$^{21}$ have the meaning of R$^{18}$ and R$^{19}$ given above and are identical to or different from this meaning, or
together with the nitrogen atom form a morpholinyl ring, pyrrolidinyl ring or a radical of the formula

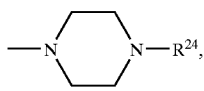

in which
R$^{24}$ has the meaning of R$^{16}$ given above and is identical to or different from this meaning,
E represents a straight-chain alkylene group having up to 4 carbon atoms,
R$^{22}$ and R$^{23}$ have the meaning of R$^{18}$ and R$^{19}$ given above and are identical to or different from this meaning, and/or
R$^3$ or R$^4$ represent radicals of the formulae

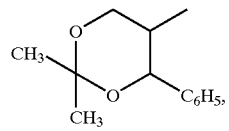  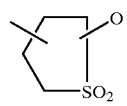

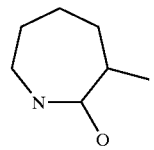 or 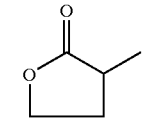, or represent cyclopentyl, cyclohexyl, naphthyl, phenyl, pyridyl, or quinolyl or tetrazolyl attached via the phenyl ring,
and where the ring systems given above are optionally mono- to disubstituted by identical or different substituents from the group consisting of fluorine, chlorine, trifluoromethyl, trifluoromethoxy, carboxyl, straight-chain or branched acyl and alkoxycarbonyl having in each case up to 4 carbon atoms and/or by groups of the formulae —SO$_3$H, —OR$^{26}$, (SO$_2$)$_f$R$^{27}$R$^{28}$, —P(O)(OR$^{29}$)(OR$^{30}$),
in which
R$^{26}$ represents a radical of the formula

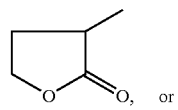 or represents cyclopentyl or cyclohexyl, or
represents hydrogen or straight-chain or branched alkyl having up to 4 carbon atoms which is optionally substituted by straight-chain or branched alkoxy or alkoxycarbonyl having in each case up to 4 carbon atoms, hydroxyl, carboxyl or phenyl, which for its part may be mono- to disubstituted by identical or different substituents from the group consisting of straight-chain or branched alkoxy having up to 3 carbon atoms, hydroxyl and halogen,
f represents a number 0 or 1,
R$^{27}$ and R$^{28}$ have the meaning of R$^{18}$ and R$^{19}$ given above and are identical to or different from this meaning or represent a radical of the formula —CO—NH$_2$,
R$^{29}$ and R$^{30}$ have the meaning of R$^{10}$ and R$^{11}$ given above and are identical to or different from this meaning,
and/or the ring systems given above are optionally substituted by straight-chain or branched alkyl having up to 4 carbon atoms, which are optionally substituted by hydroxyl, carboxyl, morpholine, pyridyl or by groups of the formula —SO$_2$—R$^{31}$, P(O)(OR$^{32}$)(OR$^{33}$) or —NR$^{34}$R$^{35}$,
in which
R$^{33}$ represents hydrogen or has the meaning of R$^9$ given above and is identical to or different from this meaning,
R$^{32}$ and R$^{33}$ have the meaning of R$^{10}$ and R$^{11}$ given above and are identical to or different from this meaning, $R^{34}$ and $R^{35}$ are identical or different and represent hydrogen or straight-chain or branched alkyl having up to 4 carbon atoms which is optionally substituted by hydroxyl or straight-chain or branched alkoxy having up to 3 carbon atoms, or $R^{34}$ and $R^{35}$ together with the nitrogen atom form a morpholinyl, pyrrolidinyl, piperidinyl ring or a radical of the formula

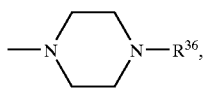

in which
$R^{36}$ has the meaning of $R^{16}$ given above and is identical to or different from this meaning, or
$R^3$ and $R^4$ together with the nitrogen atom form a piperidinyl, pyrrolidinyl or morpholinyl ring, or a radical of the formula

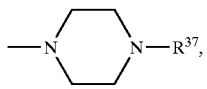

in which
$R^{37}$ represents hydrogen, hydroxyl, formyl, trifluoromethyl, straight-chain or branched acyl, alkoxy or alkoxycarbonyl having in each case up to 4 carbon atoms, or
represents cyclopropyl, cyclobutyl, cyclopentyl or cyclohexyl, or
represents straight-chain or branched alkyl having up to 4 carbon atoms which is optionally mono- to trisubstituted by identical or different substituents from the group consisting of hydroxyl, trifluoromethyl, pyridyl, carboxyl, straight-chain or branched alkoxy and alkoxycarbonyl having in each case up to 4 carbon atoms, or
$R^{37}$ represents a radical of the formula —$(CO)_g$—G,
in which
g represents a number 0 or 1,
G represents naphthyl, phenyl, pyridyl or pyrimidyl, where the ring systems listed above are optionally mono- to trisubstituted by identical or different substituents from the group consisting of fluorine, chlorine, straight-chain or branched alkoxy, alkyl or alkylthio having in each case up to 4 carbon atoms, hydroxyl and trifluoromethyl,
and the heterocycles listed above under $R^3$ and $R^4$ are optionally mono- to trisubstituted, optionally also seminally, by identical or different substituents from the group consisting of hydroxyl, formyl, carboxyl, straight-chain or branched acyl or alkoxycarbonyl having in each case up to 4 carbon atoms and groups of the formulae —$P(O)(OR^{38})(OR^{39})$ or —$(CO)_g$—$NR^{40}R^{41}$,
in which
$R^{38}$ and $R^{39}$ have the meaning of $R^{10}$ and $R^{11}$ given above and are identical to or different from this meaning,
g represents a number 0 or 1,
and
$R^{40}$ and $R^{41}$ are identical or different and have the meaning of $R^{18}$ and $R^{19}$ given above, and/or the heterocycles listed under $R^3$ and $R^4$ are optionally substituted by straight-chain or branched alkyl having up to 4 carbon atoms which is optionally mono- to trisubstituted by identical or different substituents from the group consisting of hydroxyl, fluorine, chlorine, carboxyl, cyclopropyl, cyclobutyl, cyclopentyl, cyclohexyl, cyclopentyloxy, cyclohexyloxy, straight-chain or branched alkoxy and alkoxycarbonyl having in each case up to 4 carbon atoms or by a radical of the formula —$SO_3H$, —$NR^{42}R^{43}$ or $P(O)OR^{44}OR^{45}$,
in which
$R^{42}$ and $R^{43}$ are identical or different and: represent hydrogen, phenyl, carboxyl, benzyl or straight-chain or branched-alkyl or alkoxy having in each case up to 4 carbon atoms,
$R^{44}$ and $R^{45}$ are identical or different and have the meaning of $R^{10}$ and $R^{11}$ given above,
and/or the alkyl is optionally substituted by benzyloxy, naphthyl or phenyl, which for its part may be mono- to trisubstituted by identical or different substituents from the group consisting of fluorine, chlorine, hydroxyl, straight-chain or branched alkoxy and alkylthio having, in each case up to 4 carbon atoms, or by a group of the formula —$NR^{42'}R^{43'}$,
in which
$R^{42'}$ and $R^{43'}$ have the meaning of $R^{42}$ and $R^{43}$ given above and are identical to or different from this meaning,
and/or the heterocycles listed under $R^3$ and $R^4$ are optionally substituted by phenyl, naphthyl or by radicals of the formulae

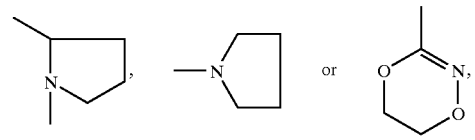

where the ring systems for their part may be substituted by fluorine, chlorine, hydroxyl or by straight-chain or branched alkyl, alkylthio or alkoxy having in each case up to 4 carbon atoms, or
$R^3$ and $R^4$ together with the nitrogen atom form radicals of the formulae

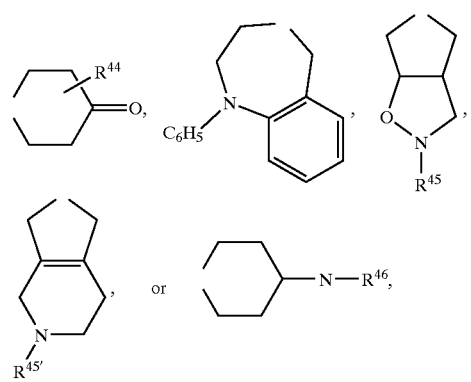

in which
$R^{44}$ represents hydrogen or straight-chain or branched alkyl or alkoxycarbonyl having in each case up to 3 carbon atoms, $R^{45}$ and $R^{45'}$ are identical or different and represent hydrogen or methyl, $R^{46}$ represents hydroxyl or straight-chain or branched alkoxy having up to 4 carbon atoms, $R^5$ and $R^6$ are identical or different and represent hydrogen, straight-chain or branched alkyl having up to 4 carbon atoms, hydroxyl or represent straight-chain or branched alkoxy having up to 4 carbon atoms, and their salts and isomeric forms.

Particular preference is given to compounds of the general formula (I) according to the invention, in which $R^1$ represents straight-chain or branched alkyl having up to 3 carbon atoms, $R^2$ represents straight-chain [lacuna] having 5 to 12 carbon atoms or branched alkyl having 3 to 12 carbon atoms, or represents cyclopropyl, cyclobutyl, cyclopentyl, cyclohexyl, cycloheptyl or cyclooctyl, $R^3$ and $R^4$ are identical or different and represent hydrogen, or represent straight-chain or branched alkenyl having up to 4 carbon atoms, or represent a straight-chain or branched alkyl chain having up to 6 carbon atoms which is optionally interrupted by an oxygen atom and which is optionally mono- to trisubstituted by identical or different substituents from the group consisting of hydroxyl, carboxyl, straight-chain or branched alkoxy, alkoxycarbonyl and alkylthio having in each case up to 4 carbon atoms and/or by radicals of the formulae $-SO_3H$, $-(A)_a-NR^7R^8$, $-O-CO-NR^{7'}R^{8'}$, $-S(O)_b-R^9$, $HN=SO-R^{9'}$, $-P(O)(OR^{10})(OR^{11})$,

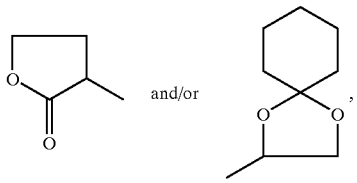

in which a and b are identical or different and represent a number 0 or 1,

A represents a radical CO or SO, $R^7$, $R^{7'}$, $R^8$ and $R^{8'}$ are identical or different and represent hydrogen, or represent phenyl, naphthyl, or pyridyl, where the ring systems listed above are optionally mono- to disubstituted by identical or different substituents from the group consisting of hydroxyl, nitro, trifluoromethyl, trifluoromethoxy, carboxyl, halogen, straight-chain or branched alkoxy and alkoxycarbonyl having in each case up to 4 carbon atoms, or represent straight-chain or branched alkoxy having up to 4 carbon atoms, or represent straight-chain or branched alkyl having up to 6 carbon atoms which is optionally mono- or polysubstituted by identical or different substituents from the group consisting of hydroxyl, fluorine, chlorine bromine, phenyl, straight-chain or branched alkoxy and alkoxycarbonyl having in each case up to 4 carbon atoms or by a group of the formula $-(CO)_d-NR^{14}R^{15}$, in which $R^{14}$ and $R^{15}$ are identical or different and represent hydrogen or straight-chain or branched alkyl having up to 3 carbon atoms, and d represents a number 0 or 1, or $R^7$ and $R^8$ and/or $R^{7'}$ and $R^{8'}$ together with the nitrogen atom form a pyrrolidinyl, piperidinyl or morpholinyl ring or a radical of the formula

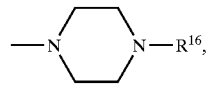

in which $R^{16}$ represents hydrogen, phenyl, naphthyl or straight-chain or branched alkyl having up to 4 carbon atoms which is optionally substituted by hydroxyl, $R^9$ and $R^{9'}$ are identical or different and represent phenyl or benzyl, or represent straight-chain or branched alkyl having up to 3 carbon atoms, $R^{10}$ and $R^{11}$ are identical or different and represent hydrogen or straight-chain or branched alkyl having up to 3 carbon atoms, and/or the alkyl chain listed above under $R^3/R^4$ is optionally substituted by phenyl, naphthyl, morpholinyl, pyridyl, tetrahydropyranyl, tetrahydrofuranyl or thienyl, where the attachment to the alkyl chain may optionally also take place via a ring nitrogen atom, and where aryl and the heterocycle are optionally mono- to disubstituted by identical or different substituents from the group consisting of nitro, fluorine, chlorine, bromine, $-SO_3H$, straight-chain or branched monohydroxy-substituted alkyl, alkylthio or alkoxy having in each case up to 4 carbon atoms, hydroxyl, trifluoromethyl, trifluoromethoxy and/or by a radical of the formula $-(SO_2)_e-NR^{18}R^{19}$, in which e represents a number 0 or 1, $R^{18}$ and $R^{19}$ are identical or different and represent hydrogen, phenyl, benzyl or straight-chain or branched alkyl or acyl having in each case up to 4 carbon atoms, and/or $R^3$ or $R^4$ represents radicals of the formulae $-NR^{20}R^{21}$ or $-(O)-E-NR^{22}R^{23}$, in which $R^{20}$ and $R^{21}$ have the meaning of $R^{18}$ and $R^{19}$ given above and are identical to or different from this meaning, or together with the nitrogen atom form a morpholinyl ring, pyrrolidinyl ring or a radical of the formula

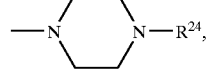

in which $R^{24}$ has the meaning of $R^{16}$ given above and is identical to or different from this meaning, E represents a straight-chain alkylene group having up to 4 carbon atoms, $R^{22}$ and $R^{23}$ have the meaning of $R^{18}$ and $R^{19}$ given above and are identical to or different from this meaning and/or $R^3$ or $R^4$ represent the radicals of the formulae

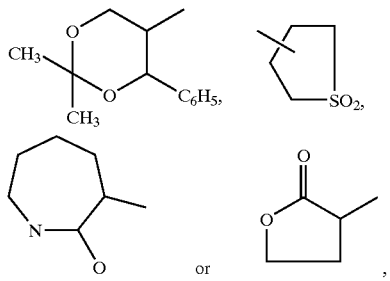

or or represent cyclopentyl, cyclohexyl, naphthyl, phenyl, pyridyl, or quinolinyl or tetrazolyl attached via the phenyl ring, and where the ring systems given above are optionally mono- to disubstituted by identical or different substituents from the group consisting of fluorine, chlorine, trifluoromethyl, trifluoromethoxy, carboxyl, straight-chain or branched acyl and alkoxycarbonyl having in each case up to 4 carbon atoms and/or by groups of the formulae —$SO_3H$, —$OR^{26}$, $(SO_2)_fNR^{27}R^{28}$, —$P(O)(OR^{29})(OR^{30})$, in which $R^{26}$ represents a radical of the formula

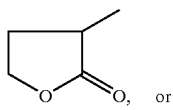 or represents cyclopentyl or cyclohexyl, or represents hydrogen or straight-chain or branched alkyl having up to 4 carbon atoms which is optionally substituted by straight-chain or branched alkoxy or alkoxycarbonyl having in each case up to 4 carbon atoms, hydroxyl, carboxyl or phenyl, which for its part may be mono- to disubstituted by identical or different substituents from the group consisting of straight-chain or branched alkoxy having up to 3 carbon atoms, hydroxyl and halogen, f represents a number 0 or 1, $R^{27}$ and $R^{28}$ have the meaning of $R^{18}$ and $R^{19}$ given above and are identical to or different from this meaning or represent a radical of the formula —CO—$NH_2$, $R^{29}$ and $R^{30}$ have the meaning of $R^{10}$ and $R^{11}$ given above and are identical to or different from this meaning, and/or the ring systems given above are optionally substituted by straight-chain or branched alkyl having up to 4 carbon atoms which are optionally substituted by hydroxyl, carboxyl, morpholine, pyridyl or by groups of the formula —$SO_2$—$R^{31}$, $P(O)(OR^{32})((OR^{33})$ or —$NR^{34}R^{35}$, in which $R^{31}$ represents hydrogen or has the meaning of $R^9$ given above and is identical to or different from this meaning, $R^{32}$ and $R^{33}$ have the meaning of $R^{10}$ and $R^{11}$ given above and are identical to or different from this meaning, $R^{34}$ and $R^{35}$ are identical or different and represent hydrogen or straight-chain or branched alkyl having up to 4 carbon atoms which is optionally substituted by hydroxyl or straight-chain or branched alkoxy having up to 3 carbon atoms, or $R^{34}$ and $R^{35}$ together with the nitrogen atom form a morpholinyl, pyrrolidinyl, piperidinyl ring or a radical of the formula

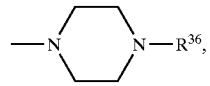

in which $R^{36}$ has the meaning of $R^{16}$ given above and is identical to or different from this meaning, or $R^3$ and $R^4$ together with the nitrogen atom form a piperidinyl, pyrrolidinyl or morpholinyl ring, or a radical of the formula

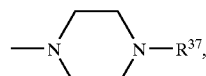

in which $R^{37}$ represents hydrogen, hydroxyl, formyl, trifluoromethyl, straight-chain or branched acyl, alkoxy or alkoxycarbonyl having in each case up to 4 carbon atoms, or represents cyclopropyl, cyclobutyl, cyclopentyl or cyclohexyl, or represents straight-chain or branched alkyl having up to 4 carbon atoms which is optionally mono- to trisubstituted by identical or different substituents from the group consisting of hydroxyl, trifluoromethyl, pyridyl, carboxyl, straight-chain or branched alkoxy and alkoxycarbonyl having in each case up to 4 carbon atoms, or $R^{37}$ represents a radical of the formula —$(CO)_g$—G, in which g represents a number 0 or 1, G represents naphthyl, phenyl, pyridyl or pyrimidyl, where the ring systems listed above are optionally mono- to trisubstituted by identical or different substituents from the group consisting of fluorine, chlorine, straight-chain or branched alkoxy, alkyl or alkylthio having in each case up to 4 carbon atoms, hydroxyl and trifluoromethyl, and the heterocycles listed under $R^3$ and $R^4$ are optionally mono- to trisubstituted, optionally also geminally, by identical or different substituents from the group consisting of hydroxyl, formyl, carboxyl, straight-chain or branched acyl or alkoxycarbonyl having in each case up to 4 carbon atoms and groups of the formulae —$P(O)(OR^{38})(OR^{39})$ or —$(CO)_g$—$NR^{40}R^{41}$, in which $R^{38}$ and $R^{39}$ have the meaning of $R^{10}$ and $R^{11}$ given above and are identical to or different from this meaning, g represents a number 0 or 1, and $R^{40}$ and $R^{41}$ are identical or different and have the meaning of $R^{18}$ and $R^{19}$ given above, and/or the heterocycles listed under $R^3$ and $R^4$ are optionally substituted by straight-chain or branched alkyl having up to 4 carbon atoms which is optionally mono- to trisubstituted by identical or different substituents from the group consisting of hydroxyl, fluorine, chlorine, carboxyl, cyclopropyl, cyclobutyl, cyclopentyl, cyclohexyl, cyclopentyloxy, cyclohexyloxy, straight-chain or branched alkoxy and alkoxycarbonyl having in each case up to 4 carbon atoms or by a radical of the formula $-SO_3H$, $-NR^{42}R^{43}$ or $P(O)OR^{44}OR^{45}$, in which
$R^{42}$ and $R^{43}$ are identical or different and represent hydrogen, phenyl, carboxyl, benzyl or straight-chain or branched alkyl or alkoxy having in each case up to 4 carbon atoms,
$R^{44}$ and $R^{45}$ are identical or different and have the meaning of $R^{10}$ and $R^{11}$ given above.

and/or the alkyl is optionally substituted by benzyloxy, naphtyl or phenyl, which for its part may be mono- to trisubstituted by identical or different substituents from the group consisting of fluorine, chlorine, hydroxyl, straight-chain or branched alkoxy or alkylthio having in each case up to 4 carbon atoms, or by a group of the formula $-NR^{42'}R^{43'}$ in which
$R^{42'}$ and $R^{43'}$ have the meaning of $R^{42}$ and $R^{43}$ given above and are identical to or different from this meaning, and/or the heterocycles listed under $R^3$ and $R^4$ are optionally substituted by phenyl, naphthyl or by radicals of the formulae

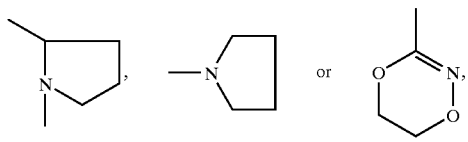

where the ring systems for their part may be substituted by fluorine, chlorine, hydroxyl or by straight-chain or branched alkyl, alkylthio or alkoxy having in each case up to 4 carbon atoms, or
$R^3$ and $R^4$ together with the nitrogen atom form radicals of the formulae

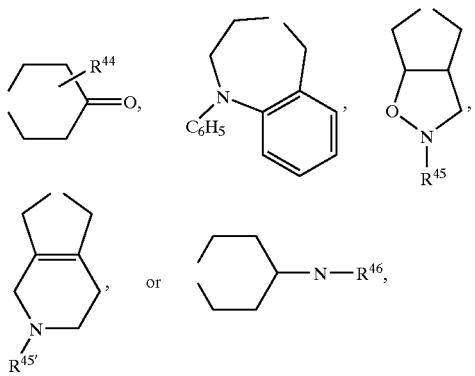

in which
$R^{44}$ represents hydrogen or straight-chain or branched alkyl or alkoxycarbonyl having in each case up to 3 carbon atoms, $R^{45}$ and $R^{45'}$ are identical or different and represent hydrogen or methyl,
$R^{46}$ represents hydroxyl or straight-chain or branched alkoxy having up to 4 carbon atoms,
$R^5$ and $R^6$ are identical or different and represent hydrogen, straight-chain or branched alkyl having up to 4 carbon atoms, hydroxyl or represent straight-chain or branched alkoxy having up to 4 carbon atoms, and their salts and isomeric forms.

Particular preference is also given to compounds of the general formula (I)
in which
$R^1$ represents methyl or ethyl,
$R^2$ represents straight-chain [lacuna] having 5 to 11 carbon atoms or branched alkyl having 3 to 11 carbon atoms, or represents cyclopentyl, cyclohexyl, cycloheptyl,
$R^3$ and $R^4$ are identical or different and represent straight-chain or branched alkyl having up to 4 carbon atoms which is optionally substituted by hydroxyl, morpholinyl, methoxy, ethoxy, N,N-dimethylamino, N,N-diethylamine or phenyl, which for its part may be substituted up to 3 times by identical or different substituents from the group consisting of methoxy, or
represents cyclopropyl, or
or represents phenyl which is optionally substituted up to 3 times by identical or different substituents from the group consisting of fluorine, chlorine or hydroxyl, methoxy, ethoxy, fluorine or by straight-chain or branched alkyl having up to 3 carbon atoms, which for its part may be substituted by hydroxyl, or
$R^3$ and $R^4$ together with the nitrogen atom form a morpholinyl, pyrrolidinyl or piperidinyl ring which are optionally substituted by hydroxyl or by radicals of the formulae $-P(O)(OC_2H_5)_2$ or $-CH_2-P(O)OH(OC_2H_5)$ or by straight-chain or branched alkyl having up to 3 carbon atoms, which for its part may be substituted by hydroxyl or methoxy, or or
$R^3$ and $R^4$ together with the nitrogen atom form a radical of the formula

in which
$R^{37}$ represents pyrimidyl, ethoxycarbonyl or a radical of the formula $-CH_2-P(O)(OCH_3)_2$ or represents straight-chain or branched alkyl having up to 3 carbon atoms which is optionally substituted by hydroxyl or methoxy,
$R^5$ represents hydrogen,
and
$R^6$ represents ethoxy,
and their salts and isomeric forms.

Particular preference is furthermore given to compounds of the general formula (I) according to the invention in which $R^5$ represents hydrogen and the ethoxy group is in the O position to the point of attachment of the heterocycle.

Very particular preference is given to compounds according to the invention having the following structures:

Structure
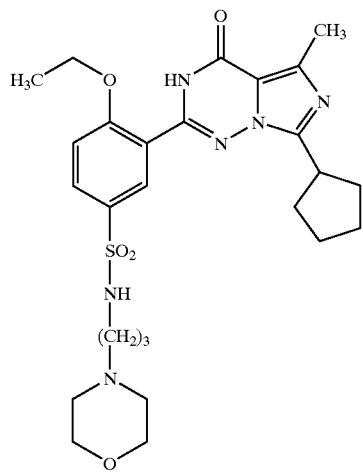
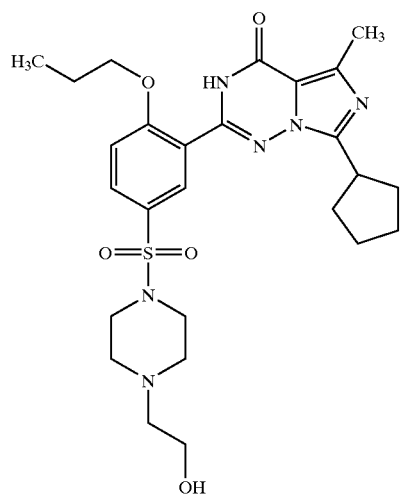
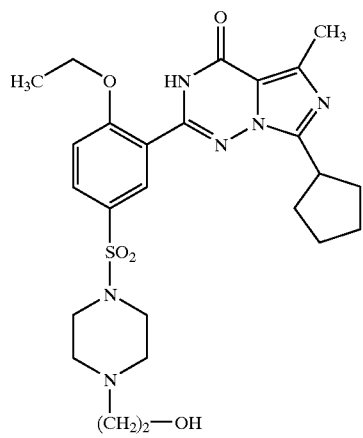
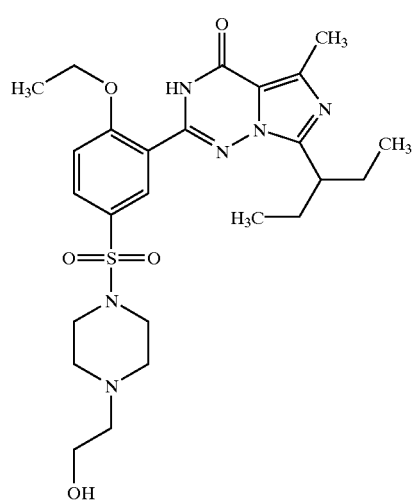
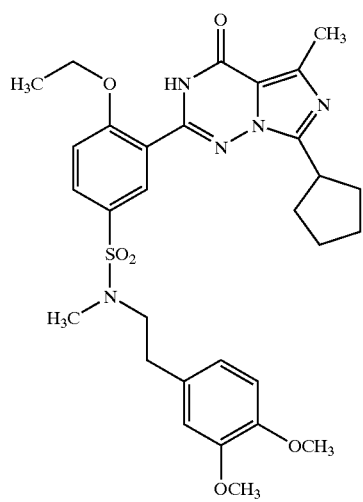
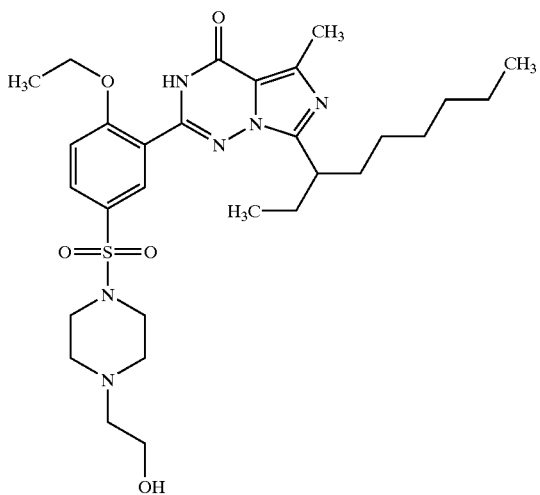

-continued
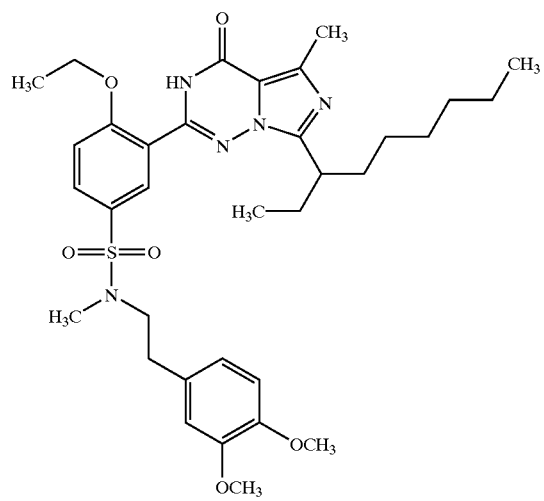
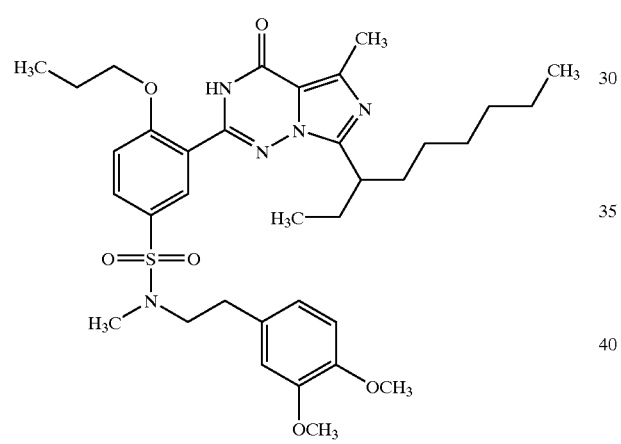
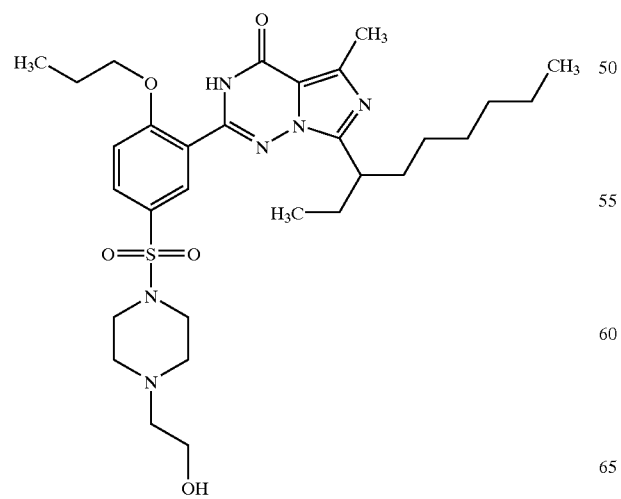
-continued
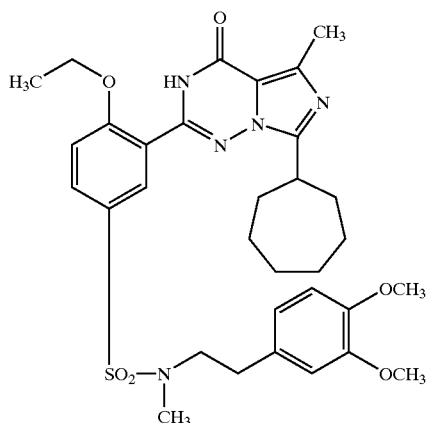
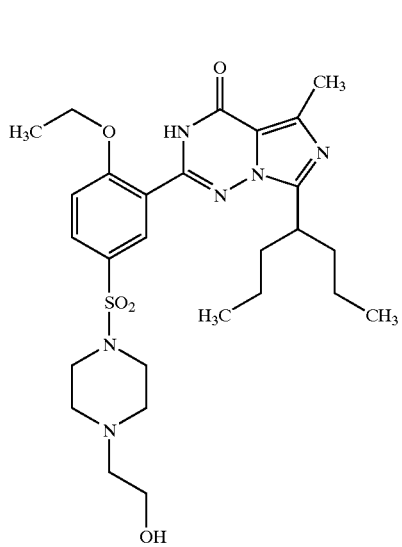
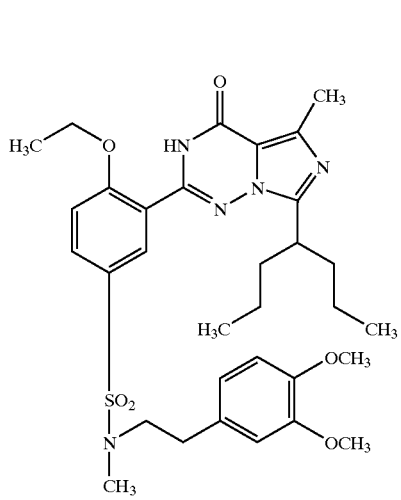

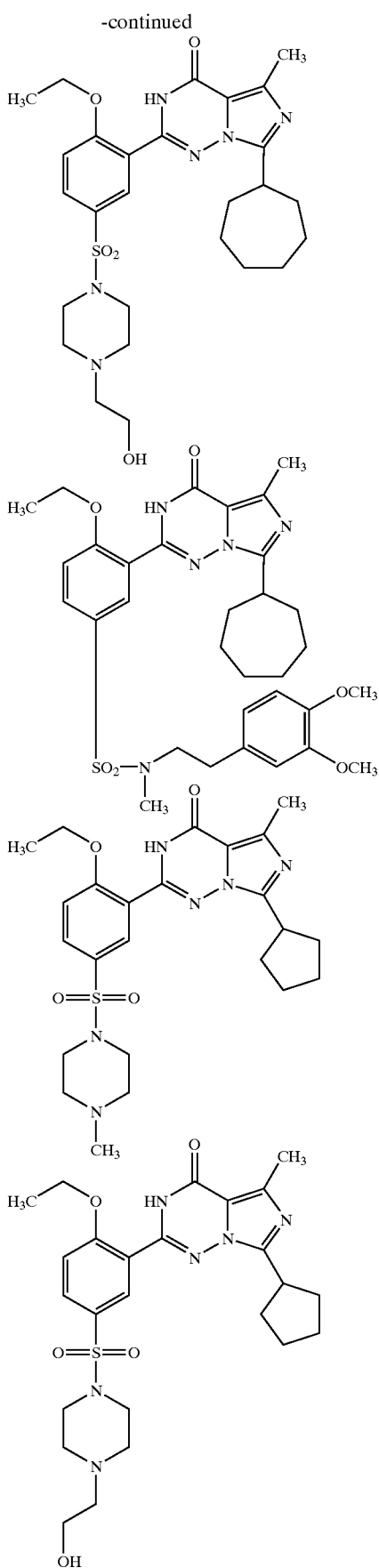

Moreover, we have found a process for preparing the compounds of the general formula (I) according to the invention, characterized in that

[A] initially compounds of the general formula (II)

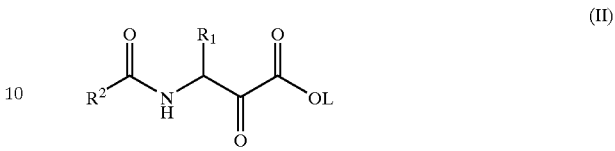

in which $R^3$ and $R^4$ are as defined above and

L represents straight-chain or branched alkyl having up to 4 carbon atoms, are converted with compounds of the general formula (III)

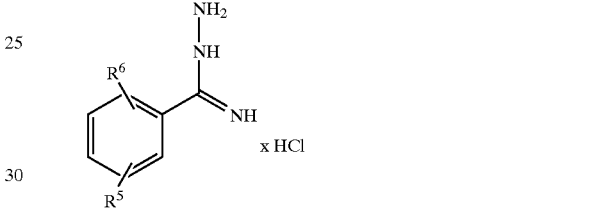

in which $R^3$ and $R^6$ are as defined above in a two-step reaction, preferably using the system ethanol and then phosphorus oxytrichloride/dichloroethane, into the compounds of the general formula (IV)

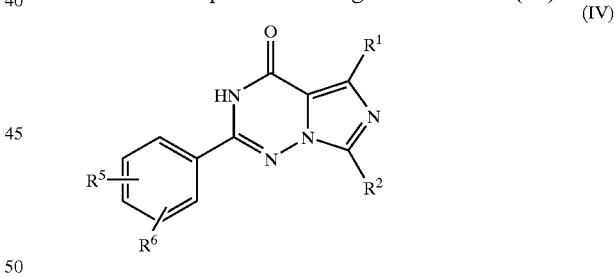

in which $R^1$, $R^2$, $R^3$ and $R^4$ are as defined above, in a further step reacted with chlorosulphonic acid to give the compounds of the general formula (V)

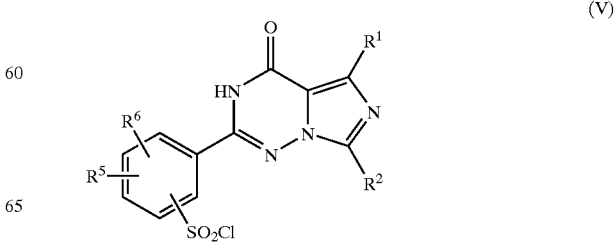

in which

R¹, R², R⁵ and R⁶ are as defined above, and then reacted with amines of the general formula (VI)

$$HN^3R^4 \quad (VI)$$

in which

R³ and R⁴ are as defined above in inert solvents.

The process according to the invention can be illustrated in an exemplary manner by the equations below:

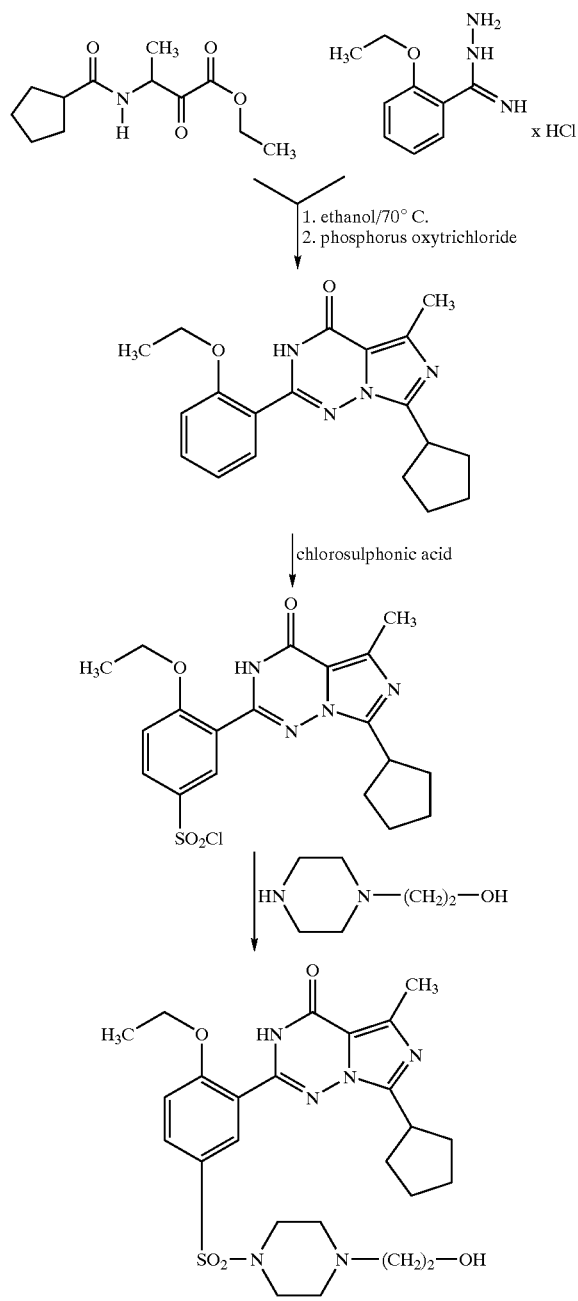

Solvents which are suitable for the individual steps are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, hexamethylphosphoric triamide, acetonitrile, acetone, dimethoxyethane or pyridine. It is also possible to use mixtures of the abovementioned solvents. Particular preference is given to ethanol for the first step and dichloroethane for the second step.

The reaction temperature can generally be varied within a relatively wide range. In general, the reaction is carried out in a range of from −20° C. to 200° C., preferably of from 0° C. to 70° C.

The process steps according to the invention are generally carried out under atmospheric pressure. However, it is also possible to operate under superatmospheric pressure or under reduced pressure (for example, in a range of from 0.5 to 5 bar).

The reaction to give the compounds of the general formula (V) is carried out in a temperature range of from 0° C. to room temperature, and at atmospheric pressure.

The reaction with the amines of the general formula (VI) is carried out in one of the abovementioned chlorinated hydrocarbons, preferably in dichloromethane.

The reaction temperature can generally be varied within a relatively wide range. In general, the reaction is carried out at temperatures in a range of from −20° C. to 200° C., preferably of from 0° C. to room temperature.

The reaction is generally carried out at atmospheric pressure. However, it is also possible to operate under superatmospheric pressure or under reduced pressure (for example in a range of from 0.5 to 5 bar).

Some of the compounds of the general formula (II) are known, or they are novel, and they can then be prepared by converting compounds of the general formula (VII)

$$R^2—CO—T \quad (VII)$$

in which

R² is as defined above and

T represents halogen, preferably represents chlorine, initially by reaction with compounds of the general formula (VIII)

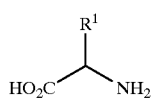

in which

R¹ is as defined above in inert solvents, if appropriate in the presence of a base and trimethylsilyl chloride, into the compounds of the general formula (IX)

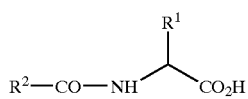

in which

R$^1$ and R$^2$ are each as defined above, and finally reacting with the compound of the formula (X)

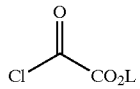
(X)

in inert solvents, if appropriate in the presence of a base.

Suitable solvents for the individual steps of the process are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl, acetate, dimethylformamide, hexamethylphosphoric triamide, acetonitrile, acetone, dimethoxyethane or pyridine. It is also possible to use mixtures of the abovementioned solvents. Particular preference is given to dichloromethane for the first step and to a mixture of tetrahydrofuran and pyridine for the second step.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or $C_1$–$C_4$ alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (X).

The reaction temperature can generally be varied within a relatively wide range. In general, the reaction is carried out in a range of from −20° C. to 200° C., preferably of from 0° C. to 100° C.

The compounds of the general formulae (VII), (VIII), (IX) and (X) are known per se, or they can be prepared by customary methods.

The compounds of the general formula (III) can be prepared by reacting compounds of the general formula (XI)

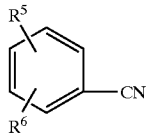
(XI)

in which

R$^5$ and R$^6$ are each as defined above with ammonium chloride in toluene and in the presence of trimethylaluminium in hexane in a temperature range of from −20° C. to room temperature, preferably at 0° C. and atmospheric pressure, and reacting the resulting amidine, if appropriate in situ, with hydrazine hydrate, to give the compounds of the general formula (III).

The compounds of the general formula (XI) are known per se, or they can be prepared by customary methods.

Most of the compounds of the general formula (IV) and (V) are novel, and they can be prepared as described above.

The amines of the general formula (VI) are known or can be prepared by customary methods.

The compounds of the general formula (I) according to the invention have an unforeseeable useful pharmacological activity spectrum.

They inhibit either one or more of the cGMP-metabolizing phosphodiesterases (PDE I, PDE II and PDE V). This results in an increase of cGMP. The differentiated expression of the phosphodiesterases in different cells, tissues and organs, as well as the differentiated subcellular localization of these enzymes, in combination with the selective inhibitors according to the invention make it possible selectively address the various cGMP-regulated processes.

Moreover, the compounds according to the invention enhance the activity of substances such as, for example EDRF (endothelium derived relaxing factor), ANP (atrial natriuretic peptide), of nitrovasodilators and all other substances which increase the cGMP concentration in a manner different from that of phosphodiesterase inhibitors.

They can therefore be employed in pharmaceuticals for treating cardiovascular disorders, such as, for example, for treating hypertension, neuronal hypertonic stable and unstable angina, peripheral and cardial vasculopathies, arrhythmiae, for treating thromboembolic disorders and ischaemias such as myocardial infarction, stroke, transistory and ischaemic attacks, angina pectoris, obstruction of peripheral circulation, prevention of restenoses after thrombolysis therapy, percutaneous transluminal angioplasty (PTA), percutaneous transluminal coronary angioplasties (PTCA) and bypass. Furthermore, they may also be of significance for cerebrovascular disorders.

They are also suitable for treating all disorders in which a relaxing action on smooth muscles is of importance, such as, for example, erectile dysfunction and female sexual dysfunction.

Activity of the Phosphodiesterases (PDEs)

The cGMP-stimulated PDE II, the cGMP-inhibited PDE III and the cAMP-specific PDE IV were isolated either from porcine or bovine heart myocardium. The Ca$^{2+}$-calmodulin-stimulated PDE I was isolated from porcine aorta, porcine brain or, preferably, from bovine aorta. The cGMP-specific PDE V was obtained from porcine small intestine, porcine aorta, human platelets and, preferably, from bovine aorta. Purification was carried out by anion exchange chromatography over MonoQ® Pharmacia, essentially following the method of M. Hoey and Miles D. Houslay, Biochemical Pharmacology, Vol. 40, 193–202 (1990) and C. Lugman et al., Biochemical Pharmacology, Vol. 35. 1743–1751 (1986).

The "phosphodiesterase [$^3$H] cAMP-SPA enzyme assay" and the "phosphodiesterase [$^3$H] cGMP-SPA enzyme assay" from Amersham Life Science were used for determining enzyme activity and IC$_{50}$ values of the various substances. The test was carried out according to the test protocol of the manufacturer. To determine the activity of PDE2, the [$^3$H] cAMP SPA assay was used, and $10^{-6}$ M cGMP were added to the reaction mixture to activate the enzyme. To measure PDE 1, $10^{-7}$ M calmodulin and 1 mM CaCl, were added to the reaction mixture. PDE5 was measured using the [$^3$H] cGMP SPA assay.

The substances preferably inhibit phosphodiesterases I and V. For both enzymes, the IC$_{50}$ values are in the range from 500 [lacuna] to 1 mM for PDE V preferably in the range from 1 to 100, for PDE I preferably in the range from 10 to 300 mM.

In principle, inhibition of one or more phosphodiesterases of this type results in an increase of the cGMP concentration. Thus, the compounds are of interest for all therapies in which an increase in the cGMP concentration is considered to be beneficial.

The cardiovascular effects were investigated using SH rats and dogs. The substances were administered intravenously or orally.

The novel active compounds and their physiologically acceptable salts (for example hydrochlorides, maleates or lactates) can be converted in a known manner into the customary formulations, such as tablets, coated tablets, pills, granules, aerosols, syrups, emulsions, suspensions and solutions, using inert non-toxic, pharmaceutically suitable excipients or solvents. In this case the therapeutically active compound should in each case be present in a concentration of from approximately 0.5 to 90% by weight of the total mixture, i.e., in amounts which are sufficient in order to achieve the dosage range indicated.

The formulations are prepared, for example, by extending the active compounds using solvents and/or excipients, if appropriate using emulsifiers and/or dispersants, it optionally being possible, for example, to use organic solvents as auxiliary solvents if the diluent used is water.

Administration is carried out in a customary manner, preferably orally, transdermally or parenterally, for example perlingually, buccally, intravenously, nasally, rectally or inhalatively.

In spite of this, if appropriate it may be necessary to depart from the amounts mentioned, namely depending on the body weight or the type of administration route, on the individual response towards the medicament, the manner of its formulation and the time or interval at which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

For human use, in the case of oral administration, doses of from 0.001 to 30 mg/kg, preferably of 0.01 mg/kg–10 mg/kg are administered. In the case of parenteral administration, it is good practice to use doses of 0.001 mg/kg–½ mg/kg.

The compounds according to the invention are also suitable for use in veterinary medicine. For use in veterinary medicine, the compounds or their non-toxic salts can be administered in a suitable formulation in accordance with general veterinary practice. Depending on the kind of animal to be treated, the veterinary surgeon can determine the nature of use and the dosage.

STARTING MATERIALS

Example 1A
2-Cyclopentanoylamino-propionic acid

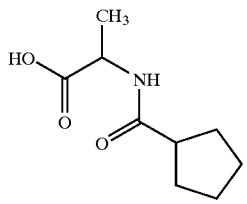

16.8 g (0.189 mol) of D,L-alanine and 41.98 g (0.415 mol) of triethylamine are initially charged in 200 ml of dichloromethane. At 0° C., 45.07 g (0.415 mol) of trimethylsilyl chloride are added dropwise, and the mixture is then stirred at room temperature for 1 h and then at 40C for 1 h. The solution is cooled to −10° C. and 25 g (0. 89 mol) of cyclopentanecarbonyl chloride are added dropwise. The mixture is stirred at −10° C. for 2 h and at room temperature for 1 h. With ice-cooling, 100 ml of water are added, and the mixture is then stirred for 10 min and the resulting precipitate is filtered off with suction. The precipitate is washed with 300 ml of water and then with 300 ml of diethyl ether and subsequently dried at 60° C.

Yield: 25.8 g (73.90% of theory).

$^1$H-NMR (CD$_3$OD): 1.35 (d, 3H); 1.5–1.9 (m, 8H); 2.7 (quin, 1H); 4.5 (quar., 1H);

Example 2A
2-Cyclopentanoylamino-butyric acid

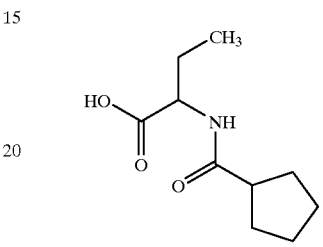

10.31 g of 2-aminobutyric acid (100 mmol) and 22.26 g (220 mmol) of triethylamine are dissolved in 100 ml of dichloromethane, and the solution is cooled to 0° C. 23.90 g (220 mmol) of trimethylsilyl chloride are added dropwise, and the solution is stirred at room temperature for 1 hour and at 40° C. for 1 hour. After cooling to −10° C. 13.26 g (100 mmol) of cyclopentanecarbonyl chloride are added dropwise, and the resulting mixture is stirred at −10° C. for 2 hours and at room temperature for 1 hour.

With ice-cooling, 50 ml of water are added dropwise and the reaction mixture is stirred at room temperature for 15 minutes. The mixture is diluted with water and dichloromethane and the resulting precipitate is filtered off with suction: 11.1 g (55%) of a colourless solid. The dichloromethane phase is dried over sodium sulphate and the solvent is removed under reduced pressure. The residue is stirred with toluene and the precipitate is filtered off with suction: 5.75 g (28%) of a colourless solid:

200 MHz $^1$H-NMR (DMSO$_6$): 0.88 (t, 3H) 1.61 (m, 10H); 2.66 (m, 1H): 4.09 (hex., 1H); 7.97 (d, 1H); 12.44 (s, 1H).

Example 3A
2-(2-Ethyl)-butanoylaminopropionic acid

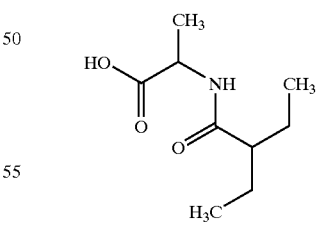

24.5 g (0.275 mol) of D,L-alanine are initially charge in 250 ml of dichloromethane, and 61.2 g (0.605 mol) of triethylamine are added. The mixture is cooled to 0° C. and 65.7 g (0.605 mol) of trimethylsilyl chloride are added. The mixture is stirred at room temperature for 1 hour and at 40° C. for 1 hour. The mixture is cooled to −10° C. and 37 g (0.275 mol) of 2-ethylbutyryl chloride are added dropwise. The mixture is stirred at −10° C. for 2 hours and at room temperature overnight. The mixture is cooled in an ice-bath and 150 ml of water are added dropwise, 50 g (1.25 mol) of NaOH dissolved in 100 ml of water, are added, and the aqueous phase is separated off and concentrated. The residue is again taken up in water and acidified with concentrated hydrochloric acid, the aqueous solution is extracted repeatedly with dichloromethane and the organic phase is dried over $Na_2SO_4$ and concentrated.

Yield: 43.55 g (84.6% of theory).

200 MHz $^1$H-NMR ($CDCl_3$): 0.91 (t, 6H); 1.5 (d, 3H); 1.52–1.73 (m, 4H); 1.99 (m, 1H); 4.61 (p, 1H); 6.25 (d, 1H); 6.76 (bs, 1H).

Example 4A
2-(2-Ethyl)-octanoylamino-propionic acid

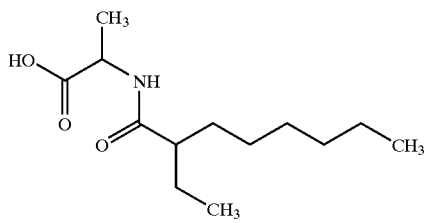

18.6 g (0.211 mol) of D,L-alanine and 46.6 g (0.41 mol) of triethylamine are initially charged in 300 ml of dichloromethane, at 0° C., 50.09 g (0.461 mol) of trimethylsilyl chloride are added dropwise, and the mixture is stirred at room temperature for 1 h and then at 40° C. for 1 h. The solution is cooled to −10° C., and 40 g (0.21 mol) of 2-ethyloctanoyl chloride in 50 ml of dichloromethane are added dropwise. The mixture is stirred at room temperature overnight, and 100 ml of water are then added dropwise with ice-cooling, and the mixture is stirred for another 10 minutes. The phases are separated, the aqueous phase is extracted twice with in each case 100 ml of dichloromethane and the combined organic phases are dried over sodium sulphate and evaporated under reduced pressure. The residue is recrystallized from toluene by adding n-hexane and dried at 60° C.

Yield: 3.9 g (78.2%).

$^1$H-NMR ($CDCl_3$): 0.9 (m, 6h); 1.25 (pseudo s, 8H); 1.45 (d, 3H); 1.4–1.7 (m, 4H); 2.0 (m, 1H); 4.6 (quin, 1H); 6.1 (d, 1H).

Example 5A
2-Hexanoylamino-propionic acid

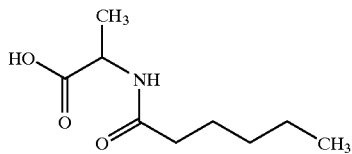

The preparation is carried out analogously to the procedure of Example 4A using 16.5 g (0.185 mol) of D,L-alanine, 41.23 g (0.407 mol) of triethylamine, 44.27 g (0.407 mol) of trimethylsilyl chloride and 24.93 g (0.185 mol) of hexanoyl chloride. The product crystallizes from toluene/n-hexane.

Yield: 33 g (95.2%).

$^1$H-NMR ($CD_3OD$): 0.9 (t, 3H); 1.2–1.4 (m, 7H); 1.6 (quin, 2H); 2.2 (t, 2H); 4.35 (quin, 1H).

Example 6A
2-Octanoylamino-propionic acid

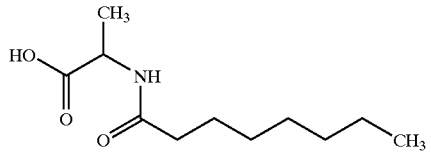

The preparation is carried out analogously to the procedure of Example 4A using 16.5 (0.185 mol) of D,L-alanine, 41.23 g (0.407 mol) of triethylamine, 44.27 g (0.407 mol) of trimethylsilyl chloride and 30.12 g (0.185 mol) of octanoyl chloride. The product crystallizes from toluene/n-hexane.

Yield: 34.3 g (86%).

$^1$H-NMR ($CD_3OD$): 0.9 (t, 3H); 1.2–1.4 (m, 11H); 1.6 (quin, 2H); 2.2 (t, 2H); 4.35 (quin, 1H).

Example 7A
2-Heptanoylamino-propionic acid

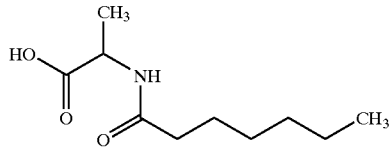

30 g (291 mmol) of methyl D,L-alaninate hydrochloride and 64.77 g (640 mmol) of triethylamine are initially charged in 300 ml of dry methylene chloride, at 0° C. 43.24 g (291 mmol) of heptanoyl chloride in 50 ml of methylene chloride are added dropwise. The mixture is allowed to warm to room temperature and stirred at this temperature for 2 h. The precipitate is filtered off, and the methylene chloride phase is extracted with saturated sodium bicarbonate solution and with saturated sodium chloride solution and dried over sodium sulphate. The solvent is removed under reduced pressure and the residue is dissolved in 300 ml of methanol, 300 ml of water, in which 46.55 g (1164 mmol) of sodium hydroxide are dissolved, is added to this solution, and the mixture is stirred at RT for 2 h. The mixture is filtered, the methanol is removed using a rotary evaporator and the aqueous phase that remains is acidified with conc. Hcl to pH 1–2. The precipitated product is filtered off and dried. A second product fraction is obtained by extracting the aqueous phase with ethyl acetate.

Yield: 50 g (85.4%).

$^1$H-NMR ($CD_3OD$): 0.9 (t, 3H); 1.2–1.4 (m, 9H); 1.6 (quin., 2H); 2.2 (t, 2H); 4.38 (quar., 1H).

Example 8A
2-Decanoylamino-propionic acid

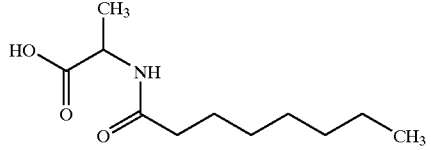

The preparation is carried out analogously to the procedure of Example 7A using 19.0 g (184 mmol) of methyl D,L-alaninate hydrochloride and 35.14 g (184 mmol) of decanoyl chloride.

Yield: 37.3 g (83.2%).
$^1$H-NMR (CD$_3$OD): 0.9 (t, 3H); 1.2–1.4 (m, 15H); 1.6 (m, 2H); 2.2 (t, 2H); 4.35 (quar., 1H).

Example 9A
2-(2-n-Propyl)-pentanoylamino-propionic acid

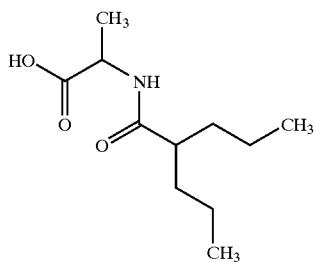

The preparation is carried out analogously to the procedure of Example 7A using 20.94 g (150 mmol) of methyl D,L-alaninate hydrochloride and 24.4 g (150 mmol) of 2-n-propylpentanoyl chloride.
Yield: 21.7 g (88.9%).
$^1$H-NMR (CD$_3$OD): 0.9 (t, 6H); 1.2–1.4 (m, 9H); 1.55 (m, 2H); 2.25 (m, 1H); 4.4 (quar., 1H).

Example 10A
2-Cycloheptanoylamino-propionic acid

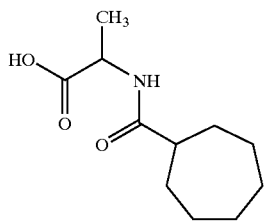

The preparation is carried out analogously to the procedure of Example 7A using 20 g (143 mmol) of methyl D,L-alaninate hydrochloride and 23.02 g (143 mmol) of cycloheptanoyl chloride.
Yield: 16 g (52.4%).
$^1$H-NMR (CD$_3$OD): 1.35 (d, 3H); 1.45–1.65 (m, 8H); 1.7–1.95 (m, 4H); 2.35 (m, 1H); 4.25 (quar., 1H).

Example 11A
2-Ethoxy-benzonitrile

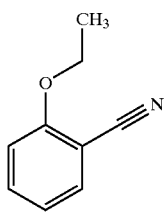

25 g (210 mmol) of 2-hydroxybenzonitrile, 87 g of potassium carbonate and 34.3 g (314.8 mmol) of ethyl bromide in 500 ml of acetone are refluxed overnight. The solid is filtered off, the solvent is removed under reduced pressure and the residue is distilled under reduced pressure. This gives 30.0 g (97%) of a colourless liquid.
200 MHz $^1$H-NMR (DMSO-d$_6$): 1.48 (t, 3H); 4.15 (quart., 2H); 6.99 (dt, 2H); 7.51 (dt, 2H).

Example 12A
2-Ethoxy-benzamidine hydrochloride

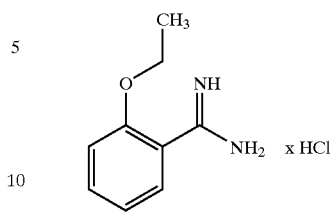

21.4 g (400 mmol) of ammonium chloride are suspended in 375 ml of toluene, and the suspension is cooled to 0° C. 200 ml of a 2M solution of trimethylaluminium in hexane are added dropwise, and the mixture is stirred at room temperature until evolution of gas has ceased, 29.44 g (200 mmol) of 2-ethoxybenzonitrile are added, and the reaction mixture is then stirred at 80° C. (bath) overnight. The cooled reaction mixture is, with ice-cooling, added to a suspension of 100 g of silica gel and 950 ml of chloroform, and the mixture is stirred at room temperature for 30 minutes. The mixture is filtered off with suction and the filter residue is washed with the same amount of methanol. The mother liquor is evaporated, the resulting residue is stirred with a mixture of dichloromethane and methanol (9:1), the solid is filtered off with suction and the mother liquor is evaporated. This gives 30.4 g (76%) of a colourless solid.
200 MHz $^1$H-NMR (DMSO-d$_6$): 1.36 (t, 3H); 4.12 (quart, 2H); 7.10 (t, 1H); 7.21 (d, 1H); 7.52 (m, 2H); 9.30 (s, broad, 4H).

Example 13A
2-Propoxybenzonitrile

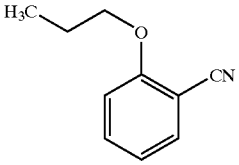

75 g (63 mmol) of 2-hydroxybenzonitrile, 174 g (1.26 mol) of potassium carbonate and 232.3 g (1.89 mol) of n-propyl bromide in 1 l of acetone are refluxed overnight. The solid is filtered off, the solvent is removed under reduced pressure and the residue is distilled under reduced pressure.
M.p.: 89° C. (0.7 mbar).
Yield: 95.1 g (93.7% of theory).

Example 14A
2-Propoxybenzamidine hydrochloride

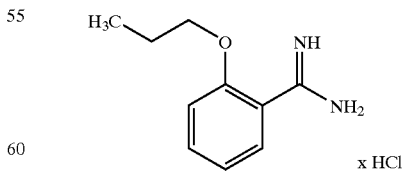

21.41 g (400 ml) of ammonium chloride are suspended in 400 ml of toluene and cooled to from 0 to 5° C. 200 ml of a 2M solution of triethylaluminium in hexane are added dropwise, and the mixture is stirred at room temperature until evolution of gas has ceased, 32.2 g (200 mmol) of 2-propoxybenzonitrile are added, and the reaction mixture is then stirred at 80° C. (bath) overnight. The cooled reaction mixture is, with ice-cooling, added to a suspension of 300 g of silica gel and 2.85 ml of ice-cold chloroform and stirred for 30 minutes. The mixture is filtered off with suction and the filter residue is washed with the same amount of methanol. The solvent is distilled off under reduced pressure, the residue is stirred with 500 ml of a mixture of dichloromethane and methanol (9:1), the solid is filtered off and the mother liquor is evaporated. The residue is stirred with petroleum ether and filtered off with suction. This gives 22.3 g (52%) of product.

200 MHz $^1$H-NMR (CD$_3$OD): 1.05 (t, 3H); 1.85 (sex, 2H); 4.1 (t, 2H); 7.0–7.2 (m, 2H); 7.5–7.65 (m, 2H).

Example 15A 2-(2-Ethoxyphenyl)-5-methyl-7-cyclopentyl-3H-imidazo[5,1-f][1,2,4]-triazin-4-one

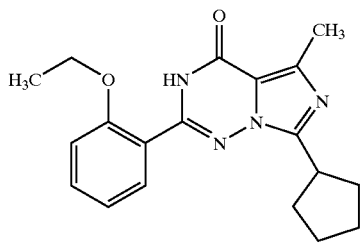

19.9 g (0.1 mol) of 2-cyclopentanoylamino-propionic acid (Example 1A), 24 ml of pyridine and 0.5 g of 4-dimethylaminopyridine are refluxed in 100 ml of absolute tetrahydrofuran, and 27.27 g (0.2 mol) of ethyl oxalyl chloride are added dropwise. The mixture is boiled at reflux for 90 minutes, cooled and put into 200 ml of ice-water. The mixture is extracted 3 times with ethyl acetate and the combined ethyl acetate phases are dried over sodium sulphate and evaporated. The residue is taken up in 30 ml of methanol and, after addition of 4.75 g of sodium bicarbonate, refluxed for 2.5 h. The mixture is filtered off and the resulting methanolic solution of the α-keto ester is directly reacted further, without further purification.

With ice-cooling, 4.99 g (0.1 mol) of hydrazine monohydrate are added dropwise to a solution of 20 g (0.1 mol) of 2-ethoxy-benzamidine hydrochloride (Example 12A) in 120 ml of ethanol, and the mixture is stirred at room temperature for 10 minutes. The methanolic solution of the α-keto ester described above is added dropwise to the suspension, and the mixture is stirred at 70° C. for 4 h. Following filtration, the solution is evaporated, the residue is partitioned between dichloromethane and water and the organic phase is, after drying over sodium sulphate, evaporated.

The residue is taken up in 150 ml of 1.2-dichloroethane, and 17 ml of phosphorus oxychloride are added dropwise. The mixture is stirred under reflux for 2 h and then cooled, washed twice with saturated sodium bicarbonate solution and dried over sodium sulphate. The organic phase is evaporated and the residue is chromatographed over silica gel using the mobile phase dichloromethane/methanol 50:1. The product-containing fractions are combined and evaporated. The product can be crystallized from ethyl acetate/petroleum ether.

Yield: 7.1 g (20.9%), white solid.

$^1$H-NMR (CD$_3$OD): 1.45 (t, 3H); 1.65–1.8 (m, 2H); 1.8–2.0 (m, 4H); 2.05–2.2 (m, 2H); 2.6 (s, 3H); 3.65 (quin., 1H); 4.2 (quar, 2H); 7.1 (t, 1H); 7.15 (d, 1H); 7.5 (t, 1H); 7.7 (d, 1H).

Example 16A 2-(2-Ethoxyphenyl)-5-ethyl-7-cyclopentyl-3H-imidazo[5,1-f][1,2,4]-triazin-4-one

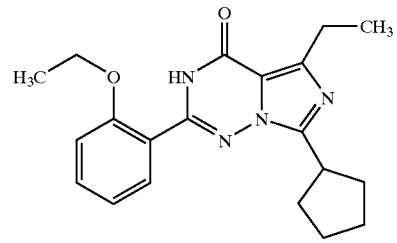

The preparation is carried out analogously to the procedure of Example 15A using 8.77 g (44 mmol) of 2-cyclopentanoylamino-butyric acid (Example 2A) and 8.83 g (44 mmol) of 2-ethoxy-benzamidine hydrochloride (Example 12A). The product is purified by silica gel chromatography using the mobile phase cyclohexane/ethyl acetate (6:4).

Yield: 0.355 g (6.7%), white solid.

$^1$H-NMR (CDCl$_3$): 1.32 (t, 3H); 1.57 (t 3H); 1.94 (m, 8H); 3.03 (quar, 2H); 3.64 (quin, 1H); 4.27 (quar, 2H); 7.06 (d, 1H); 7.12 (t, 1H); 7.50 (t, 1H); 8.16 (dd, 1H); 9.91 (s, 1H).

Example 17A 2-(2-Propoxyphenyl)-5-methyl-7-cyclopentyl-3H-imidazo[5,1-f][1,2,4]-triazin-4-one

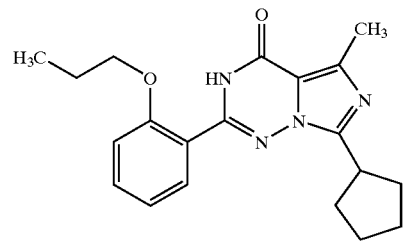

The preparation is carried out analogously to the procedure of Example 15A using 8.33 g (45 mmol) of 2-cyclopentanoylamino-propionic acid (Example 1A) and 9.65 g (45 mmol) of 2-propoxybenzamidine hydrochloride (Example 14A). The product is purified by silica gel chromatography using the mobile phase dichloromethane/methanol (50:1). The product can be crystallized from ethyl acetate/petroleum ether.

Yield: 1.82 g (11.5%), white solid.

$^1$H-NMR (CDCl$_3$): 1.95 (m, 4H); 2.15 (m, 2H); 2.65 (s, 3H); 3.65 (quin, 1H); 4.15 (t, 2H); 7.05 (d, 1H); 7.1 (t, 1H); 7.5 (td, 1H); 8.2 (dd, 1H).

Example 18A 2-(2-Ethoxyphenyl)-5-methyl-7-(2-ethylpropyl)-3H-imidazo[5,1-f][1,2,4]-triazin-4-one

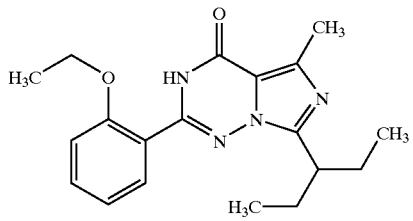

The preparation is carried out analogously to the procedure of Example 15A using 21.45 g (0.1 mol) of 2-(2-ethyl)-butyrylamino-propionic acid (Example 3A) and 20.6 g (0.1 mol) of 2-ethoxybenzamidine hydrochloride (Example 12A). The product is purified by silica gel chromatography using the mobile phase dichloromethane/methanol 60:1.

Yield: 7.22 g (21.3%).

200 MHz $^1$H-NMR (CDCl$_3$): 0.87 (t, 6H); 1.57 (t, 3H); 1.88 (m, 4H); 2.67 (s, 3H); 3.28 (m, 1h); 4.28 (q 2H); 7.05 (d, 1H); 7.13 (dt, 1H); 8.15 (dd, 1H).

Example 19A 2-(2-Ethoxyphenyl)-5-methyl-7-(2-ethyleptyl)-3H-imidazo[5,1-f][1,2,4]-triazin-4-one

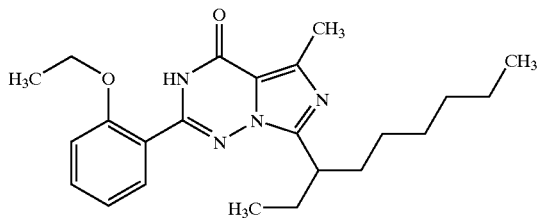

The preparation is carried out analogously to the procedure of Example 15A using 10.95 g (45 mmol) of 2-(2-ethyl)octanoylamino-propionic acid (Example 4A) and 9.03 g (45 mmol) of 2-ethoxybenzamidine hydrochloride (Example 12A). The product is purified by silica gel chromatography using the mobile phase dichloromethane/methanol 100:1.

Yield: 2.76 g (15.5%), yellow oil.

$^1$H-NMR (CDCl$_3$): 0.75–0.9 (m, 6H); 1.1–1.4 (m, 8H); 1.5 (t, 3H); 1.8–2.05 (m, 4h); 2.7 (s, 3H); 3.4 (quin, 1H); 4.3 (t, 2H); 7.05–7.2 (pseudo quar 2h); 7.5 (td, 1H); 8.2 (dd, 1H); 10.4 (broad, 1H).

Example 20A 2-(2-Propoxyphenyl)-5-methyl-7-(2-ethyleptyl)-3H-imidazo[5,1-f][1,2,4]-triazin-4-one

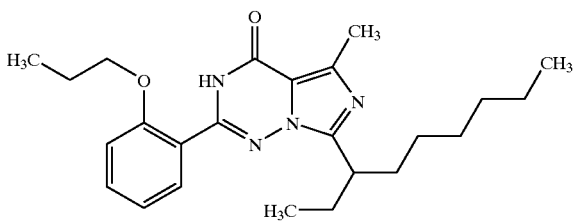

The preparation is carried out analogously to the procedure of Example 15A using 10.95 g (45 mmol) of 2-(2-ethyl)-octanoylamino-propionic acid (Example 4A) and 9.66 g (45 mmol) of 2-propoxybenzamidine hydrochloride (Example 14A). The product is purified by silica gel chromatography using the mobile phase dichloromethane/methanol 60:1.

Yield; 3.7 g (20%), yellow oil.

$^1$H-NMR (CDCl$_3$): 0.75–0.9 (m, 6H); 1.15 (t, 3h); 11–1.35 (m, 8H); 1.75–2.1 (m, 6h); 2.7 (s, 3H); 3.4 (quin, 1H); 4.2 (t, 2H); 7.05–7.2 (pseudo quar, 2H); 7.5 (td, 1H); 8.2 (dd, 1H); 10.2 (broad, 1H).

Example 21A 2-(2-Ethoxyphenyl)-5-methyl-7-pentyl-3H-imidazo[5,1-f][1,2,4]-triazin-4-one

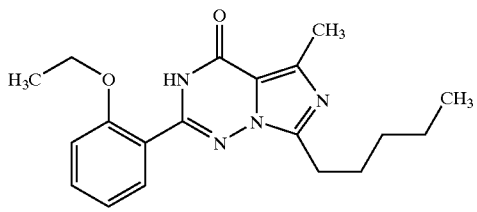

The preparation is carried out analogously to the procedure of Example 15A using 9.36 g (50 mmol of 2-hexanoylamino-propionic acid (Example 5A) and 10.1 g (50 mmol) of 2-ethoxybenzamidine hydrochloride (Example 12A). The product is purified, by silica gel chromatography using the mobile phase dichloromethane/methanol 50:1.

Yield: 3.1 g (18.3%), oil.

$^1$H-NMR (CD$_3$OD): 0.9 (t, 3H); 1.3–1.4 (m, 4h); 1.45 (t, 3H); 1.8 (quin, 2H); 2.1 (s, 3H); 3.0 (t, 2H); 4.2 (quar, 2H); 7.1 (t, 1H); 7.15 (d, 1H); 7.5 (td, 1H); 7.7 (dd, 1H).

Example 22A 2-(2-Ethoxyphenyl)-5-heptyl-3H-imidazo[5,1-f][1,2,4]-triazin-4-one

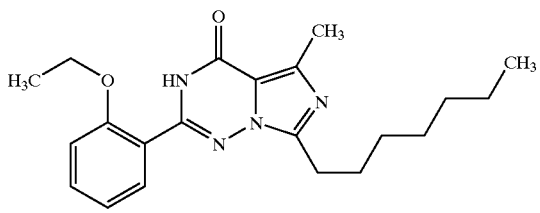

The preparation is carried out analogously to the procedure of Example 15A using 14.7 g (68.1 mmol) of 2-octanoylamino-propionic acid (Example 6A) and 13.66 g (68.1 mmol) of 2-ethoxybenzamidine hydrochloride (Example 12A). The product is purified by silica gel chromatography using the mobile phase dichloromethane/methanol 50:1.

Yield: 4.65 g (18.5%), oil.

$^1$H-NMR (CD$_3$OD): 0.85 (t, 3H); 1.2–1.4 (m, 8H); 1.45 (t, 3H); 2.8 (quin, 2H); 2.6 (s, 3H); 3.0 (t, 2H); 4.2 (quar, 2H); 7.1 (t, 1H); 7.2 (d, 1H); 7.55 (td, 1H); 7.7 (dd, 1H).

Example 23A

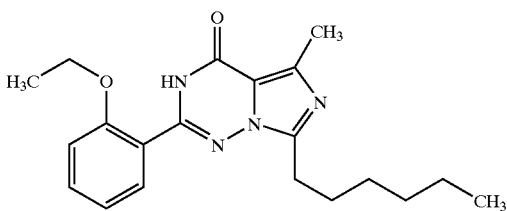

The preparation is carried out analogously to the procedure of Example 15A using 14.1 g (70 mmol) of 2-heptanoylamino-propionic acid (Example 7A) and 14.05 g (70 mmol) of 2-ethoxybenzamidine hydrochloride (Example 12A). The product is purified by silica gel chromatography using the mobile phase petroleum ether/ethyl acetate 1:1.

Yield: 3.5 g (14.1%).

$^1$H-NMR (CD$_3$OD): 0.9 (t, 3H); 1.3–1.45 (m, 6H); 1.4 (t, 3H); 1.7–1.9 (m, 2H); 2.15 (s, 3H); 3.1 (t, 2H); 4.2 (quar, 2H); 7.1 (t, 1H); 7.15 (d, 1H); 7.05 (td, 1H); 7.7 (dd, 1H).

Example 24A
2-(2-Ethoxyphenyl)-5-methyl-7-n-3H-imidazo[5,1-f]-[1,2,4]-triazin-4-one

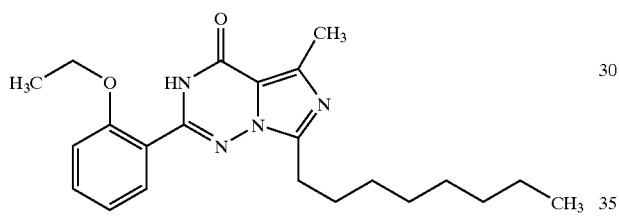

The preparation is carried out analogously to the procedure of Example 15A using 17.0 g (70 mmol) of 2-decanoylamino-propionic acid (Example 8A) and 14.05 g (70 mmol) of 2-ethoxybenzamidine hydrochloride (Example 12A). The product is purified by silica gel chromatography using the mobile phase petroleum ether/ethyl acetate 1:1.

Yield: 3.5 g (14.1%).

$^1$H-NMR (CD$_3$OD): 0.9 (t, 3H); 1.3–1.45 (m, 6H); 1.4 (t, 3H); 1.7–1.9 (m, 2H); 2.15 (s, 3H); 3.1 (t, 2H); 4.2 (quar., 2H); 7.1 (t, 1H); 7.15 (d, 1H); 7.05 (td, 1H); 7.7 (dd, 1 H).

Example 24B
2-(2-Ethoxyphenyl)-5-methyl-7-n-3H-imidazo[5,1-f][1,2,4]-triazin-4-one

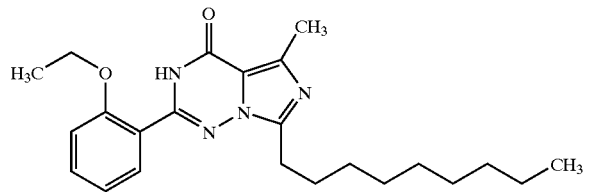

The preparation is carried out analogously to the procedure of Example 15A using 17.0 g (70 mmol) of 2-decanoylamino-propionic acid (Example 8A) and 14.05 g (70 mmol) of 2-ethoxybenzamidine hydrochloride (Example 12A). The product is purified by silica gel chromatography using the mobile phase methylene chloride/methanol 50:1. The product can then be crystallized from petroleum ether.

Yield: 4.64 g (16.7%).

$^1$H-NMR (CD$_3$OD): 0.85 (t, 3H); 1.2–1.4 (m, 12H); 1.45 (t, 3H); 1.86 (quin., 2H); 2.6 (s, 3H); 3.0 (t, 2H); 4.2 (quar., 2H); 7.05 (t, 1H); 7.15 (d, 1H); 7.5 (td, 1H); 7.7 (dd, 1H).

Example 25A 2-(2-Ethoxyphenyl)-5-methyl-7-(2-n-propylbutyl)-3H-imidazo[5,1-f][1,2,4]-triazin- 4-one

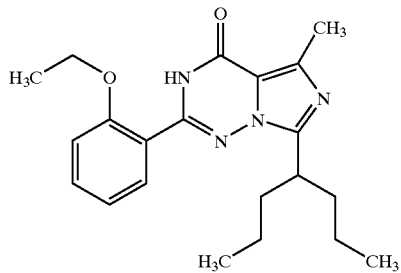

The preparation is carried out analogously to the procedure of Example 15A using 10.72 g (49.8 mmol) of 2-(2-n-propyl)pentanoylamino-propionic acid (Example 9A) and 10.0 g (49.8 mmol) of 2-ethoxybenzamidine hydrochloride (Example 12A). The product is purified by silica gel chromatography using the mobile phase methylene chloride/methanol 100:1, then 50:1. The product can be recrystallized from diethyl ether.

Yield: 1.8 g (9.8%).

M.p.: 150° C.

Example 26A 2-(Ethoxyphenyl)-5-methyl-7-cycloheptyl-3H-imidazo[5,1-f][1,2,4]-triazin-4-one

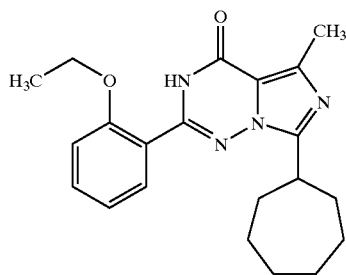

The preparation is carried out analogously to the procedure of Example 15A using 14.9 g (70 mmol) of 2-cycloheptanoylamino-propionic acid (Example 10A) and 14 g (70 mmol) of 2-ethoxybenzamnidine hydrochloride (Example 12A). The product is purified by silica gel chromatography using the mobile phase methylene chloride/methanol 10:1, and then 50:1.

Yield: 5.35 g (20.9%).

$^1$H-NMR (CD$_3$OD): 1.45 (t, 3H); 1.6–2.0 (m, 10H); 2.1–2.2 (m, 2H); 2.7 (s, 3H); 3.65 (quin., 1H); 4.2 (quar., 2H); 7.1 (t, 1H); 7.2 (d, 1H); 7.6 (td, 1H); 7.75 (dd, 1H).

Example 27A

4-Ethoxy-3-(5-methyl-4-oxo-7-cyclopentyl-3,4-dihydro-imidazo[5,1-f][1,2,4]-triazin-2-yl)-benzenesulphonyl chloride

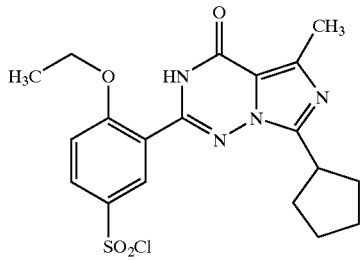

At 0° C. 7.0 g (20.7 mmol) of 2-(2-ethoxyphenyl)-5-methyl-7-cyclopentyl-3H-imidazo-[5,1-f][1,2,4]-triazin-4-one (Example 15A) are added carefully to 24.1 g (207 mmol) of chlorosulphuric acid. The mixture is allowed to warm to room temperature and stirred overnight. The solution is carefully added to 200 ml of ice-water and extracted twice with dichloromethane. The combined organic phases are dried over sodium sulphate and the solvent is distilled off under reduced pressure. The sulphonyl chloride is dried under reduced pressure and reacted further to the sulphonamides without further purification.

Yield: 7.95 g (88%), white foam.

$^1$H-NMR (CDCl$_3$): 1.6 (t, 3H); 1.7 (m, 2H); 1.95 (m, 4H); 2.15 (m, 2H); 2.65 (s, 3H); 3.71 (quin, 1H); 4.4 (quar, 2H); 7.25 (d, 1H); 8.2 (dd, 1H); 8.7 (d, 1H); 9.9 (s, 1H).

Example 28A

4-Ethoxy-3-(5-ethyl-4-oxo-7-cyclopentyl-3,4-dihydro-imidazo[5,1-f][1,2,4]- triazin-2-yl)-benzenesulphonyl chloride

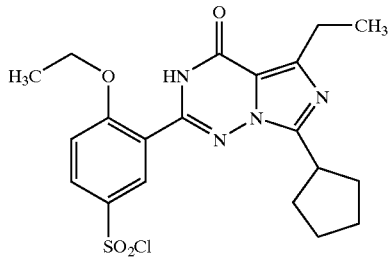

The preparation is carried out analogously to the procedure of Example 27A using 0.34 g (0.96 mmol) of 2-(2-ethoxyphenyl)-5-ethyl-7-cyclopentyl-3H-imidazo-[5,1-f][1,2,4]-triazin-4-one (Example 16A). This gives 0.43 g (98%) of sulphonyl chloride as a colourless foam which is directly reacted further.

Example 29A

4-Propoxy-3-(5-methyl-4-oxo-7-cyclopentyl-3,4-dihydro-imidazo[5,1-f][1,2,4]-tri-azin-2-yl)-benzenesulphonyl chloride

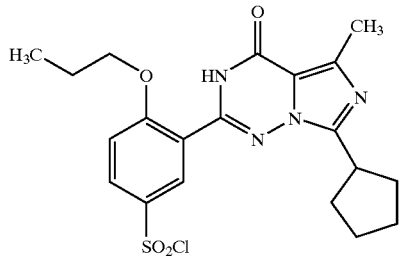

The preparation is carried out analogously to the procedure of Example 27A using 0.7 g (2 mmol) of 2-(2-propoxyphenyl)-5-methyl-7-cyclopentyl-3H-imidazo-[5,1-f][1,2,4]-triazin-4-one (Example 17A). This gives 0.8 g (89.3%) of sulphonyl chloride as a white foam which is directly reacted further.

Example 30A

4-Ethoxy-3-(5-methyl-4-oxo-7-(2-ethylpropyl)-3,4-dihydro-imidazo[5,1-f][1,2,4]-triazin-2-yl)-benzenesulphonyl chloride

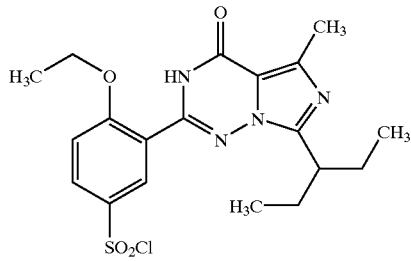

The preparation is carried out analogously to the procedure of Example 27A using 7.23 g (0.12 mmol) of 2-(2-ethoxyphenyl)-5-methyl-7-(2-ethylpropyl)-1H-imidazo-[5,1-f][1,2,4]-triazin-4-one (Example 18A). This gives 8.56 g (91.9%) of sulphonyl chloride as a white solid which is directly reacted further.

Example 31A

4-Ethoxy-3-(5-methyl-4-oxo-7-(2-ethylheptyl)-3,4-dihydro-imidazo[5,1-f][1,2,4]-triazin-2-yl)-benzenesulphonyl chloride

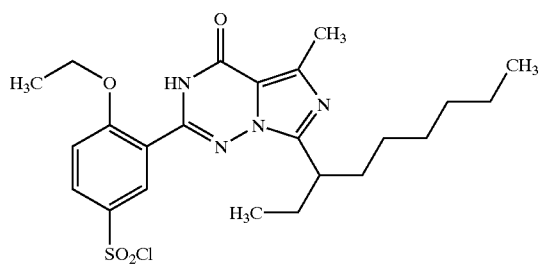

The preparation is carried out analogously to the procedure of Example 27A using 5.6 g (14.1 mmol) of 2-(2-ethoxyphenyl)-5-methyl-7-(2-ethylheptyl)-3H-imidazo-[5,1-f][1,2,4]-triazin-4-one (Example 19A). This gives 3.7 g (52.9%) of sulphonyl chloride as a slightly yellow foam which is directly reacted further.

Example 32A

4-Propoxy-3-(5-methyl-4-oxo-7-(2-ethylheptyl)-3,4-dihydro-imidazo[5,1-f][1,2,4]-triazin-2-yl)-benzenesulphonyl chloride

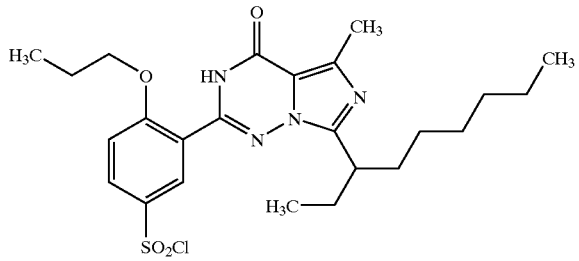

The preparation is carried out analogously to the procedure of Example 27A using 1.4 g (3.41 mmol) of 2-(2-propoxyphenyl)-5-methyl-7-(2-ethyl)-3H-imidazo-[5,1-f][1,2,4]-triazin-4-one (Example 20A). This gives 1.4 g (80.6%) of sulphonyl chloride as a white foam which is directly reacted further.

Example 33A

4-Ethoxy-3-(5-methyl-4-oxo-7-pentyl-3H-imidazo[5,1-f][1,2,4]-triazin-2-yl)- benzenesulphonyl chloride

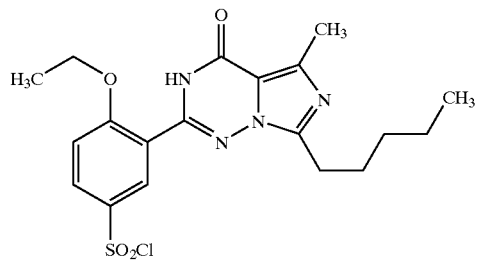

The preparation is carried out analogously to the procedure of Example 27A using 0.3 g (0.88 mmol) of 2-(2-ethoxyphenyl)-5-methyl-7-pentyl-3H-imidazo[5,1-f][1,2,4]triazin-4-one (Example 21A). This gives 0.3 g (77.6%) of sulphonyl chloride as a white foam which is directly reacted further.

Example 34A

4-Ethoxy-3-(5-methyl-4-oxo-7-heptyl-3H-imidazo[5,1-f][1,2,4]-triazin-2-yl)- benzenesulphonyl chloride

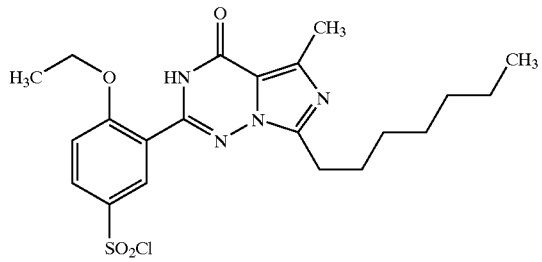

The preparation is carried out analogously to the procedure of Example 27A using 0.3 g (0.81 mmol) of 2-(2-ethoxyphenyl)-5-methyl-7-heptyl-3H-imidazo[5,1-f][1,2,4]triazin-4-one (Example 22A). This gives 0.3 g (78.9%) of sulphonyl chloride as a white foam which is directly reacted further.

Example 35A

4-Ethoxy-3-(5-methyl-4-oxo-7-n-hexyl-3,4-dihydro-imidazo[5,1-f][1,2,4]- triazin-2-yl)-benzenesulphonyl chloride

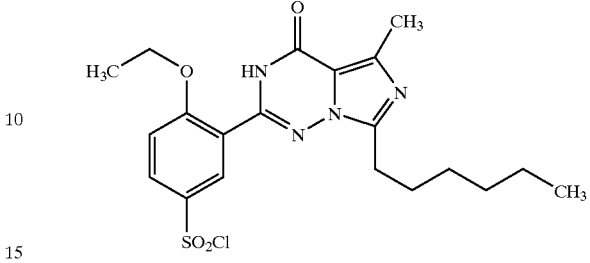

The preparation is carried out analogously to the procedure of Example 27A using 300 mg (0.84 mmol) of 2-(2-ethoxyphenyl)-5-methyl-7-n-hexyl-3H-imidazo-[5,1-f][1,2,4]-triazin-4-one (Example 23A) and 0.98 g (8.4 mmol) of chlorosulphuric acid. This gives 300 mg (78.7%) of sulphonyl chloride which is directly reacted further.

Example 36A

4-Ethoxy-3-(5-methyl-4-oxo-7-n-nonyl-3,4-dihydro-imidazo[5,1-f][1,2,4]- triazin-2-yl)-benzenesulphonyl chloride

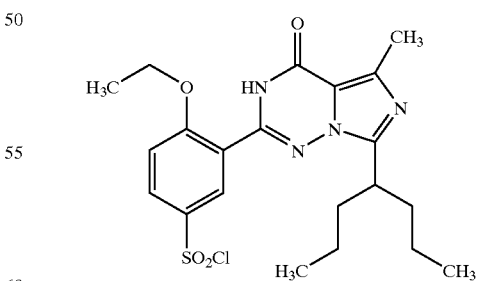

The preparation is carried out analogously to the procedure of Example 27A using 400 mg (1 mmol) of 2-(2-ethoxyphenyl)-5-methyl-7-n-nonyl-3H-imidazo[5,1-f][1,2,4]triazin-4-one (Example 24A) and 1.18 g (10 mmol) of chlorosulphuric acid. This gives 402 mg (80.1%) of sulphonyl chloride which is directly reacted further.

Example 37A

4-Ethoxy-3-(5-methyl-4-oxo-7-(2-n-propylbutyl)-3,4-dihydro-imidazo[5,1-f][1,2,4]-triazin-2-yl)-benzenesulphonyl chloride The preparation is carried out analogously to the procedure of Example 27A using 300 mg (0.81 mmol) of 2-(2-ethoxyphenyl)-5-methyl-7-(2-n-propylbutyl)-3H-imidazo[5,1-f][1,2,4]-triazin-4-one (Example 25A) and 950 mg. (8.1 mmol) of chlorosulphuric acid. This gives 300 g (78.9%) of sulphonyl chloride which is directly reacted further.

Example 38A

4-Ethoxy-(5-methyl-4-oxo-7-cycloheptyl-3,4-dihydro-imidazo[5,1-f][1,2,4]- triazin-2-yl)-benzenesulphonyl chloride

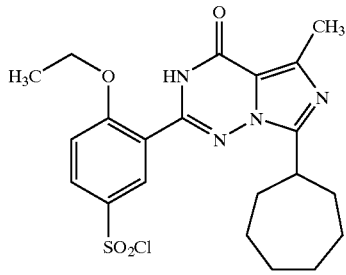

The preparation is carried out analogously to the procedure of Example 27A using 400 mg (1.1 mmol) of 2-(2-ethoxyphenyl)-5-methyl-7-cycloheptyl-3H-imidazo[5,1-f][1,2,4]triazin-4-one (Example 26A) and 1.27 g (11 mmol) of chlorosulphuric acid. This gives 402 mg (78.6%) of sulphonyl chloride which is directly reacted further.

PREPARATION EXAMPLES

Example 1

2-[2-Ethoxy-5-(4-methylpiperazine-1-sulphonyl)-phenyl]-5-methyl-7-cyclopentyl- 3H-imidazo[5,1-f][1,2,4]-triazin-4-one

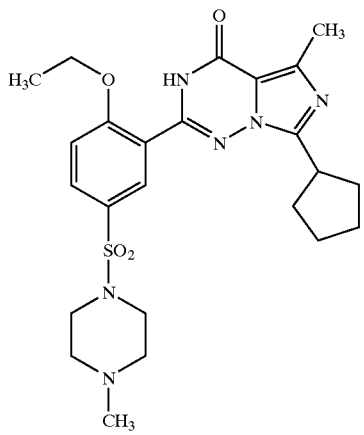

60 mg (0.137 mmol) of 4-ethoxy-3-(5-methyl-4-oxo-7-cyclopentyl-3,4-dihydro[5,1-f][1,2,4]triazin-2-yl)-benzenesulphonyl chloride are dissolved in 10ml of dichloromethane, 30 mg (0.343 mmol) of N-methylpiperazine are added, and the mixture is stirred at room temperature overnight. The mixture is washed twice with saturated ammonium chloride solution, dried over sodium sulphate and evaporated. The residue is purified by silica gel flash chromatography (dichloromethane/methanol 50:1).

Yield: 52 mg (75.6%).

$R_f$=0.52 ($CH_2Cl_2$/MeOH 10:1).

$^1$H-NMR ($CD_3OD$): 1.45 (t, 3H); 1.6–1.75 (m, 2H); 1.8–2.0 (m, 4H); 2.05–2.2 (m, 2H); 2.3 (s, 3H); 2.5–2.55 (m, 4H); 2.6 (m, 3H); 3.0 (s broad, 3H); 3.6 (quin, 1H); 4.3 (quar, 2H); 7.4 (d, 1H); 7.6 (dd, 1H); 8.0 (d, 1H).

Example 2

2-[2-Ethoxy-5-(N,N-bis-2-hydroxyethyl-sulphonyl)-phenyl]-5-methyl-7-cyclopentyl- 3H-imidazo[5,1-f][1,2,4]-triazin-4-one

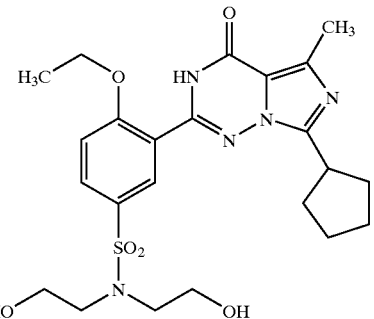

The preparation is carried out analogously to the procedure of Example 1 using 800 mg (1.83 mmol) of 4-ethoxy-3-(5-methyl-4-oxo-7-cyclopentyl-3,4-dihydro[5,1-f][1,2,4]triazin-2-yl)-benzenesulphonyl chloride and 420 mg (4.03 mmol) of N,N-bis-2-hydroxyethylamine. This gives 530 mg (57.3%) of sulphonamide.

$R_f$=0.51 ($CH_2Cl_2$/MeOH 10:1).

$^1$H-NMR ($CD_3OD$): 1.45 (t, 3H); 1.65–1.75 (m, 2H); 1.8–1.95 (m, 4H); 2.05–2.2 (m, 2H); 2.6 (s, 3H); 3.2–3.3 (m, 4H); 3.6 (quin 1H); 3.7 (t, 4H); 4.3 (quar, 2H); 7.35 (d, H); 8.0 (dd, 1H); 8.13 (d, 1H).

Example 3

2-[2-Ethoxy-5-(3-(4-morpholino)-propyl)-sulphonyl)-phenyl]-5-methyl-7- cyclopentyl-3H-imidazo[5,1-f][1,2,4]-triazin-4-one

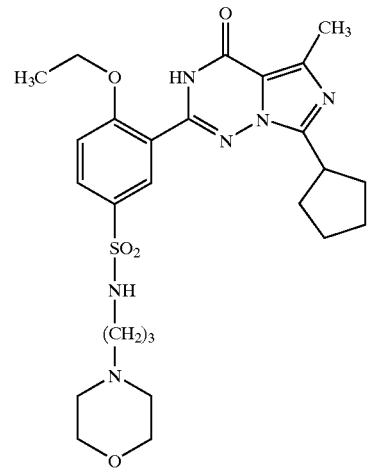

The preparation is carried out analogously to the procedure of Example 1 using 2.0 g (4.58 mmol) of 4-ethoxy-3-(5-methyl-4-oxo-7-cyclopentyl-3,4-dihydro[5,1-f][1,2,4]triazin-2-yl)-benzenesulphonyl chloride and 2.2 g (10.07 mmol) of 4-(3-aminopropyl)-morpholine. This gives 1.67 g (67%) of sulphonamide.

$R_f$=0.45 ($CH_2Cl_2$/MeOH 10:1).

$^1$H-NMR ($CD_3OD$): 1.45 (t, 3H); 1.55–2.2 (m, 10H); 2.3–2.45 (m, 4H); 2.6 (s, 3H); 2.9 (t, 2H); 3.55–3.7 (m, 4H); 4.3 (quar, 2H); 7.3 (d, 1H); 8.0 (dd,); 8.1 (d, 1H).

Example 4
2-[2-Ethoxy-5-(4-(2-hydroxyethyl)-piperazine-1-sulphonyl)-phenyl]-5-methyl-7- cyclopentyl-3H-imidazo[5,1-f][1,2,4]-triazin-4-one

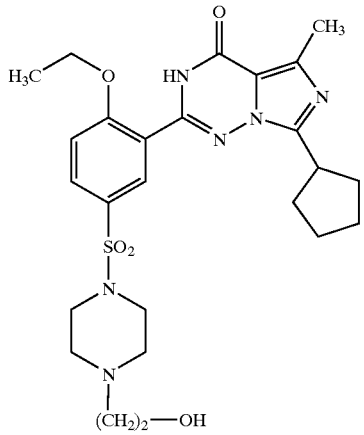

The preparation is carried out analogously to the procedure of Example 1 using 2.0 g (4.58 mmol) of 4-ethoxy-3-(5-methyl-4-oxo-7-cyclopentyl-3,4-dihydro[5,1-f][1,2,4]triazin-2-yl)-benzenesulphonyl chloride and 2.2 g (10.1 mmol) of N-(2-hydroxyethyl)piperazine. This gives 1.8 g (74.1%) of sulphonamide.

$R_f$=0.51 (CH$_2$Cl$_2$/MeOH 10:1).
$^1$H-NMR (CD$_3$OD): 1.45 (t, 3H); 1.6–2.2 (m, 8H); 2.5 (t, 2H); 2.55–2.65 (m, 7H); 3.0–3.1 (m, 4H); 3.6 (t,+quin, 3H); 4.3 (quar, 2H); 7.35 (d, 1H); 7.9 (dd, 1H); 8.0 (d, 1H).

Example 5
2-[2-Ethoxy-5-(4-N-ethoxycarbonylmethyl-piperazine-1-sulphonyl)-phenyl]-5- methyl-7-cyclopentyl-3H-imidazo[5,1-f][1,2,4]-triazin-4-one

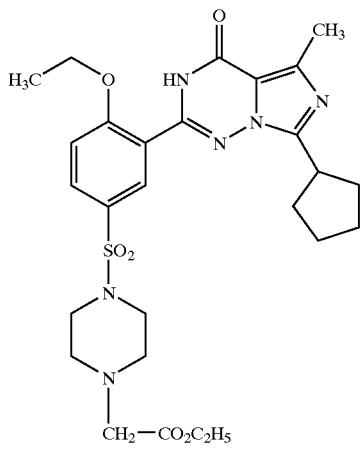

The preparation is carried out analogously to the procedure of Example 1 using 100 mg (0.23 mmol) of 4-ethoxy-3-(5-methyl-4-oxo-7-cyclopentyl-3,4-dihydro[5,1-f][1,2,4]triazin-2-yl)-benzenesulphonyl chloride and 90 mg (0.504 mmol) of N-(carboethoxymethyl)piperazine. This gives 57 mg (43.5%) of sulphonamide.

$R_f$=0.53 (CH$_2$Cl$_2$/MeOH 10:1).
$^1$H-NMR (CD$_3$OD): 1.25 (t, 3H); 1.45 (t, 3H); 1.65–2.2 (m, 8H); 2.5 (s, 3H); 2.6–2.7 (m, 4H); 3.0–3.1 (m, 4H); 3.25 (s, 2H); 3.6 (quin., 1H); 4.15 (quar, 2h); 4.3 (quar, 2H); 7.35 (d, 1H); 7.95 (dd, 1H); 8.0 (d, 1H).

Example 6
2-[2-Ethoxy-5-(4-N-carboxymethyl-piperazine-1-sulphonyl)-phenyl]-5-methyl-7- cyclopentyl-3H-imidazo[5,1-f][1,2,4]-triazin-4-one

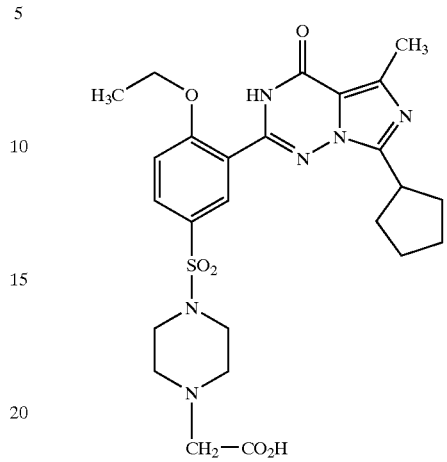

50 mg (0.084 mmol) of the ester from Example 5 and 10 mg (0.335 mmol) of sodium hydride are stirred at room temperature in 4 ml of methanol/water 3:1 for 30 minutes. The mixture is evaporated and the residue is purified by silica gel chromatography (mobile phase: methanol/dichloromethane 10:1).

Yield: 39 mg (85.4%).
$R_f$=0.671 (CH$_2$Cl$_2$/MeOH 10:1+1% AcOH).
$^1$H-NMR (CD$_3$OD): 1.45 (t, 3H); 1.65–2.2 (m, 2H); 2.1 (s, 3H); 2.15–2.25 (m, 4H); 3.05 (s, 2H); 3.05–3.15 (m, 4H); 3.6 (quin, 1H); 4.3 (quar, 2H); 7.4 (d, 1H); 7.95 (dd, 1H); 8.05 (d, 1H).

Example 7
2-[2-Ethoxy-5-(N-methyl-N-dimethylaminoethyl)-sulphonamido)-phenyl]-5- methyl-7-cyclopentyl-3H-imidazo[5,1-f][1,2,4]-triazin-4-one

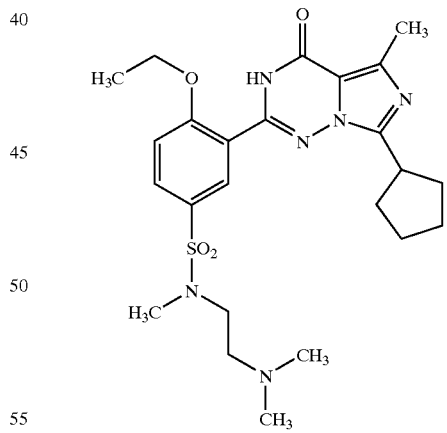

The preparation is carried out analogously to the procedure of Example 1 using 60 mg (0.137 mmol) of 4-ethoxy-3-(5-methyl-4-oxo-7-cyclopentyl-3,4-dihydro[5,1-f][1,2,4]triazin-2-yl)-benzenesulphonyl chloride and 40 mg (0.343 mmol) of N-methyl-N-(2-dimethylamino-ethyl)-amine. This gives 52 mg (75.3%) of sulphonamide.

$R_f$=0.29 (CH$_2$C$_2$/MeOH 10:1).
$^1$H-NMR (CD$_3$OD): 1.45 (t, 3H); 1.65–2.2 (m, 8H); 2.3 (s, 6H); 2.55 (t, 2H); 2.6 (s, 3H); 2.8 (s, 3H); 3.15 (t, 2H); 3.6 (quin, 1H); 4.3 (quar, 2H); 7.4 (d, 1H); 7.95 (dd, 1H); 1 8.1 (d, 1H).

Example 8
2-[2-Ethoxy-5-(4-ethoxycarbonylpiperadine-1-sulphonyl)-phenyl]-5-methyl-7-cyclopentyl-3H-imidazo[5,1-f][1,2,4]-triazin-4-one

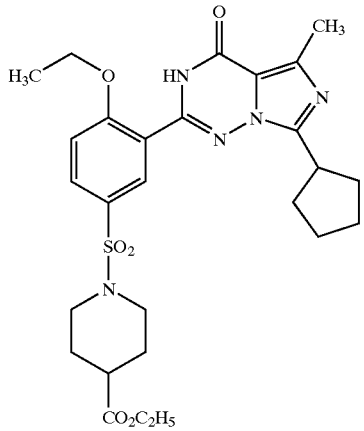

The preparation is carried out analogously to the procedure of Example 1 using 200 mg (0.458 mmol) of 4-ethoxy-3-(5-methyl-4-oxo-7-cyclopentyl-3,4-dihydro[5,1-f][1,2,4]triazin-2-yl)-benzenesulphonyl chloride and 160 mg (1 mmol) of methyl piperidine-4-carboxylate. This gives 190 mg (74.4%) of sulphonamide.

$^1$H-NMR (CD$_3$OD): 1.2 (t, 3H); 1.45 (t, 3H); 1.65–2.2 (m, 10H); 2.3 (m, 1H); 2.5–2.6 (m, 2H); 2.6 (s, 3H); 3.55–3.7 (m, 3H); 4.1 (quar, 2H); 4.3 (quar, 2H); 7.4 (d, 1H); 7.9 (dd, 1H); 8.0 (d, 1H).

Example 9
2-[2-Ethoxy-5-(4-carboxypiperadine-1-sulphonyl)-phenyl]-5-methyl-7-cyclopentyl-3H-imidazo[5,1-f][1,2,4]-triazin-4-one

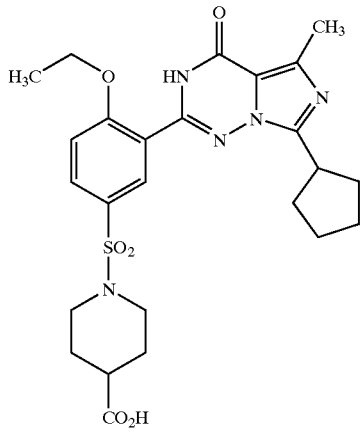

180 mg (0.323 mmol) of the ester from Example 8 and 50 mg (1.29 mmol) of sodium hydroxide are stirred at room temperature in 20 ml of methanol/water 3:1 for minutes, 10 ml of water are added and the mixture is extracted once with dichloromethane. The aqueous phase is acidified using 2 n HCl and extracted twice with dichloromethane. The combined dichloromethane phases are dried over sodium sulphate and evaporated. The residue is recrystallized from diethyl ether.

Yield: 120 mg (70.2%).
M.p.: 170° C. (decomp.).

Example 10
2-[2-Ethoxy-5-(4-hydroxymethylpiperazine-1-sulphonyl)-phenyl]-5-methyl-7-cyclopentyl-3H-imidazo[5,1-f][1,2,4]-triazin-4-one

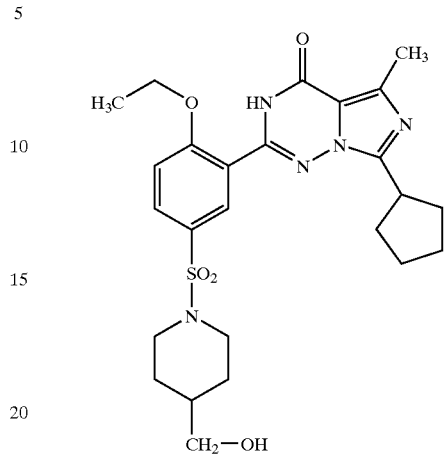

The preparation is carried out analogously to the procedure of Example 1 using 60 mg (0.137 mmol) of 4-ethoxy-3-(5-methyl-4-oxo-7-cyclopentyl-3,4-dihydro[5,1-f][1,2,4]triazin-2-yl)-benzenesulphonyl chloride and 30 mg (0.302 mmol) of 4-hydroxymethylpiperidine. This gives 55 mg (77.7%) of sulphonamide.

R$_f$=0.46 (toluene/acetone 1:1).

Example 11
2-[2-Ethoxy-5-(-N-methyl-N-(2-(3,4-dimethoxyphenyl)ethyl)-sulphonamido)-phenyl]-5-methyl-7-cyclopentyl-3H-imidazo[5,1-f][1,2,4]-triazin-4-one

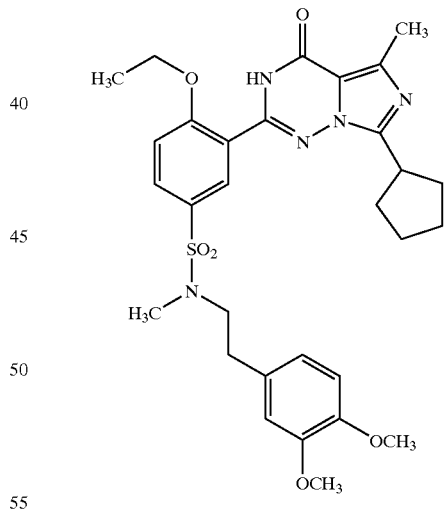

The preparation is carried out analogously to the procedure of Example 1 using 60 mg (0.137 mmol) of 4-ethoxy-3-(5-methyl-4-oxo-7-cyclopentyl-3,4-dihydro[5,1-f][1,2,4]triazin-2-yl)-benzenesulphonyl chloride and 60 mg (0.302 mmol) of N-methyl-N-(2-(3,4-dimethoxyphenyl)ethylamine. This gives 66 mg (80.9%) of sulphonamide.

R$_f$=0.64 (toluene/acetone 1:1).

$^1$H-NMR (CD$_3$OD): 1.45 (t, 3H); 1.6–2.15 (m, 8H); 2.55 (s, 3H); 2.75 (s, 3H); 2.8 (t, 2H); 3.3 (t, 2H); 3.55 (quin, 1H); 3.8 (s, 6H); 4.25 (quar, 2H); 6.7–6.85 (m, 3H); 7.3 (d, 1H); 7.9 (dd, 1H); 8.0 (d, 1H).

Example 12
2-[2-Ethoxy-5-(4-ethoxyphenyl-sulphonamido)-phenyl]-5-methyl-7-cyclopentyl-3H- imidazo[5,1-f][1,2,4]-triazin-4-one

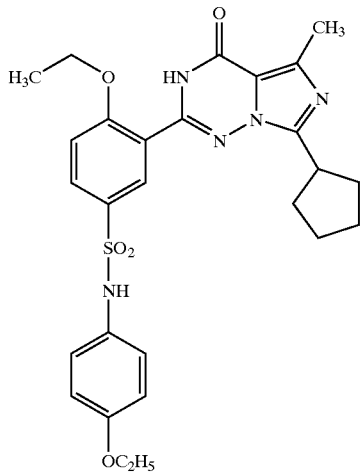

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 70 mg (0.504 mmol) of 4-ethoxy-aniline. This gives 62 mg (50.4%) of sulphonamide which is purified by recrystallization from ethyl acetate/petroleum ether.

Yield: 62 mg (50.4%).
M.p.: 245° C.

Example 13
2-[2-Ethoxy-5-(3-fluoro-4-methoxyphenyl-sulphonamido)-phenyl]-5-methyl-7- cyclopentyl-3H-imidazo[5,1-f][1,2,4]-triazin-4-one

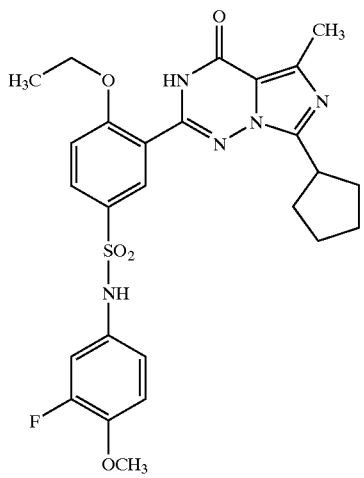

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 70 mg (0.5 mmol) of 3-fluoro-4-methoxyaniline. This gives 73 mg (58.9%) of sulphonamide which is purified by recrystallization from diethyl ether.

Yield: 73 mg (58.9%).
M.p.: 180° C. (decomp.).

Example 14
2-[2-Ethoxy-5-(2-methoxyethyl-sulphonamido)-phenyl]-5-methyl-7- cyclopentyl-3H-imidazo[5,1-f][1,2,4]-triazin-4-one

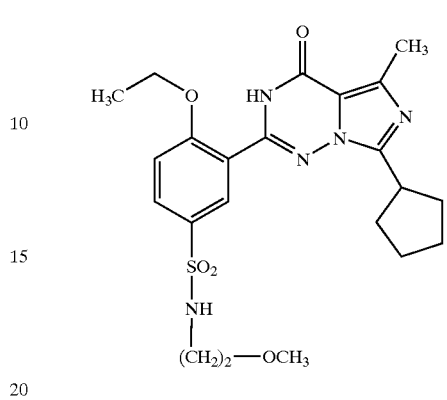

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 37.5 mg (0.05 mmol) of 2-methoxy-ethylamine. This gives 80 mg (73.2%) of sulphonamide.

$R_f$=0.47 (toluene/acetone 4:1).

$^1$H-NMR (CD$_3$OD): 1.45 (t, 3H); 1.65–2.2 (m, 8H); 2.6 (s, 3H); 3.05 (t, 2H); 3.25 (s, 3H); 3.4 (t, 2H); 3.65 (quin, 1H); 4.3 (quin, 2H); 7.3 (d, 1H); 8.0 (dd, 1H); 8.1 (d, 1H).

Example 15
2-[2-Ethoxy-5-(N-(4-morphinolinyl)-sulphonamido)-phenyl]-5-methyl-7- cyclopentyl-3H-imidazo[5,1-f][1,2,4]-triazin-4-one

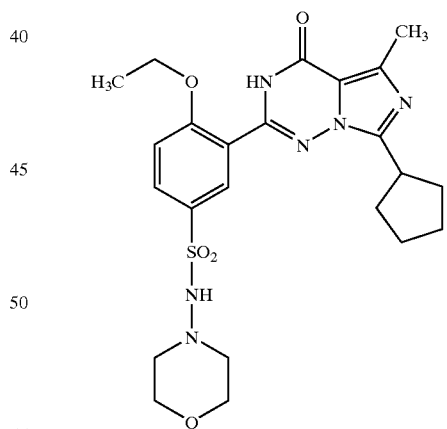

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 50 mg (0.5 mmol) of 4-aminomorpholine. This gives 108 mg (93.9%) of sulphonamide.

$R_f$=0.24 (toluene/acetone 4:1).

$^1$H-NMR (CD$_3$OD): 1.45 (t, 3H); 1.65–2.2 (m, 8H); 2.6 (s, 3H); 2.9–3,0 (m, 4H); 3.65 (quin, 1H); 3.65–3.75 (m, 4H); 4.3 (quar, 2H); 7.4 (d, 1H); 7.95 (dd, 1H); 8.05 (d, 1H).

Example 16
2-[2-Ethoxy-5-(4-methoxybenzyl-sulphonamido)-phenyl]-5-methyl-7- cyclopentyl-3H-imidazo[5,1-f][1,2,4]-triazin-4-one

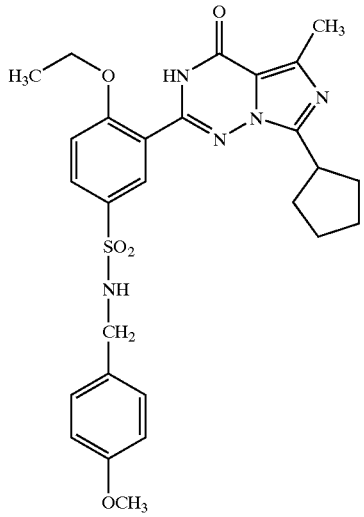

The preparation is carried out analogously to the procedure of Example 1 using 400 mg (0.915 mmol) of 4-ethoxy-3-(5-methyl-4-oxo-7-cyclopentyl-3,4-dihydro[5,1-f][1,2,4] triazin-2-yl)-benzenesulphonyl chloride and 310 mg (2.29 mmol) of 4-methoxybenzylamine. This gives 260 mg (52.8%) of sulphonamide.

$R_f$=0.25 (toluene/acetone 4:1).

$^1$H-NMR (CD$_3$OD): 1.45 (t, 3H); 1.65–1.75 (m, 2H); 1.8–1.95 (m, 4H); 2.1–2.2 (m, 2H); 2.55 (s, 3H); 3.63 (quin, 1H); 3.67 (s, 3H); 4.05 (s, 2H); 4.25 (quar, 2H); 6.75 (d, 2H); 7.1 (d, 2H); 7.25 (d, 1H); 7.9 (dd, 1H); 7.95 (d, 1H).

Example 17
2-[2-Ethoxy-5-(3-ethoxypropyl-sulphonamido)-phenyl]-5-methyl-7- cyclopentyl-3H-imidazo[5,1-f][1,2,4]-triazin-4-one

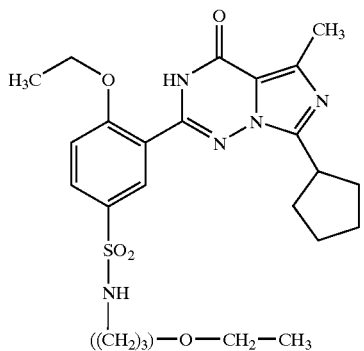

The preparation is carried out analogously to the procedure of Example 1 using 300 mg (0.687 mmol) of 4-ethoxy-3-(5-methyl-4-oxo-7-cyclopentyl-3,4-dihydro[5,1-f][1,2,4] triazin-2-yl)-benzenesulphonyl chloride and 180 mg (1.717 mmol) of 3-ethoxy-propylamine. This gives 230 mg (66.5%) of sulphonamide.

$R_f$=0.19 (toluene/acetone).

$^1$H-NMR (CD$_3$OD): 1.1 (t, 3H); 1.45 (t, 3H); 1.65–2.2 (m, 10H); 2.6 (s, 3H); 2.95 (t, 2H); 3.35–3.5 (m, 4H); 3.65 (quin, 1H); 4.25 (quar, 2H); 7.3 (d, 1H); 7.95 (dd, 1H); 8.1 (d, 1H).

Example 18
2-[2-Ethoxy-5-(3,4-dimethoxyphenyl-sulphonamido)-phenyl]-5-methyl-7- cyclopentyl-3H-imidazo[5,1-f][1,2,4]-triazin-4-one

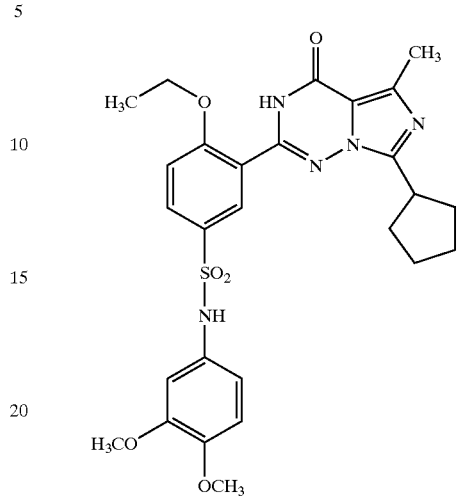

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4] triazin-2-yl)-benzenesulphonyl chloride and 80 mg (0.5 mmol) of 3,4-dimethoxyaniline. This gives 70 mg (55.2%) of sulphonamide.

$R_f$=0.17 (toluene/acetone 4:1).

$^1$H-NMR (CD$_3$OD): 1.45 (t, 3H); 1.75–1.95 (m, 6H); 2.15–2.3 (m, 2H); 2.7 (s, 3H); 3.65–3.8 (m, 7H); 4.2 (quar, 2H); 6.55 (dd, 1H); 6.7–6.8 (m, 2H); 7.3 (d, 1H); 7.9–8.0 (m, 2H).

Example 19
2-[2-Ethoxy-5-(2,3,4-trimethoxyphenyl-sulphonamido)-phenyl]-5-methyl-7- cyclopentyl-3H-imidazo[5,1-f][1,2,4]-triazin-4-one

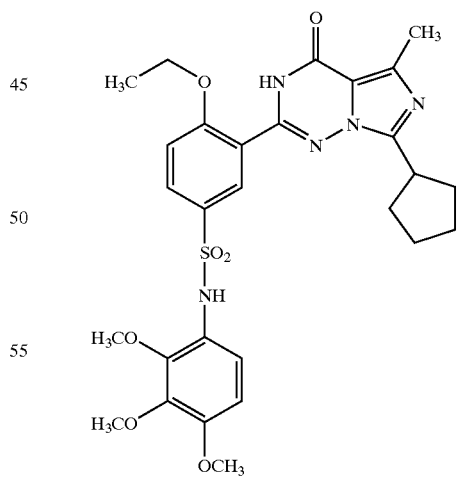

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4] triazin-2-yl)-benzenesulphonyl chloride and 90 mg (0.5 mmol) of 2,3,4-trimethoxyaniline. This gives 61 mg (45.7%) of sulphonamide.

$R_f$=0.25 (toluene/acetone 4:1).

$^1$H-NMR (CD$_3$OD): 1.4 (t, 3H); 1.65–1.95 (m, 6H); 2.05–2.2 (m, 2H); 2.55 (s, 3H); 3.5 (s, 3H); 3.6 (quin, 1H); 3.7 (s, 3H); 3.8 (s, 3H); 4.2 (quar, 2H); 6.7 (d, 1H); 7.15 (d, 1H); 7.2 (d, 1H); 7.8 (dd, 1H); 8.0 (d, 1H).

Example 20
2-[2-Ethoxy-5-(3-picolyl-sulphonamido)-phenyl]-5-methyl-7-cyclopentyl-3H-imidazo[5,1-f][1,2,4]-triazin-4-one

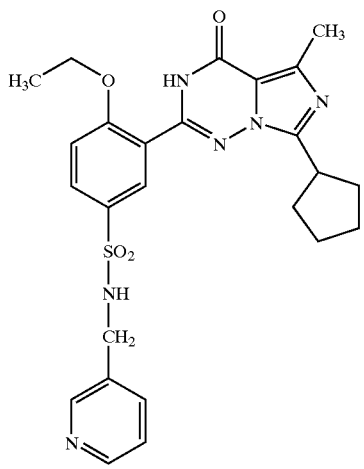

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 50 mg (0.5 mmol) of 3-picolylamine. This gives 50 mg (43%) of sulphonamide which is purified by recrystallization from ethyl acetate/diethyl ether.

M.p.: 128–130° C. (decomp.).

Example 21
2-[2-Ethoxy-5-(2-(2,6-dichlorophenyl)ethyl-sulphonamido)-phenyl]-5-methyl-7-cyclopentyl-3H-imidazo[5,1-f][1,2,4]-triazin-4-one

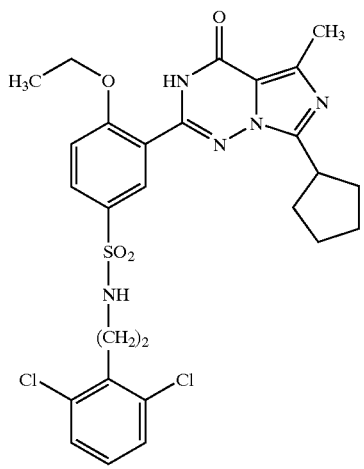

The preparation is carried out analogously to the procedure of Example 1 using 400 mg (0.915 mmol) of 4-ethoxy-3-(5-methyl-4-oxo-7-cyclopentyl-3,4-dihydro[5,1-f][1,2,4]triazin-2-yl)-benzenesulphonyl chloride and 440 mg (2.29 mmol) of 2-(2,6-dichlorophenyl)ethylamine. This gives 380 mg (70.3%) of sulphonamide which is purified by recrystallization from ethyl acetate/diethyl ether.

M.p.: 202° C.

Example 22
2-[2-Ethoxy-5-(N-ehtyl-N-(2-hydroxyethyl)-sulphonamido)-phenyl]-5-methyl-7-cyclopentyl-3H-imidazo[5,1-f][1,2,4]-triazin-4-one

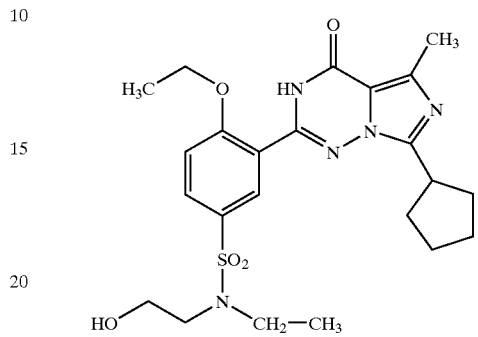

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 50 mg (0.57 mmol) of N-ethyl-N-(2-hydroxyethyl)amine. This gives 57 mg (50.9%) of sulphonamide which is recrystallization from ethyl acetate/diethyl ether.

M.p.: 193° C.

Example 23
2-[2-Ethoxy-5-(2-(4-sulphonamidophenyl)-ethyl-sulphonamido)-phenyl]-5-methyl-7-cyclopentyl-3H-imidazo[5,1-f][1,2,4]-triazin-4-one

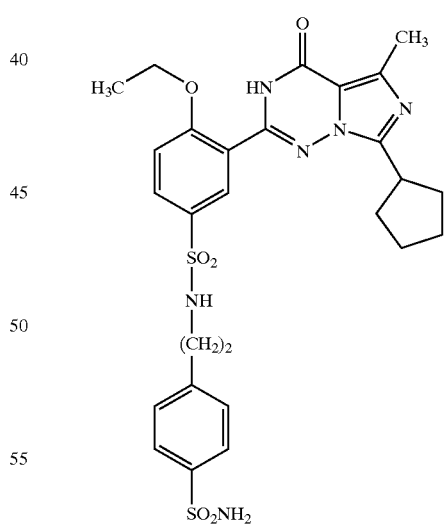

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 10 mg (0.572 mmol) of 2-(4-sulphonamidophenyl)-ethylamine, This gives 67 mg (48.7%) of sulphonamide which is purified by recrystallization from ethyl acetate/diethyl ether.

M.p.: 141–143° C. (decomp.).

Example 24
2-[2-Ethoxy-5-(7-quinolinyl-sulphonamido)-phenyl]-5-methyl-7-cyclopentyl-3H-imidazo[5,1-f][1,2,4]-triazin-4-one

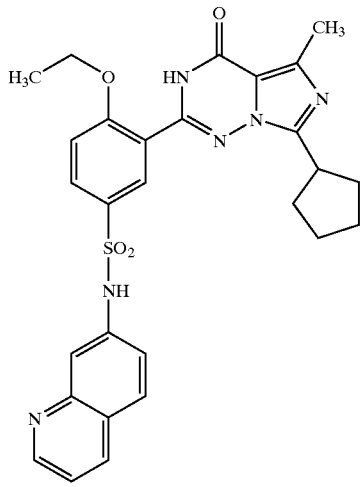

The preparation is carried out analogously to the procedure of Example 1 using 400 mg (0.915 mmol) of 4-ethoxy-3-(5-methyl-4-oxo-7-cyclopentyl-3,4-dihydro[5,1-f][1,2,4]triazin-2-yl)-benzenesulphonyl chloride and 290.4 mg (2.014 mmol) of 7-aminoquinoline. This gives 264 mg (52.9%) of sulphonamide which is purified by recrystallization from ethyl acetate.

M.p.: 184° C.

Example 25
2-[2-Ethoxy-5-(1-(4-diethoxyphosphonylmethyl-piperidinyl)-sulphonyl)-phenyl]-5-methyl-7-cyclopentyl-3H-imidazo[5,1-f][1,2,4]-triazin-4-one

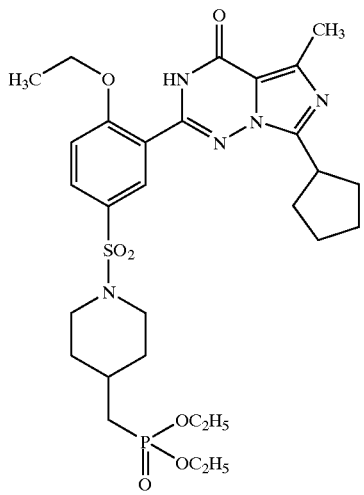

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 120 mg (0.5 mmol) of 4-dimethoxyphosphonyl-methyl-piperidine. This gives 62 mg (42.6%) of sulphonamide.

$^1$H-NMR (CD$_3$OD): 1.25 (t, 6H); 1.45 (t, 3H); 1.5–2.2 (m, 15H); 2.3 (t, 2H); 2.6 (s, 3H); 3.5–3.8 (m, 3H); 4.05 (m, 4H); 4.8 (quar, 2H); 7.35 (d, 1H); 7.9 (dd, 1H); 8.0 (d, 1H).

Example 26
2-[2-Ethoxy-5-(1-(4-dimethoxyphosphonylmethyl-piperazinyl)-sulphonyl)-phenyl]-5-methyl-7-cyclopentyl-3H-imidazo[5,1-f][1,2,4]-triazin-4-one

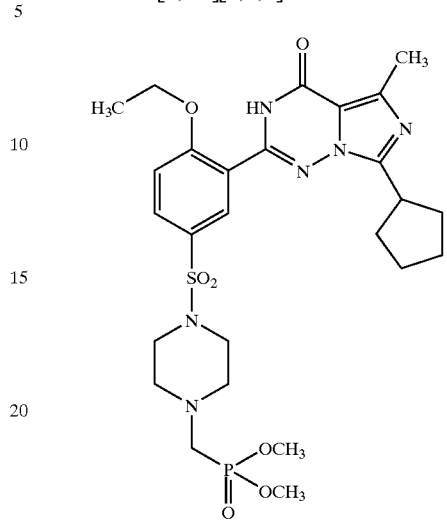

The preparation is carried out analogously to the procedure of Example 1 using 100 mg (0.229 mmol) of 4-ethoxy-3-(5-methyl-4-oxo-7-cyclopentyl-3,4-dihydro[5,1-f][1,2,4]triazin-2-yl)-benzenesulphonyl chloride and 100 mg (0.5 mmol) of (4-dimethoxyphosphonylmethyl)-piperazine. This gives 53 mg (38%) of sulphonamide.

$R_f$=0.57 (dichloromethane/methanol 10:1).

$^1$H-NMR (CD$_3$OD): 1.45 (t, 3H), 1.65–2.0 (m, 6H); 2.05–2.2 (m, 2H); 2.55 (s, 3H); 2.65–2.75 (m, 4H); 2.9 (d, 3H); 3.0–3.1 (m, 4H); 3.6 (quin, 1H); 3.7 (s, 3H); 3.75 (s, 6H); 4.3 (quar, 2H); 7.35 (d, 1H); 7.9 (dd, 1H); 8.0 (d, 1H).

Example 27
2-[2-Ethoxy-5-(methylpiperazine-1-sulphonyl)-phenyl]-5-methyl-7-cyclopentyl-3H-imidazo[5,1-f][1,2,4]-triazin-4-one hydrochloride

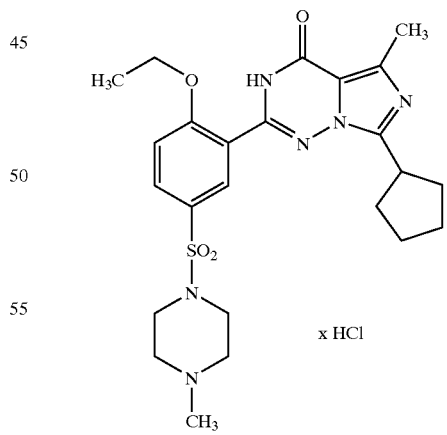

220 mg (0.42 mmol) of 2-[2-ethoxy-5-(4-methylpiperazine-1-sulphonyl)-phenyl]-5-methyl-7-cyclopentyl-3H-imidazo[5,1-f][1,2,4]-triazin-4-one (Example 1) are suspended in 20 ml of diethyl ether and, after addition of 20 mg (0.462 mmol) of 1 molar ethereal HCl solution, stirred at room temperature for 30 minutes.

The solvent is distilled off under reduced pressure and the residue is dried under high vacuum.

Yield: 236 mg (990%).

Example 28
2-[2-Ethoxy-5-(4-methylpiperazine-1-sulphonyl)-phenyl]-5-methyl-7-cyclopentyl-3H-imidazo[5,1-f][1,2,4]-triazin-4-one

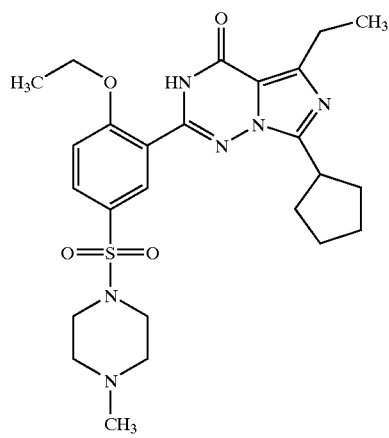

0.42 g (0.92 mmol) of 3-(7-cyclopentyl-5-ethyl-4-oxo-3,4-dihydroimidazo[5,1-f][1,2,4]triazin-2-yl)-4-ethoxybenzenesulphonyl chloride are dissolved in 15 ml of dichloromethane and cooled to 0° C. After addition of a spatula tip of 4-dimethylaminopyridine, 0.28 g (2.76 mmol) of N-methylpiperazine are added, and the reaction mixture is stirred at room temperature overnight. The mixture is diluted with dichloromethane, the organic phase is washed with ammonium chloride solution and dried over sodium sulphate and the solvent is removed under reduced pressure. Crystallization from ether gives 0.395 g (80%) of a colourless solid.

200 MHz $^1$H-NMR (DMSO-$d_6$): 1.21 (t, 3H); 1.32 (t, 3H); 1.79 (m, 8H); 2.13 (s, 3H); 2.48 (s, 4H); 2.86 (m, 6H); 4.21 (quart., 2H); 7.48 (m, 1H); 7.85 (m, 2H); 11.70 (s, 1H).

Example 29
2-[2-Ethoxy-5-N-ethyl-N-(2-hydroxyethyl)-amino-1-sulphonyl]-phenyl]-5-ethyl-7-cyclopentyl-3H-imidazo[5,1-f][1,2,4]-triazin-4-one

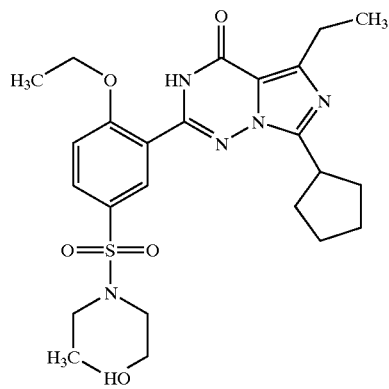

In an analogous manner, starting from 1.3) g (3 mmol) of 3-(7-cyclopentyl-5-ethyl-4-oxo-3,4-dihydroimidazo[5,1-f][1,2,4]triazin-2-yl)-4-ethoxybenzene-sulphonyl chloride and 800 mg (9 mmol) of N-ethyl-N-(2-hydroxyethyl)-amine, 1.07 g (71%) of 2-(2-ethoxy-5-N-ethyl-N-(2-hydroxyethyl)-amino-1-sulphonyl)-phenyl]-5-ethyl-7-cyclopentyl-3H-imidazo[5,1-f][1,2,4]triazin-4-one are obtained.

$R_f$=0.31 (dichloromethane/methanol=19:1).

200 MHz $^1$H-NMR (CDCl$_3$): 1.20 (t, 3H); 1.32 (t, 3H); 1.61 (t, 3H); 1.95 (m, 9H); 2.41 (m, 1H); 3.02 (quart., 2H); 3.35 (m, 4H); 3.65 (m, 1H); 3.80 (m, 2H); 4.33 (quart., 2H); 7.15 (d, 1H); 7.95 (dd, 1H); 8.50 (d, 1H); 9.81 (s, 1H).

Example 30

2-[2-Ethoxy-5-(4-(2-hydroxyethyl)-piperazine)-1-sulphonyl)-phenyl]-5-ethyl-7-cyclopentyl-3H-imidazo[5,1-f][1,2,4]-triazin-4-one

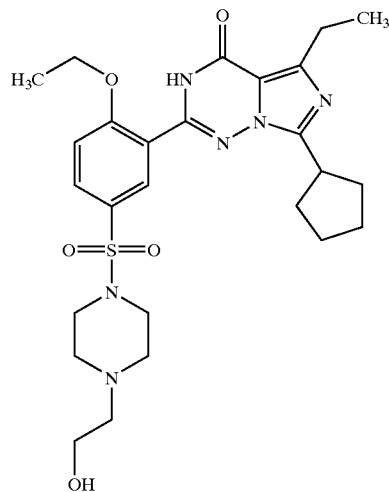

In an analogous manner, starting from 1.35 g (3 mmol) of 3-(7-cyclopentyl-5-ethyl-4-oxo-3,4-dihydroimidazo[5,1-f][1,2,4]triazin-2-yl)-4-ethoxybenzenesulphonyl chloride and 1.17 g (9 mmol) of 4-(2-hydroxyethyl)-piperazine, 1.21 g (74%) of 2-[2-ethoxy-5-(4-(2-hydroxyethyl)-piperazine)-1-sulphonyl)-phenyl]-5-ethyl-7-cyclopentyl-3H-imidazo[5,1-f][1,2,4]triazin-4-one are obtained.

$R_f$=0.21 (dichloromethane/methanol=19:1).

200 MHz $^1$H-NMR (CDCl$_3$): 1.31 (t 3H); 1.60 (t, 3H); 1.96 (m, 9H); 2.58 (m, 7H); 3.02 (quart., 2H); 3.10 (m, 4H); 3.61 (m, 3H); 4.35 (quart., 2H); 7.19 (d, 1H); 7.89 (dd, 1H); 8.45 (d, 1H); 9.75 (s, 1H).

Example 31
2-[2-Ethoxy-5-(3-(4-morpholino)-propyl)-sulphonamido)-phenyl]-5-ethyl-3H-7- cyclopentyl-imidazo[5,1-f][1,2,4]-triazin-4-one

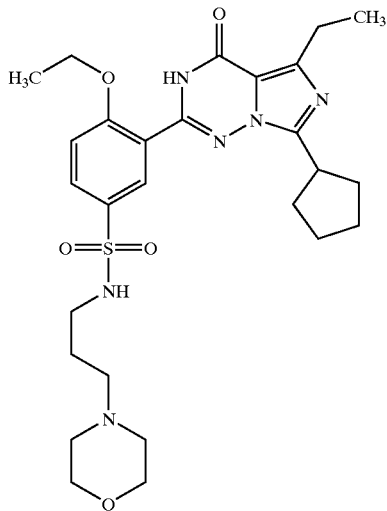

In an analogous manner, starting from 1.35 g (3 mmol) of 3-(7-cyclopentyl-5-ethyl-4-oxo-3,4-dihydroimidazo[5,1-f][1,2,4]triazin-2-yl)-4-ethoxybenzenesulphonyl chloride and 1.30 g (9 mmol) of 4-(3-aminopropyl)-morpholine, 1.44 g (86%) of 2-[2-ethoxy-5-(3-(1-morpholino)-propyl)-sulphonamido)-phenyl]-5-ethyl-7-cyclopentyl-3H-imidazo[5,1-f][1,2,4]triazin-4-one are obtained.

$R_f$=0.29 (dichloromethane/methanol=19:1).

200 MHz $^1$H-NMR (CDCl$_3$): 1.31 (t, 3H); 1.60 (t, 3H); 2.02 (m, 12H); 2.46 (m, 8H); 3.02 (quart., 2H); 3.13 (t, 2H); 3.62 (m, 5H); 4.35 (quart., 2H); 7.15 (d, 1H); 7.89 (dd, 1H); 8.55 (d, 1H); 9.82 (s).

Example 32
2-[2-Propoxy-5-(4-hydroxypiperidine-1-sulphonyl)-phenyl]-5-methyl-7-cyclopentyl- 3H-imidazo[5,1-f][1,2,4]-triazin-4-one

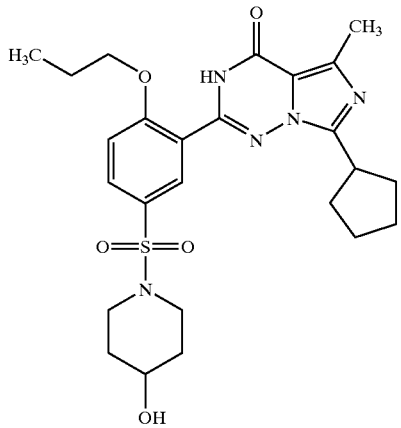

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 28 mg (0.227 mmol) of 4-hydroxypiperidine. This gives 46 mg (80.5%) of sulphonamide.

$R_f$=0.53 (CH$_2$Cl$_2$/MeOH 10:1).
$^1$H-NMR (CD$_3$OD): 1.05 (t, 3H); 1.5–1.6 (m, 2H); 1.65–1.75 (m, 2H); 1.8–2.0 (m, 8H); 1.05–2.2 (m, 2H); 2.6 (s, 3H); 2.8–2.9 (m, 2H); 3.3–3.4 (m, 2H); 3.6–3.7 (m, 2H); 4.15 (t, 2H); 7.35 (d, 1H); 7.9 (dd, 1H); 8.0 (d, 1H).

Example 33
2-[2-Propoxy-5-(4-(2-hydroxyethyl)-piperazine-1-sulphonyl)-phenyl]-5-methyl-7- cyclopentyl-3H-imidazo[5,1-f][1,2,4]-triazin-4-one

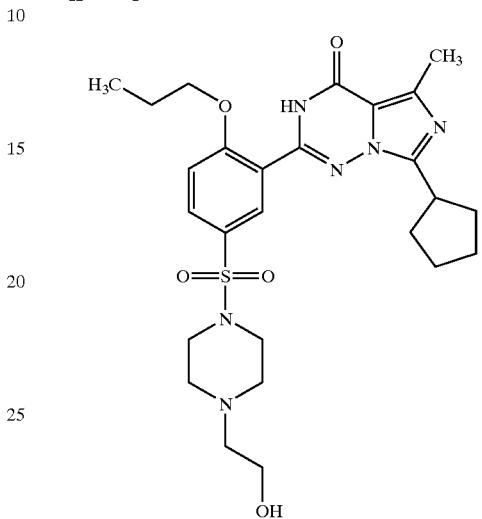

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 32.4 mg (0.249 mmol) of N-(2-hydroxyethyl)-piperazine. This dives 40 mg (73.6%) of sulphonamide which is purified by recrystallization from ethyl acetate/diethyl ether.

M.p.: 210° C.

Example 34
2-[2-Propoxy-5-(4-methylpiperazine-1-sulphonyl)-phenyl]-5-methyl-7-cyclopentyl- 3H-imidazo[5,1-f][1,2,4]-triazin-4-one

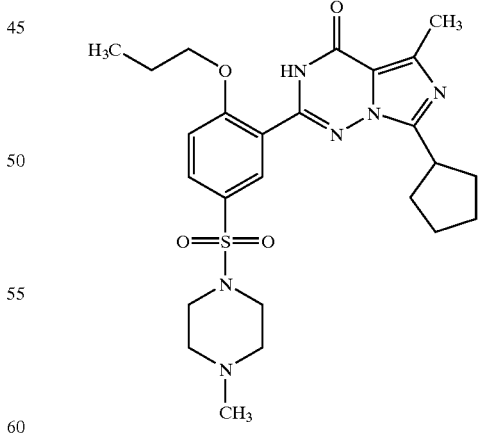

The preparation is carried out analogously to the procedure of Example 1 using 50° m (0.111 mmol) of 4-propoxy-3-(5-methyl-4-oxo-7-cyclopentyl-3,4-dihydro[5,1-f][1,2,4]triazin-2-yl)-benzenesulphonyl chloride and 24.9 mg (0.249 mmol) of N-methylpiperazine. This gives 49 mg (95.4%) of sulphonamide.

$R_f$=0.49 (CH$_2$Cl$_2$/MeOH 10:1).
$^1$H-NMR (CD$_3$OD): 1.05 (t, 3H); 1.65–2.2 (m, 2H); 2.3 (s, 3H); 2.45–2.55 (m, 4H); 2.6 (s, 3H); 3.0–3.1 (m, 4H); 3.6 (quin, 1H); 4.2 (t, 2H); 7.4 (d, 1H); 7.95 (dd, 1H); 8.0 (d, 1H).

Example 35
2-[2-Propoxy-5-(3-(4-morpholino)-propyl-sulphonamido)-phenyl]-5-methyl-7-cyclo- pentyl-3H-imidazo[5,1-f][1,2,4]-triazin-4-one

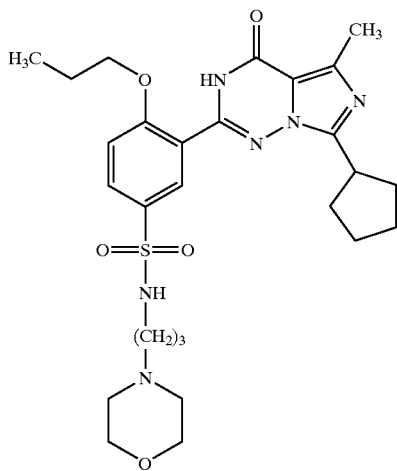

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 36.7 mg (0.255 mmol) of 3-(4-morpholino)propylamine. This gives 16 mg (28.1%) of sulphonamide.

$R_f$=0.41 (CH$_2$Cl$_2$/MeOH 10:1).
$^1$H-NMR (CD$_3$OD): 1.05 (t, 3H); 1.6–2.2 (m, 12H); 2.3–2.45 (m, 6H); 2.6 (s, 3H); 2.95 (t, 2H); 3.6–3.7 (m, 5H); 4.15 (t, 2H); 7.35 (d, 1H); 8.0 (d, 1H); 8.1 (d, 1H).

Example 36
2-[2-Propoxy-5-(4-hydroxymethylpiperidine-1-sulphonyl)-phenyl]-5-methyl-7- cyclopentyl-3H-imidazo[5,1-f][1,2,4]-triazin-4-one

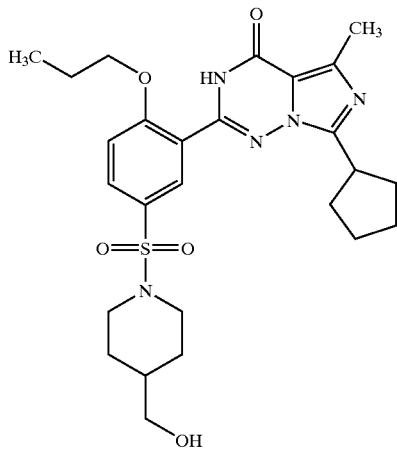

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 29.3 mg (0.255 mmol) of 4-hydroxymethylpiperidine. This gives 46 mg (85.1%) of sulphonamide.

$R_f$=0.46 (CH$_2$Cl$_2$/MeOH 10:1).
$^1$H-NMR (CD$_3$OD): 1.05 (t,3H); 1.65–2.0 (m, 13H); 2.05–2.15 (m, 2H); 2.3 (t, 2H); 2.6 (s, 3H); 3.4 (d, 2H); 3.65 (m, 1H); 3.8 (d, 2H); 4.2 (t, 2H); 7.4 (d, 1H); 7.9 (dd, 1H); 8.0 (d, 1H).

Example 37
2-[2-Propoxy-5-(N,N-2-hydroxyethyl-sulphonamide)-phenyl]-5-methyl-7-cyclo- pentyl-3H-imidazo[5,1-f][1,2,4]-triazin-4-one

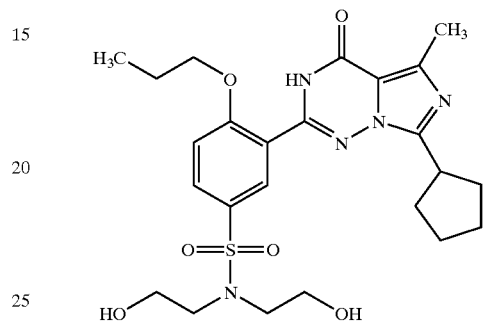

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 26.8 mg (0.255 mmol) of diethanolanine. This gives 30 mg (56.6%) of sulphonamide.

$R_f$=0.43 (CH$_2$Cl$_2$/MeOH 10:1).
$^1$H-NMR (CD$_3$OD): 1.05 (t, 3H); 1.65–2.2 (m, 10H); 2.6 (s, 3H); 3.3 (m, 4H); 3.65 (quin, 1H); 3.7 (t, 4H); 4.2 (t, 2H); 7.35 (d, 1H); 8.0 (dd, 1H); 8.1 (d, 1H).

Example 38
2-[2-Propoxy-5-(N-methyl-N-(2-dimethylaminoethyl)-sulphonamido)-phenyl]-5- methyl-7-cyclopentyl-3H-imidazo[5,1-f][1,2,4]-triazin-4-one

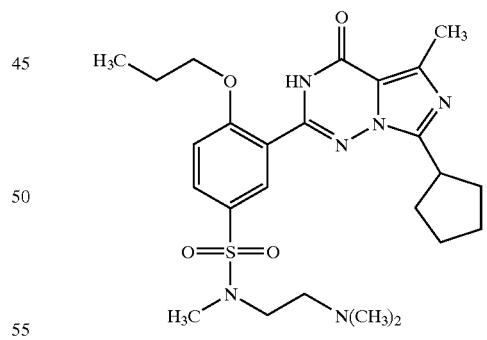

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4]triazin-2-yl)-benzenesulphonyl chloride and 26 mg (0.255 mmol) of N-methyl-N-(2-dimethylaminoethyl)-amine. This gives 26 mg (49.3%) of sulphonamide.

$R_f$=0.3 (CH$_2$Cl$_2$/MeOH 10:1).
$^1$H-NMR (CD$_3$OD): 1.05 (t, 3H); 1.65–2.2 (m, 10H); 2.3 (s, 6H); 2.55 (t, 2H); 2.6 (s, 3H); 2.8 (s, 3h); 3.15 (t 2H); 3.65 (quin, 1H); 4.2 (t, 2H); 7.4 (d, 1H); 7.95 (dd, 1H); 8.05 (d, 1H).

Example 39
2-[2-Propoxy-5-(4-ethoxycarbonylpiperidine-1-sulphonyl)-phenyl]-5-methyl-7- cyclopentyl-3H-imidazo[5,1-f][1,2,4]-triazin-4-one

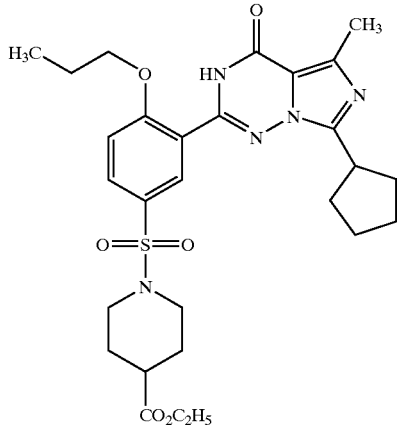

The preparation is carried out analogously to the procedure of Example 1 using 50 mg (0.111 mmol) of 4-propoxy-3-(5-methyl-4-oxo-7-cyclopentyl-3,4-dihydro[5,1-f][1,2,4] triazin-2-yl)-benzenesulphonyl chloride and 48.7 mg (0.31 mmol) of ethyl 4-piperidinecarboxylate. This gives 80 mg (90.1%) of sulphonamide.

$^1$H-NMR (CD$_3$OD): 1.05 (t, 2H); 1.2 (t, 2H); 1.65–2.0 (m, 12H); 2.15–2.35 (m, 3H); 2.6 (td, 2H); 2.7 (s, 3H); 3.5–3.6 (, 2H); 3.75 (quin., 1H); 4.1 (quar, 2H); 4.2 (quar., 2H); 7.4 (d, 1H); 7.95 dd, 1H); 8.05 (d, 1H).

Example 40
2-[2-Propoxy-5-(4-carboxypiperidine-1-sulphonyl)-phenyl]-5-methyl-7-cyclopentyl- 3H-imidazo[5,1-f][1,2,4]-triazin-4-one

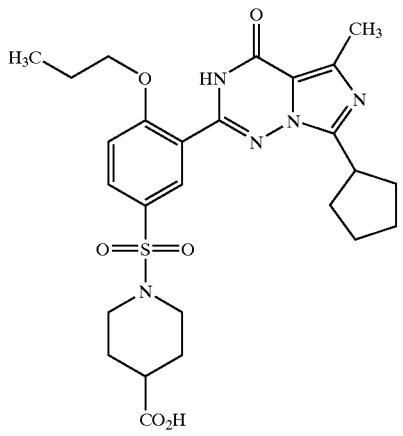

80 mg (0.14 mmol) of the ester from Example 39 are stirred at room temperature in a mixture of 5 ml of methanol and 1 ml of 4 n NaOH for 30 minutes, 10 ml of dichloromethane are added, the mixture is extracted with 10 ml of 2 n HCl solution and the organic phase is separated off, dried over sodium sulphate and evaporated. The residue is recrystallized from diethyl ether.

Yield: 50 mg (65.7%).
R$_f$=0.47 (CH$_2$Cl$_2$/MeOH 10:1).
$^1$H-NMR (CD$_3$OD): 1.05 (t, 3H); 1.65–2.0 (m, 12H); 2.2–2.35 (m, 3h); 2.6 (td, 2H); 2.7 (s, 3H); 3.55–3.6 (m, 2H); 3.75 (quin., 1H); 4.2 (t, 2H); 7.4 (d, 1H); 7.95 (dd, 1H); 8.05 (d, 1H).

Example 41
2-[2-Ethoxy-5-(4-methylpiperazine-1-sulphonyl)-phenyl]-7-(1-ethylpropyl)-5- methyl-3H-imidazo[5,1-f][1,2,4]-triazin-4-one

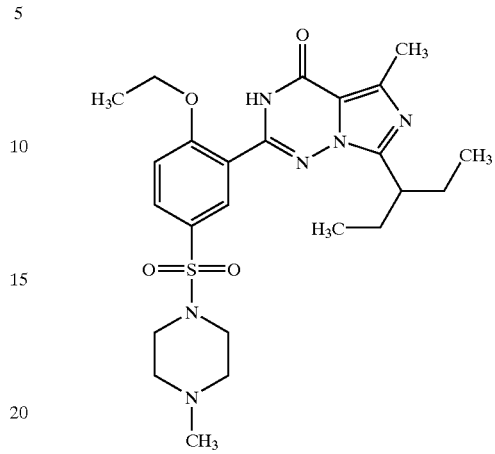

50 mg (0.114 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride arc initially charged in 5 ml of dichloromethane and a spatula tip of 4 dimethylaminopyridine is added, followed by 30 mg (0.342 mmol) of N-methylpiperazine. The mixture is stirred at room temperature overnight, diluted with dichloromethane, washed twice with saturated ammonium chloride solution, dried over sodium sulphate, concentrated and filtered through silica gel (methanol).

Yield: 45 mg (78.6% of theory).
200 MHz $^1$H-NMR (CDCl$_3$): 0.85 (t, 6H); 1.63 (t, 3H); 1.85 (m, 4H); 2.39 (s, 3H); 2.65 (m, 7H); 3.17 (m, 5H); 4.35 (q, 2H); 7.18 (d, 1H); 7.88 (dd, 1H); 8.49 (d, 1H); 9.64 (bs, 1H).

Example 42
2-[2-Ethoxy-5-(4-(2-hydroxyethyl)-piperazine-1-sulphonyl)-phenyl]-7-(1- ethylpropyl)-5-methyl-3H-imidazo[5,1-f][1,2,4]-triazin-4-one

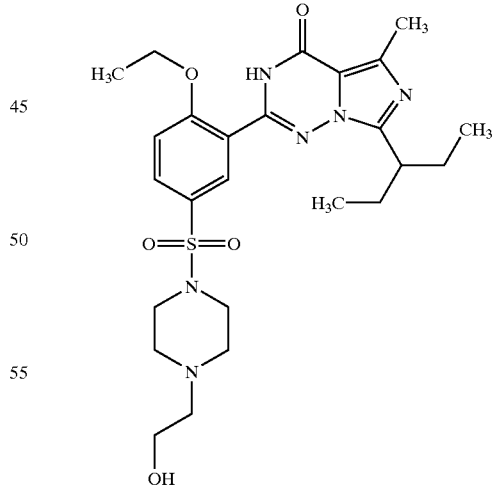

Analogously, using 100 mg (0.221 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 90 mg (0.662 mmol) of N-(2-hydroxyethyl)-piperazine, 99 mg (84.2% of theory) of 2-[2-ethoxy-5-(4-(2-hydroxyethyl)-piperazine-1-sulphonyl)phenyl]-7-(1-ethylpropyl)-5-methyl-3H-imidazo[5,1-f][1,2,4]triazin-4-one are obtained.

200 MHz $^1$H-NMR (CDCl$_3$): 0.87 (t, 6H); 1.62 (t, 3H); 1.84 (m, 4H); 2.56–2.74 (m, 9H); 3.08–3.32 (m, 5H); 3.63 (t, 2H); 4.37 (q, 2H); 7.18 (d, 1H); 7.9 (dd, 1H); 8.5 (d, 1H); 9.67 (bs, 1H).

Example 43
2-[2-Ethoxy-5-(4-(2,2,2-trifluoroethyl)-piperazine-1-sulphonyl)-phenyl]-7-(1-ethyl- propyl)-5-methyl-3H-imidazo[5,1-f][1,2,4]-triazin-4-one

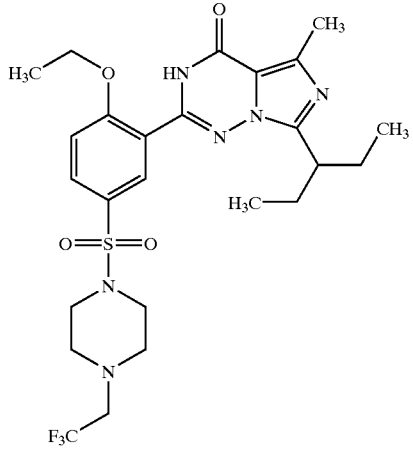

Analogously, using 100 mg (0.228 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 120 mg (0.69 mmol) of (2,2,2-trifluoroethyl)-piperazine, 72 mg (18.2% of theory) of 2-[2-ethoxy-5-(4-(2,2,2-trifluoroethyl)-piperazine-1-sulphonyl)-phenyl]-7-(1-ethylpropyl)-5-methyl-3H-imidazo-[5,1-f][1,2,4]triazin-4-one are obtained.

200 MHz $^1$H-NMR (CDCl$_3$): 0.87 (t, 6H); 1.63 (t, 3H); 1.89 (m, 4H); 2.71 (s, 3H); 2.8 (m, 4H); 2.97 (q, 2H); 3.1 (m, 4H); 3.25 (m, 1H); 4.38 (q, 2H); 7.19 (s, 1H); 7.89 (dd, 1H); 8.49 (d, 1H); 9.71 (bs, 1H).

Example 44
2-[2-Ethoxy-5-(1-(4-diethoxyphosphonylmethyl-piperidinyl)-sulphonyl)-phenyl]-7- (1-ethylpropyl)-5-methyl-3H-imidazo[5,1-f][1,2,4]-triazin-4-one

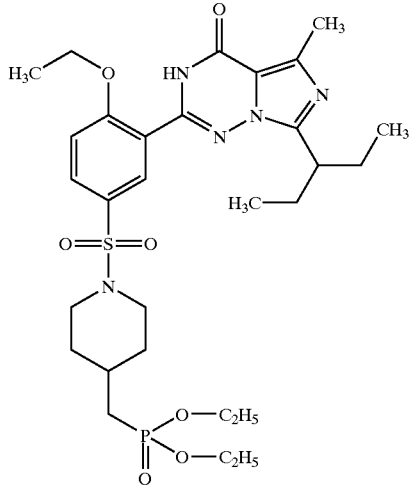

Analogously, using 100 mg (0.228 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 161 mg (0.683 mmol) of 4-diethoxyphosphonylmethyl-pipenrdine, 96.2 mg (66.2% of theory) of 2-[2-ethoxy-5-(1-(4-diethoxyphosphonylmethylpiperidine)-sulphonyl)-phenyl]-7-(1-ethylpropyl)-5-methyl-3H-imidazo[5,1-f][1,2,4]triazin-4-one are obtained.

200 MHz $^1$H-NMR (CDCl$_3$): 0.86 (t, 6H); 1.3 (t, 6H); 1.38–2.02 (m, 14H); 2.35 (dt, 2H); 2.68 (s, 3H); 3.23 (m, 1H); 3.8 (d, 2H); 4.08 (m, 4H); 4.36 (q, 2H); 7.17 (d, 1H); 7.88 (dd, 1H); 8.49 (d, 1H); 9.7 (bs, 1H).

Example 45
2-[2-Ethoxy-5-(1-(4-monoethoxyphosphonylmethyl-piperidinyl)-sulphonyl)-phenyl]- 7-(1-ethylpropyl)-5-methyl-3H-imidazo[5,1-f][1,2,4]-triazin-4-one

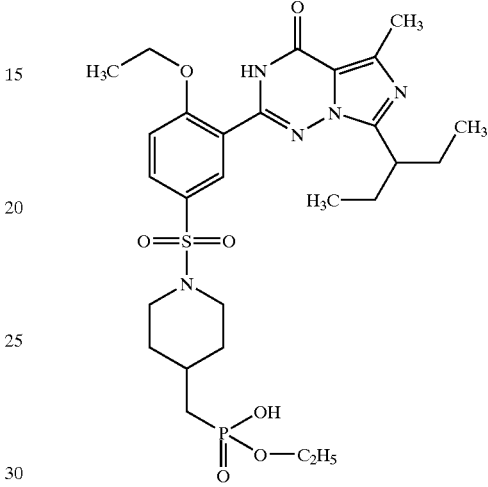

61.4 mg (96.2 μmol) of 2-[2-ethoxy-5-(1-(4-diethoxyphosphonylmethylpiperidinyl)-sulphonyl)-phenyl]-7-(1-ethylpropyl)-5-methyl-3H-imidazo[5,1-f][1,2,4]-triazin-4-one are heated under reflux with 21.6 mg (0.385 mmol) of KOH powder in 5 ml of ethanol overnight. The mixture is concentrated, taken up in water, acidified with 1N hydrochloric acid and extracted three times with dichloromethane. The extracts are dried and concentrated.

Yield: 42 mg (71.6% of theory).

Example 46
2-[2-Ethoxy-5-(4-oxopiperidine-1-sulphonyl)-phenyl]-7-(1-ethylpropyl)-5-methyl- 3H-imidazo[5,1-f][1,2,4]-triazin-4-one

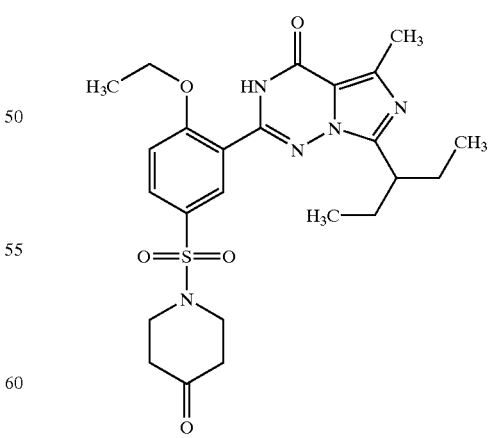

Analogously using 300 mg (0.683 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 310 mg (2.05 mmol) of 4,4-dihydroxipiperidine hydrochloride, 18 mg (5.2% of theory) of 2-[2-ethoxy-5-(4-oxopiperidine-1-sulphonyl)-phenyl]-7-(1-ethylpropyl)-5-methyl-3H-imidazo[5,1-f][1,2,4]triazin-4-one are obtained.

Example 47
2-[2-Ethoxy-5-(3-hydroxypyrrolidine-1-sulphonyl)-phenyl]-7-(1-ethylpropyl)-5- methyl-3H-imidazo[5,1-f][1,2,4]-triazin-4-one

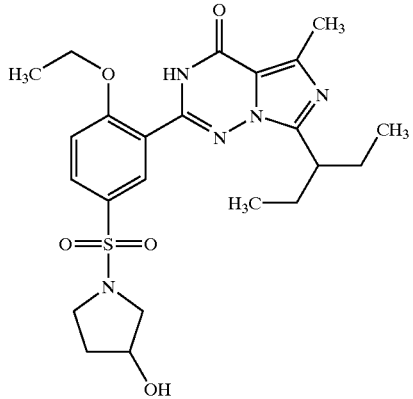

Analogously, using 100 mg (0.228 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 60 mg (0.683 mmol) of 3-hydroxypyrrolidine, 55 mg (49.1% of theory) of 2-[2-ethoxy-5-(3-hydroxy-pyrrolidine-1-sulphonyl)-phenyl]-7-(1-ethylpropyl)-5-methyl-3H-imidazo[5,1-f][1,2,4]triazin-4-one are obtained.

200 MHz $^1$H-NMR (CDCl$_3$): 0.85 (t, 6H); 1.61 (t, 3H); 1.72–2.1 (m, 7H); 2.69 (s, 3H); 3.22–3.55 (m, 5H); 4.35 (q, 2H); 4.45 (m, 1H); 7.18 (d, 1H); 7.99 (dd, 1H); 8.57 (d, 1H); 9.8 (bs, 1H).

Example 48
2-[2-Ethoxy-5-(N,N-diethyl-sulphonamido)-phenyl]-5-methyl-7-(1-ethylpropyl)-3H- imidazo [5,1-f][1,2,4]-triazin-4-one

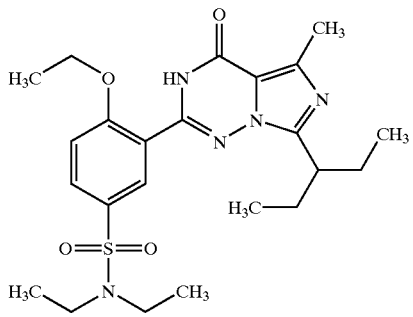

Analogously, using 100 mg (0.228 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 50 mg (0.683 mmol) of diethylamine, 78 mg (72.3% of theory) of 2-[-ethoxy-5-(N,N-diethyl-sulphonamido)phenyl]-5-methyl-7-(1-ethylpropyl)-3H-imidazo[5,1-f][1,2,4]triazin-4-one are obtained.

200 MHz $^1$H-NMR (CDCl$_3$): 0.87 (t, 6H); 1.2 (t, 6H); 1.62 (t, 3H); 1.88 (m, 4H); 2.69 (s, 3H); 3.3 (m, 5H); 4.35 (q, 2H); 7.14 (d, 1H); 7.96 (dd, 1H); 8.57 (d, 1H); 9.78 (bs, 1H).

Example 49
2-[2-Ethoxy-5-(3-hydroxy-3-methoxymethylpyrrolidine-1-sulphonyl)-phenyl]-7- (1-ethylpropyl)-5-methyl-3H-imidazo[5,1-f][1,2,4]-triazin-4-one

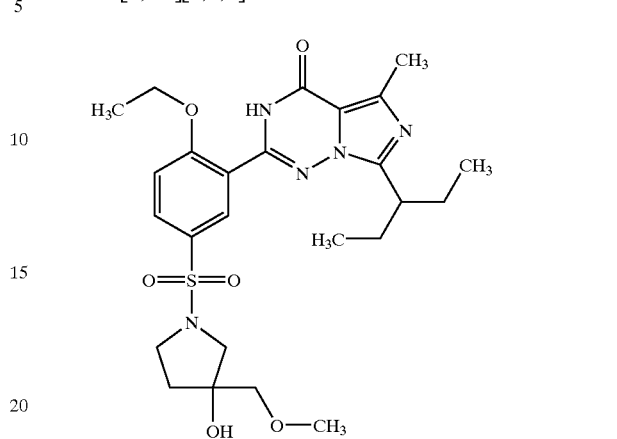

Analogously, using 100 mg (0.228 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 90 mg (0.683 mmol) of 3-hydroxy-3-methoxymethylpyrrolidine, 89 mg (72.9% of theory) of 2-[2-ethoxy-5-(3-hydroxy-3-methoxymethylpyrrolidine-1-sulphonyl)-phenyl]-7-(1-ethylpropyl)-5-methyl-3H-imidazo[5,1-f][1,2,4]triazin-4-one are obtained.

200 MHz $^1$H-NMR (CDCl$_3$): 0.88 (t, 6H); 1.62 (t, 3H); 1.72–2.08 (m, 6H); 2.47 (s, 1H); 2.7 (s, 3H); 3.13–3.63 (m, 10H); 4.36 (q, 2H); 7.17 (d, 1H); 7.98 (dd, 1H); 8.57 d, 1H); 9.78 (bs, 1H).

Example 50
2-[2-Ethoxy-5-(N-2-methoxyethyl-sulphonamido)-phenyl]-5-methyl-7-(1-ethyl- propyl)-3H-imidazo[5,1-f][1,2,4]-triazin-4-one

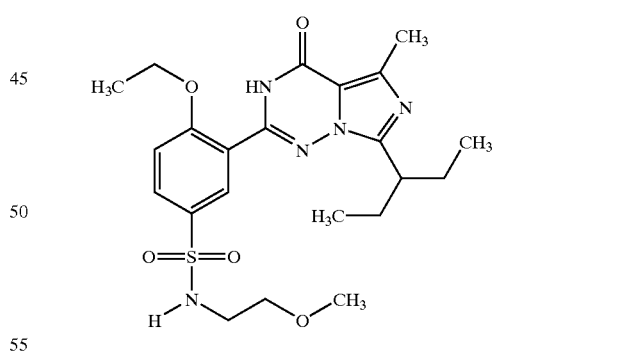

Analogously, using 350 mg (0.797 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 180 mg (2.392 mmol) of methoxyethylamine, 251 mg (66% of theory) of 2-[2-ethoxy-5-(N-2-methoxyethyl-sulphonamide)-phenyl]-5-methyl-7(1-ethylpropyl)-3H-imidazo[5,1-f][1,2,4]-triazin-4-one are obtained.

200 MHz $^1$H-NMR (DMSO-d$_6$): 0.75 (t, 6H); 1.32 (t, 3H); 1.61–1.72 (m, 4H); 2.93 (q, 2H); 3.1 (m, 1H); 3.18 (s, 3H); 3.26–3.4 (m, 5H); 4.19 (q, 2H); 7.35 (d, 1H); 7.76 (t, 1H); 7.86–7.96 (m, 2H); 11.7 (bs, 1H).

Example 51

2-[2-Ethoxy-5-(N-ethyl-N-(2-hydroxyethyl)-sulphonamido)-phenyl]-5-methyl-7-(1-ethylpropyl)-3H-imidazo[5,1-f][1,2,4]-triazin-4-one

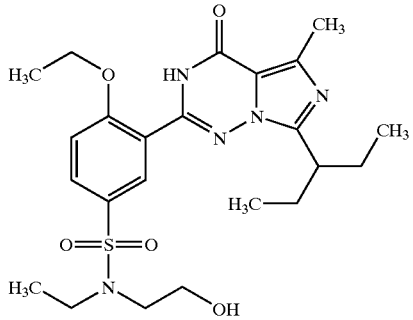

Analogously, using 400 mg (0.911 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 240 mg (2.734 mmol) of 2-(ethylamino)-ethanol, 261 mg (58.3% of theory) of 2-[2-ethoxy-5-(N-2-ethyl-N-(2-hydroxyethyl)-sulphonamide)-phenyl]-5-methyl-7-(1-ethylpropyl)-3H-imidazo[5,1-f][1,2,4]-triazin-4-one are obtained.

200 MHz $^1$H-NMR (DMSO-$d_6$): 0.78 (t, 6H); 1.08 (t, 3H); 1.33 (t, 3H); 1.6–1.88 (m, 4H); 2.99–3.28 (m, 7H); 3.38 (m, 1H); 3.52 (q, 2H); 4.2 (q, 2H); 4.81 (t, 1H); 7.34 (d, 1H); 7.86–8.0 (m, 2H); 11.69 (bs, 1H).

Example 52

2-[2-Ethoxy-5-(N-(4-morpholino)sulphonamido)-phenyl]-5-methyl-7-(1-ethyl-propyl)-3H-imidazo[5,1-f][1,2,4]-triazin-4-one

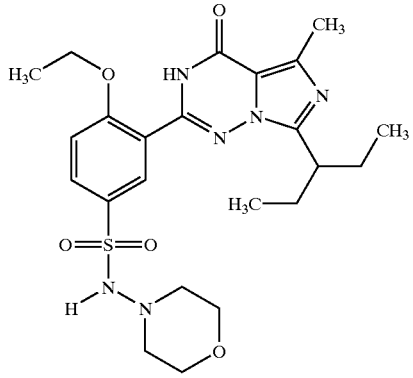

Analogously, using 400 mg (0.911 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and 280 mg (2.734 mmol) of 4-aminomorpholine, 109 mg (21.1% of theory) of 2-[2-ethoxy-5-(N-(morpholinyl)sulphonamido)-phenyl]-5-methyl-7-(1-ethylpropyl)-3 H-imidazo[5,1-f][1,2,4]-triazin-4-one are obtained.

200 MHz $^1$H-NMR (CDCl$_3$): 0.88 (t, 6H); 1.63 (t, 3H); 1.85–2.28 (m, 4H); 2.88 (s, 3H); 3.05 (m, 4H); 3.45 (m, 1H); 3.76 (m, 4H); 4.42 (q, 2H); 7.2–7.35 (m, 2H); 7.96 (m, 1H); 8.45 (m, 1H); 10.23 (bs, 1H).

Example 53

2-[2-Ethoxy-5-(4-hydroxymethylpiperidine-1-sulphonyl)-phenyl]-7-(1-ethylpropyl)-5-methyl-3H-imidazo[5,1-f][1,2,4]triazin-4-one

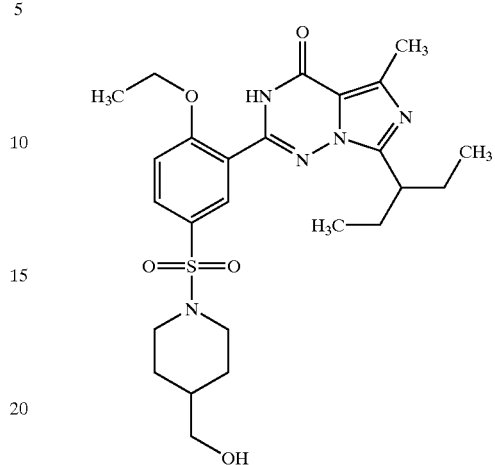

Analogously, using 400 mg (0.911 mmol) of 4-ethoxy-3-(5-methyl-4-oxo-7-(1-ethylpropyl)-3,4-dihydroimidazo[5,1-f][1,2,4]triazin-2-yl)-benzenesulphonyl chloride and; 10 mg (2.734 mmol) of 4-hydroxymethylpiperidine, 270 mg (57.3% of theory) of 2-[2-ethoxy-5-(4-hydroxymethylpiperidine-1-sulphonyl)-phenyl]-7-(1-ethylpropyl)-5-methyl-3H-imidazo[5,1-f][1,2,4]triazin-4-one.

200 MHz $^1$H-NMR (DMSO): 0.77 (t, 6H); 1.05–1.43 (m, 6H); 1.58–1.85 (m, 6H); 2.12–2.38 (m, 2H); 2.52 (s, 3H); 3.08 (m, 1H); 3.22 (t, 2H); 3.55–3.72 (m, 2H); 4.2 (q, 2H); 4.51 (t, 1H); 7.38 (d, 1H); 7.78–7.92 (m, 2H); 11.7 (bs, 1H).

Example 54

2-[2-Ethoxy-5-(3-(1-morpholino)-propyl)-sulphonamido)-phenyl]-5-methyl-7-(1-ethylpropyl)-3H-imidazo[5,1-f][1,2,4]triazin-4-one

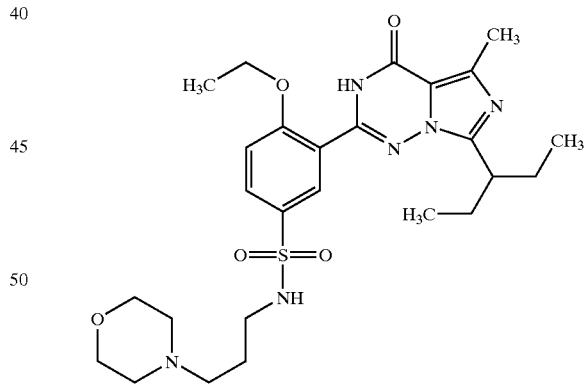

In an analogous manner, starting from 0.44 g (1 mmol) of 3-(1-ethylpropyl)-5-methyl-4-oxo-3,4-dihydroimidazo[5,1-f][1,2,4]triazin-2-yl)-4-ethoxy-benzenesulphonyl chloride and 0.43 (3 mmol) of 4-(3-aminopropyl)-morpholine 0.45 g (81%) of 2-[2-ethoxy-5-(3-(1-morpholino)-propyl)-sulphonamido)-phenyl]-5-methyl-7-(1-ethylpropyl)-3H-imidazo[5,1-f][1,2,4]triazin-4-one are obtained.

$R_f$=0.18 (dichloromethane/methanol=19:1).

200 MHz $^1$H-NMR (CDCl$_3$): 1.31 (t, 3H); 1.61 (t, 3H); 1.87 (m, 14H); 2.66 (s, 3H); 3.00 (m 2H); 3.28 (m, 3H); 3.85 (m, 1H); 4.35 (quart., 2H); 7.17 (d, 1H); 7.90 (dd, 1H); 8.50 (d, 1H); 9.72 (s, 1H).

Example 55

2-[2-Ethoxy-5-(4-hydroxypiperidine-1-sulphonyl)-phenyl]-5-methyl-7-(1-ethyl- propyl)-3H-imidazo[5,1-f][1,2,4]triazin-4-one

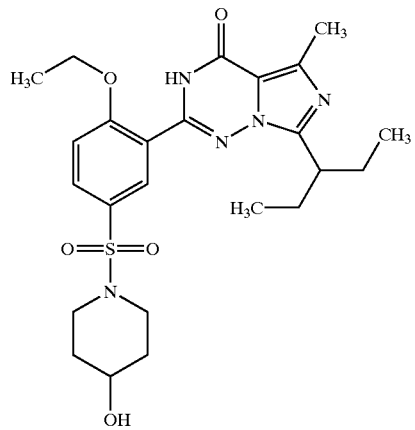

In an analogous manner, starting from 0.44 g (1 mmol) of 3-(7-(1-ethylpropyl)-5-methyl-4-oxo-3,4-dihydroimidazo[5,1-f][1,2,4]triazin-2-yl)-4-ethoxy-benzenesulphonyl chloride and 0.30 g (3 mmol) of 4-hydroxypiperidine, 0.33 g (65%) of 2-[2-ethoxy-5-(4-hydroxypiperidine-1-sulphonyl)-phenyl]-5-methyl-7-(1-ethylpropyl)-3H-imidazo[5,1-f][1,2,4]triazin-4-one are obtained.

$R_f$=0.25 (dichloromethane/methanol=19:1).

Example 56

2-[2-Ethoxy-5-(4-bishydroxyethylamino-1-sulphonyl)-phenyl]-5-methyl-7-(1-ethyl- propyl)-3H-imidazo[5,1-f][1,2,4]triazin-4-one

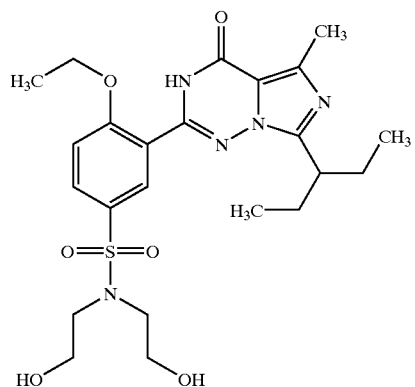

In an analogous manner, starting from 0.3 g (0.68 mmol) of 3-(7-(1-ethylpropyl)-5-ethyl-4-oxo-3,4-dihydroimidazo[5,1-f][1,2,4]triazin-2-yl)-4-ethoxy-benzenesulphonyl chloride and 0.22 g (2.01 mmol) of diethanolamine, 0.147 g (42%) of 2-[2-ethoxy-5-(bishydroxyethylamino-1-sulphonyl)-phenyl]-5-methyl-7-(1-ethylpropyl)-3H-imidazo-[5,1-f][1,2,4]triazin-4-one are obtained.

$R_f$=0.57 (dichloromethane/methanol=9:1).

200 MHz $^1$H-NMR (CDCl$_3$): 0.98 (t, 6H); 1.62 (t, 3H); 1.89 (m, 4H); 2.67 (s, 3H); 3.23 (m, 3H); 3.36 (t, 4H); 3.90 (t, 4H); 4.36 (quart., 2H); 7.18 (d, 1H); 7.96 (dd, 1H); 8. 5 (d, 1H); 9.68 (s, 1H).

Example 57

2-[2-Ethoxy-5-(4-(2-hydroxyethyl)-piperazine-1-sulphonyl)-phenyl]-5-methyl-7- (2-ethylheptyl)-3H-imidazo[5,1-f][1,2,4]triazin-4-one

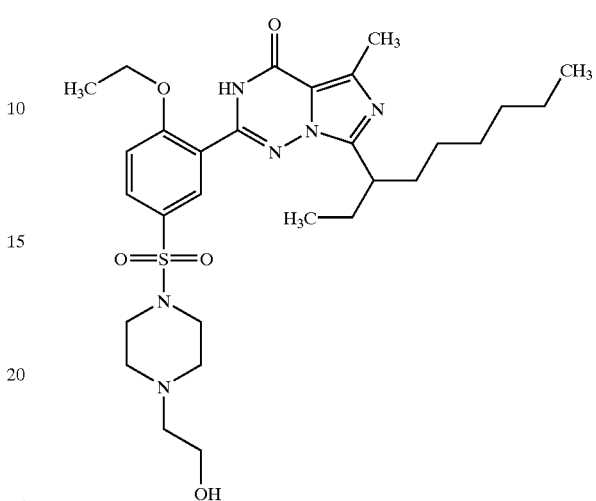

The preparation is carried out analogously to the procedure of Example 1 using 500 mg (1.01 mmol) of 4-ethoxy-3-(5-methyl-4-oxo-7-(2-ethylheptyl)-3,4-dihydro[5.1-f][1,2,4]-triazin-2-yl)-benzenesulphonyl chloride and 290 mg (2.2 mmol) of 4-(2-hydroxyethyl)-piperazine. This gives 170 mg (28.6%) of sulphonamide.

$R_f$=0.56(CH$_2$Cl$_2$/MeOH 10:1).

$^1$H-NMR (CD$_3$OD): 0.75–0.85 (2t, 6H); 131–1.35 (m, 8H); 1.45 (t, 3H); 1.65–1.95 (m, 4H); 2.0 (t, 2H); 2.55–2.65 (m, 7H); 3.0–3.1 (m, 4H); 3.3 (quin., 1H); 3.6 (t, 2H); 4.3 (quar., 2H); 7.4 (d, 1H); 7.95 (dd, 1H); 8.0 (d, 1H).

Example 58

2-[2-Ethoxy-5-(N-methyl-N-(2-(3,4-dimethoxyphenyl)-ethyl)sulphonamido-phenyl]- 5-methyl-7-(2-ethylheptyl)-3H-imidazo[5,1-f][1,2,4]triazin-4-one

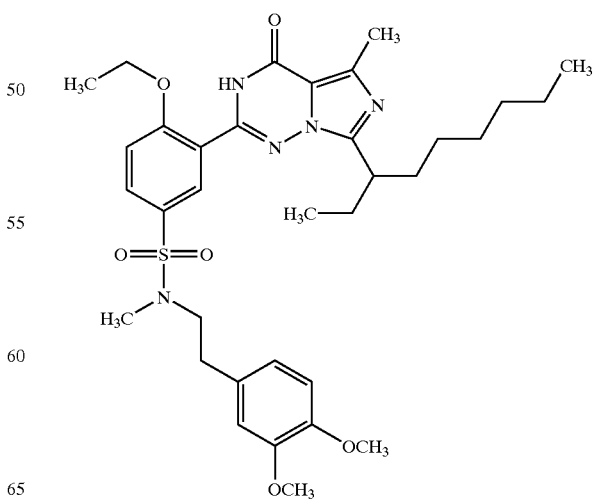

The preparation is carried out analogously to the procedure of Example 1 using 500 mg (1.01 mol) of 4-ethoxy-3-(5-methyl-4-oxo-7-(2-ethylheptyl)-3,4-dihydro-[5,1-f][1,2,4]-triazin-2-yl)-benzenesulphonyl chloride and 433 mg (2.2 mmol) of N-methyl-N-2-(3,4-dimethoxyphenyl)-ethylamine. This gives 153 mg (23.2%) of sulphonamide.

$R_f$=0.78 (CH$_2$Cl$_2$/MeOH 10:1).

$^1$H-NMR (CD$_3$OD): 0.7–0.5 (t, 6H); 1.0–1.35 (m, 8H); 1.45 (t,2H); 1.6–1.95 (m, 4H); 2.6 (s, 3h); 2.75 (s, 3H); 2.8 (t, 2H); 3.15–3.35 (m, 3H); 3.75 (s, 6H); 4.3 (quar., 2H); 6.7–6.85 (m, 3H); 7.3 (d, 1H); 7.9 (dd, 1H); 8.0 (d, 1H).

Example 59

2-[2-Ethoxy-5-(3-(4-morpholino)-propyl-sulphonamido)-phenyl]-5-methyl-7- (2-ethylheptyl)-3H-imidazo[5,1-f][1,2,4]triazin-4-one

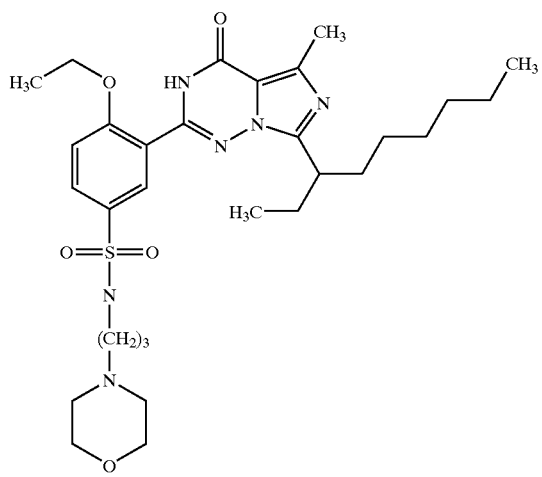

The preparation is carried out analogously to the procedure of Example 1 using 500 mg (1.01 mmol) of 4-ethoxy-3-(5-methyl-4-oxo-7-(2-ethylheptyl)-3,4-dihydro-[5,1-f][1,2,4]-triazin-2-yl)-benzenesulphonyl chloride and 320 mg (2.2 mmol) of 3-(4-morpholino)-propylamine. This gives 175 mg (28.7%) of sulphonamide.

$R_f$=0.58 (CH$_2$Cl$_2$/MeOH 10:1).

$^1$H-NMR (CD$_3$OD): 0.5–0.9 (t, 6H); 1.1–1.35 (m, 8H); 1.45 (t, 3H); 1.65 (quin., 2H); 1.7–1.9 (m, 4H); 2.3–2.45 (m, 6h); 2.6 (s, 3H); 2.95 (t, 2H); 3.35 (m, 1H); 3.665 (2t, 4H); 4.3 (quar., 2h); 7.35 (d, 1H); 8.0 (dd, 1H); 8.1(D, 1H).

Example 60
2-[2-Propoxy-5-(N-methyl-N(2-(3,4-dimethoxyphenyl)-ethyl)-sulphonamido)- phenyl]-5-methyl-7-(2-ethylheptyl)-3H-imidazo[5,1-f][1,2,4]triazin-4-one

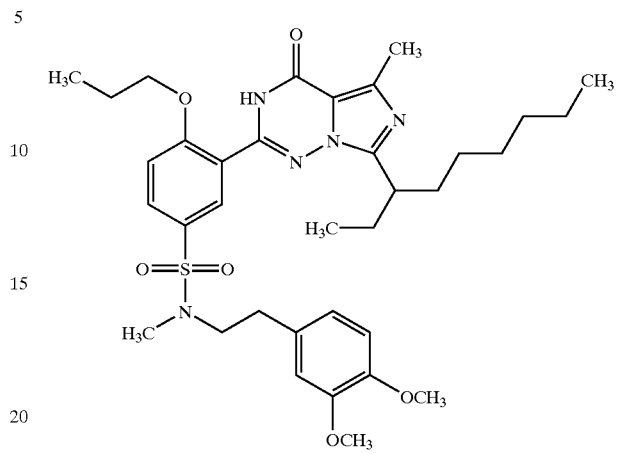

The preparation is carried out analogously to the procedure of Example 1 using 50 mg (0.1 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 50 mg (0.25 mmol) of N-methyl-N-2-(3,4-dimethoxyphenyl)-ethylamine. This gives 45 mg (66%) of sulphonamide.

$R_f$=0.74 (CH$_2$Cl$_2$/MeOH 10:1).
$^1$H-NMR (CD$_3$OD): 0.75 (t, 3H); 0.8 (t, 3h); ,105 (t, 3H); 10–1.3 (m, 8H); 1.6–1.9 (m, 6H); 2.6 (s, 3H); 2.8 (s, 3H); 2.85 (t, 2H); 3.2–3.4 (m, 3H); 3.8 (s, 6H); 4.2 (t, 2H); 6.7–6.85 (m, 3H); 7.3 (d, 1H); 7.9 (dd, 1H); 8.0 (d, 1H).

Example 61
2-[2-Propoxy-5-(4-pyridyl-sulphonamido)-phenyl]-5-methyl-7-(2-ethylheptyl)-3H- imidazo[5,1-f][1,2,4]triazin-4-one

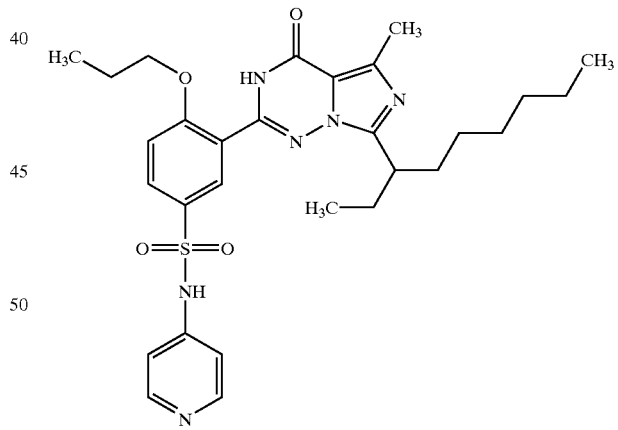

The preparation is carried out analogously to the procedure of Example 1 using 100 mg (0.196 mmol) of 4-propoxy-3-(5-methyl-4oxo-7-(2-ethylheptyl)-3,4-dihydro[5,1-f][1,2,4]-triazin-2-yl)-benzenesulphonyl chloride and 27 mg (0.236 mmol) of 4-aminopyridine in the presence of 40 mg (0.4 mmol) of triethylamine. This gives 35 mg (31.4%) of sulphonamide which can be recrystallized from ethyl acetate/diethyl ether.
$^1$H-NMR (CD$_3$OD): 0.8 (2t, 6h); 1.0 (t, 3H); 1.05–1.35 (m, 8); 1.7–1.9 (m, 6H); 2.6 (s, 3H); 3.35 (m, 1H); 4.15 (t., 2H); 7.1 (d, 1h); 7.3 (d, 1H); 8.0 (m, 2H); 8.05 (dd, 1H); 8.1 (d, 1H).

Example 62
2-[2-Propoxy-5-(4-hydroxypiperidine-1-sulphonyl)-phenyl]-5-methyl-7-(2-ethyl-heptyl)-3H-imidazo[5,1-f][1,2,4]triazin-4-one

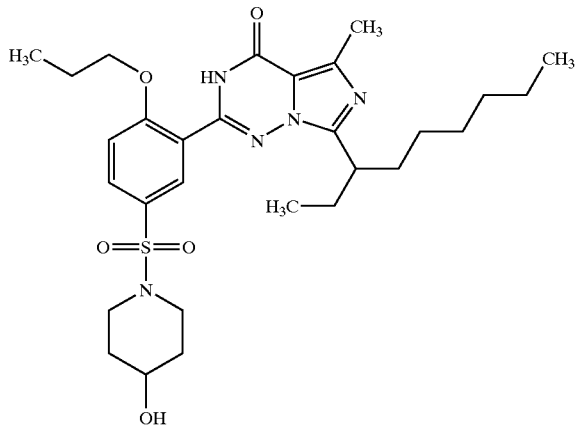

The preparation is carried out analogously to the procedure of Example 1 using 50 mg (0.1 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 20 mg (0.2 mmol) of 4-hydroxypiperidine. This gives 43 mg (76.3%) of sulphonamide.

$R_f$=0.51 (CH$_2$Cl$_2$/MeOH 10:1).

$^1$H-NMR (CDCl$_3$): 0.7–0.85 (m, 6H); 1.05–1.3 (m, 11H); 1.35–2.05 (m, 14H); 2.65 (s, 3H); 2.85–3.0 (m, 2H); 3.15–3.35 (m, 3H); 3.6–3.7 (m, 1H); 4.2 (t, 2H); 7.1 (d, 1h); 7.85 (dd, 1H); 7.95 (d, 1H); 9.8 (broad, 1H).

Example 63
2-[2-Propoxy-5-(4-(2-hydroxyethyl)-piperazine-1-sulphonyl)-phenyl]-5-methyl-7-(2-ethylheptyl)-3H-imidazo[5,1-f][1,2,4]triazin-4-one

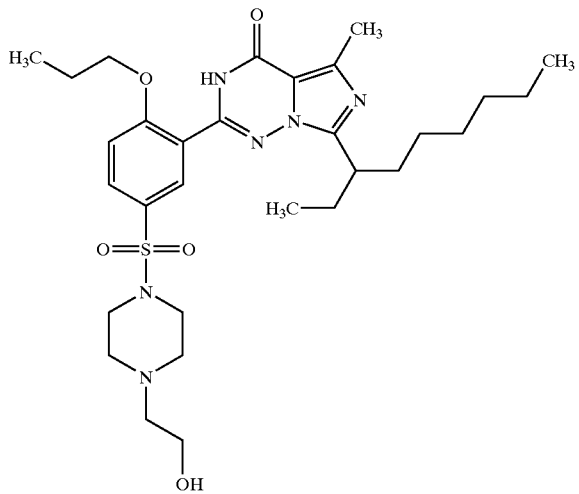

The preparation is carried out analogously to the procedure of Example 1 using 50 mg (0.1 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 26 mg (0.2 mmol) of N-(2-hydroxy-ethyl)-piperazine. This gives 13 mg (22%) of sulphonamide.

$R_f$=0.46 (CH$_2$Cl$_2$/MeOH 10:1).

$^1$H-NMR (CDCl$_3$): 0.7–0.85 (m, 6H); 1.0–1.3 (m, 11H); 1.6–2.0 (m, 6H); 2.55 (s, 3H); 2.5–2.7 (m, 4H); 3.0–3.1 (m, 3H); 3.15–3.3 (m, 1H); 3.6 (t, 2H); 4.2 (t, 2H); 7.15 (d, 1H); 7.7 (dd, 1H); 7.9 (d, 1H); 9.7 (broad, 1H).

Example 64
2-[2-Propoxy-5-(4-methylpiperazine-1-sulphonyl)-phenyl]-5-methyl-7-(2-ethyl-heptyl)-3H-imidazo[5,1-f][1,2,4]triazin-4-one

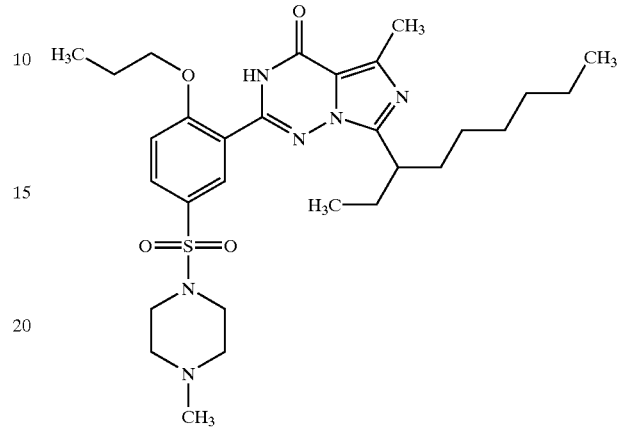

The preparation is carried out analogously to the procedure of Example 1 using 50 mg (0.1 mmol) of 4-propoxy-3-(5-methyl-4-oxo-7-(2-ethylheptyl)-3-(4-dihydro-[5,1-f][1,2,4]-triazin-2-yl)-benzenesulphonyl chloride and 20 mg (0.2 mmol) of N-methyl-piperazine. This gives 42 mg (74.7%) of sulphonamide.

$R_f$=0.46 (CH$_2$Cl$_2$/MeOH 10:1).

$^1$H-NMR (CDCl$_3$): 0.75–0.9 (m, 6H); 1.1–1.35 (m, 11H); 1.6–2.1 (m, 10H); 2.4 (s, 3H); 2.65 (s, 3H); 2.6–2.75 (m, 2H); 3.1–3.4 (m, 4H); 4.25 (t, 2H); 7.2 (d, 1H); 7.9 (d, 1H); 8.5 (d, 1H); 9.7 (broad, 1H).

Example 65
2-[2-Propoxy-5-(4-ethoxycarbonylpiperazine-1-sulphonyl)-phenyl]-5-methyl-7-(2-ethylheptyl)-3H-imidazo[5,1-f][1,2,4]triazin-4-one

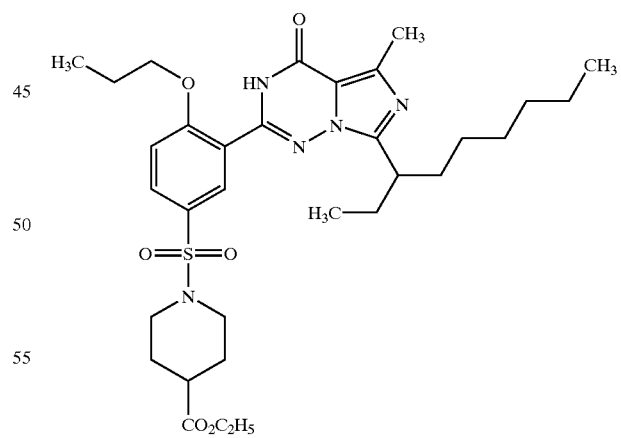

The preparation is carried out analogously to the procedure of Example 1 using 70 mg (0.138 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 43 mg of ethyl piperidinecarboxylate. This gives 55 mg (63.5%) of sulphonamide.

$^1$H-NMR (CD$_3$OD): 0.85 (t, 3H); 0.9 (t, 3H); 1.1 (t, 3H); 172 (t, 3H); 1.2–1.4 (m, 8H); 1.65–2.05 (m, 10H); 2.3 (m,

1H); 2.6 (td, 2H); 2.75 (s, 3H); 3.5 (quin., 1H); 3.6 (m, 2H); 4.1 (quar., 2H); 4.2 (t, 2H); 7.4 (d, 1H); 7.95–8.05 (m, 2H).

Example 66
2-[2-Propoxy-5-(4-carboxypiperazine-1-sulphonyl)-phenyl]-5-methyl-7-(2-ethyl-heptyl)-3H-imidazo[5,1-f][1,2,4]triazin-4-one

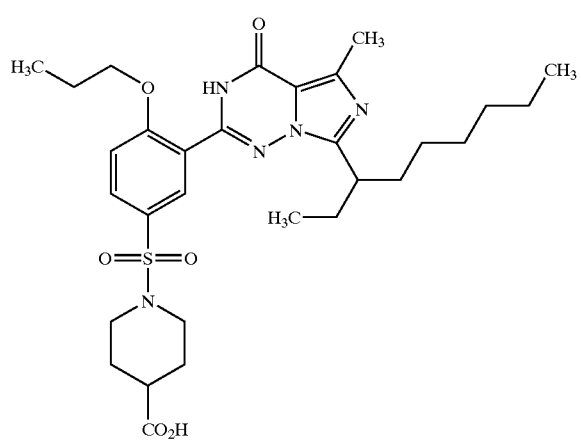

62 mg (0.098 mmol) of the ester from Example 65 are stirred at room temperature in 6 ml of 4 n $NaOH_2O$ (1:5) for 30 minutes. 20 ml of dichloromethane are added, the mixture is extracted with 2 n HCl solution, the organic phase is dried with sodium sulphate and the solvent is removed under reduced pressure.

$R_f$=0.44 ($CH_2Cl_2$/MeOH 10:1).

$^1$H-NMR ($CD_3OD$): 0.85 (t, 3H); 0.9 (t, 3H); 1.05 (t, 3H); 1.2–1.4 (m, 8H); 1.7–2.05 (m, 10H); 2.75–2.9 (m, 1H); 2.6 (td, 2H); 2.75 (s, 3H); 3.5 (quin., 1H); 3.55–3.65 (m, 2H); 4.2 (t, 2H); 7.4 (d, 1H); 7.95–8.0 (m, 2H).

Example 67
2-[2-Propoxy-5-(3-(4-morpholino)-propyl)-sulphonamido)-phenyl]-5-methyl-7-(2-ethylheptyl)-3H-imidazo[5,1-f][1,2,4]triazin-4-one

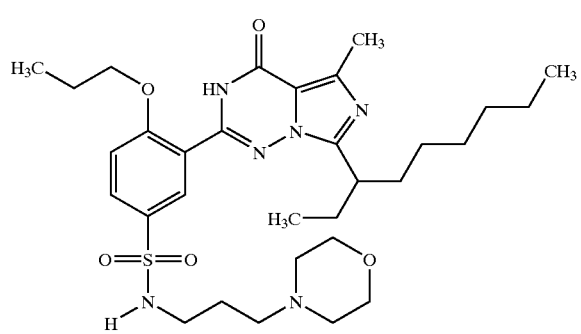

The preparation is carried out analogously to the procedure of Example 1 using 52 mg (0.102 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 37 mg (0.255 mmol) of 3-(4-morpholino)-propylamine. This gives 45 mg (71.4% of sulphonamide.

$R_f$=0.41 ($CH_2Cl_2$/MeOH 10:1).

$^1$H-NMR ($CD_3OD$): 0.75–0.95 (m, 6H); 1.05 (t, 3H); 1.05–1.35 (m, 8H); 1.65 (t, 2H); 1.6–1.95 (m, 6H); 2.3–2.45 (m, 6H); 2.6 (s, 3H); 2.95 (t, 2H); 3.2 (m, 1H); 3.6–3.7 (m, 4H); 4.2 (t, 2H); 7.35 (d, 1H); 8.0 (dd, 1H); 8.1 (d, 1H).

Example 68
2-[2-Propoxy-5-(4-hydroxymethylpiperidine-1-sulphonyl)-phenyl]-5-methyl-7-(2-ethylheptyl)-3H-imidazo[5,1-f][1,2,4]triazin-4-one

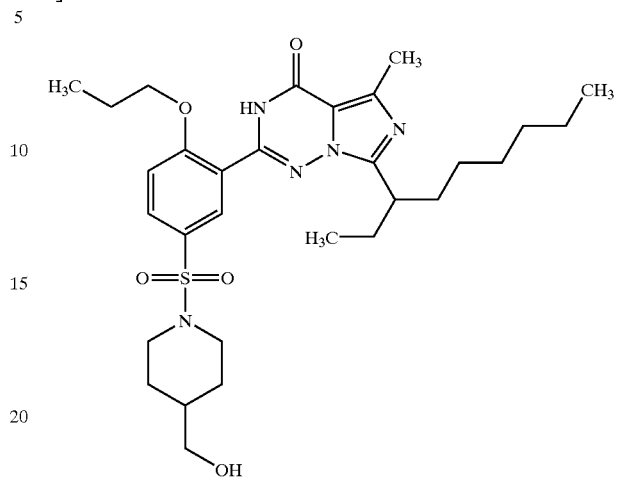

The preparation is carried out analogously to the procedure of Example 1 using 52 mg (0.102 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 29.3 mg (0.255 mmol) of 4-hydroxymethylpiperidine. This gives 45 mg (74.9%) of sulphonamide.

$R_f$=0.44 ($CH_2Cl_2$/MeOH 10:1).

$^1$H-NMR ($CD_3OD$): 0.75–0.9 (m, 6H); 1.05 (t, 3H); 1.0–1.45 (m, 10H); 1.7–1.95 (m, 8H); 2.35 (t, 2H); 2.6 (s, 3H); 3.2–3.4 (m, 2H); 3.8 (d, 2H); 4.2 (t, 2H); 7.4 (d, 1H); 7.9–8.0 (m, 2H).

Example 69
2-[2-Propoxy-5-(N,N-bis-2-hydroxyethyl-sulphonamido)-phenyl]-5-methyl-7-(2-ethylheptyl)-3H-imidazo[5,1-f][1,2,4]triazin-4-one

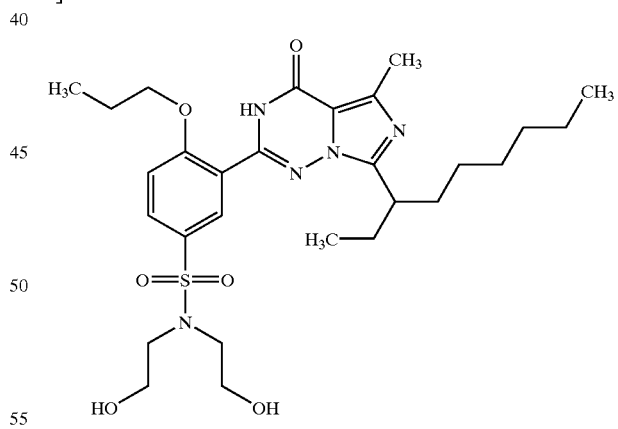

The preparation is carried out analogously to the procedure of Example 1 using 52 mg (0.102 mmol) of 4-propoxy-3-(5-methyl-4oxo-7-(2-ethylheptyl)-3,4-dihydro-[5,1-f][1,2,4]-triazin-2-yl)-benzenesulphonyl chloride and 27 mg (0.255 mmol) of diethanolamine. This gives 41 mg (69.5%) of sulphonamide.

$R_f$=0.36 ($CH_2Cl_2$/MeOH 10:1).

$^1$H-NMR ($CD_3OD$): 0.75–0.9 (m, 6H); 1.05 (t, 3H); 1.0–1.9 (m, 8H); 1.7–1.95 (m, 6H); 2.6 (s, 3H); 3.3 (t, 4H); 3.75 (t, 4H); 4.2 (t, 2H); 7.35 (d, 1H); 8.0 (dd, 1H); 8.1 (d, 1H).

Example 70
2-[2-Propoxy-5-(N-methyl-N-(2-dimethylaminoethyl)-sulphonamido)-phenyl]-5- methyl-7-(2-ethylheptyl)-3H-imidazo[5,1-f][1,2,4]triazin-4-one

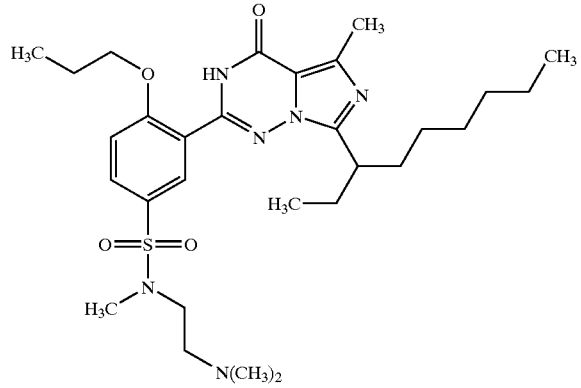

The preparation is carried out analogously to the procedure of Example 1 using 52 mg (0.102 mmol) of 4-propoxy-3-(5-methyl-4-oxo-7-(2-ethylheptyl)-3,4-dihydro-[5,1-f][1,2,4]-triazin-2-yl)-benzenesulphonyl chloride and 26 mg (0.255 mmol) of N-methyl-N-(2-dimethylaminoethyl) amine. This gives 42 meg (71.5%) of sulphonamide.

$R_f$=0.29 (CH$_2$Cl$_2$/MeOH 10:1).

$^1$H-NMR (CD$_3$OD): 0.75–0.85 (m, 6H); 1.05 (t, 3H); 1.1–1.35 (m, 8H); 1.7–1.95 (m, 6H); 2.3 (s, 6H); 2.55 (t, 2H); 2.6 (s, 3H); 2.8 (s, 3H); 3.15 (t, 2H); 3.3 (m, 1H); 4.2 (t, 2H); 7.4 (d, 11H); 8.0 (dd, 1H); 8.05 (d, 1H).

Example 71
2-[2-Ethoxy-5-(N-methyl-N-(2-(3,4-dimethoxyphenyl)-ethyl)-sulphonamido)- phenyl]-5-methyl-7-pentyl-3H-imidazo[5,1-f][1,2,4]triazin-4-one

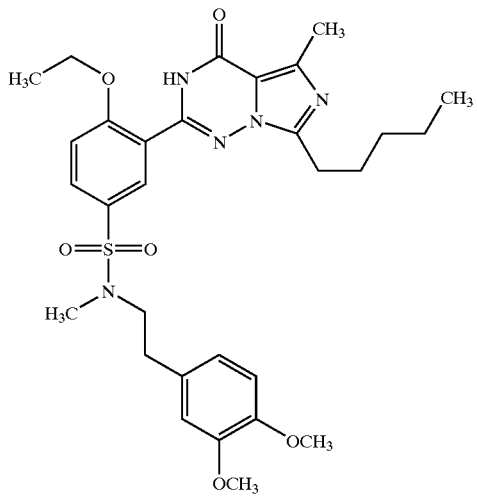

The preparation is carried out analogously to the procedure of Example 1 using 150 mg (0.342 mmol) of 4-ethoxy-3-(5-methyl-4-oxo-7-pentyl-3,4-dihydro-[5,1-f][1,2,4]-triazin-2-yl)-benzenesulphonyl chloride and 167 mg (0.854 mmol) of N-methyl-N-(2-(3,4-dimethoxyphenyl)-ethylamine. This gives 195 mg (95.5%) of sulphonamide.

$R_f$=0.75 (CH$_2$Cl$_2$/MeOH 10:1).

$^1$H-NMR (CD$_3$OD): 0.75 (t, 3H); 1.25–1.4 (m, 4H); 1.45 (t, 3H); 1.75 (quin, 2H); 2.55 (s, 3H); 2.75 (s, 3H1); 2.8 (t, 2H); 2.95 (t, 2H); 3.75 (s, 6H); 4.25 (quar, 2H); 6.7 (dd, 1H); 6.8 (d, 1H); 6.85 (d, 1H); 7.3 (d, 1H); 7.9 (dd, 1H); 8.0 (d, 1H).

Example 72
2-[2-Ethoxy-5-(4-(2-hydroxyethyl)-piperazine-1-sulphonyl)-phenyl]-5-methyl-7- pentyl-3H-imidazo[5,1-f][1,2,4]triazin-4-one

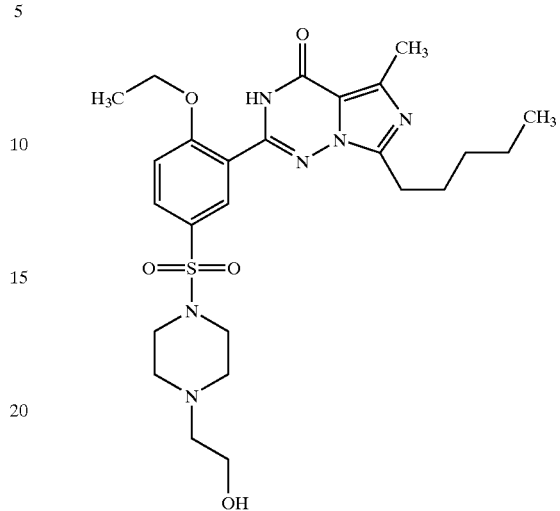

The preparation is carried out analogously to the procedure of Example 1 using 150 mg (0.342 mmol) of 4-ethoxy-3-(5-methyl-4-oxo-7-pentyl-3,4-dihydro-[5,1-f][1,2,4]-triazin-2-yl)-benzenesulphonyl chloride and 111 mg (0.854 mmol) of 2-hydroxyethyl-piperazine. This gives 95 mg (52.4%) of sulphonamide.

$R_f$=0.55 (CH$_2$Cl$_2$/MeOH 10:1).

$^1$H-NMR (CD$_3$OD): 0.9 (t, 3H); 1.3–1.4 (m, 4H); 1.45 (t, 3H); 2.95 (t, 2H); 3.05–3.1 (m, 4H); 3.6 (t, 2H); 4.3 (quar., 2H); 7.4 (d, 1H); 7.9 (dd, 1H); 8.0 (d, 1H).

Example 73
2-[2-Ethoxy-5-(N-methyl-N-(2-(3,4-dimethoxyphenyl)-ethyl)-sulphonamido)- phenyl]-5-methyl-7-pentyl-3H-imidazo[5,1-f][1,2,4]triazin-4-one

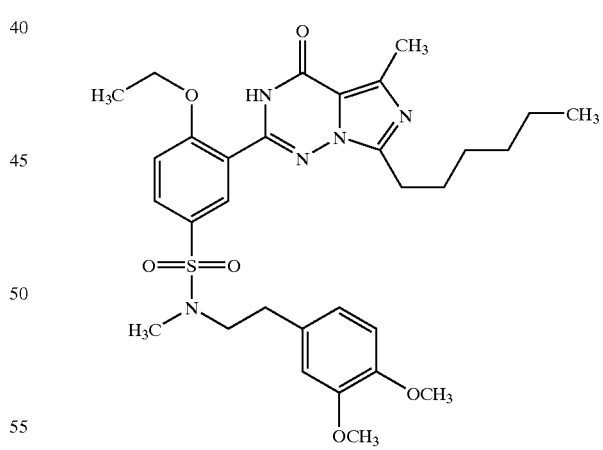

The preparation is carried out analogously to the procedure of Example 1 using 150 mg (0.321 mmol) of 4-ethoxy-3-(5-methyl-4-oxo-7-heptyl-3,4-dihydro-[5,1-f][1,2,4]-triazin-2-yl)-benzenesulphonyl chloride and 140 mg (0.707 mmol) of N-methyl-N-(2-(3,4-dimethoxyphenyl) ethylamine. This gives 112 mg (55.7%) of sulphonamide.

$R_f$=0.74 (CH$_2$Cl$_2$/MeOH 10:1).

$^1$H-NMR (CD$_3$OD): 0.7–0.9 (t, 6H); 1.2–1.35 (m, 8H); 1.45 (t, 3H); 1.75 (quin., wH); 2.6 (s, 3H); 2.75 (s, 3H); 2.8 (t, 2H); 2.95 (t, 2H); 3.8 (s, 6H); 4.3 (quar., 2H); 6.7 (dd, 1H); 6.8–6.9 (m, 2H); 7.3 (d, 1H); 7.9 (dd, 1H); 8.0 (d, 1H).

Example 74
2-[2-Ethoxy-5-(4-(2-hydroxyethyl)-piperazine-1-sulphonyl)-phenyl]-5-methyl-7- heptyl-3H-imidazo[5,1-f][1,2,4]triazin-4-one

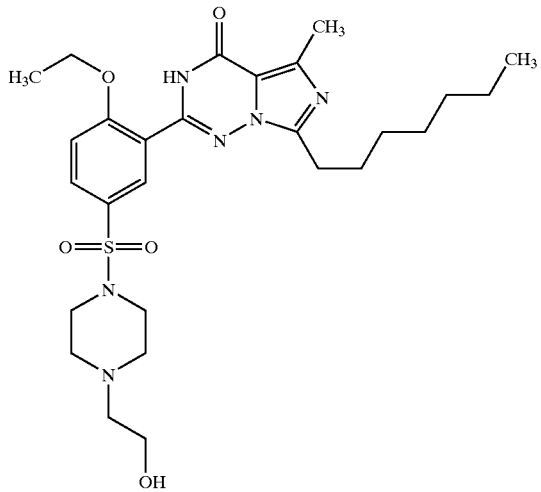

The preparation is carried out analogously to the procedure of Example 1 using 150 mg (0.321 mmol) of 4-ethoxy-3-(5-methyl-4-oxo-7-heptyl-3,4-dihydro-[5,1-f][1,2,4]-triazin-2-yl)-benzenesulphonyl chloride and 92 mg (0.707 mmol) of 2-hydroxyethylpiperazine. This gives 160 mg (88.8%) of sulphonamide.

$R_f$=0.55 ($CH_2Cl_2$/MeOH 10:1).
$^1$H-NMR ($CD_3OD$): 1.35 (t, 6H); 1.2–1.4 (m, 8H); 1.45 (t, 3H); 1.8 (quin., 2H); 2.5 (t, 2H); 3.0 (t, 2H); 3.05–3.1 (m, 4H); 3.3 (t, 2H); 3.6 (t, 2H); 4.3 (quar., 2H); 7.4 (d, 1H); 7.9 (dd, 1H); 8.0 (d, 1H).

Example 75
2-[2-Ethoxy-5-(4-(2-hydroxyethylpiperazine-1-sulphonyl)-phenyl]-5-methyl-7- hexyl-3H-imidazo[5,1-f][1,2,4]-triazin-4-one

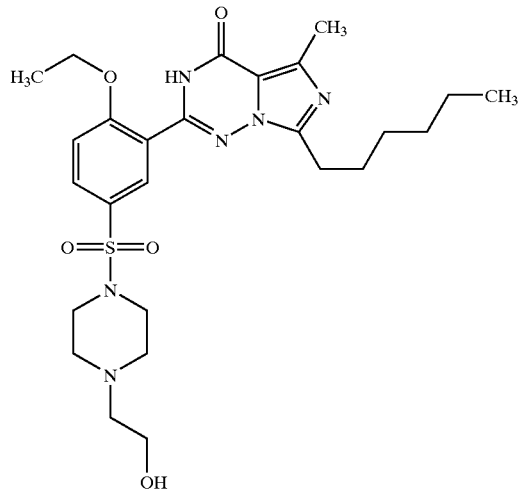

The preparation is carried out analogously to the procedure of Example 1 using 150 mg (0.33 mmol) of 4-ethoxy-3-(5-methyl-4-oxo-7-n-hexyl-3,4-dihydroimidazo[5,1-f][1,2,4]-triazin-2-yl)-benzenesulphonyl chloride and 90 mg (0.725 mmol) of 2-hydroxyethylpiperazine. This gives 90 mg (49.8%) of sulphonamide.

$R_f$=0.57 ($CH_2Cl_2$/MeOH 10:1).
$^1$H-NMR ($CD_3OD$): 0.75 (t, 3H); 1.15–1.3 (m, 6H); 1.35 (t, 3H); 1.7 (quin., 2H); 2.4 (t, 2H); 2.5 (s, 3H); 2.5–2.55 (m, 4H); 2.9 (t, 2H); 2.95–3.0 (m, 4H); 3.5 (t, 2H); 0.2 (quar., 2H); 7.3 (d, 1H); 7.85 (dd, 1H); 7.9 (d, 1H).

Example 76
2-[2-Ethoxy-5-(N-methyl-N-(2-(3,4-dimethoxyphenyl)-ehtyl)sulphonamido)- phenyl]-5-methyl-7-hexyl-3H-imidazo[5,1-f][1,2,4]-triazin-4-one

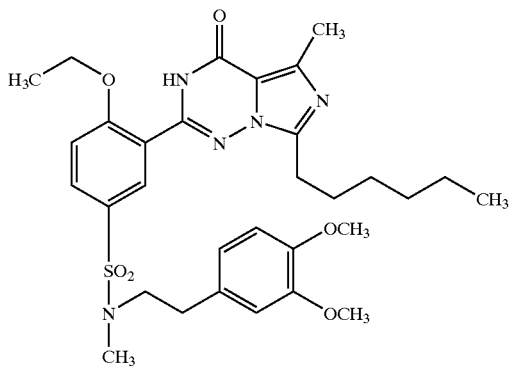

The preparation is carried out analogously to the procedure of Example 1 using 150 mg (0.33 mmol) of 4-ethoxy-3-(5-methyl-4-oxo-7-n-hexyl-3,4-dihydro-imidazo-[5,1-f][1,2,4]-triazin-2-yl)-benzenesulphonyl chloride and 140 mg (0.725 mmol) of N-methyl-N-(2-(3,4-dimethoxyphenyl)-ethylamine. This gives 24.7%) of sulphonamide.

$R_f$=0.72 ($CH_2Cl_2$/MeOH 10:1).
$^1$H-NMR ($CD_3OD$): 0.75 (t, 3H); 1.1–1.25 (m, 6H); 1.35 (t, 3H); 1.65 (quin, 2H1); 2.5 (s, 3H); 2.65 (s, 3H); 2.7 (t, 2H); 2.85 (t, 2H); 3.65 (s, 6H); 4.15 (quar., 2H); 6.6–6.75 (m, 3H); 7.2 (d, 1H); 7.75 (dd, 1H); 7.9 (d, 1H).

Example 77
2-[2-Ethoxy-5-(4-(2-hydroxyethylpiperazine-1-sulphonyl)-phenyl]-5-methyl-7- nonyl-3H-imidazo[5,1-f][1,2,4]-triazin-4-one

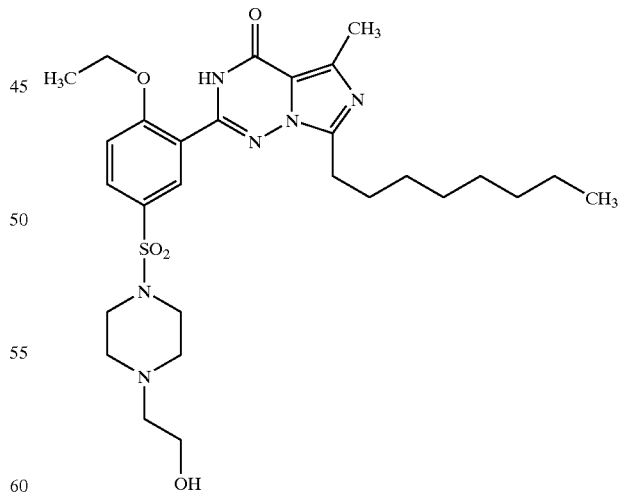

The preparation is carried out analogously to the procedure of Example 1 using 200 mg (0.4 mmol) of 4-ethoxy-3-(5-methyl-4-oxo-7-n-nonyl-3,4-dihydro-imidazo-[5,1-f][1,2,4]triazin-2-yl)-benzenesulphonyl chloride and 120 mg (0.89 mmol) of 2-hydroxyethyl-piperazine. This gives 85 mg (35.7%) of sulphonamide.

R_f=0.45 (CH_2Cl_2/MeOH 10:1).
$^1$H-NMR (CD_3OD): 0.75 (t, 3H); 1.1–1.3 (m, 12H); 1.4 (t, 3H); 1.7 (quin., 2H); 2.4 (t, 2H); 2.5 (s, 3H); 2.5–2.6 (m, 4H); 2.9 (t, 214); 2.95–3.05 (m, 4H); 3.5 (t, 2H); 4.3 (quar., 2H); 7.3 (d, 1H); 7.8 (dd, 1H); 7.9 (d, 1H).

Example 78
2-[2-Ethoxy-5-(N-methyl-N-(2-(3,4-dimethoxyphenyl-ethyl)-sulphonamido)- phenyl]-5-methyl-7-nonyl-3H-imidazo[5,1-f][1,2,4]-triazin-4-one

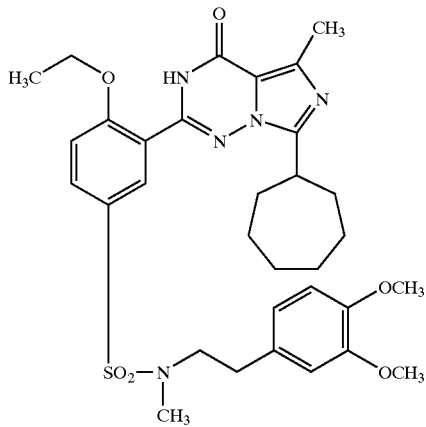

The preparation is carried out analogously to the procedure of Example 1 using 200 mg (0.4 mmol) of 4-ethoxy-3-(5-methyl-4-oxo-7-n-nonyl-3,4-dihydro-imidazo-[5,1-f][1,2,4]triazin-2-yl)-benzenesulphonyl chloride and 170 mg (0.89 mmol) of N-methyl-N-(2-(3,4-dimethoxy)phenyl)-ethylamine. This gives 142 mg (52.8%) of sulphonamide.
R_f=0.74(CH_2Cl_2/MeOH 10:1).
$^1$H-NMR (CD_3OD): 0.7 (t, 3H); 1.1–1.3 (m, 12H); 1.4 (t, 3H); 1.7 (quin., 2H); 2.5 (s, 3H); 2.7 (s, 3H); 2.75 (t, 2H); 2.9 (t, 2H); 3.3 (t, 2H); 3.7 (s, 6H); 4.7 (quar., 2H); 6.6–6.8 (m, 3H); 7.2 (d, 1H); 7.7 (dd, 1H); 7.95 (d, 1H).

Example 79
2-[2-Ethoxy-5-(4-(2-hydroxyethylpiperazine-1-sulphonyl)-phenyl]-5-methyl-7- (2-n-propylbutyl)-3H-imidazo[5,1-f][1,2,4]-triazin-4-one

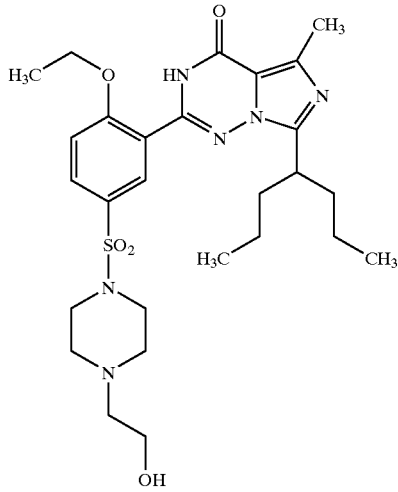

The preparation is carried out analogously to the procedure of Example 1 using 150 mg (0.32 mmol) of 4-ethoxy-3-(5-methyl-4-oxo-7-(2-n-propylbutyl)-3,4-dihydro-imidazo[5,1-f][1,2,4]-triazin-2-yl)-benzenesulphonyl chloride and 50 mg (0.385 mmol) of 2-hydroxyethyl-piperazine. This gives 150 mg (83.3%) of sulphonamide.
R_f=0.62 (CH_2Cl_2/MeOH 10:1).
$^1$H-NMR (CD_3OD): 0.75 (t, 6H); 1.1–1.25 (m, 4H); 1.4 (t, 3H); 1.6–1.7 (m, 2H); 1.75–1.85 (m, 2H); 2.45 (t, 2H); 2.5 (s, 3H); 2.5–2.55 (m, 4H); 3.0 (m 4H); 3.4 (hept., 1H); 2.55 (t, 2H); 4.25 (quar., 2H); 7.35 (d, 1H); 7.85 (dd, 1H); 7.95 (d, 1H).

Example 80
2-[2-Ethoxy-5-(N-methyl-N-(2-(3,4-dimethoxyphenyl)-ethyl)-sulphonamido)- phenyl]-5-methyl-7-(2-n-propylbutyl)-3H-imidazo[5,1-f][1,2,4]-triazin-4-one

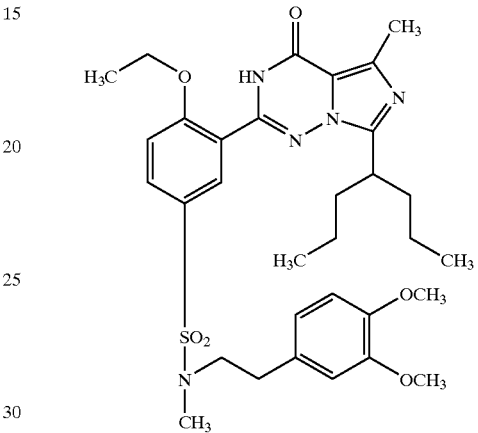

The preparation is carried out analogously to the procedure of Example 1 using 150 mg (0.32 mmol) of 4-ethoxy-3-(5-methyl-4-oxo-7-(2-n-propylbutyl)-3,4-dihydro-imidazo[5,1-f][1,2,4]-triazin-2-yl)-benzenesulphonyl chloride and 80 mg (0.385 mmol) of N-methyl-N-(2-(3,4-dimethoxyphenyl)-ethylamine. This gives 166 mg (82.6%) of sulphonamide.
M.p.: 131 ° C. (ethyl acetate/diethyl ether).

Example 81
2-[2-Ethoxy-5-(4-(2-hydroxyethylpiperazine-1-sulphonyl)-phenyl]-5-methyl-7-cyclo- heptyl-3H-imidazo[5,1-f][1,2,4]-triazin-4-one

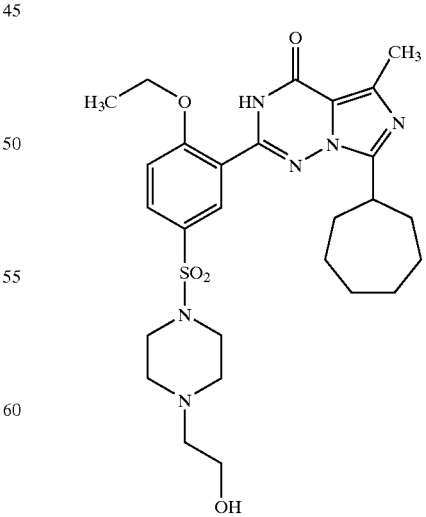

The preparation is carried out analogously to the procedure of Example 1 using 200 mg (0.43 mmol) of 4-ethoxy- 3-(5-methyl-4-oxo-7-cycloheptyl-3,4-dihydroimidazo[5,1-f]-[1,2,4]-triazin-2-yl-benzenesulphonyl chloride and 120 mg (0.946 mmol) of 2-hydroxyethyl-piperazine. This gives 158 mg (65.7%) of sulphonamide.

$R_f$=0.55 (CH$_2$Cl$_2$/MeOH 10:1).

Example 82
2-[2-Ethoxy-5-(N-methyl-N-(2-(3,4-dimethoxyphenyl)-ethyl)-sulphonamido)- phenyl]-5-methyl-7-cycloheptyl-3H-imidazo[5,1-f][1,2,4]-triazin-4-one

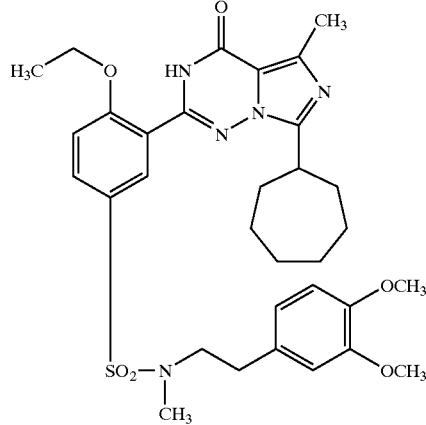

The preparation is carried out analogously to the procedure of Example 1 using 300 mg (0.645 mmol) of 4-ethoxy-3-(5-methyl-4-oxo-7-cycloheptyl-3,4-dihydroimidazo[5,1-f]-[1,2,4]-triazin-2-yl-benzenesulphonyl chloride and 280 mg (1.42 mmol) of N-methyl-N-(2-(3,4-dimethoxyphenyl)-ethylamine. This gives 256 mg (63.6%) of sulphonamide.

$R_f$=0.66 (CH$_2$Cl$_2$/MeOH 10:1).

$^1$H-NMR (CD$_3$OD): 1.45 (t, 2H); 1.5–1.7 (m, 9H); 1.7–2.0 (m, 6H); 2.55 (s, 3H); 2.75 (s, 3H); 2.8 (t, 2H); 3.35 (t, 2H); 3.45 (quin., 1H); 3.7 (s, 6H); 4.25 (quar., 2H); 6.65–6.8 (m, 3H); 7.25 (d, 1H); 7.85 (dd, 1H); 8.0 (d, 1H).

The sulphonamides listed in the tables below were prepared by automatic parallel synthesis from the corresponding sulphonyl chlorides and the corresponding amines using one of the three standard procedures below.

The purity of the final product was determined by means of HPLC, and they were characterized by LC-MS. The number given in the column % (HPLC) is the content of the end product characterized by the molecular peak. Standard procedure A was used with alnines having acidic functionalities, standard procedure B was used with amines having neutral functionalities, standard procedure C was used with amines having additional basic functionalities.

Compounds listed in the tables below and having optically a free nitrogen valency are, in principle, to be understood as —NH— radical.

Standard procedure A: Reaction of Amines Having Acidic Functionalities 0.05 mmol of amine, 0.042 mmol of sulphonyl chloride and 0.100 mmol of Na$_2$CO$_3$ are initially charged, and 0.5 ml of a mixture of THF/H$_2$O is pipetted in by hand. After 24 h at room temperature, the mixture is admixed with 0.5 ml of 1 M H$_2$SO$_4$ solution and filtered through a two-phase cartridge (500 mg of Extrelut (upper phase)) and 500 mg of SiO$_2$, mobile phase ethyl acetate). The product is obtained after concentrating the filtrate under reduced pressure.

Standard procedure B: Reaction of Amines Having Neutral Functionalities 0.125 mmol of amine are initially charged and 0.03 mmol of sulphonyl chloride as a solution in 1,2-dichloroethane is pipetted in by the synthesizer. After 24 h, the mixture is admixed with 0.5 ml of 1 M H$_2$SO$_4$ and filtered through a two-phase cartridge (500 mg of Extrelut (upper phase) and 500 mg of SiO$_2$, mobile phase: ethyl acetate). The filtrate is concentrated under reduced pressure.

Standard procedure C: Reaction of Amines Having Basic Functionalities 0.05 mmol of amine are initially charged and 0.038 mmol of sulphonyl chloride as a solution in 1,2-dichloroethane and 0.05 mmol of triethylamine, as a solution in 1,2-dichloroethane are pipetted in by the synthesizer. After 24 h, the solution is initially admixed with 3 ml of saturated NaHCO$_3$ solution and the reaction mixture is filtered through a two-phase cartridge. The product is obtained after concentrating the filtrate under reduced pressure.

All reactions are monitored by thin-layer chromatography. If the reaction is not complete after 24 h at room temperature, the mixture is heated at 60° C. for a further 12 h and the experiment is subsequently terminated.

TABLE 1

| Ex. No. | Structure | MW | % (HPLC)* |
|---|---|---|---|
| 83 | 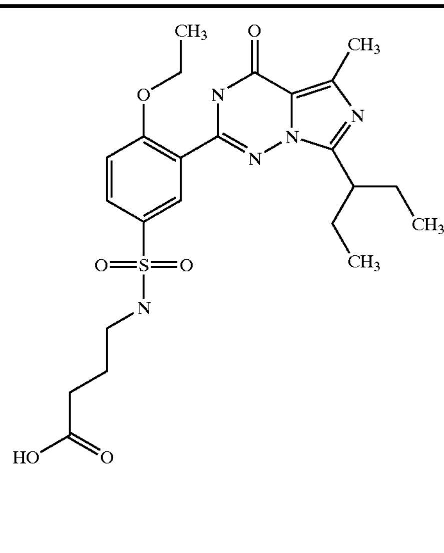 | 505.6 | 76 |

TABLE 1-continued
| | | |
|---|---|---|
| 84 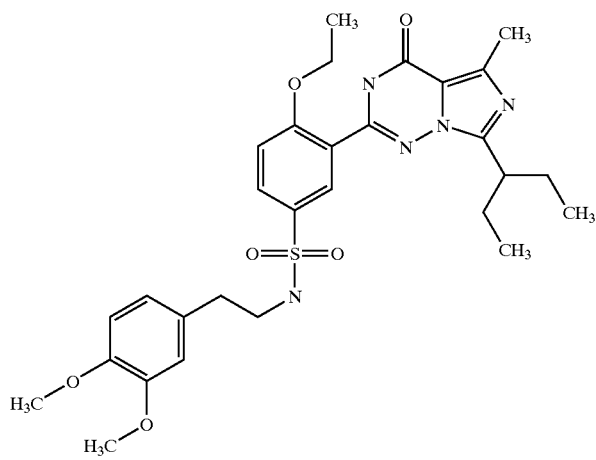 | 583.71 | 89 |
| 85 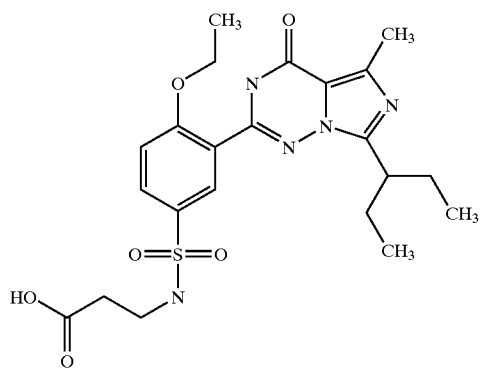 | 491.57 | 56 |
| 86 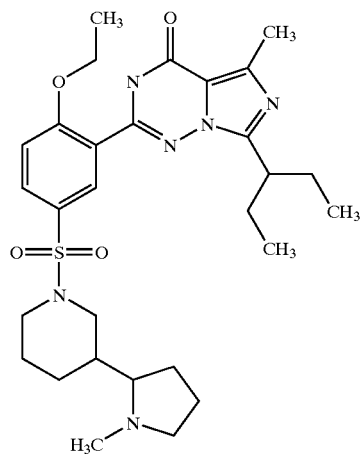 | 570.76 | 60 |

TABLE 1-continued
| | | | |
|---|---|---|---|
| 87 | 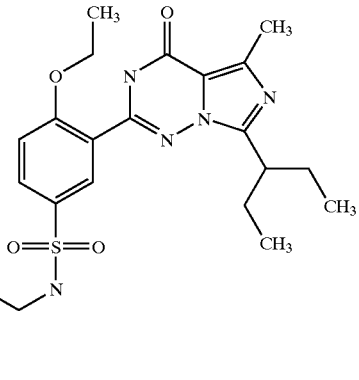 | 539.66 | 87 |
| 88 | 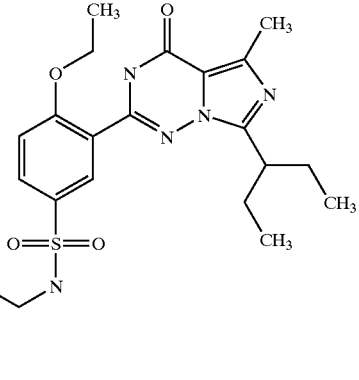 | 569.69 | 88 |
| 89 | 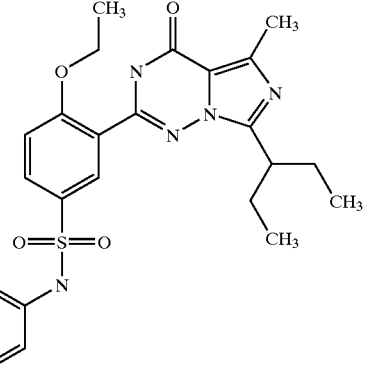 | 567.67 | 82 |
| 90 | 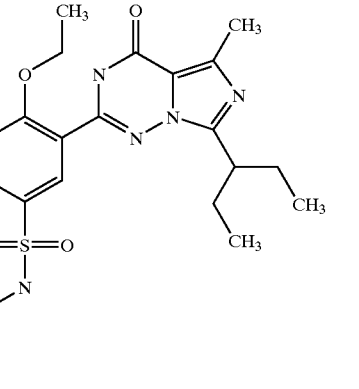 | 555.66 | 91 |

TABLE 1-continued
| | | |
|---|---|---|
| 91 | 569.69 | 77 |
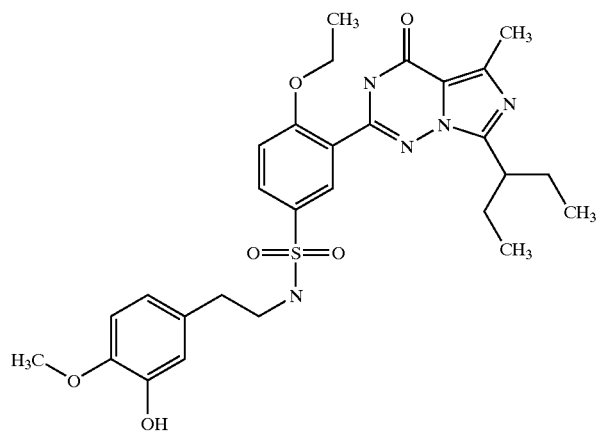
| | | |
|---|---|---|
| 92 | 553.66 | 54 |
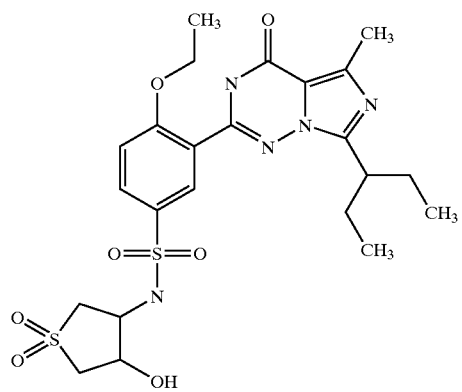
| | | |
|---|---|---|
| 93 | 551.73 | 62 |
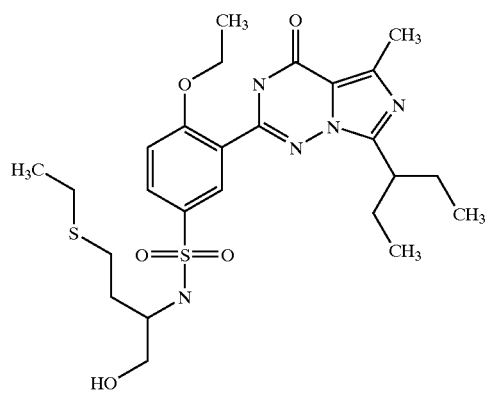

TABLE 1-continued
| 94 | | 609.73 | 60 |
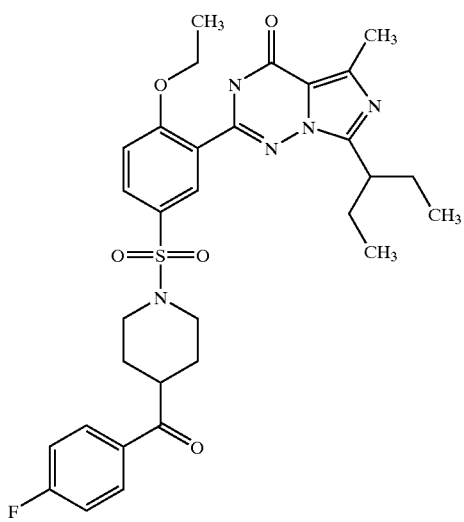
| 95 | | 537.66 | 88 |
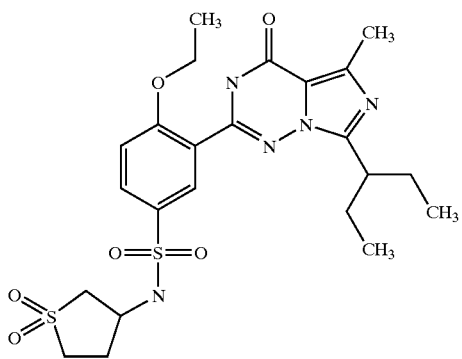
| 96 | | 477.59 | 97 |
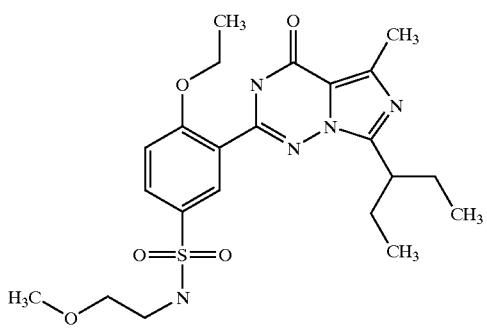

TABLE 1-continued
| | | | |
|---|---|---|---|
| 97 | 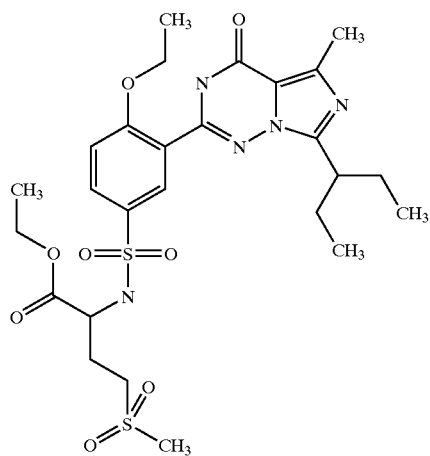 | 611.74 | 52 |
| 98 | 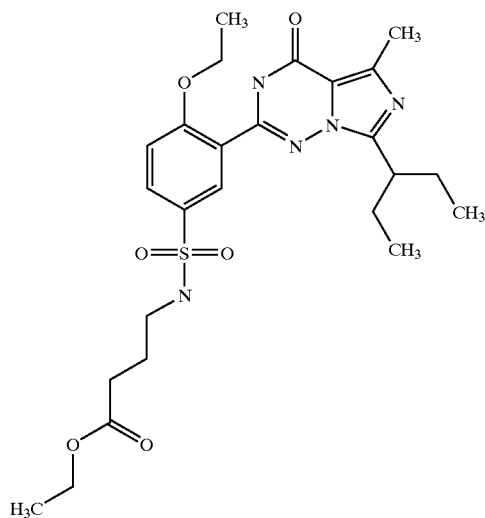 | 533.65 | 85 |
| 99 | 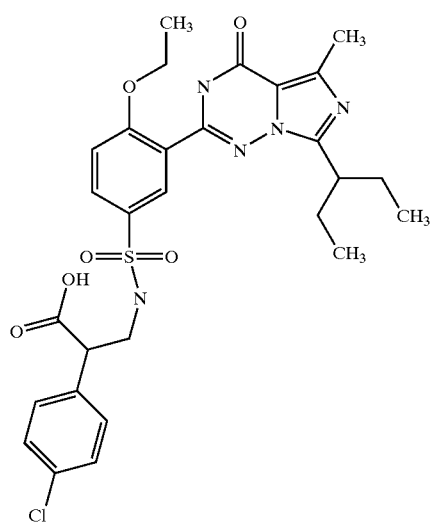 | 602.11 | NMR |

TABLE 1-continued
| | | |
|---|---|---|
| 100 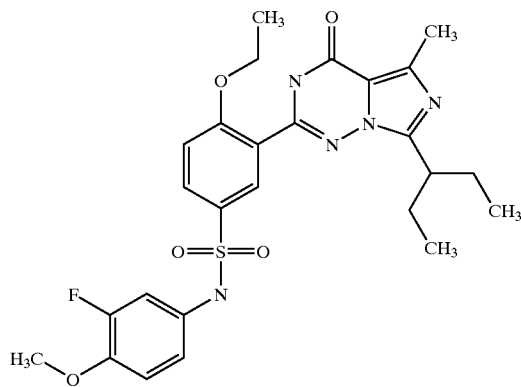 | 543.62 | 88 |
| 101 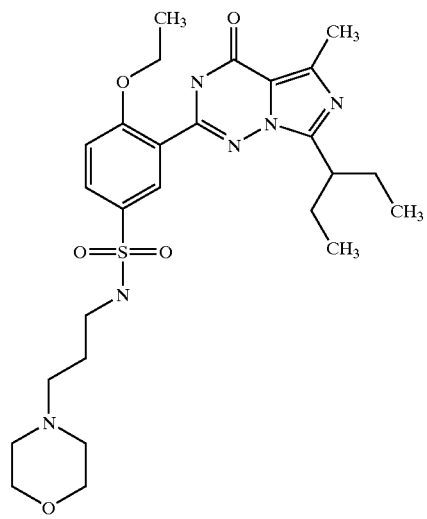 | 546.69 | 82 |
| 102 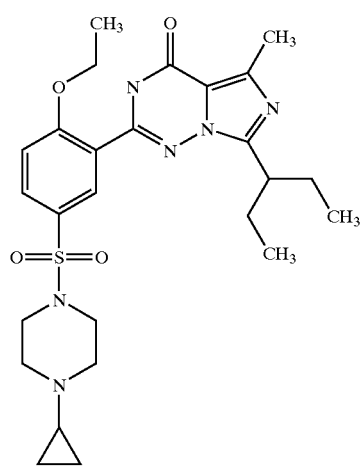 | 528.68 | 82 |

TABLE 1-continued
| | | | |
|---|---|---|---|
| 103 | 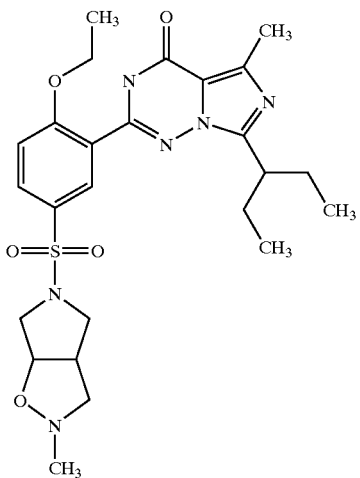 | 530.65 | 77 |
| 104 | 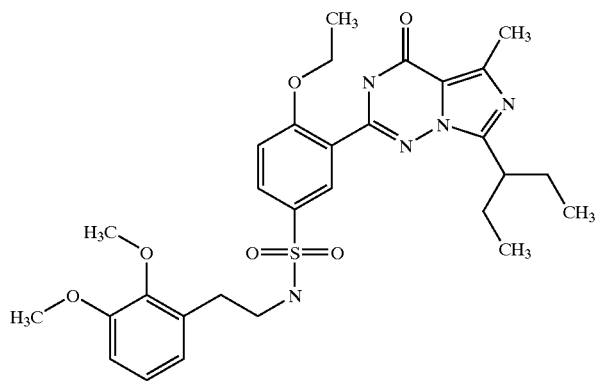 | 583.71 | 91 |
| 105 | 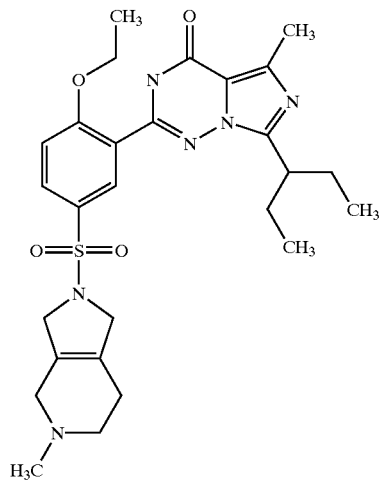 | 540.69 | 58 |

| | | |
|---|---|---|
| 106 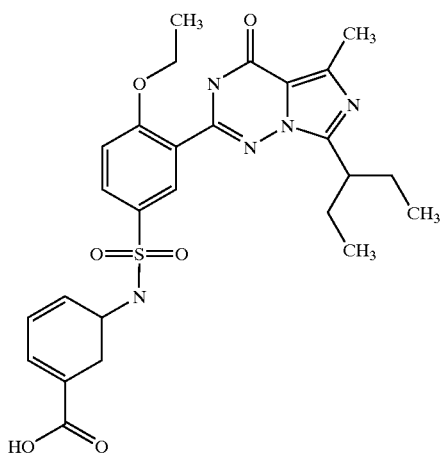 | 541.63 | 38 |
| 107 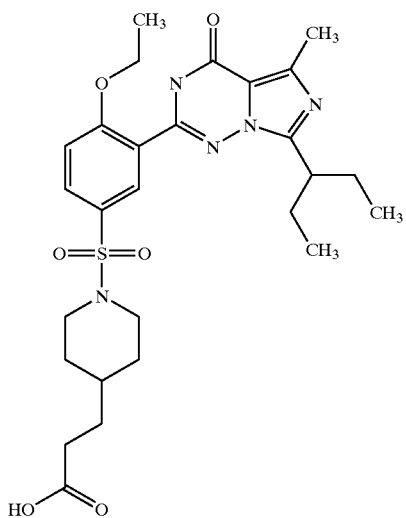 | 559.69 | 60 |
| 108 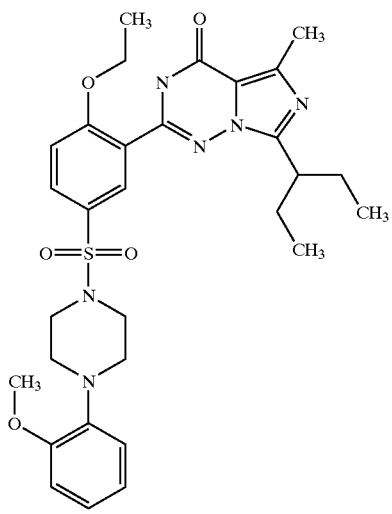 | 594.74 | 88 |

TABLE 1-continued
| | | | |
|---|---|---|---|
| 109 | 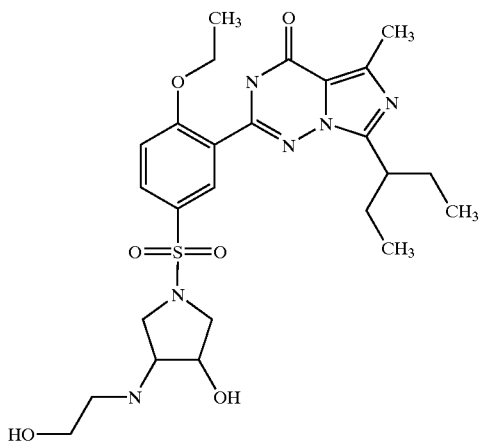 | 548.67 | 61 |
| 110 | 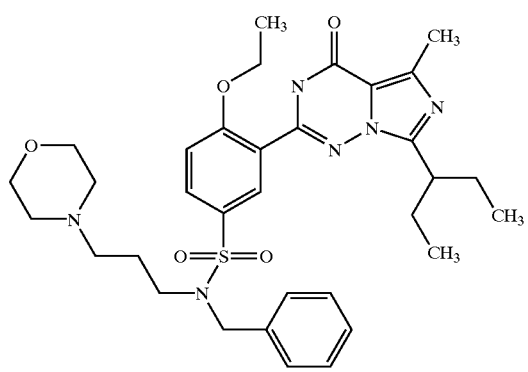 | 636.82 | 85 |
| 111 | 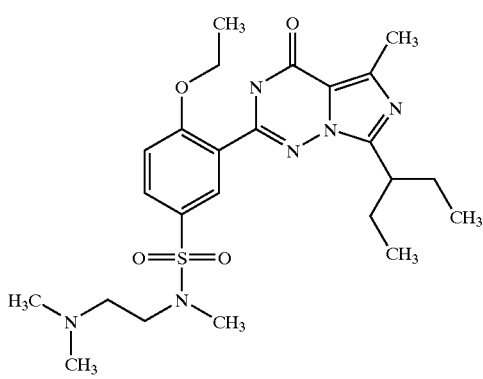 | 504.66 | 67 |
| 112 | 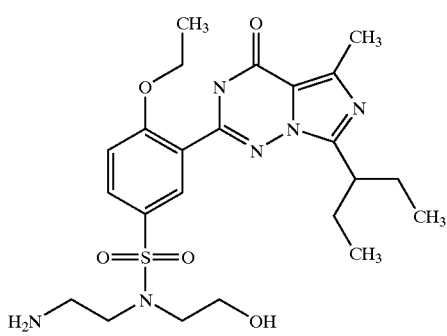 | 506.63 | 57 |

TABLE 1-continued
| | | | |
|---|---|---|---|
| 113 | 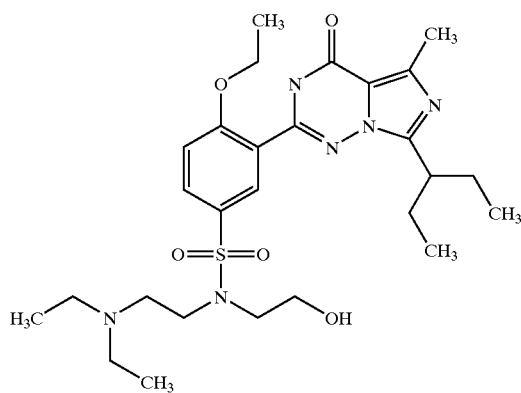 | 562.74 | 84 |
| 114 | 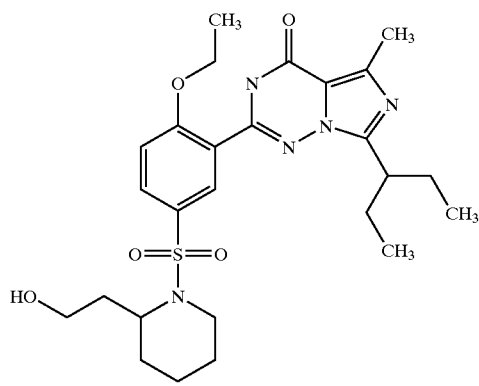 | 531.68 | 61 |
| 115 | 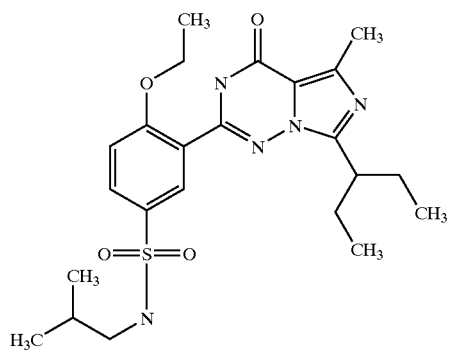 | 475.61 | 90 |

TABLE 1-continued
| 116 | 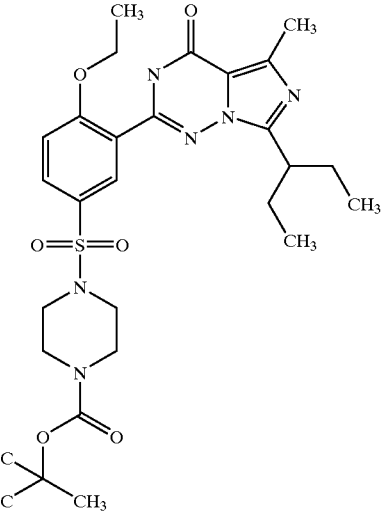 | 588.73 | 82 |
| 117 | 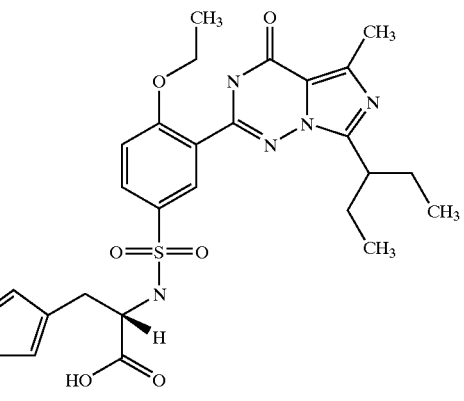 | 573.69 | 52 |
| 118 | 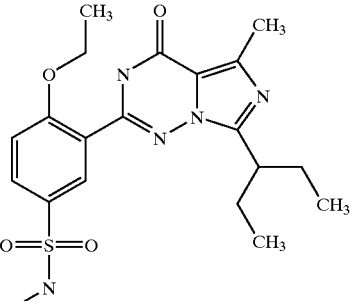 | 505.64 | 92 |
| 119 | 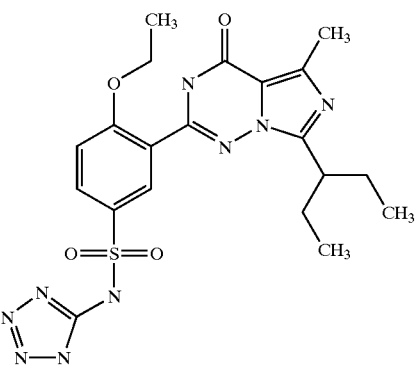 | 487.54 | >58 |

TABLE 1-continued
| | | |
|---|---|---|
| 120 | 609.75 | 86 |
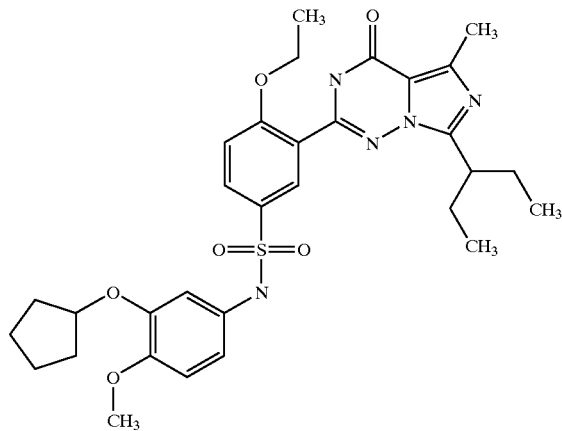
| | | |
|---|---|---|
| 121 | 625.77 | 98 |
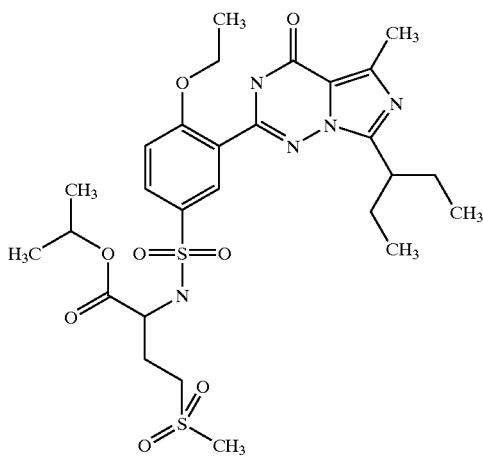
| | | |
|---|---|---|
| 122 | 560.68 | 90 |
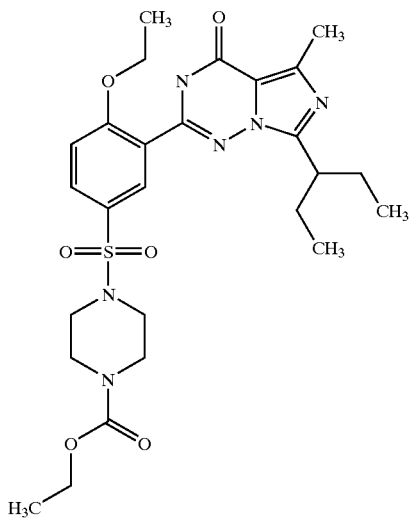

TABLE 1-continued
| 123 | 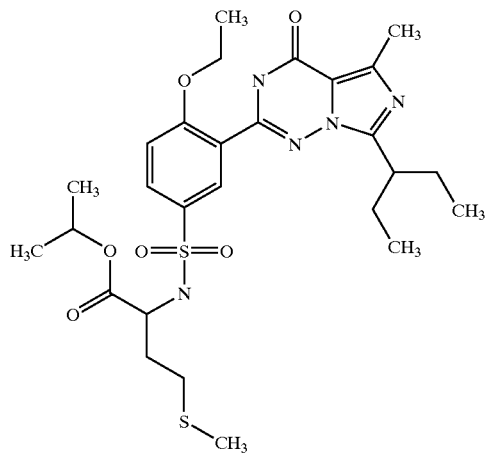 | 593.77 | 46 |
| 124 | 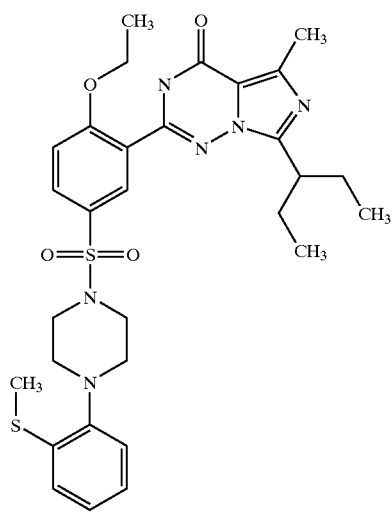 | 610.8 | 64 |
| 125 | 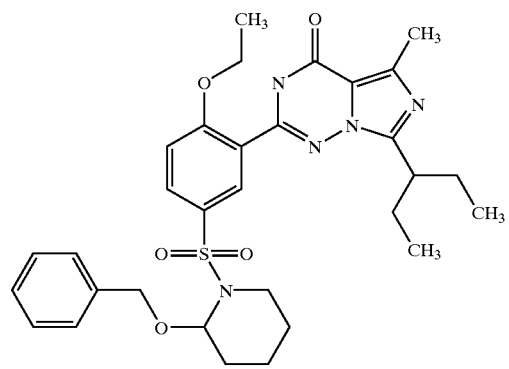 | 593.75 | 84 |

TABLE 1-continued
| 126 | 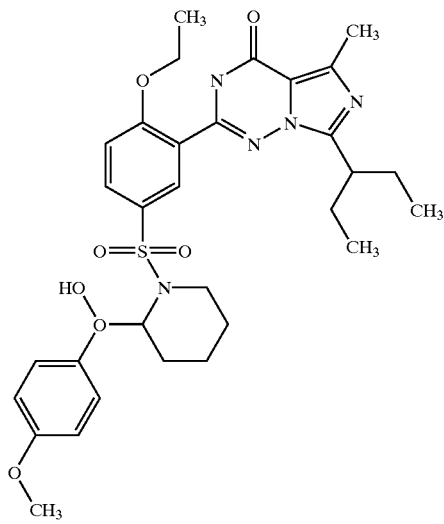 | 623.78 | 85 |
| 127 | 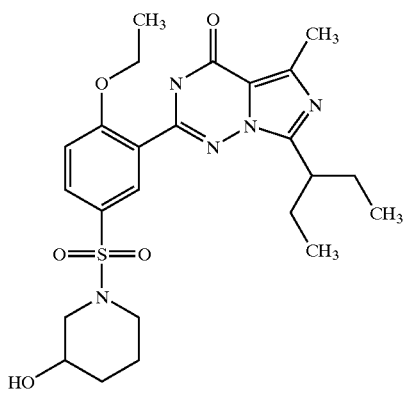 | 503.63 | 89 |
| 128 | 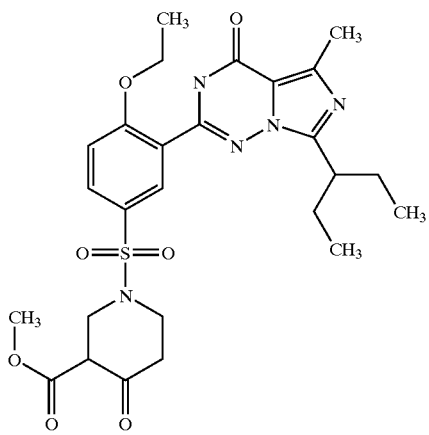 | 559.65 | 58 |

TABLE 1-continued
| | | | |
|---|---|---|---|
| 129 | 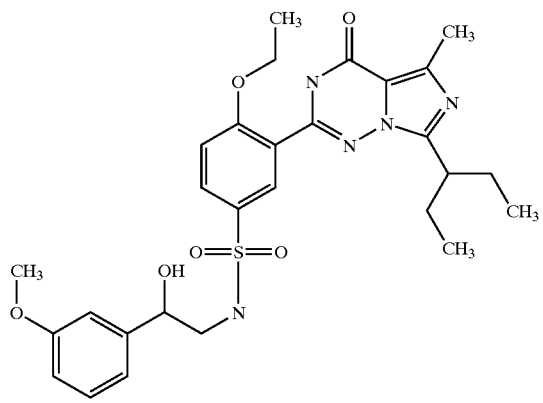 | 569.69 | 70 |
| 130 | 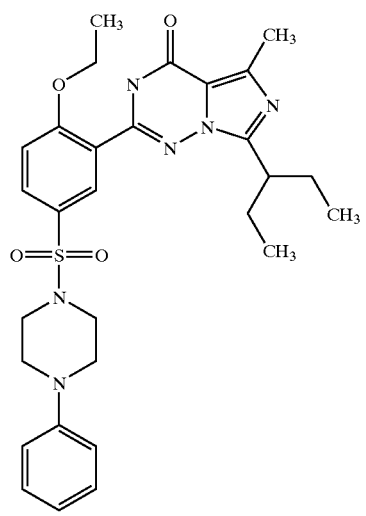 | 564.71 | 76 |
| 131 | 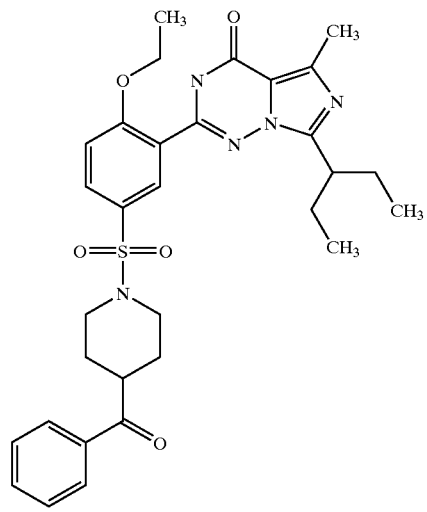 | 591.74 | 77 |

| | | | |
|---|---|---|---|
| 132 | 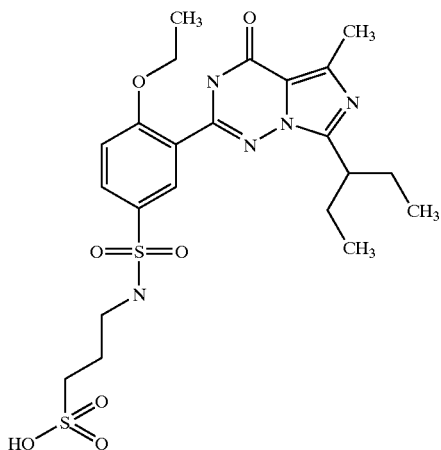 | 541.65 | 66 |
| 133 | 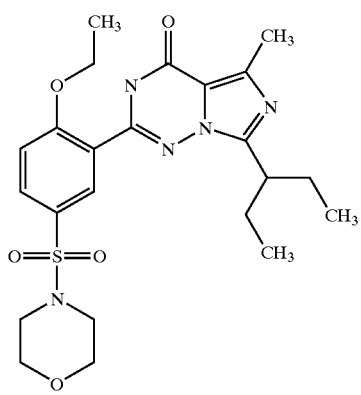 | 489.6 | 83 |
| 134 | 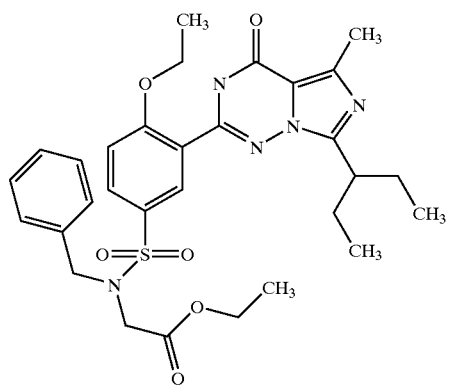 | 595.72 | 84 |
| 135 | 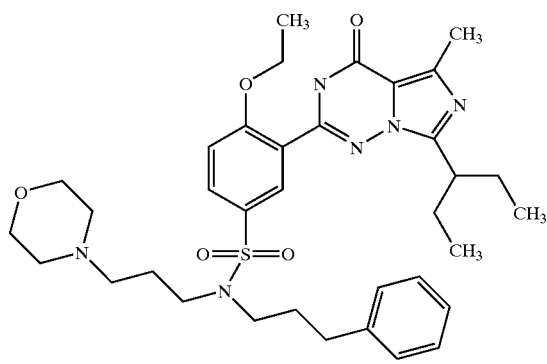 | 664.87 | 70 |

TABLE 1-continued
| 136 | 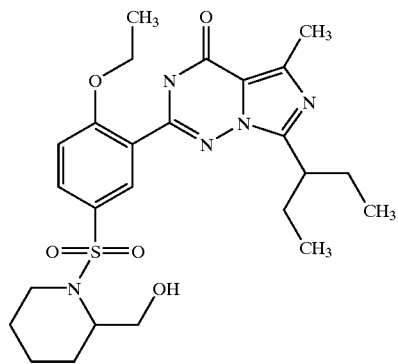 | 517.65 | 77 |
| 137 | 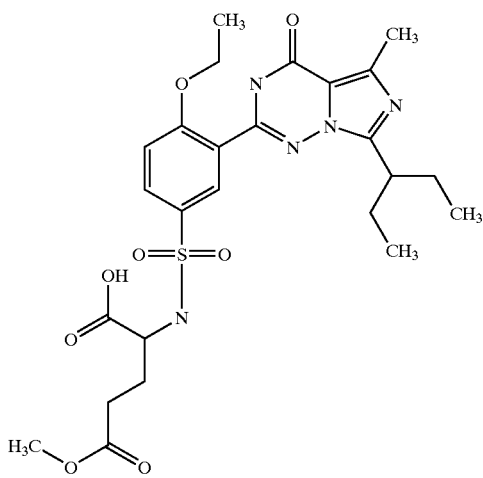 | 563.63 | 31 |
| 138 | 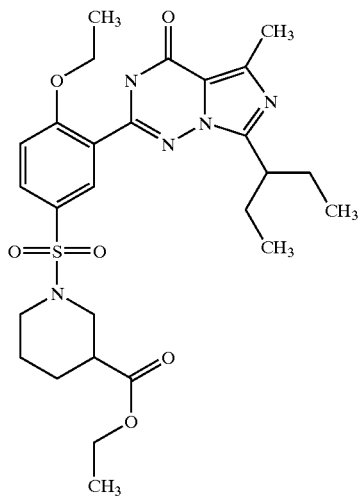 | 559.69 | 88 |

TABLE 1-continued
| 139 | 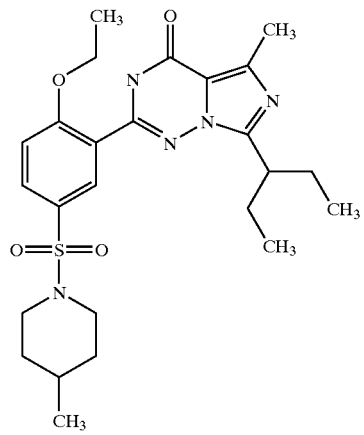 | 501.65 | 81 |
| 140 | 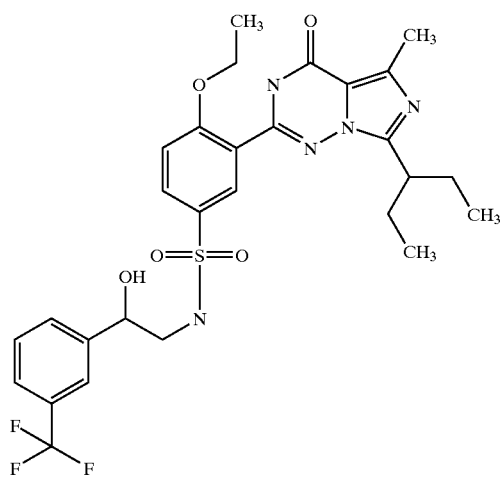 | 607.66 | 86 |
| 141 | 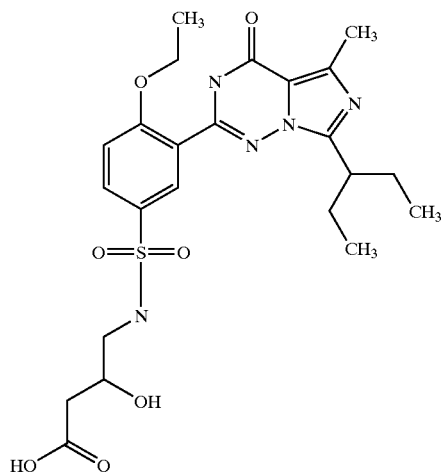 | 521.6 | 37 |

TABLE 1-continued
| | | | |
|---|---|---|---|
| 142 | 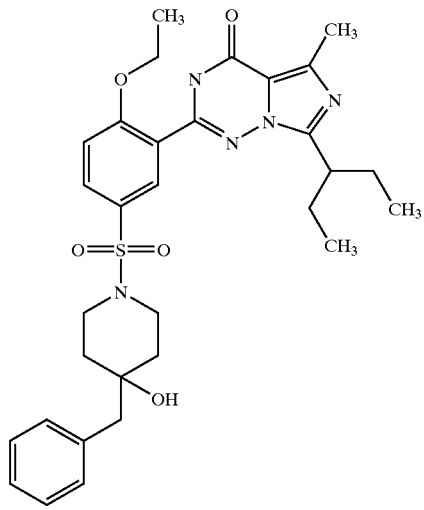 | 593.75 | 82 |
| 143 | 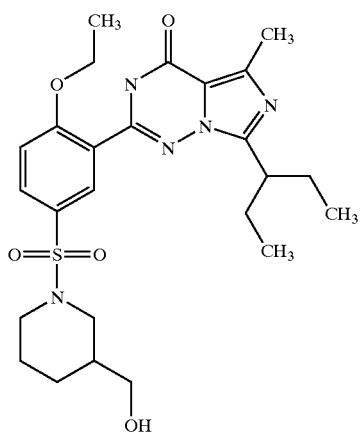 | 517.65 | 85 |
| 144 | 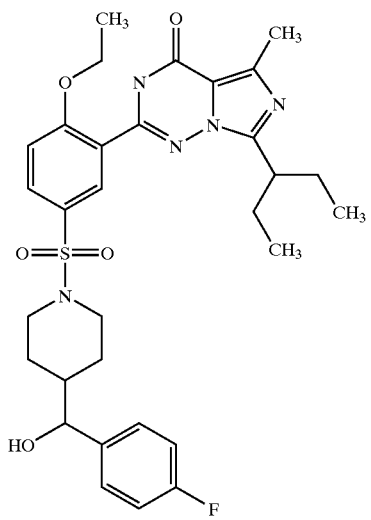 | 611.74 | 67 |

TABLE 1-continued
| | | | |
|---|---|---|---|
| 145 | 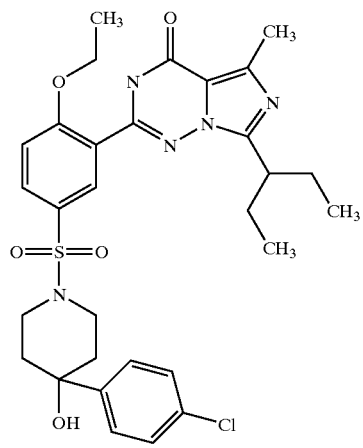 | 614.17 | 78 |
| 146 | 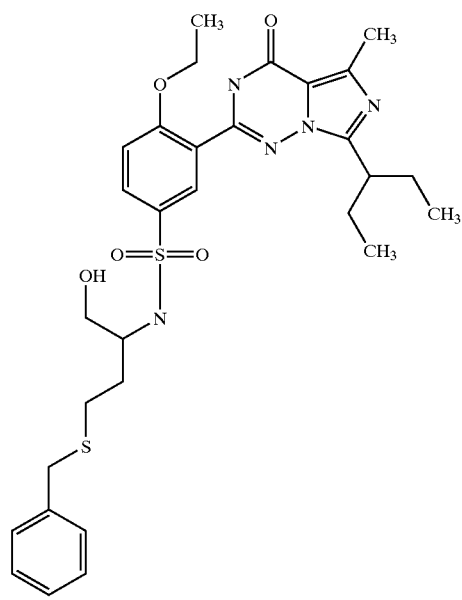 | 613.8 | 47 |
| 147 | 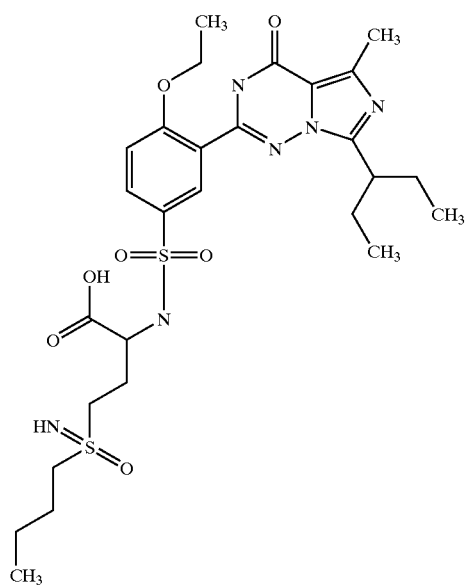 | 624.78 | 52 |

TABLE 1-continued
| 159 | 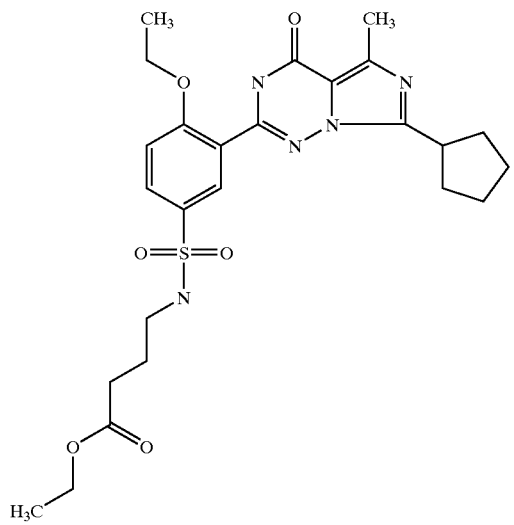 | 531.6 | 88 |
| 160 | 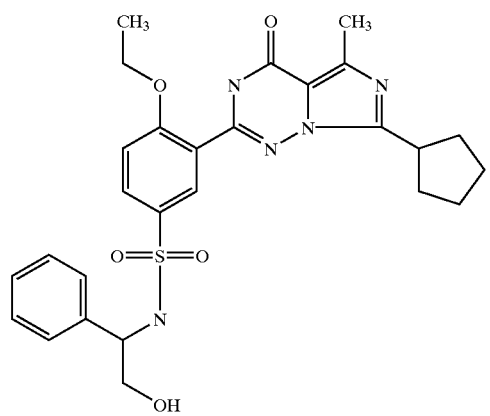 | 537.6 | 80 |
| 161 | 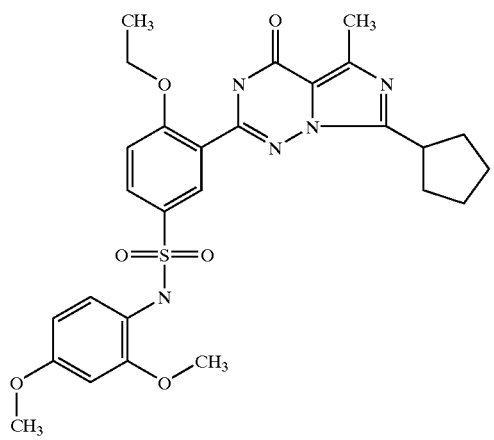 | 553.6 | 78 |

TABLE 1-continued
| | | | |
|---|---|---|---|
| 162 | 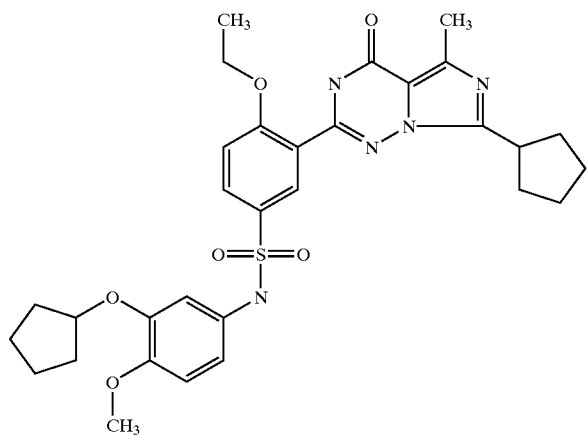 | 607.7 | 75 |
| 163 | 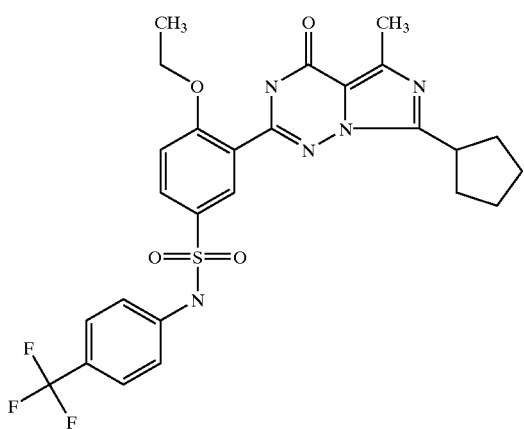 | 561.6 | 80 |
| 164 | 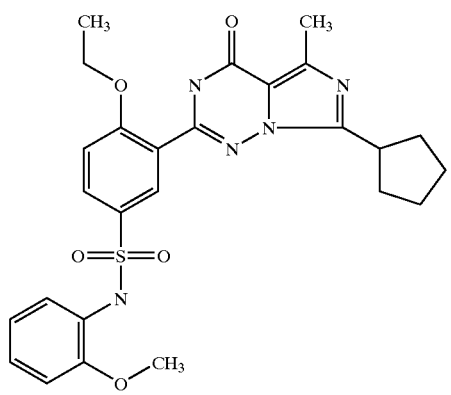 | 523.6 | 83 |
| 156 | 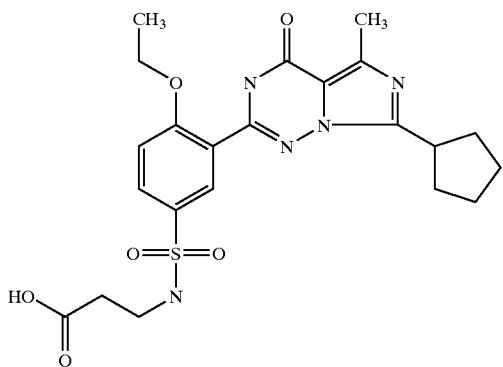 | 489.6 | 72 |

TABLE 1-continued
| 157 | 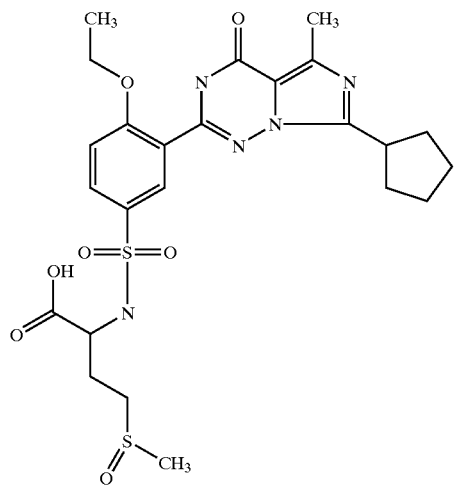 | 565.7 | 76 |
| 158 | 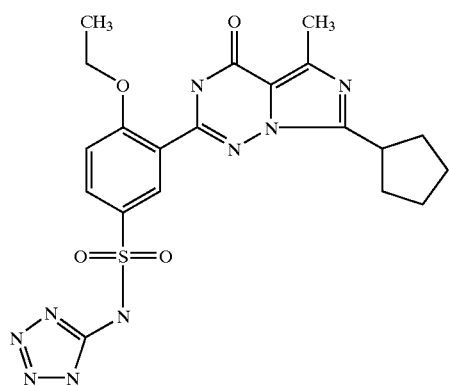 | 485.5 | 42 |
| 159 | 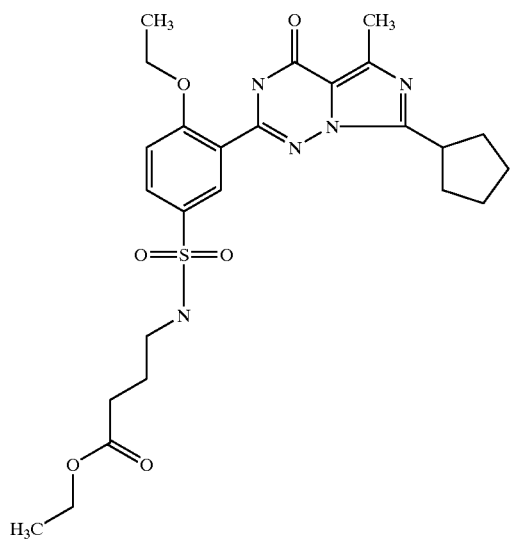 | 531.6 | 88 |

TABLE 1-continued
| 160 | 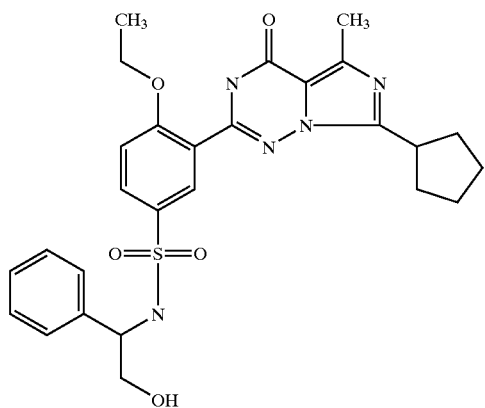 | 537.6 | 80 |
| 161 | 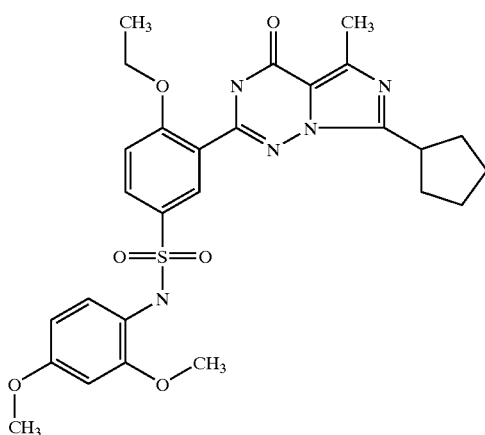 | 553.6 | 78 |
| 162 | 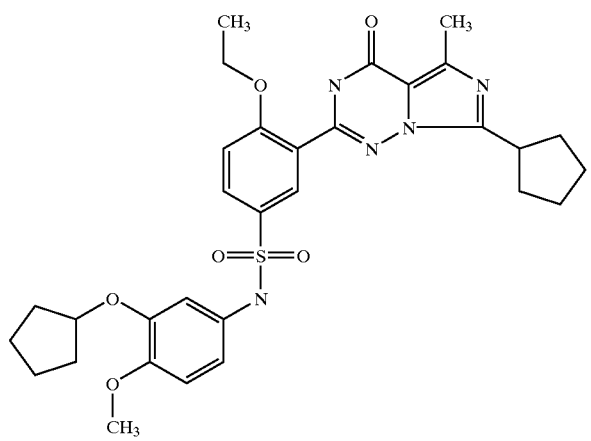 | 607.7 | 75 |

TABLE 1-continued
| 163 | | 561.6 | 80 |
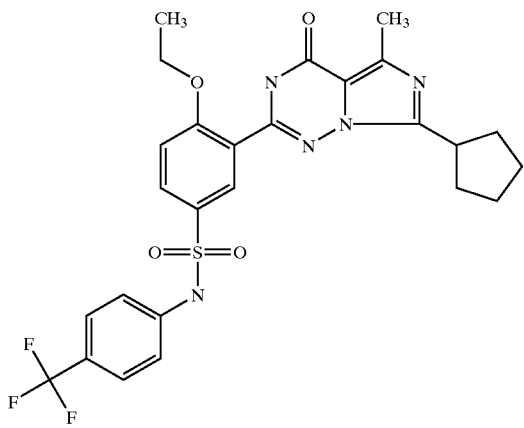
| 164 | | 523.6 | 83 |
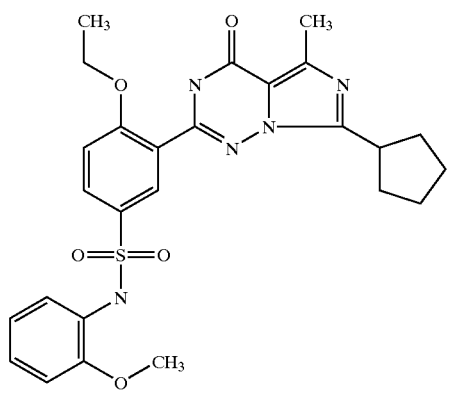
| 159 | | 531.6 | 88 |
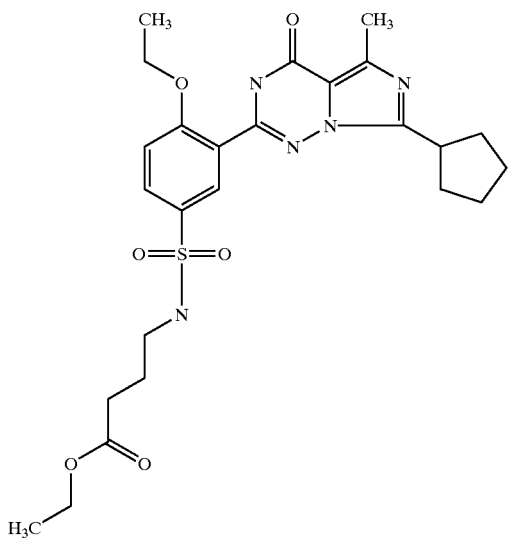

TABLE 1-continued
| | | |
|---|---|---|
| 160 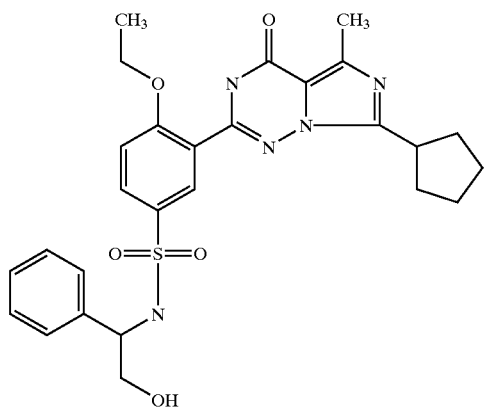 | 537.6 | 80 |
| 161 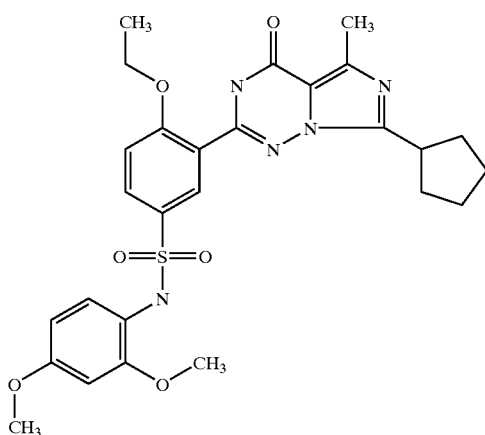 | 553.6 | 78 |
| 168 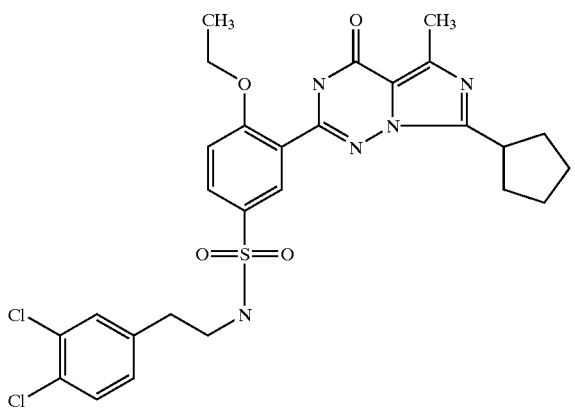 | 590.5 | 82 |

TABLE 1-continued
| | | | |
|---|---|---|---|
| 169 | 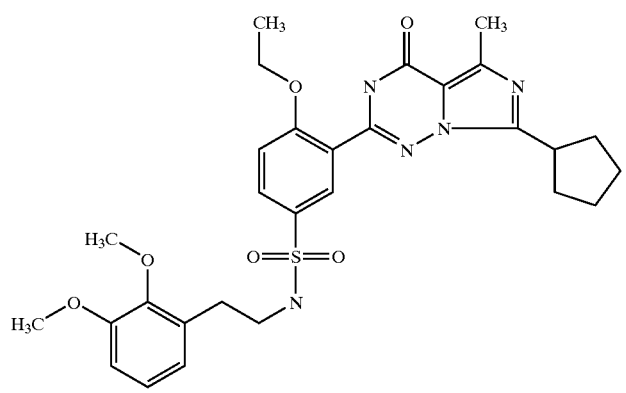 | 581.7 | 81 |
| 170 | 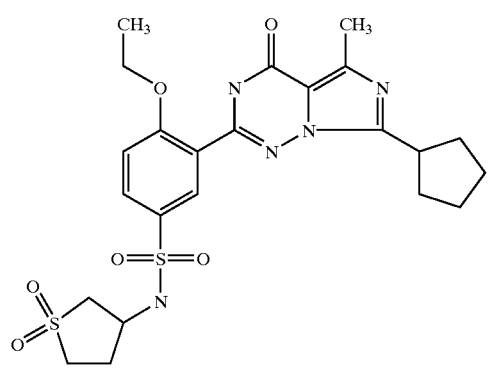 | 535.6 | 79 |
| 165 | 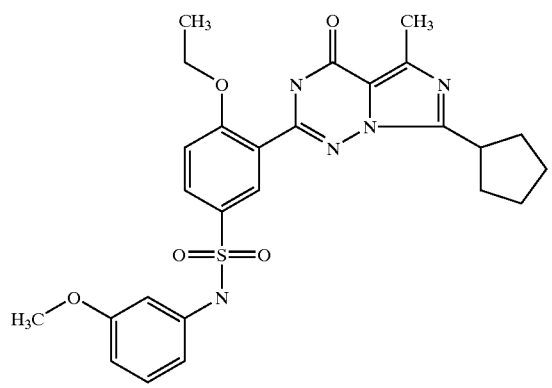 | 523.6 | 84 |
| 166 | 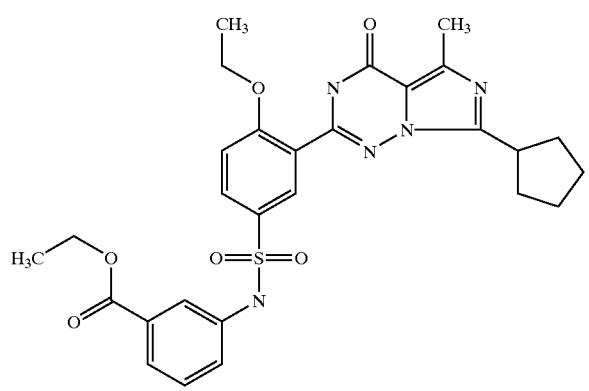 | 565.7 | 81 |

TABLE 1-continued
| | | | |
|---|---|---|---|
| 167 | | 562.5 | 63 |
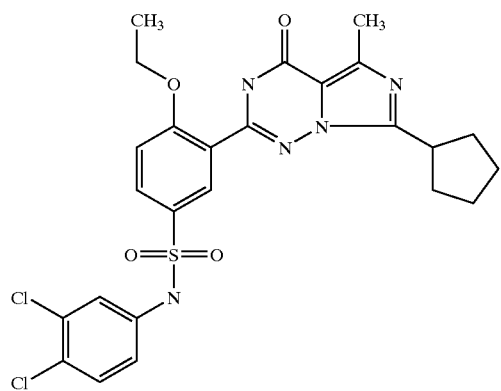
| | | | |
|---|---|---|---|
| 174 | | 623.8 | 79 |
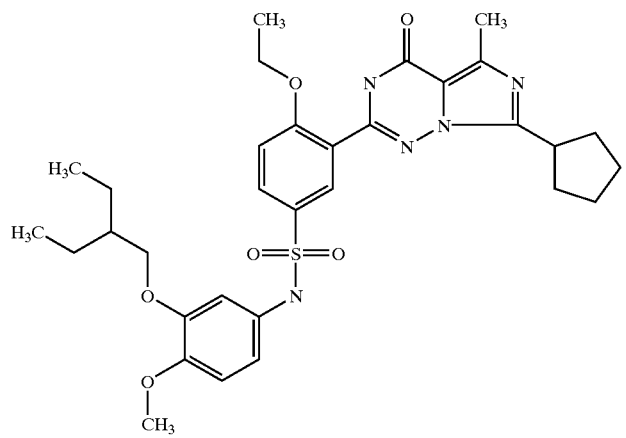
| | | | |
|---|---|---|---|
| 175 | | 597.7 | 59 |
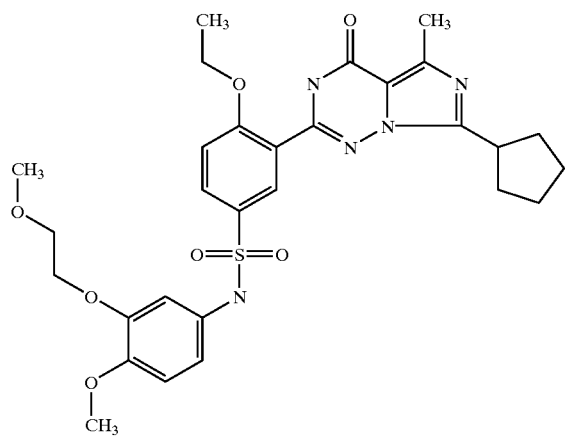

TABLE 1-continued
| 176 | | 653.8 | 41 |
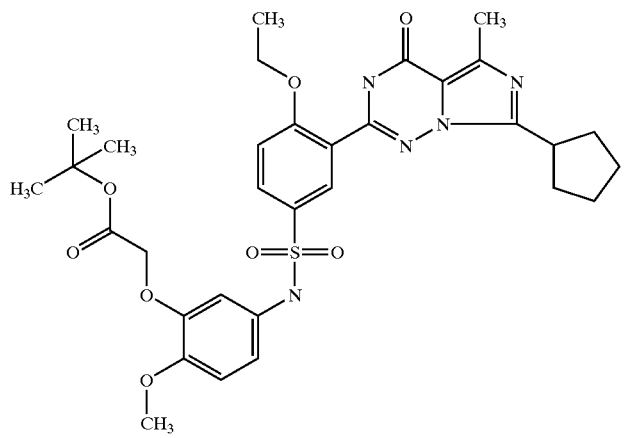
| 171 | | 567.7 | 55 |
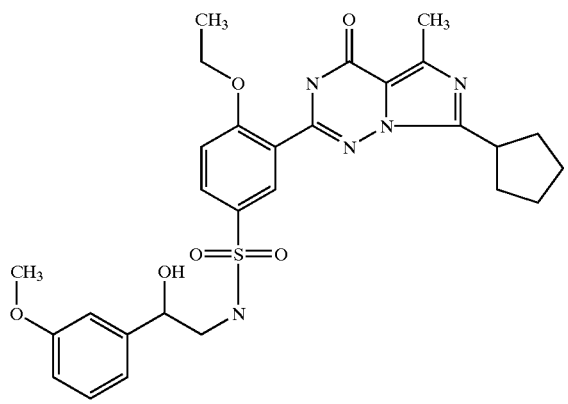
| 172 | | 605.6 | 81 |
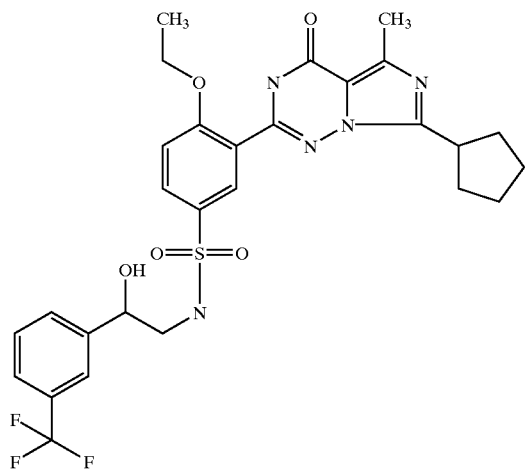

TABLE 1-continued
| | | |
|---|---|---|
| 173 | 595.7 | 79 |
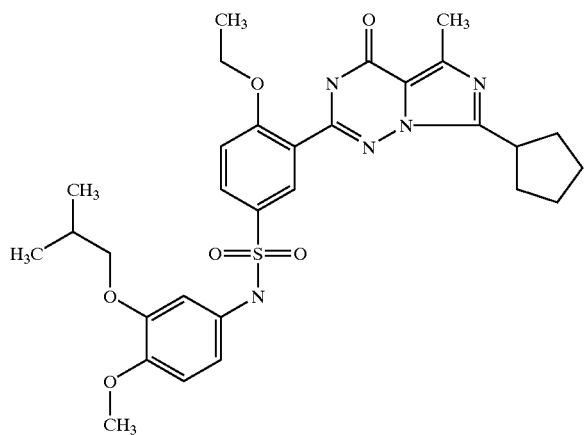
| | | |
|---|---|---|
| 180 | 529.6 | 86 |
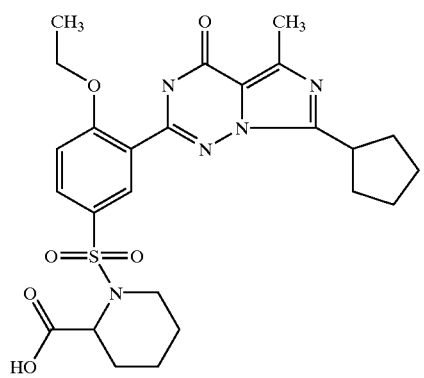
| | | |
|---|---|---|
| 181 | 560.7 | 82 |
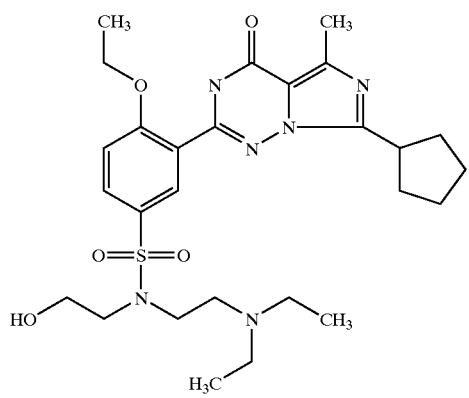

TABLE 1-continued
| | | | |
|---|---|---|---|
| 182 | 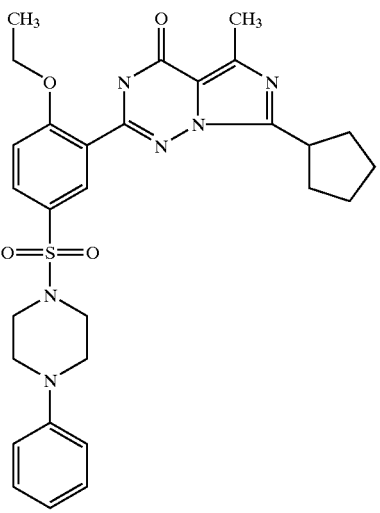 | 562.7 | 81 |
| 177 | 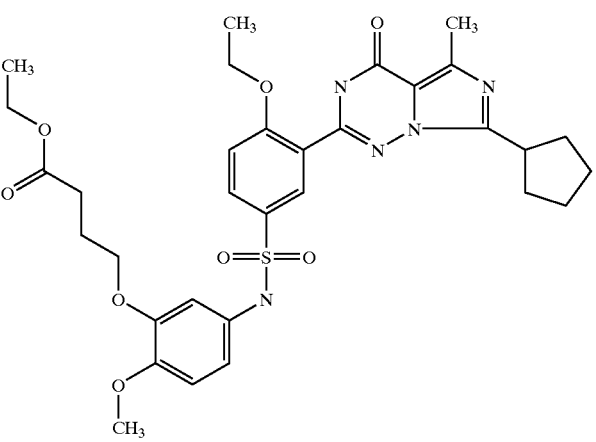 | 653.8 | 82 |
| 178 | 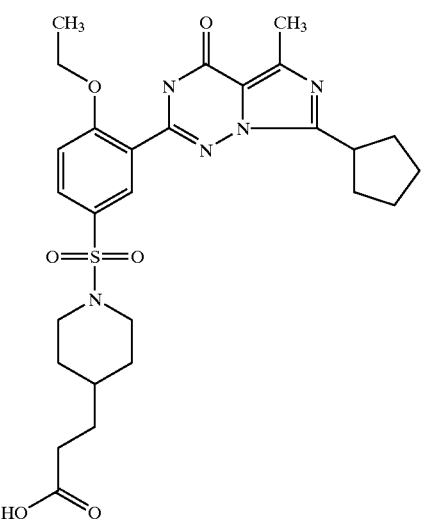 | 557.7 | 83 |

TABLE 1-continued
| | | | |
|---|---|---|---|
| 179 | 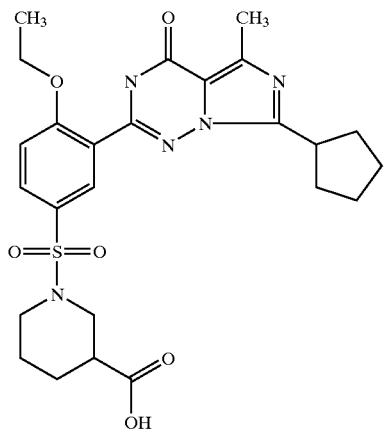 | 529.6 | 83 |
| 185 | 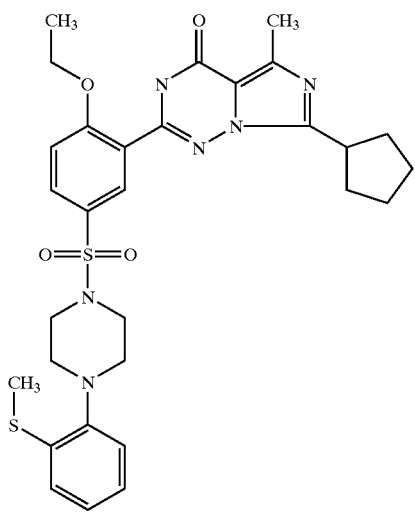 | 608.8 | 80 |
| 186 | 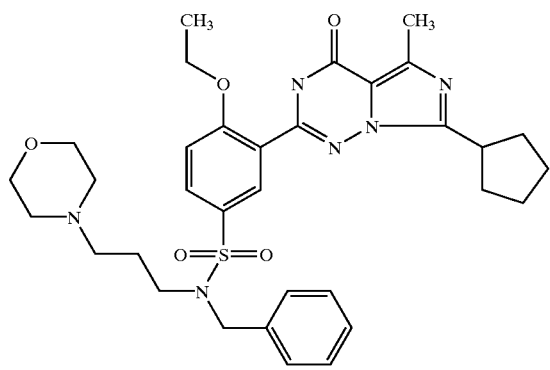 | 634.8 | 77 |

TABLE 1-continued
| | | | |
|---|---|---|---|
| 187 | 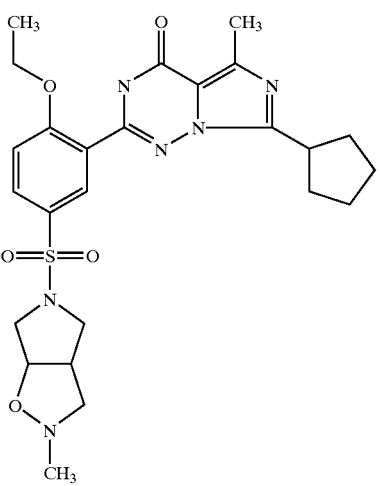 | 528.6 | 71 |
| 183 | 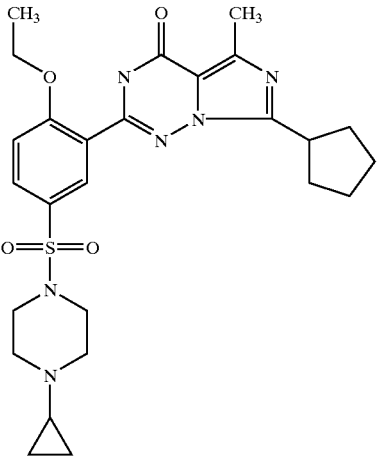 | 526.7 | 60 |
| 184 | 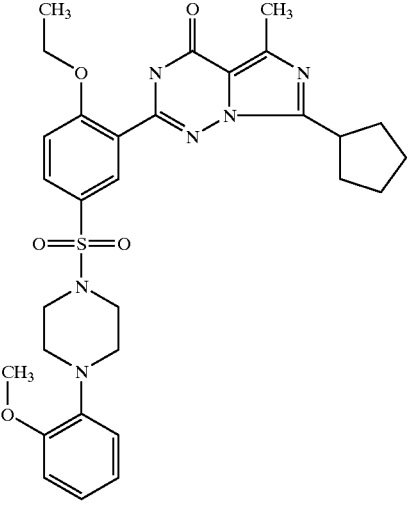 | 592.7 | 80 |

TABLE 1-continued
| | | | |
|---|---|---|---|
| 188 | 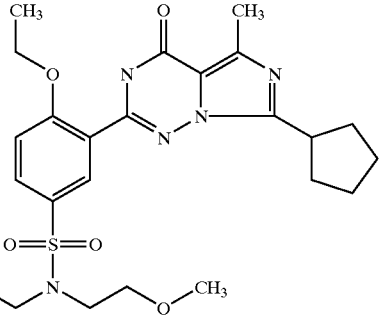 | 533.7 | 87 |
| 189 | 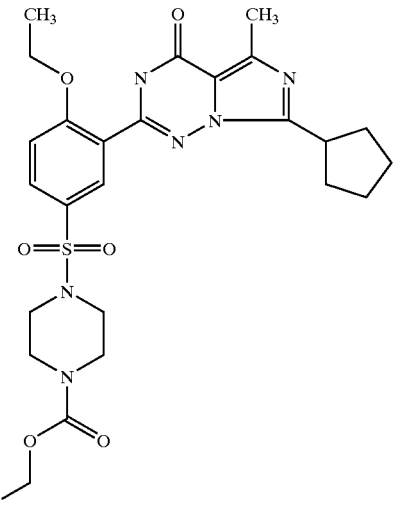 | 558.7 | 88 |
| 190 | 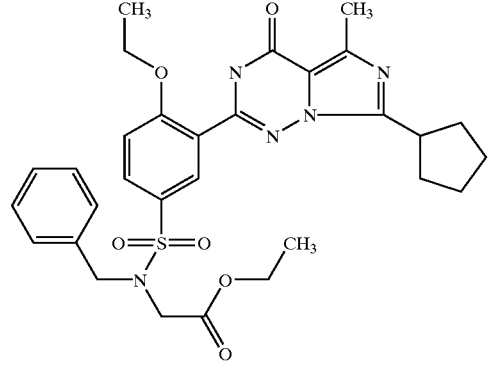 | 593.7 | 73 |
| 191 | 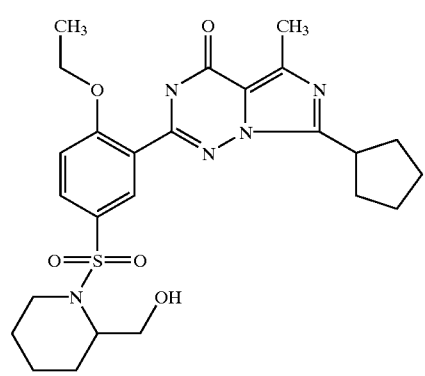 | 515.6 | 80 |

TABLE 1-continued
| 192 | 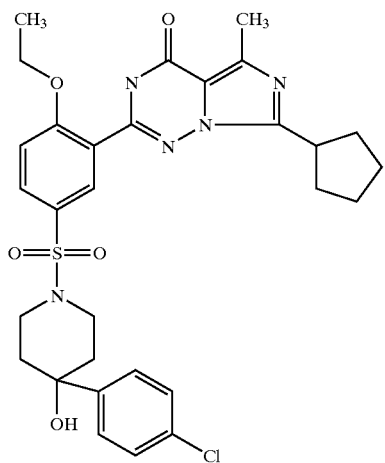 | 612.2 | 81 |
| 193 | 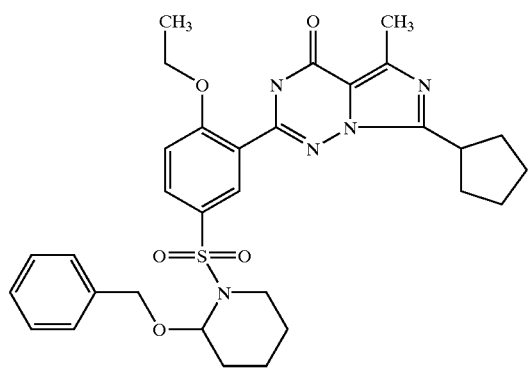 | 591.7 | 83 |
| 194 | 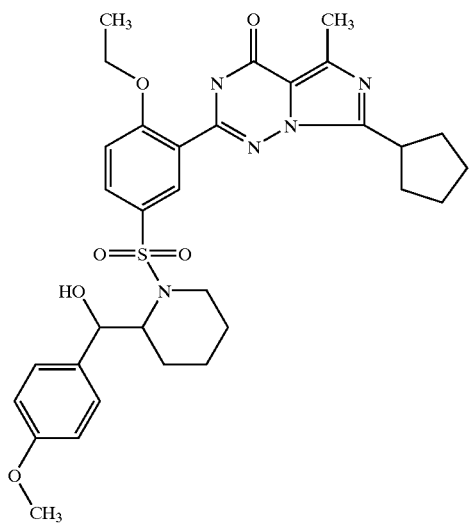 | 621.8 | 79 |

TABLE 1-continued
| # | Structure | MS | Yield |
|---|---|---|---|
| 195 | 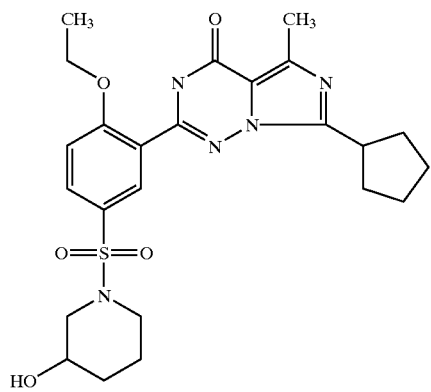 | 501.6 | 78 |
| 196 | 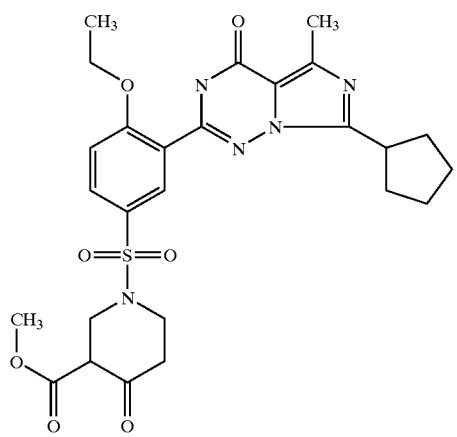 | 557.6 | 57 |
| 197 | 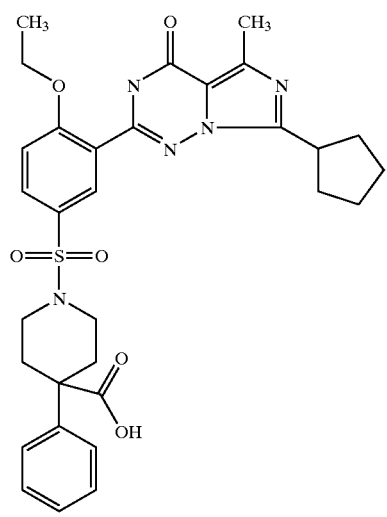 | 605.7 | 80 |

TABLE 1-continued
| | | | |
|---|---|---|---|
| 198 | 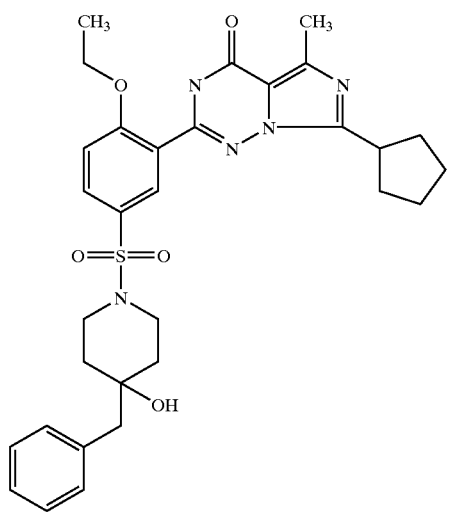 | 591.7 | 80 |
| 199 | 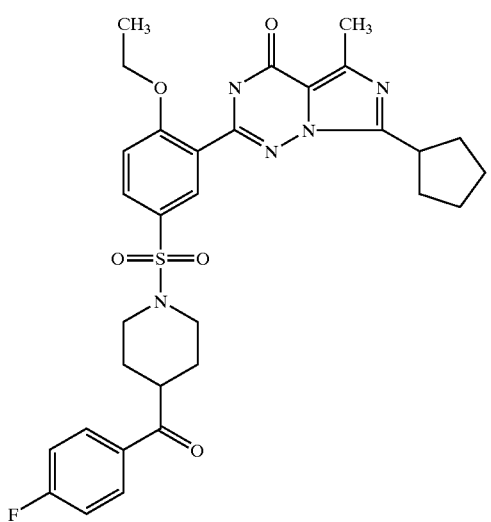 | 607.7 | 78 |
| 200 | 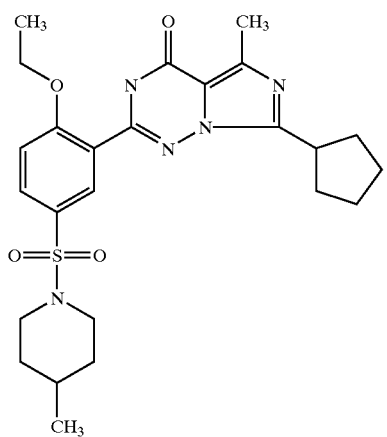 | 499.6 | 83 |

| | | |
|---|---|---|
| 201 | 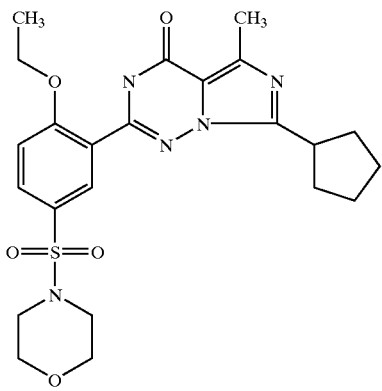 | 487.6    82 |
| 202 | 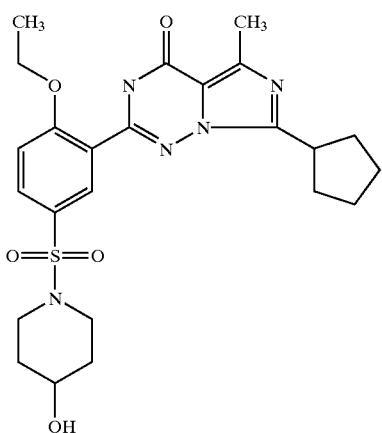 | 501.6    66 |
| 203 | 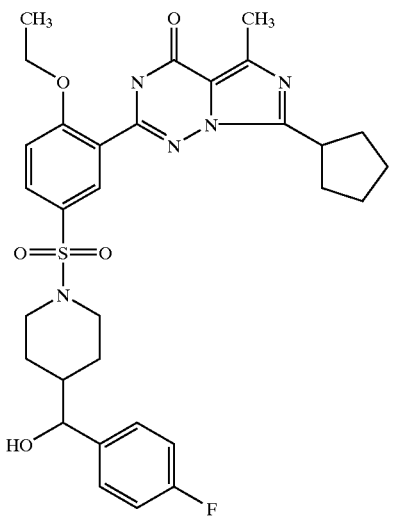 | 609.7    79 |

TABLE 1-continued
| | | | |
|---|---|---|---|
| 204 | 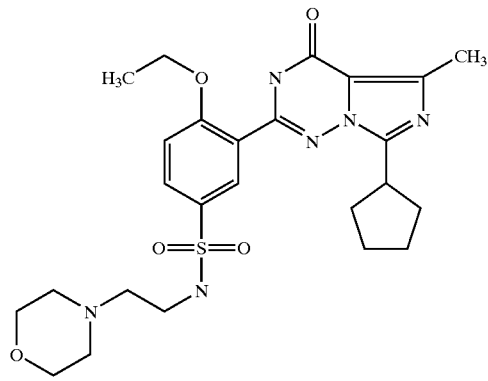 | 530.7 | 82 |
| 205 | 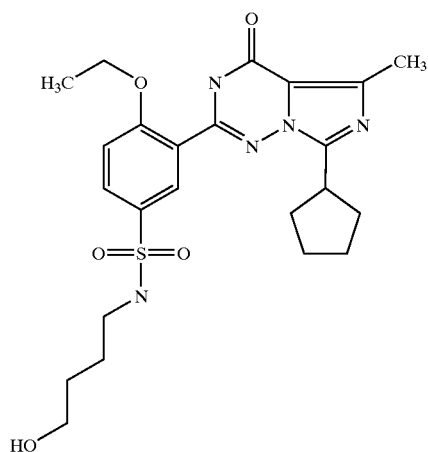 | 489.6 | 80 |
| 206 | 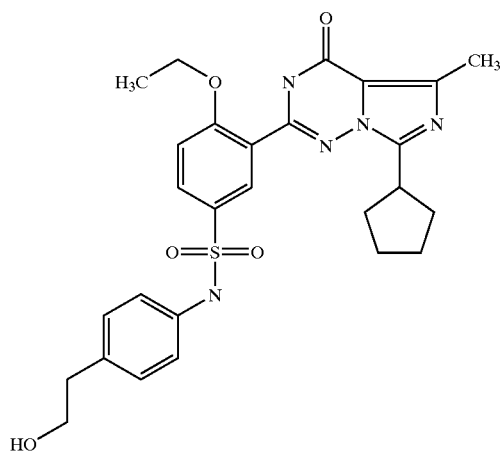 | 537.6 | 63 |

TABLE 1-continued
| 207 | 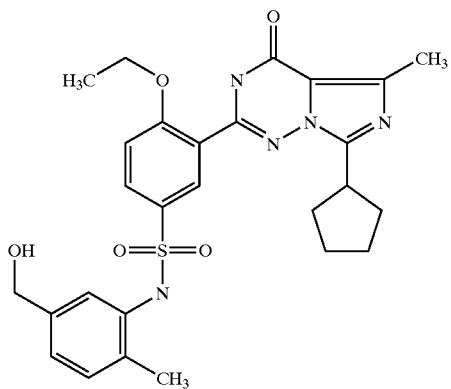 | 537.6 | 75 |
| 208 | 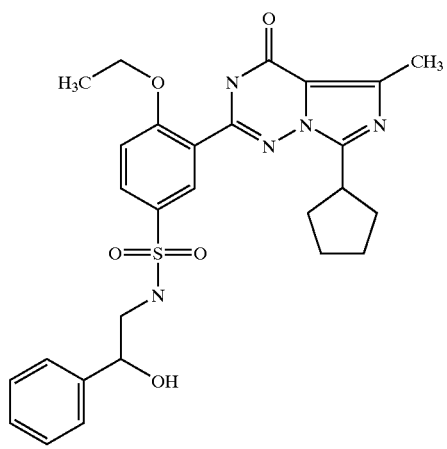 | 537.6 | 72 |
| 209 | 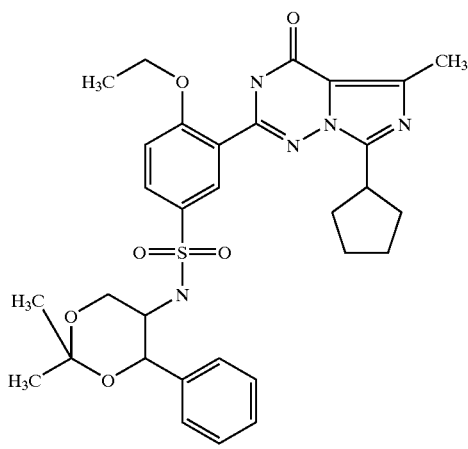 | 607.7 | 50 |

TABLE 1-continued
| | | | |
|---|---|---|---|
| 210 | 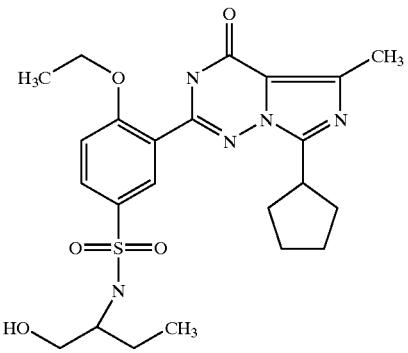 | 489.6 | 64 |
| 211 | 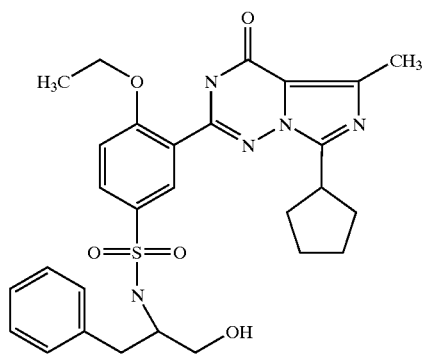 | 551.7 | 77 |
| 212 | 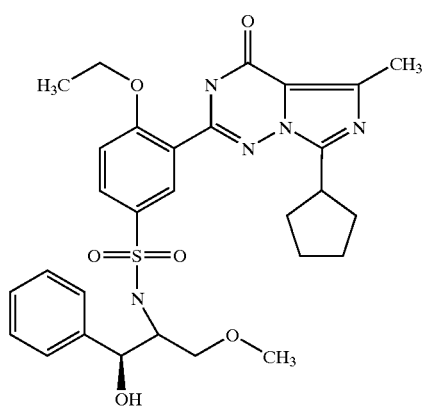 | 581.7 | 85 |
| 213 | 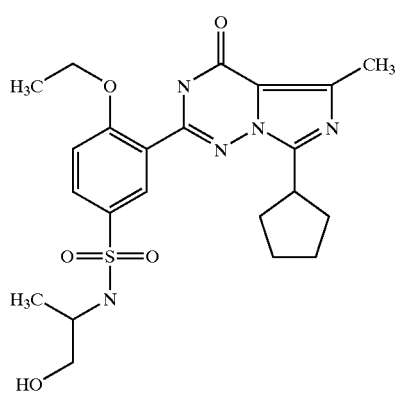 | 475.6 | 45 |

TABLE 1-continued
| | | | |
|---|---|---|---|
| 214 | 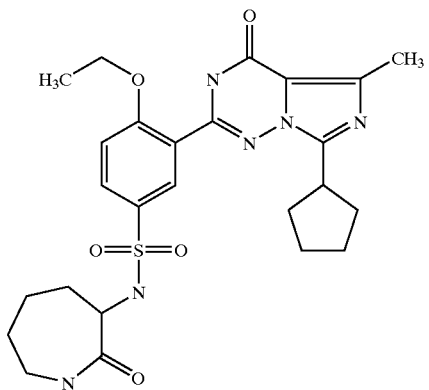 | 528.6 | 87 |
| 215 | 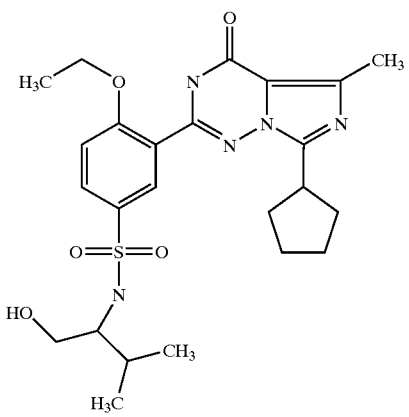 | 503.6 | 74 |
| 216 | 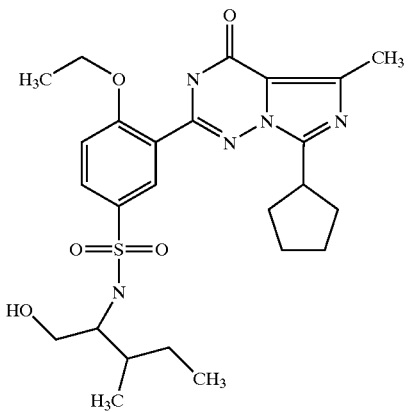 | 517.7 | 76 |
| 217 | 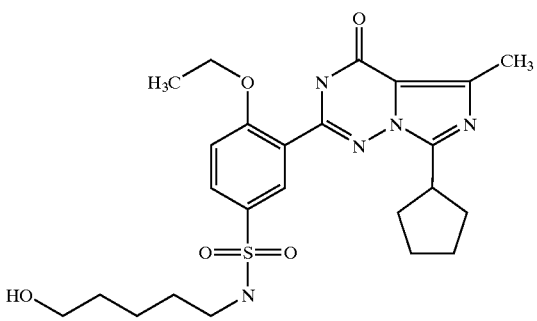 | 503.6 | 84 |

TABLE 1-continued
| | | | |
|---|---|---|---|
| 218 | 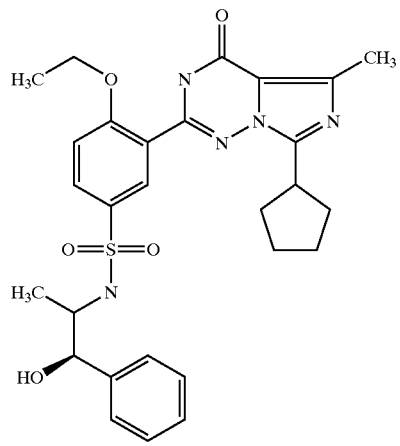 | 551.7 | 74 |
| 219 | 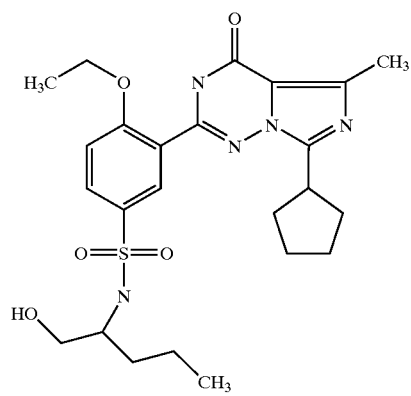 | 503.6 | 70 |
| 220 | 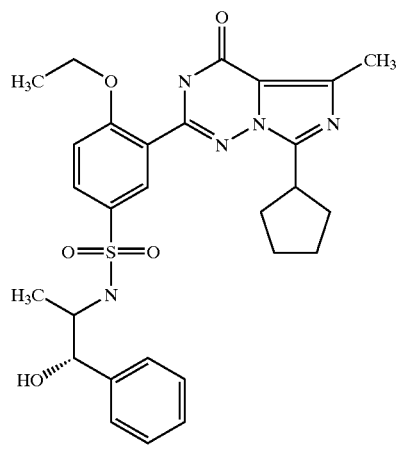 | 551.7 | 73 |

TABLE 1-continued
| | | | |
|---|---|---|---|
| 221 | | 489.6 | 57 |
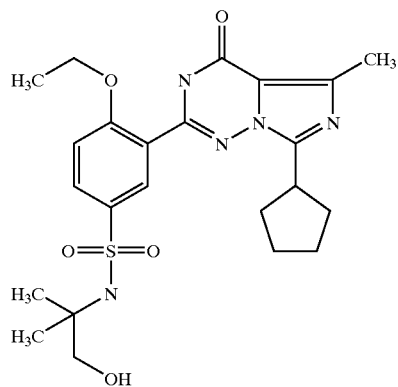
| | | | |
|---|---|---|---|
| 222 | | 475.6 | 77 |
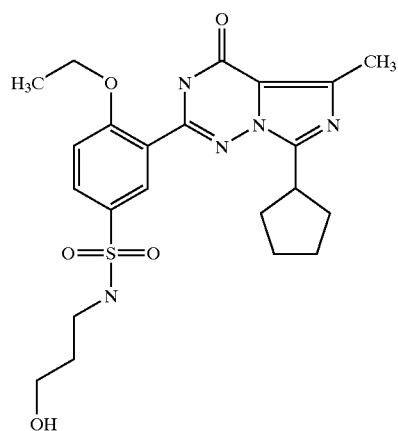
| | | | |
|---|---|---|---|
| 223 | | 593.8 | 68 |
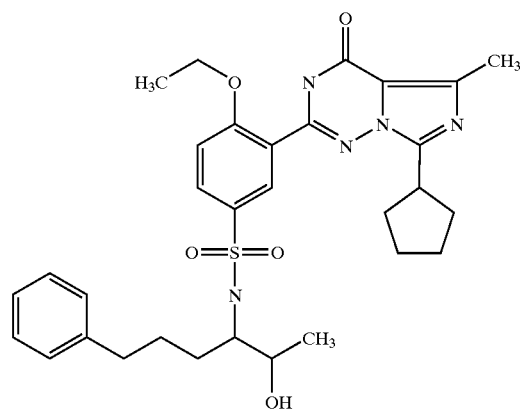

TABLE 1-continued
| | | |
|---|---|---|
| 224 | 551.7 | 77 |
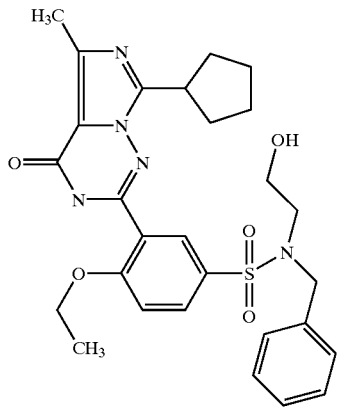
| | | |
|---|---|---|
| 225 | 615.8 | 78 |
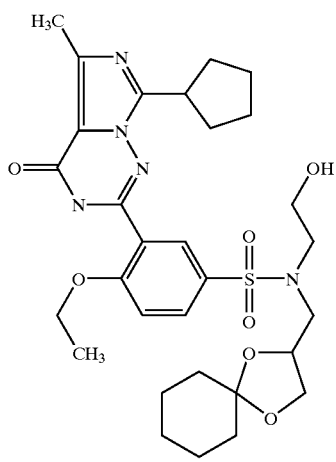
| | | |
|---|---|---|
| 226 | 503.6 | 52 |
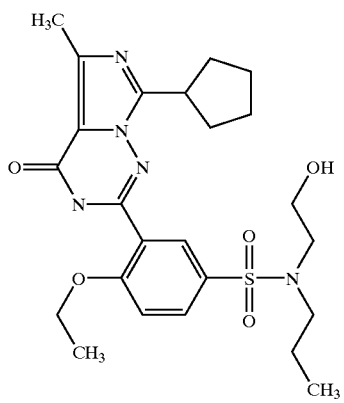

TABLE 1-continued
| | | | |
|---|---|---|---|
| 227 | 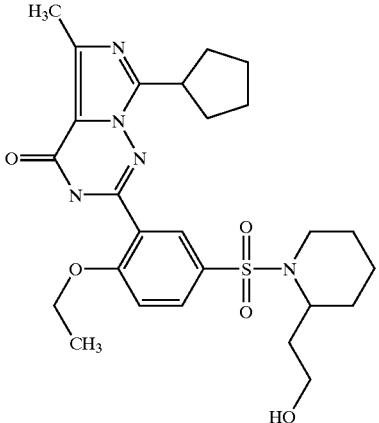 | 529.7 | 59 |
| 228 | 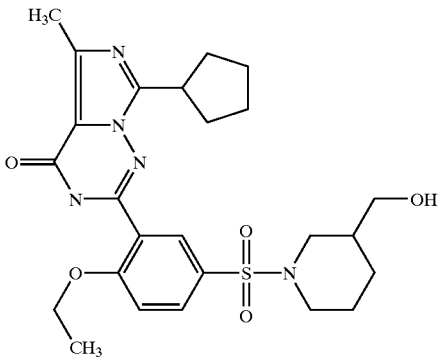 | 515.6 | 50 |
| 229 | 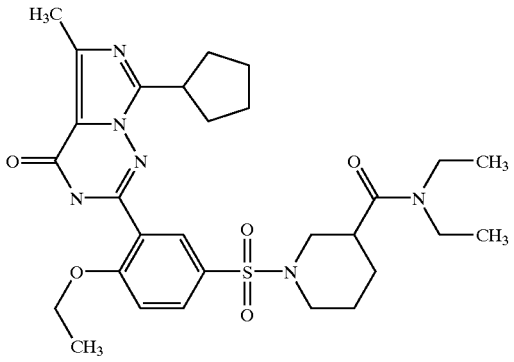 | 584.7 | 42 |
| 230 | 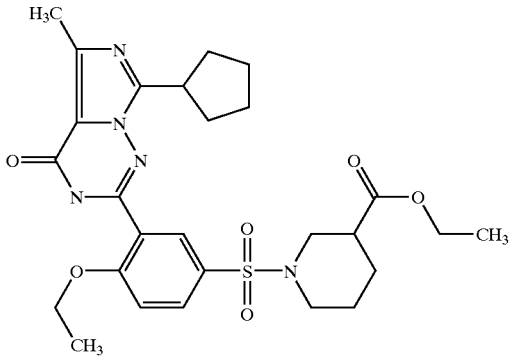 | 557.7 | 82 |

TABLE 1-continued
| 231 | 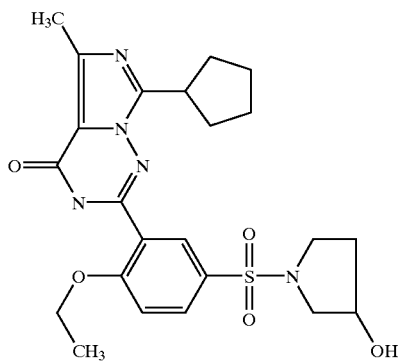 | −487.6 | 49 |
| --- | --- | --- | --- |
| 232 | 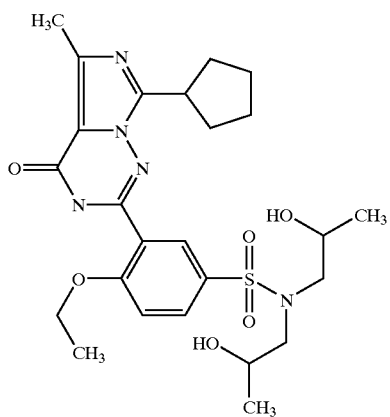 | 533.7 | 80 |
| 233 | 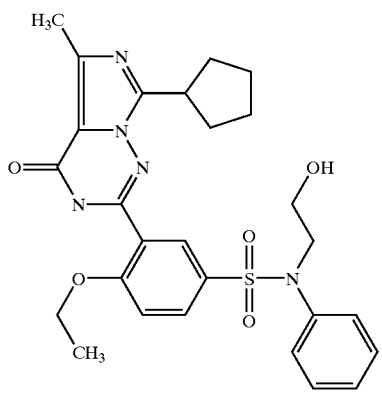 | 537.6 | 81 |

| | | |
|---|---|---|
| 234 | 565.7 | 82 |
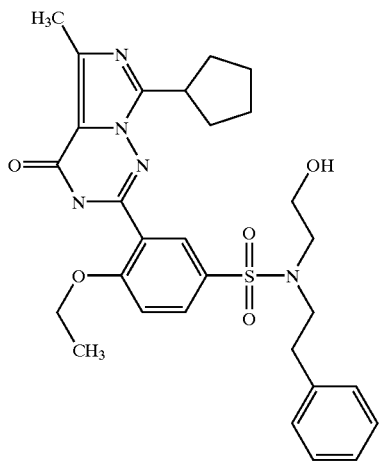
| | | |
|---|---|---|
| 235 | 565.7 | 56 |
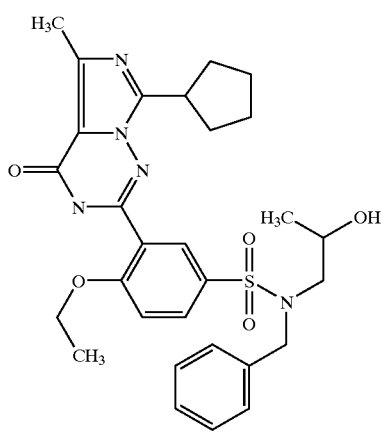
| | | |
|---|---|---|
| 236 | 669.8 | 82 |
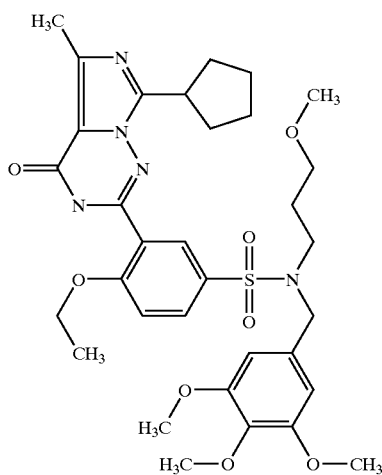

TABLE 1-continued
| | | MW [g/mol] | HPLC | Mz + H |
|---|---|---|---|---|
| 237 | 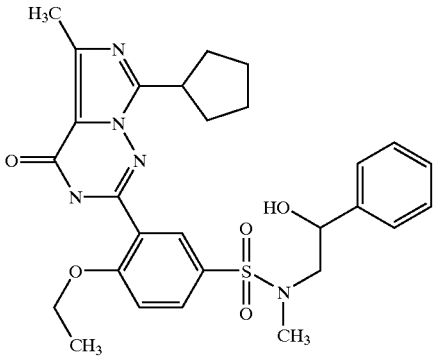 | 551.7 | 77 | |
| 238 | 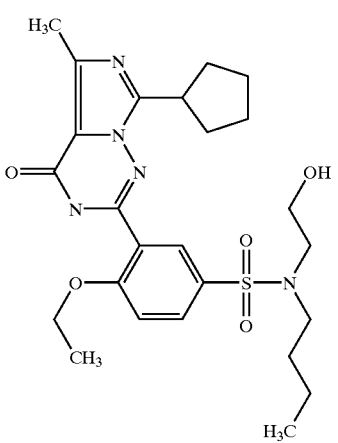 | 517.7 | 91 | |
*The yields are based on the molecular peaks determined by mass spectroscopy.
| Ex. No. | Structure | MW [g/mol] | HPLC | Mz + H |
|---|---|---|---|---|
| 239 | 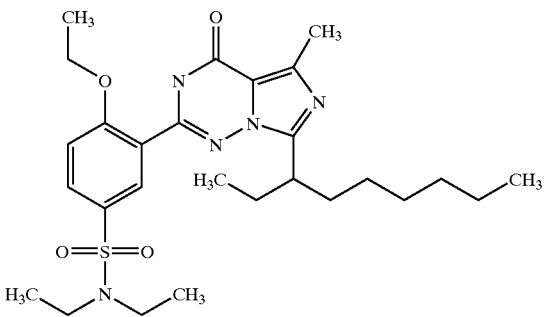 | 531.723 | 77 | 532 |
| 240 | 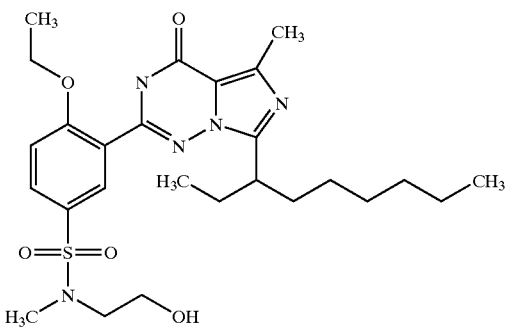 | 533.695 | 71 | 534 |

| | | | |
|---|---|---|---|
| 241 | 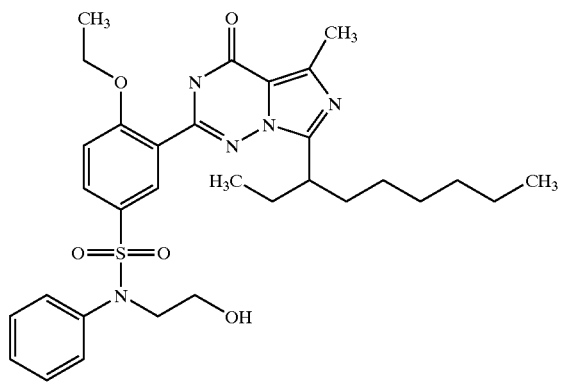 | 595.767 | 65 | 596 |
| 242 | 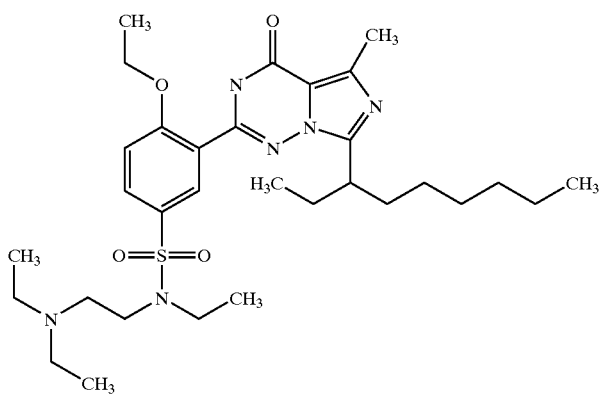 | 602.846 | 53 | 603 |
| 243 | 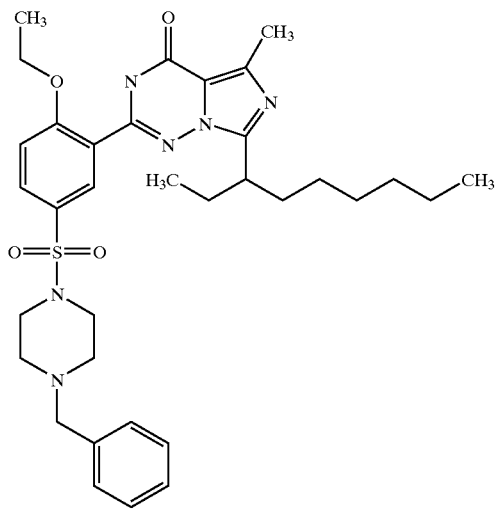 | 634.848 | 64 | 635 |

TABLE 1-continued
| | | | | |
|---|---|---|---|---|
| 244 | 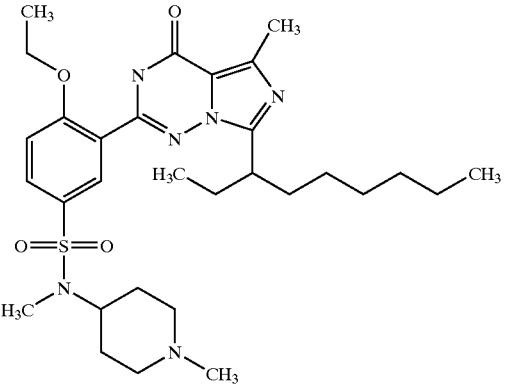 | 586.803 | 51 | 587 |
| 245 | 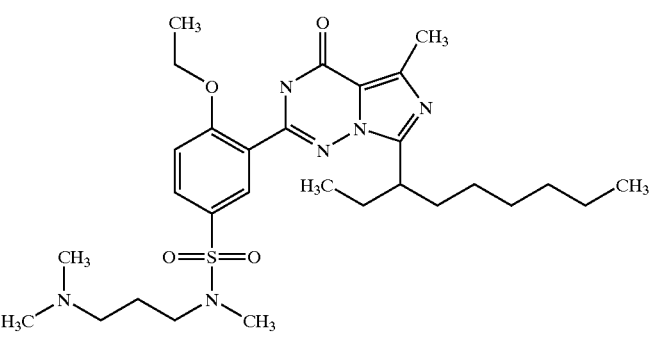 | 574.792 | 61 | 575 |
| 246 | 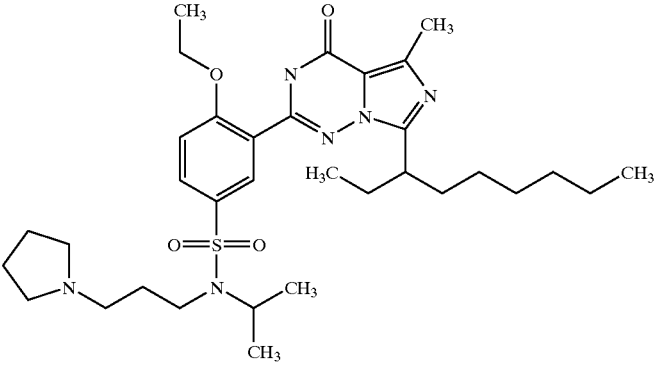 | 628.884 | 41 | 629 |
| 247 | 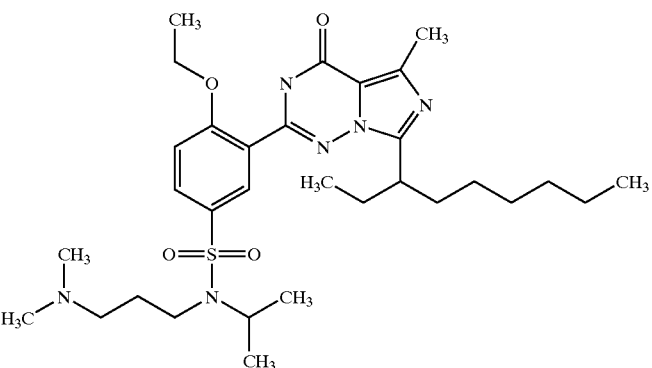 | 602.846 | 42 | 603 |

TABLE 1-continued
| | | | |
|---|---|---|---|
| 248 | 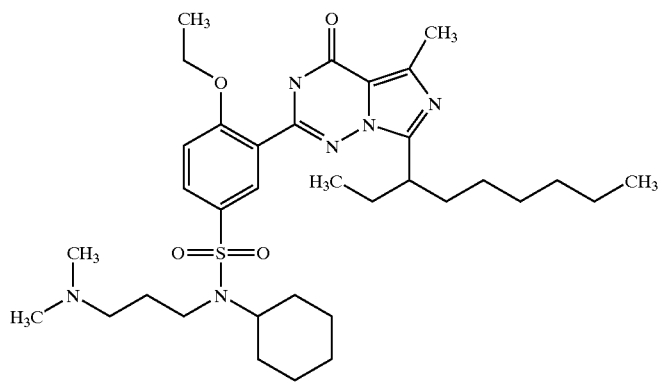 | 642.911 | 44 | 643 |
| 249 | 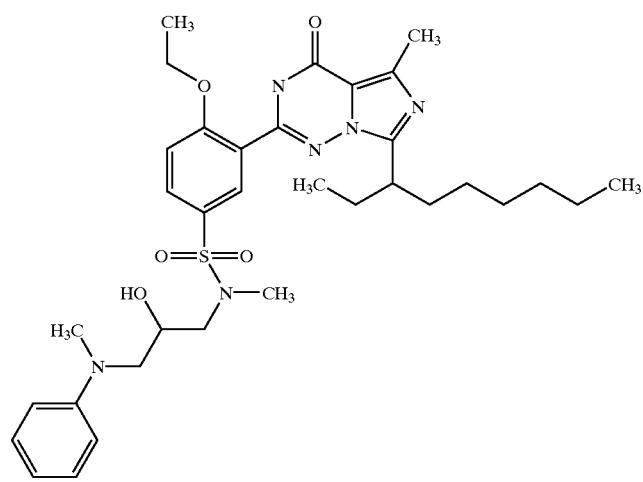 | 652.863 | 66 | 653 |
| 250 | 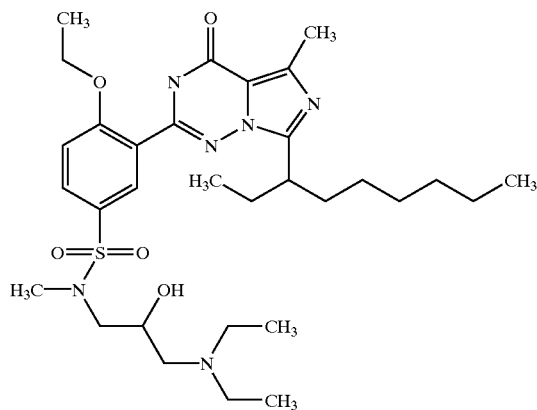 | 618.845 | 48 | 619 |

| | | | |
|---|---|---|---|
| 251 | 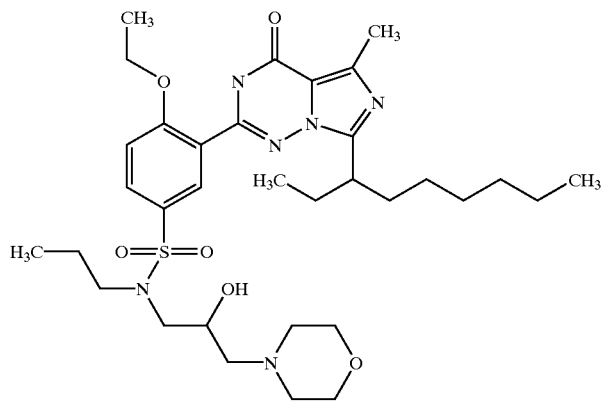 | 660.883 | 71 | 661 |
| 252 | 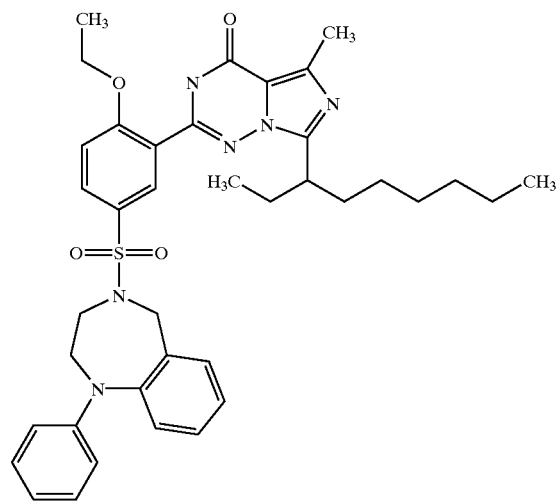 | 682.892 | 50 | 683 |
| 253 | 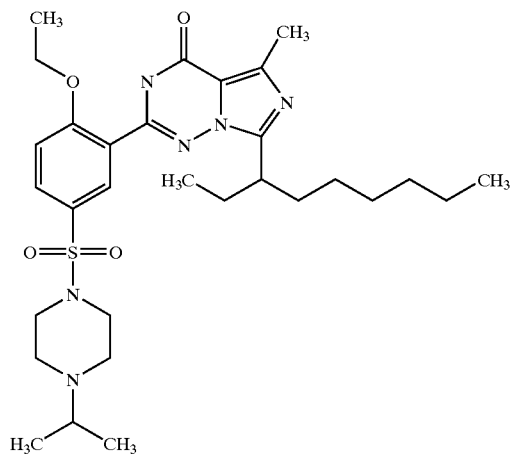 | 600.83 | 60 | 601 |

TABLE 1-continued
| | | | | |
|---|---|---|---|---|
| 254 | 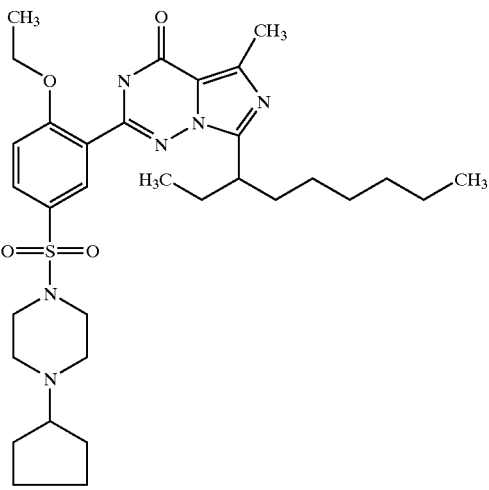 | 612.841 | 68 | 613 |
| 255 | 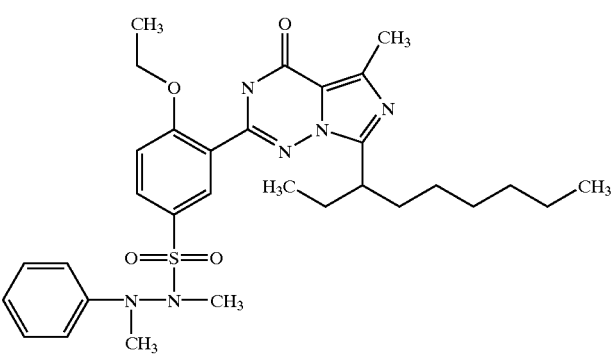 | 622.836 | 66 | 623 |
| 256 | 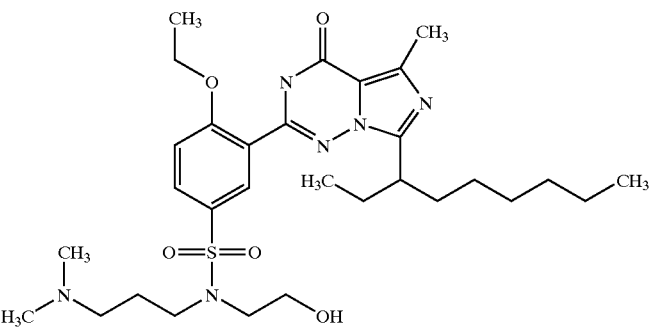 | 604.818 | 58 | 605 |
| 257 | 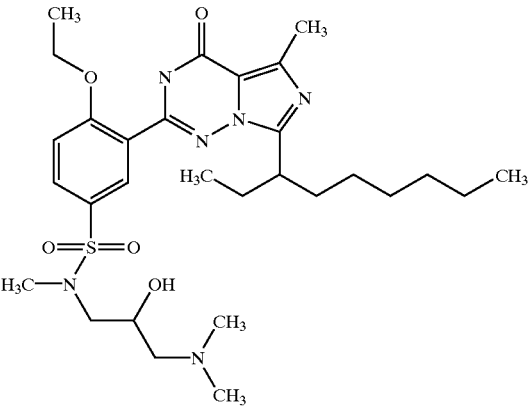 | 590.791 | 56 | 591 |

TABLE 1-continued
| 258 | 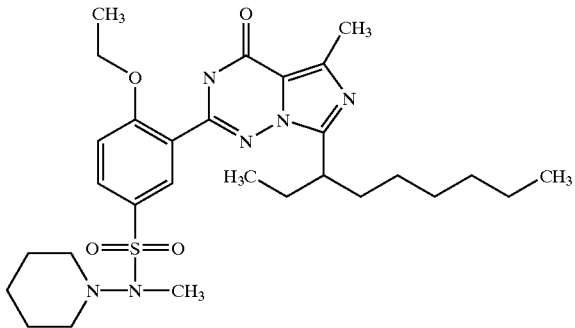 | 600.83 | 59 | 601 |
| 259 | 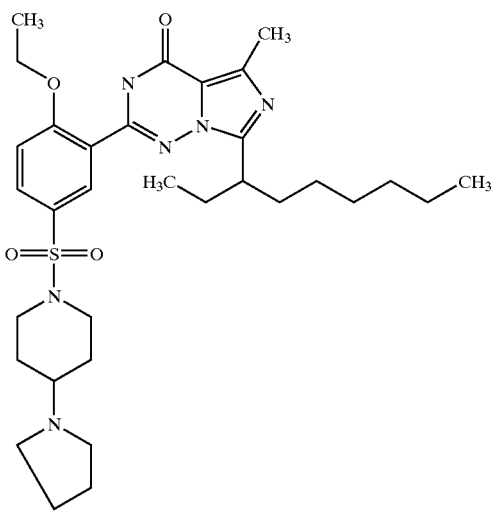 | 612.841 | 54 | 613 |
| 260 | 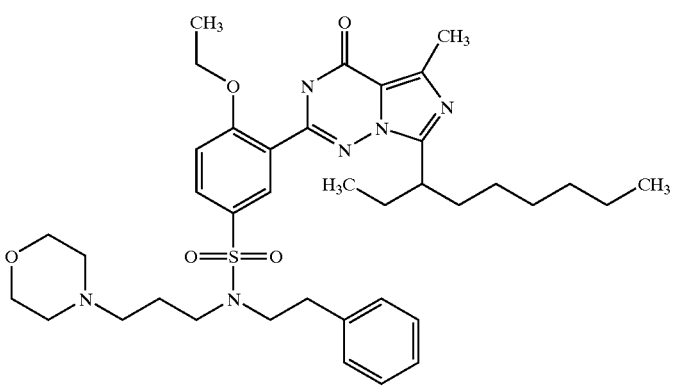 | 706.955 | 72 | 707 |
| 261 | 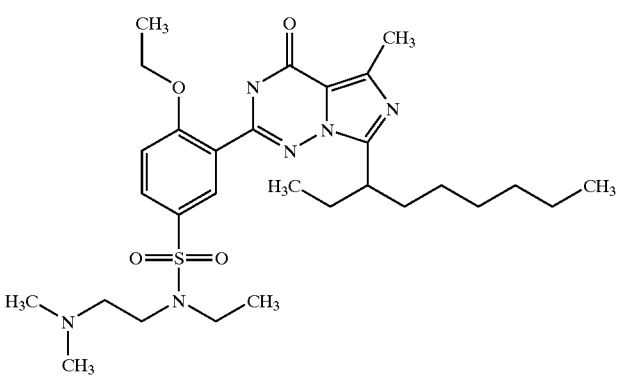 | 574.792 | 56 | 575 |

TABLE 1-continued

| | | | | |
|---|---|---|---|---|
| 262 | [structure] | 621.808 | 57 | 622 |
| 263 | [structure] | 588.819 | 52 | 589 |
| 264 | [structure] | 547.722 | 79 | 548 |
| 265 | [structure] | 561.749 | 30 | 562 |

TABLE 1-continued

| | | | | |
|---|---|---|---|---|
| 266 | [structure] | 620.82 | 68 | 621 |
| 267 | [structure] | 626.868 | 56 | 627 |
| 268 | [structure] | 584.787 | 56 | 585 |

TABLE 1-continued
| 269 | 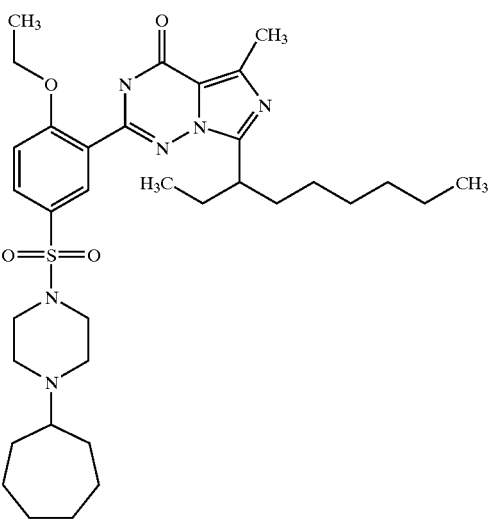 | 640.895 | 69 | 641 |
| 270 | 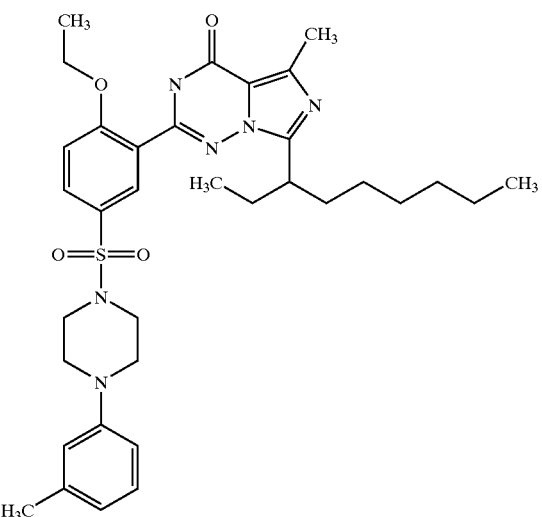 | 634.848 | 72 | 635 |
| 271 | 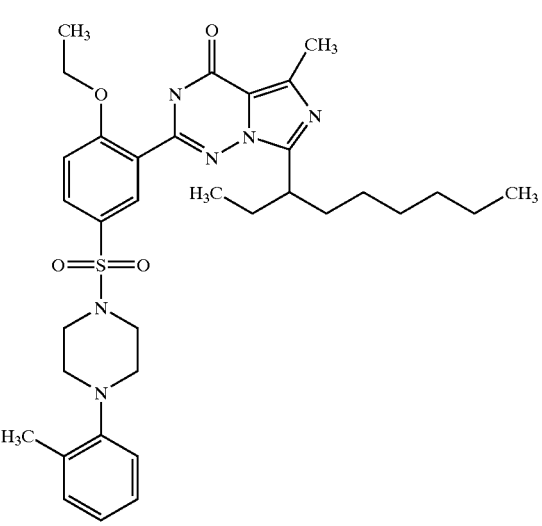 | 634.848 | 54 | 635 |

TABLE 1-continued

| 272 | [structure] | 656.801 | 64 | 657 |
| 273 | [structure] | 638.811 | 65 | 639 |
| 274 | [structure] | 650.847 | 44 | 651 |

| | | | |
|---|---|---|---|
| 275 | 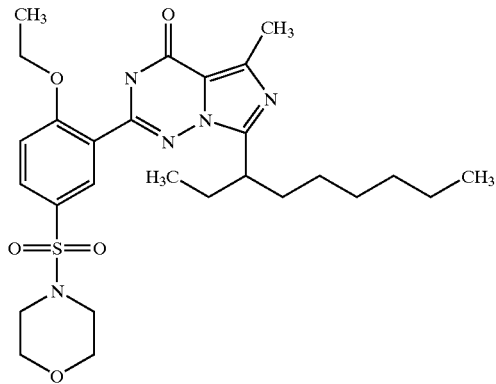 | 545.706 60 | 546 |
| 276 | 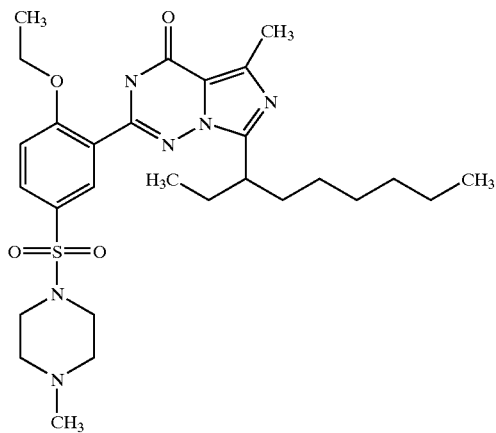 | 558.749 50 | 559 |
| 277 | 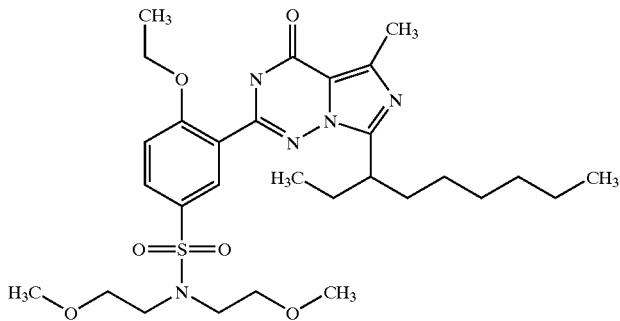 | 591.776 70 | 592 |

TABLE 1-continued
| 278 | 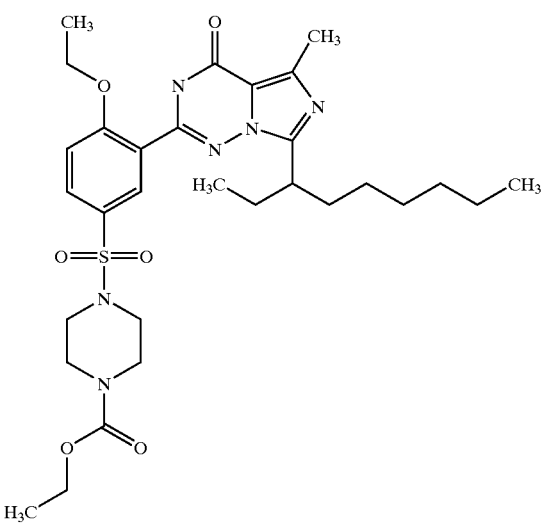 | 616.786 | 53 | 617 |
| 279 | 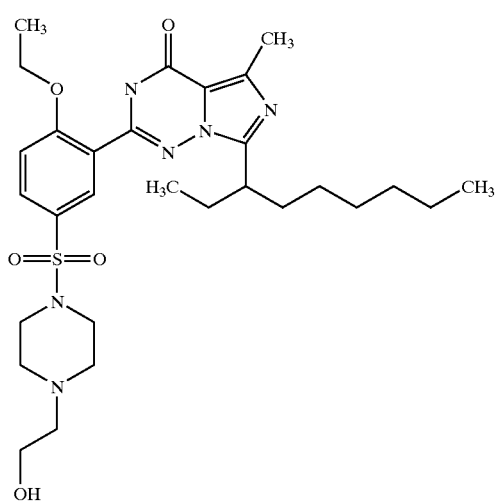 | 588.775 | 49 | 589 |
| 280 | 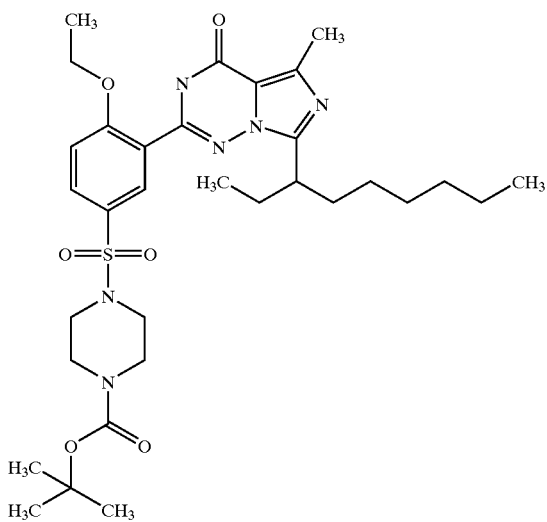 | 644.84 | 51 | 645 |

TABLE 1-continued
| 281 | 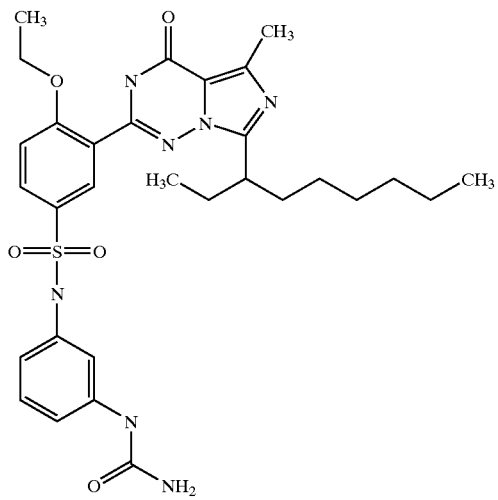 | 609.75323 | 55 | 610 |
| 282 | 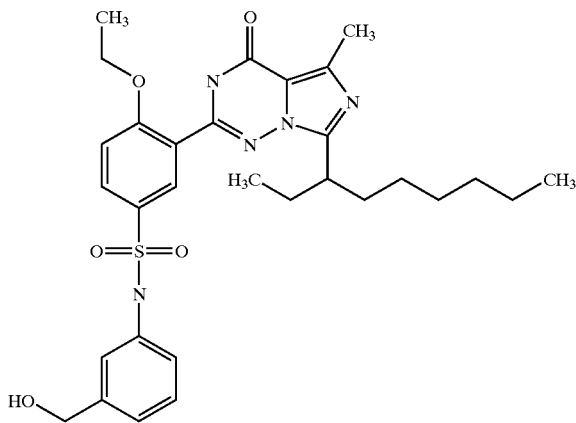 | 581.73983 | 66 | 582 |
| 283 | 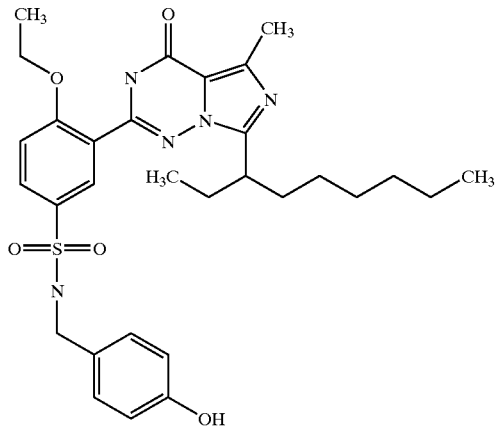 | 581.73983 | 63 | 582 |

TABLE 1-continued

| | | | |
|---|---|---|---|
| 284 [structure] | 595.76692 | 68 | 596 |
| 285 [structure] | 595.76692 | 68 | 596 |
| 286 [structure] | 593.79461 | 70 | 594 |

TABLE 1-continued
| 287 | 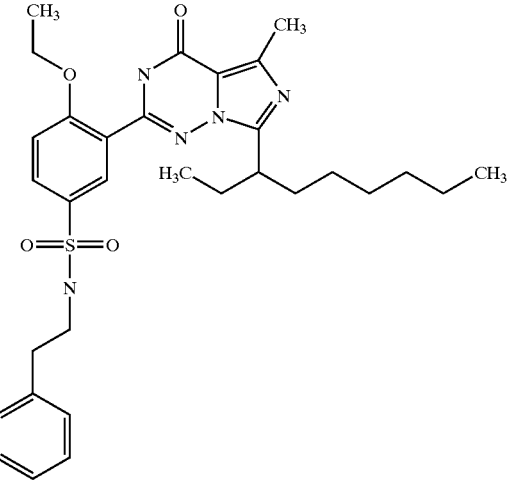 | 609.79401 | 68 | 610 |
| 288 | 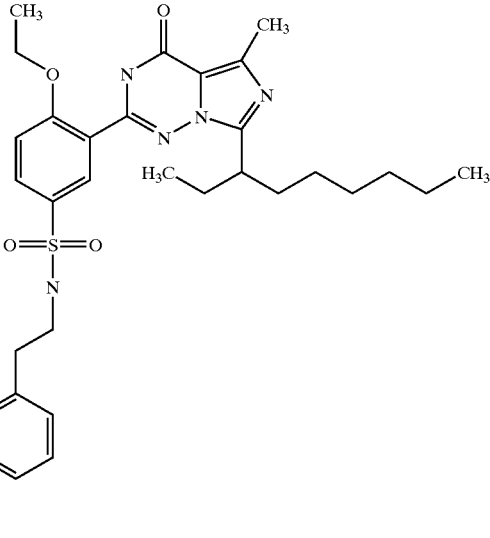 | 639.8205 | 63 | 640 |
| 289 | 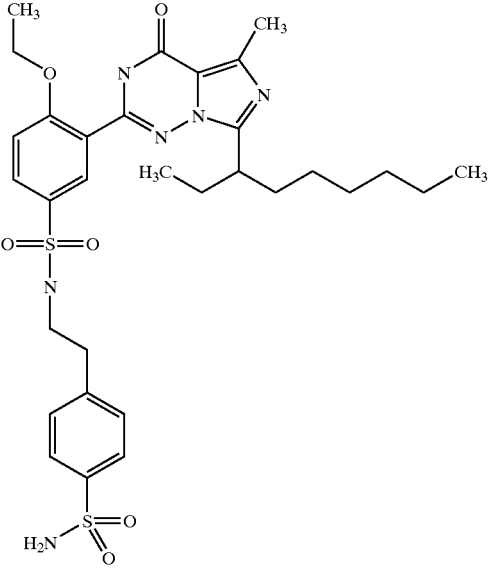 | 658.84499 | 61 | 659 |

TABLE 1-continued
| 290 | 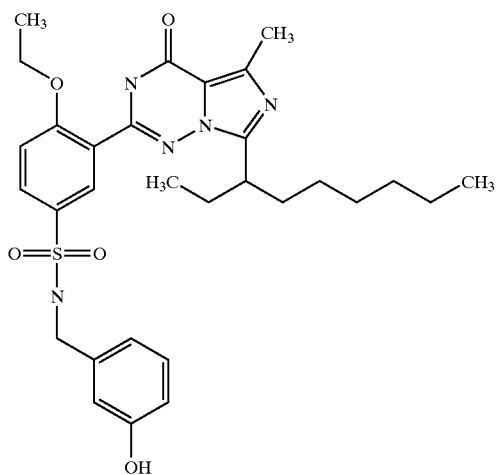 | 581.73983 | 59 | 582 |
| 291 | 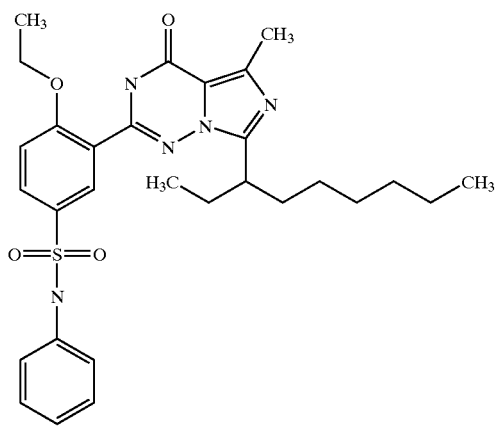 | 551.71334 | 71 | 552 |
| 292 | 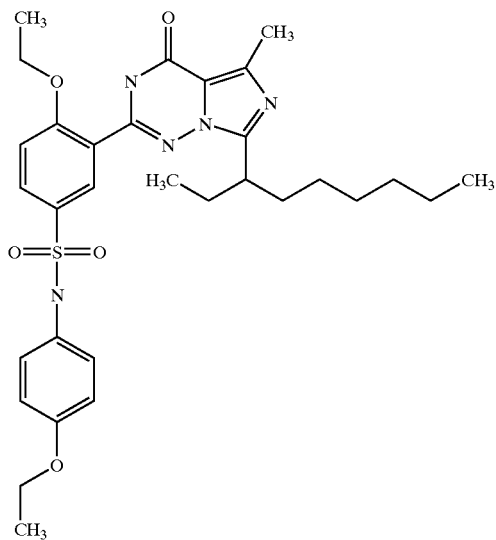 | 595.76692 | 69 | 596 |

TABLE 1-continued

| # | Structure | Mass | % | MW |
|---|---|---|---|---|
| 293 | (structure) | 609.79401 | 65 | 610 |
| 294 | (structure) | 595.76692 | 56 | 596 |
| 295 | (structure) | 665.85874 | 53 | 666 |

| | | | |
|---|---|---|---|
| 296 | 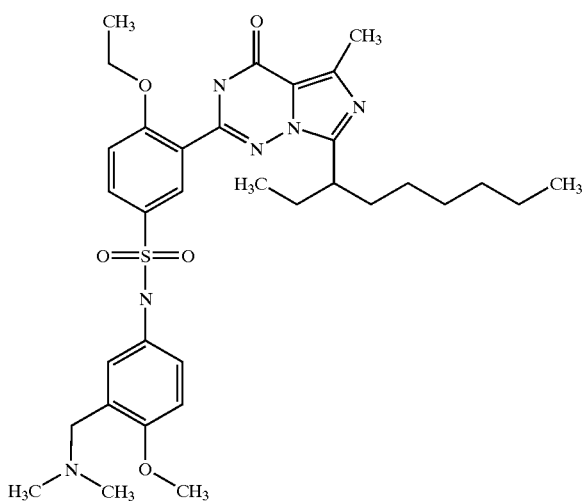 | 638.83577 | 64 | 639 |
| 297 | 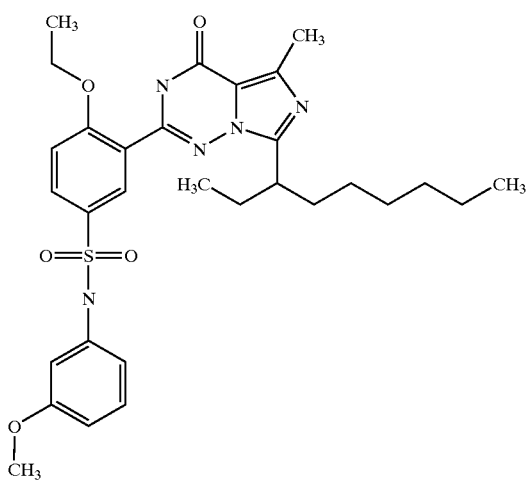 | 581.73983 | 66 | 582 |
| 298 | 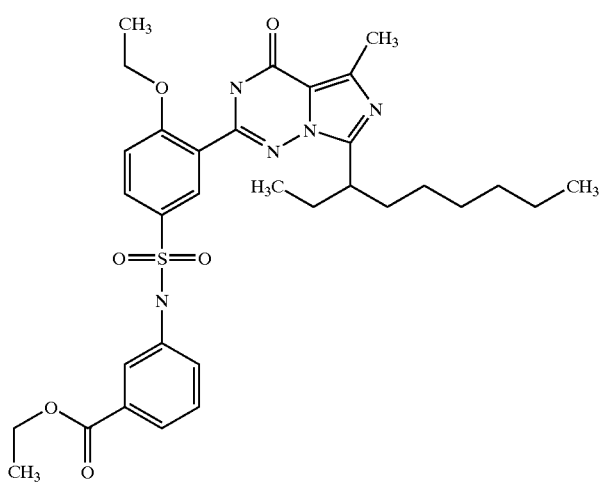 | 623.77747 | 63 | 624 |

TABLE 1-continued
| 299 | 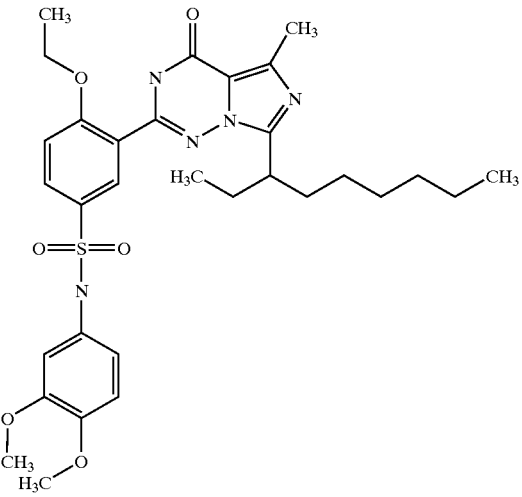 | 611.76632 | 65 | 612 |
| 300 | 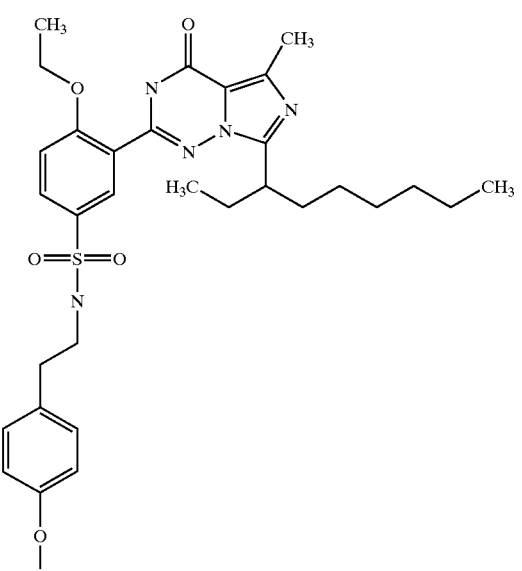 | 609.79401 | 61 | 610 |
| 301 | 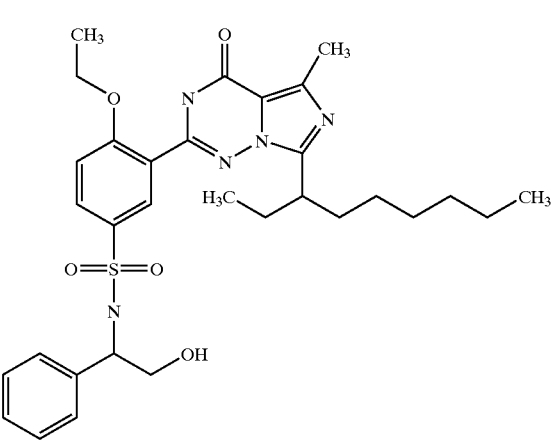 | 595.76692 | 65 | 596 |

TABLE 1-continued
| | | | |
|---|---|---|---|
| 302 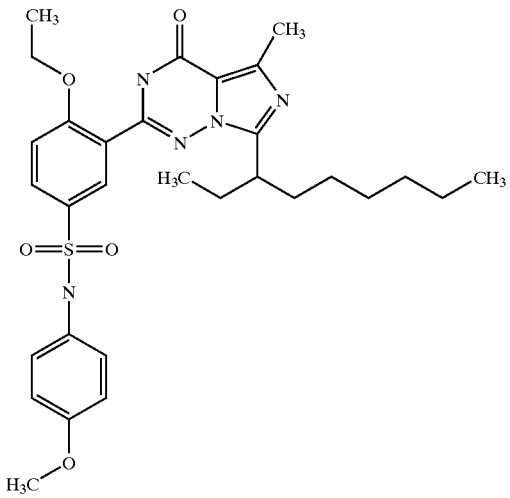 | 581.73983 | 71 | 582 |
| 303 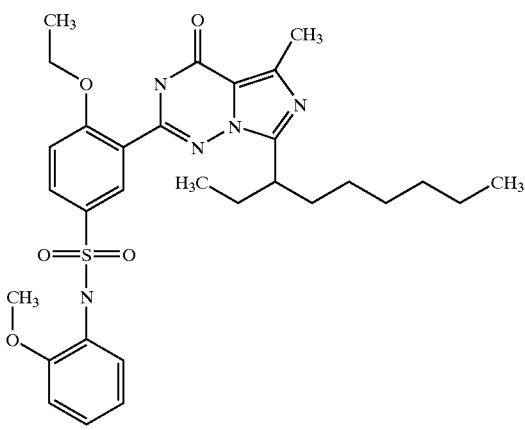 | 581.73983 | 72 | 582 |
| 304 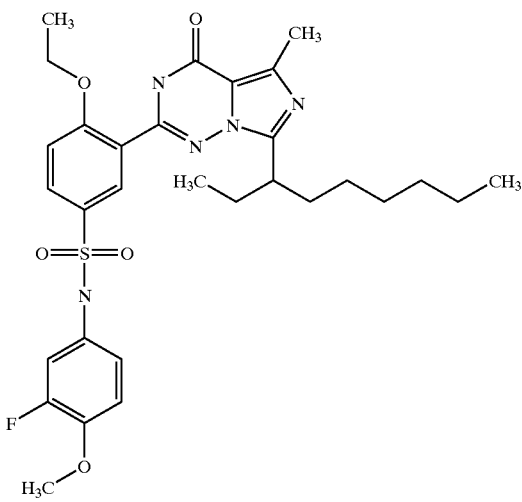 | 599.73026 | 69 | 600 |

TABLE 1-continued
| 305 | 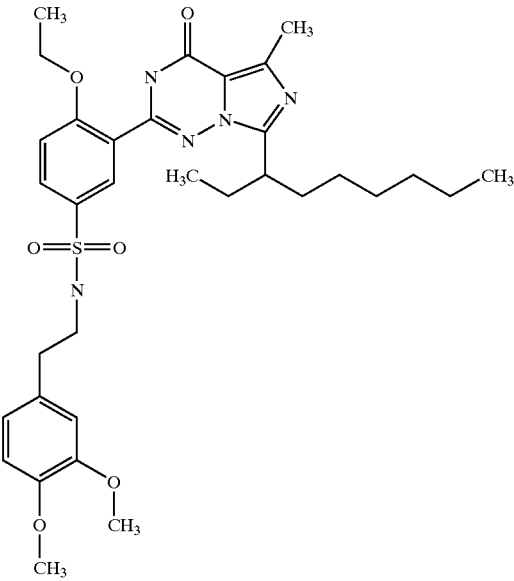 | 639.8205 | 65 | 640 |
| 306 | 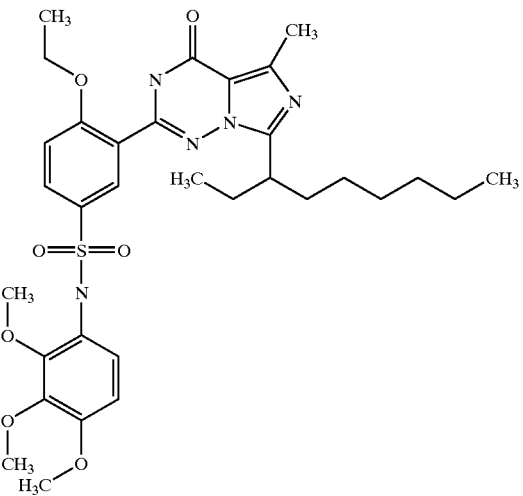 | 641.79281 | 68 | 642 |
| 307 | 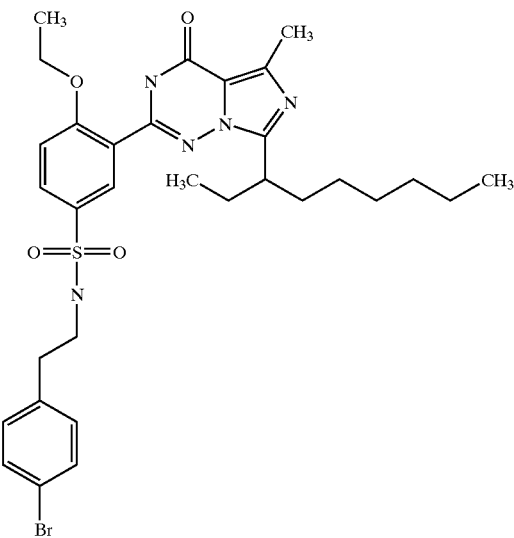 | 658.66355 | 75 | 658 |

| | | | |
|---|---|---|---|
| 308 | 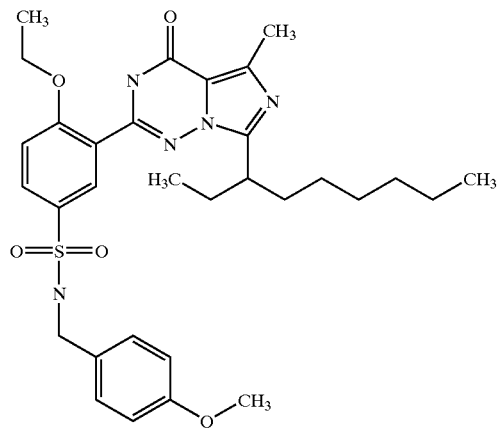 | 595.76692 72 | 596 |
| 309 | 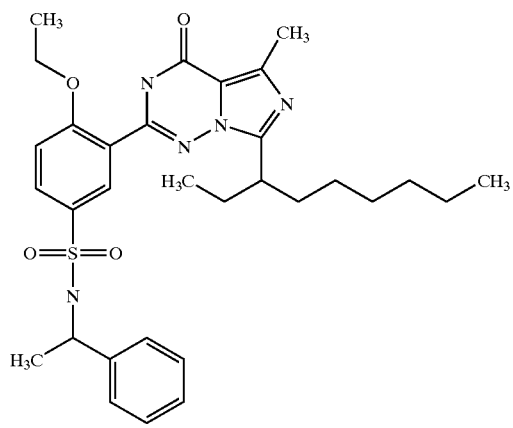 | 579.76752 74 | 580 |
| 310 | 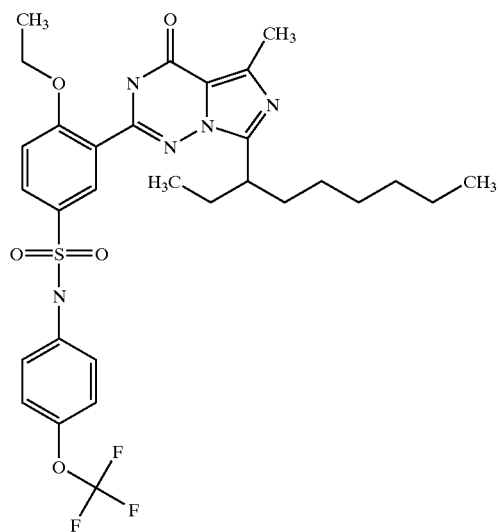 | 635.71112 69 | 636 |

TABLE 1-continued
| | | | |
|---|---|---|---|
| 311 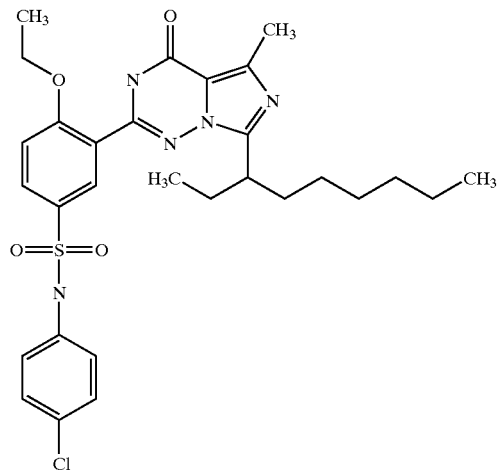 | 586.15837 | 64 | 586 |
| 312 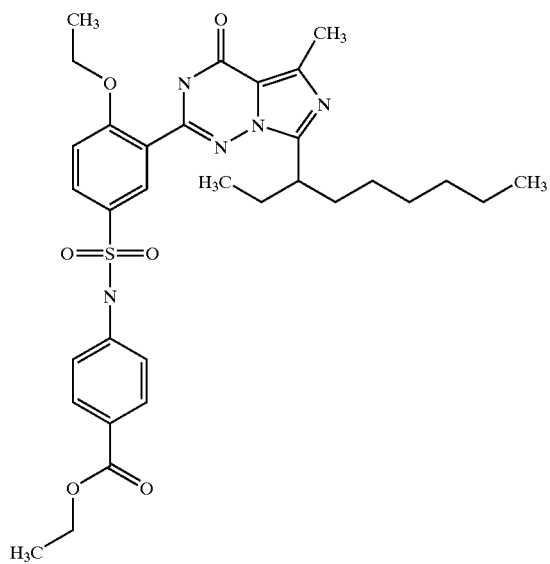 | 623.77747 | 55 | 624 |
| 313 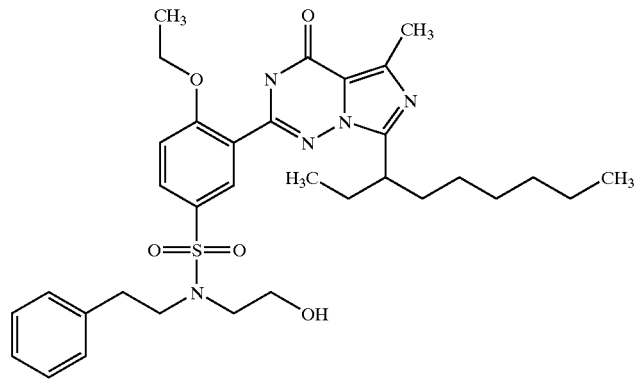 | 623.8211 | 69 | 624 |

TABLE 1-continued
| 314 | 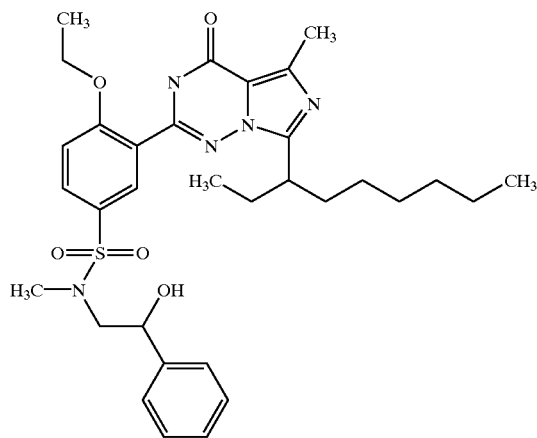 | 609.79401 | 72 | 610 |
| 315 | 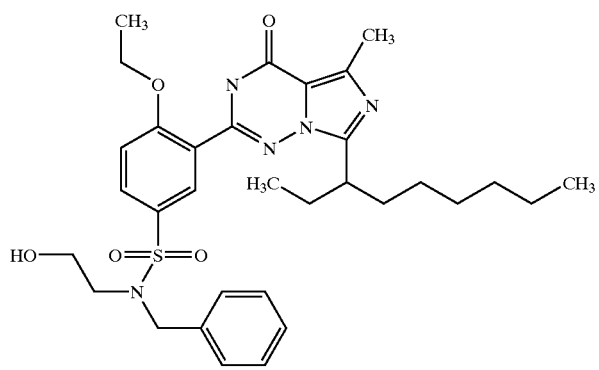 | 609.79401 | 72 | 610 |
| 316 | 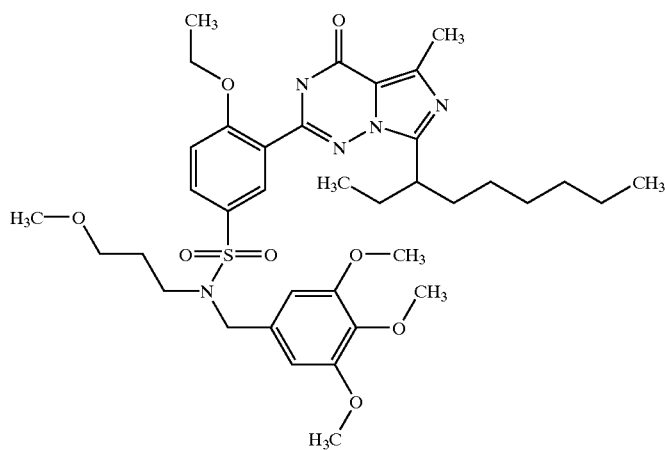 | 727.92766 | 65 | 728 |

| | | | |
|---|---|---|---|
| 317 | 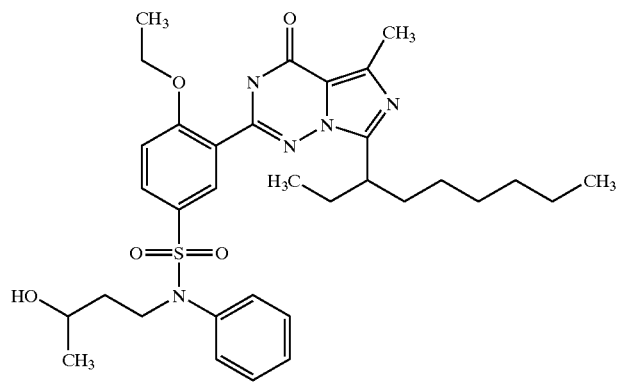 | 623.8211 54 | 624 |
| 318 | 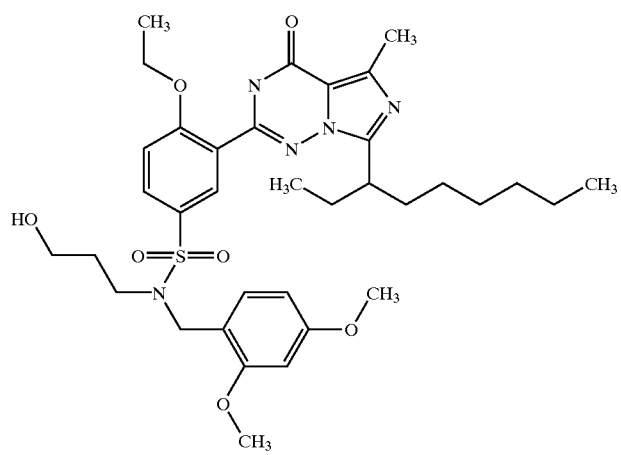 | 683.87408 68 | 684 |
| 319 | 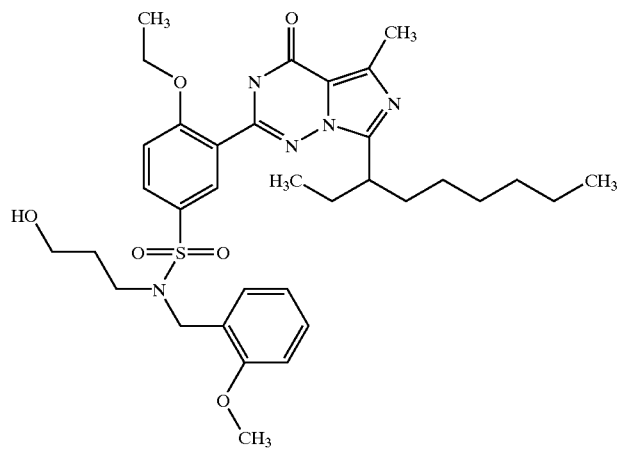 | 653.84759 71 | 654 |

TABLE 1-continued
| 320 | 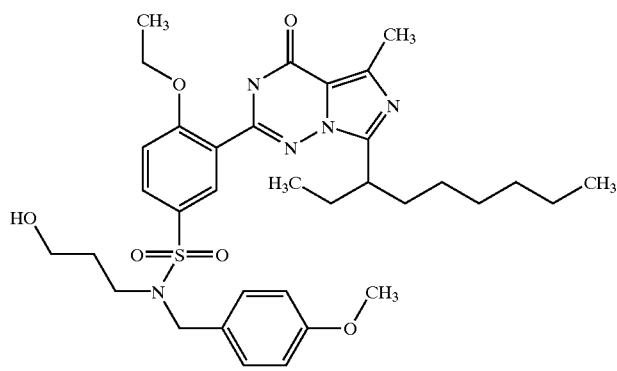 | 653.84759 | 68 | 654 |
| 321 | 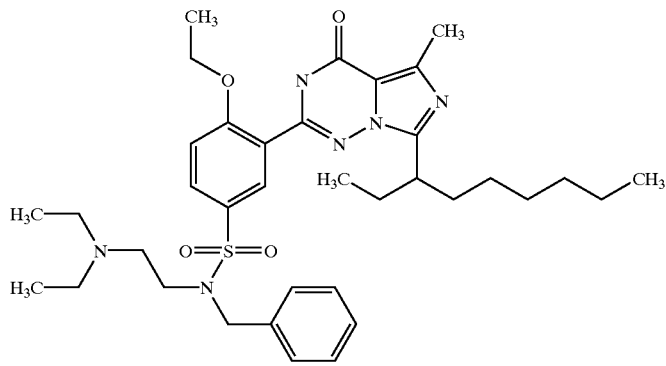 | 664.91764 | 84 | 665 |
| 322 | 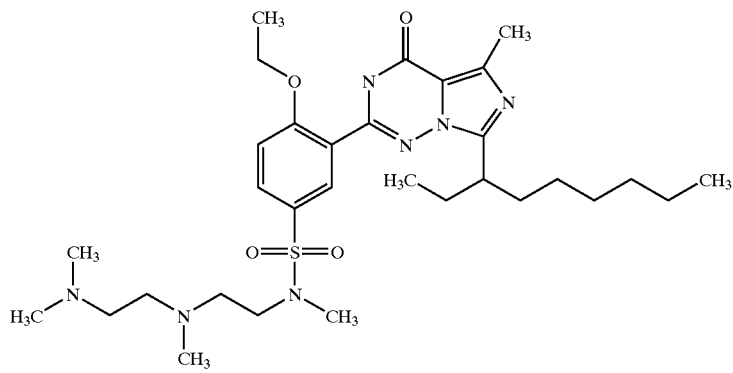 | 617.86062 | 60 | 618 |

TABLE 1-continued

| Ex. No. | Structure | MW [g/mol] | HPLC area % at 210 nm | Mz + H |
|---|---|---|---|---|
| 323 | | 650.84692 | 62 | 651 |
| 324 | 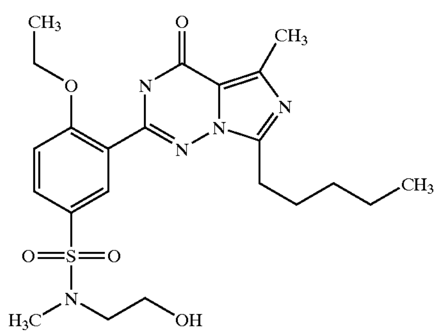 | 477.5869 | 87 | 478 |
| 325 | 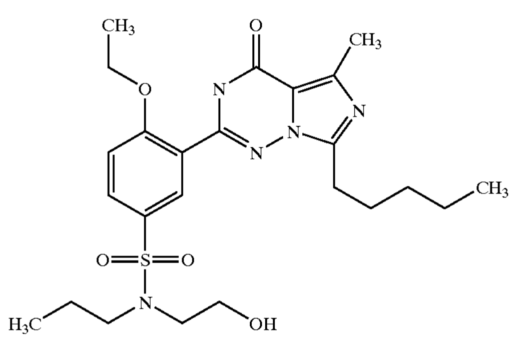 | 505.6411 | 89 | 506 |

TABLE 1-continued
| | | | | |
|---|---|---|---|---|
| 326 | 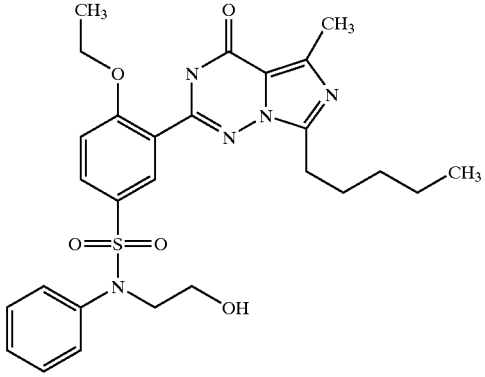 | 539.6586 | 88 | 540 |
| 327 | 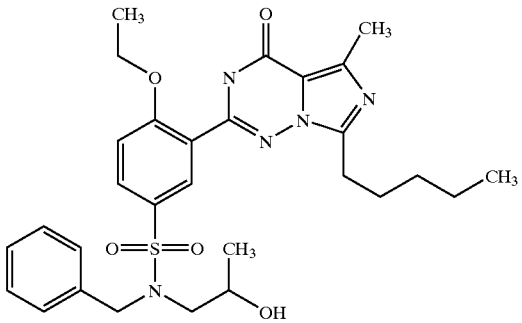 | 567.7127 | 81 | 566 |
| 328 | 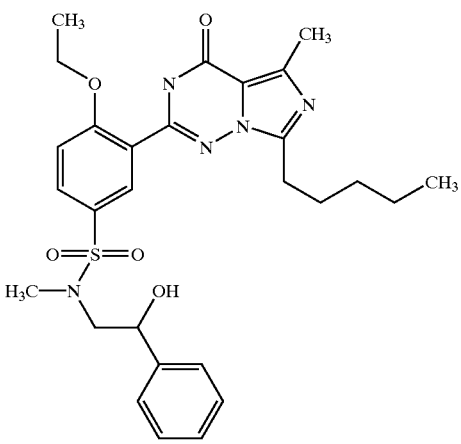 | 553.6857 | 81 | 554 |
| 329 | 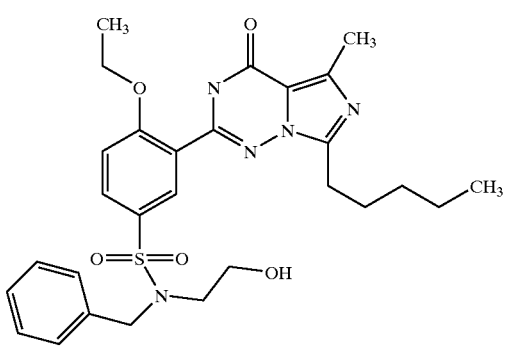 | 553.6857 | 83 | 554 |

TABLE 1-continued

| | | | | |
|---|---|---|---|---|
| 330 | (structure) | 519.6681 | 93 | 520 |
| 331 | (structure) | 579.7239 | 77 | 580 |
| 332 | (structure) | 502.6404 | 86 | 503 |
| 333 | (structure) | 489.598 | 83 | 490 |

TABLE 1-continued

| | | | | |
|---|---|---|---|---|
| 334 | (structure) | 523.6592 | 89 | 524 |
| 335 | (structure) | 594.7822 | 85 | 595 |
| 336 | (structure) | 553.6857 | 85 | 554 |
| 337 | (structure) | 579.7675 | 80 | 580 |

TABLE 1-continued
| | | | | |
|---|---|---|---|---|
| 338 | 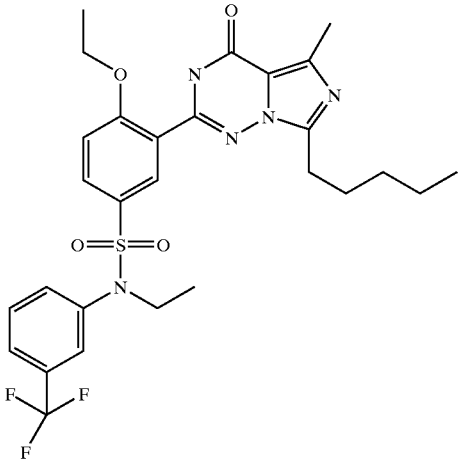 | 591.6575 | 84 | 592 |
| 339 | 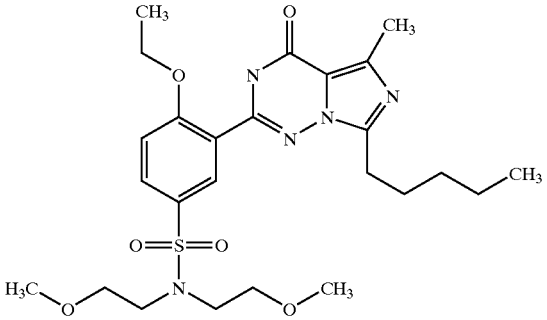 | 535.6675 | 89 | 536 |
| 340 | 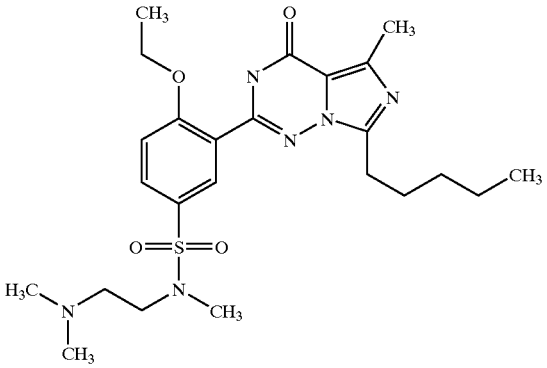 | 504.6563 | 91 | 505 |
| 341 | 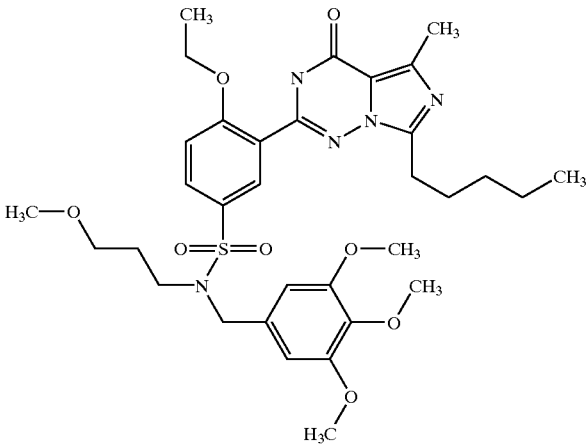 | 671.8193 | 79 | 672 |

| | | | |
|---|---|---|---|
| 342 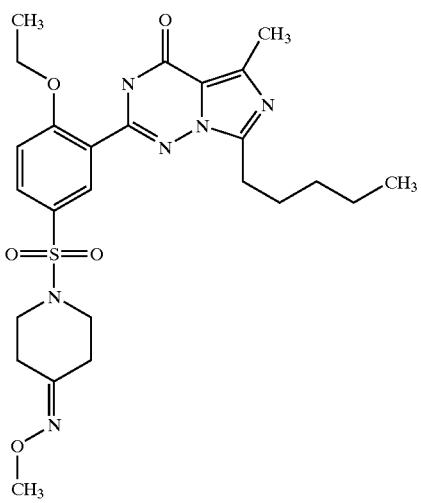 | 530.6509 | 89 | 531 |
| 343 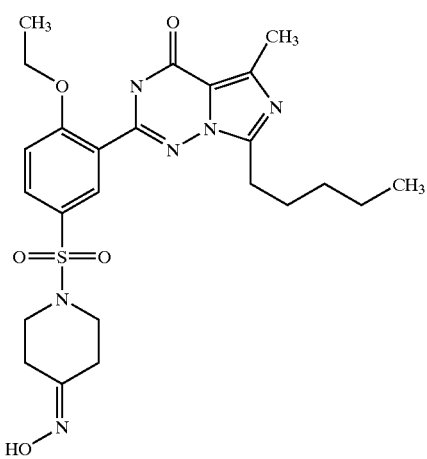 | 516.6238 | 85 | 517 |
| 344 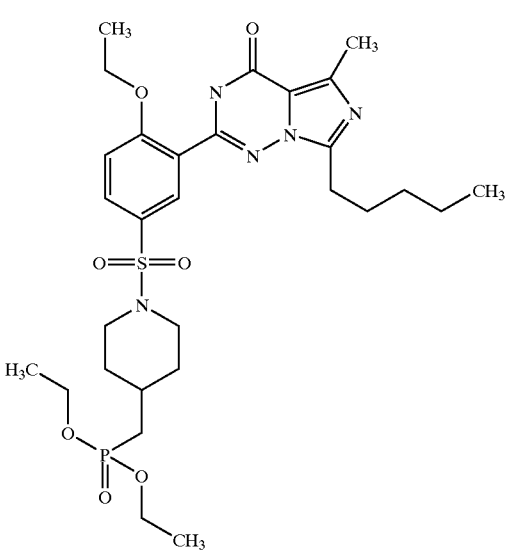 | 637.7411 | 78 | 638 |

TABLE 1-continued
| 345 | 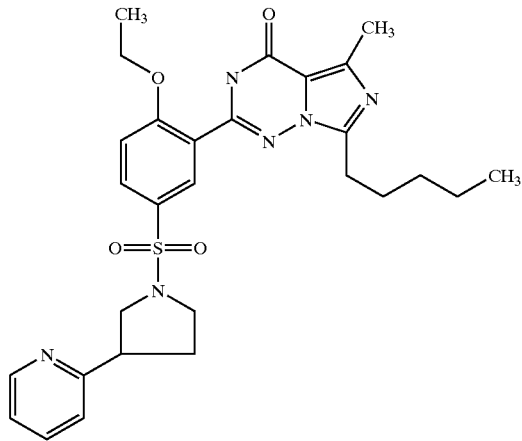 | 550.685 | 86 | 551 |
| 346 | 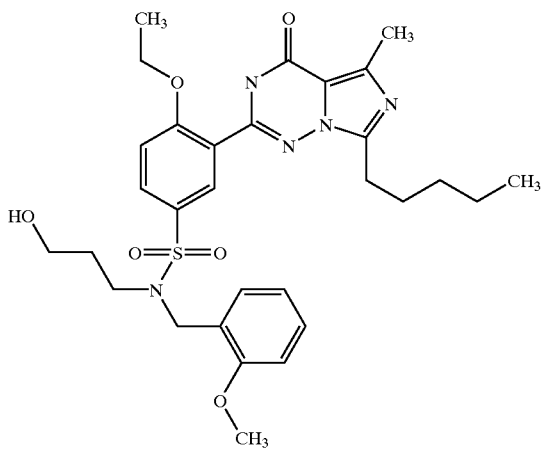 | 597.7392 | 83 | 598 |
| 347 | 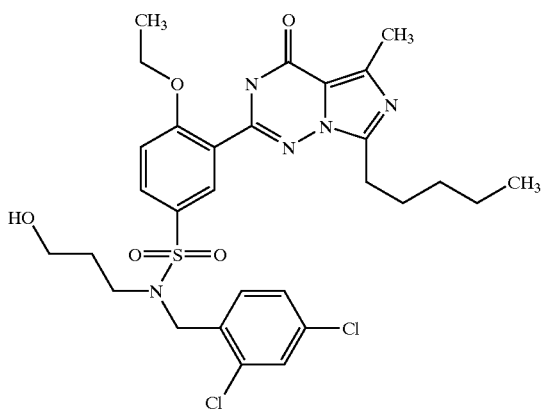 | 636.6028 | 82 | 636 |

TABLE 1-continued
| | | | | |
|---|---|---|---|---|
| 348 | 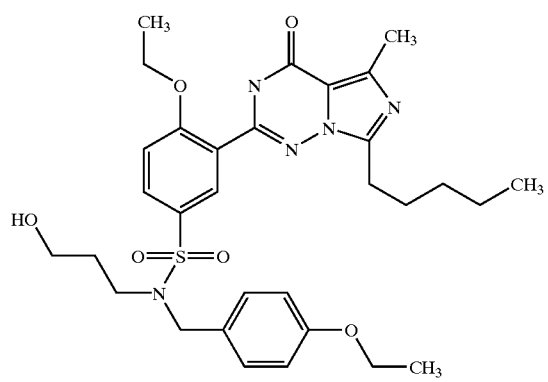 | 611.7663 | 78 | 612 |
| 349 | 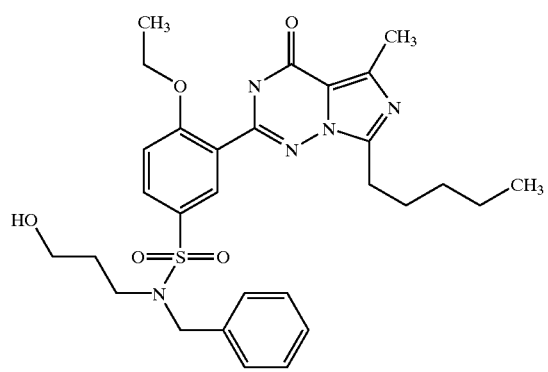 | 567.7127 | 80 | 568 |
| 350 | 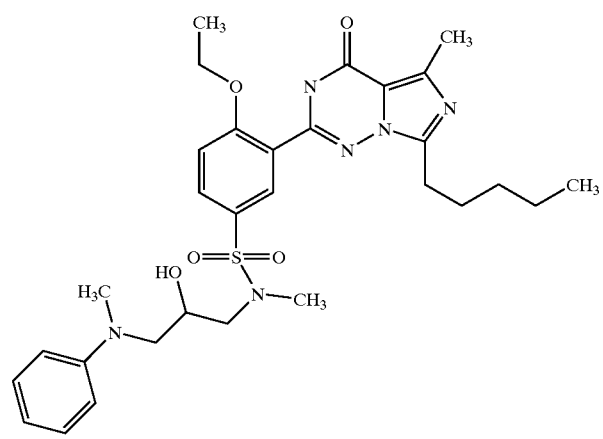 | 596.7545 | 82 | 597 |
| 351 | 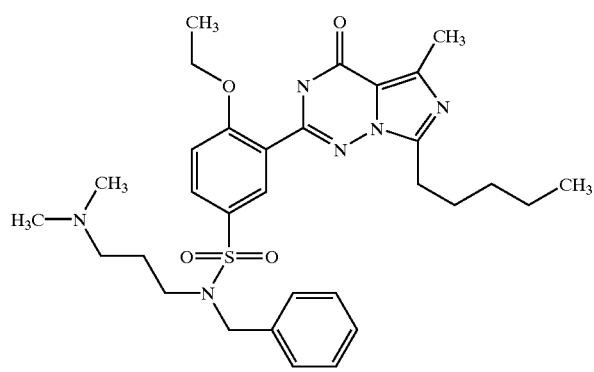 | 594.7822 | 79 | 595 |

TABLE 1-continued
| 352 | 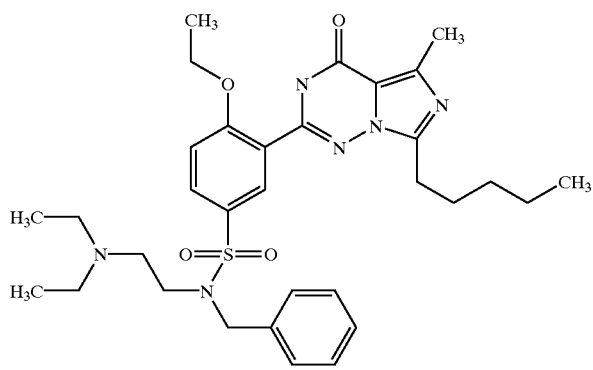 | 608.8093 | 84 | 609 |
| 353 | 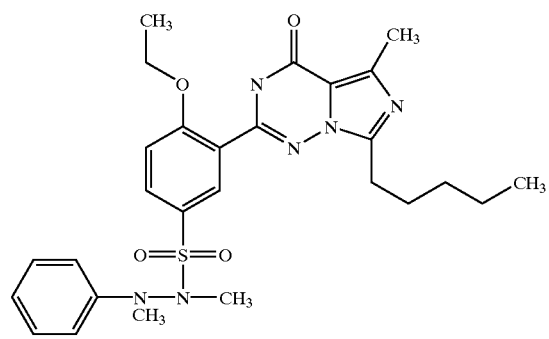 | 566.728 | 82 | 567 |
| 354 | 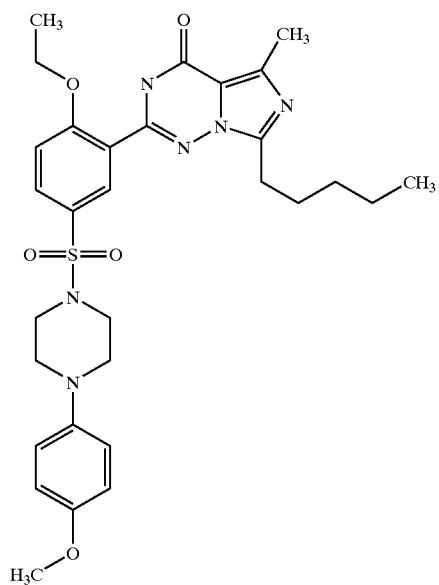 | 594.7386 | 85 | 595 |

| | | | |
|---|---|---|---|
| 355 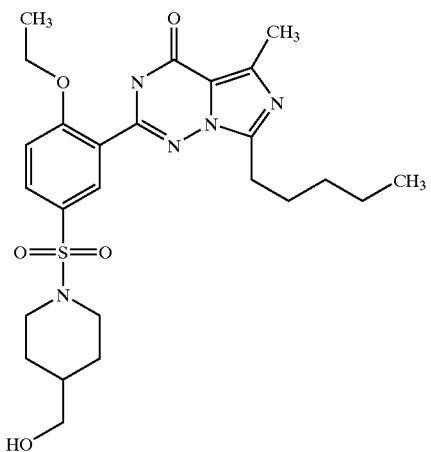 | 517.6522 | 85 | 518 |
| 356 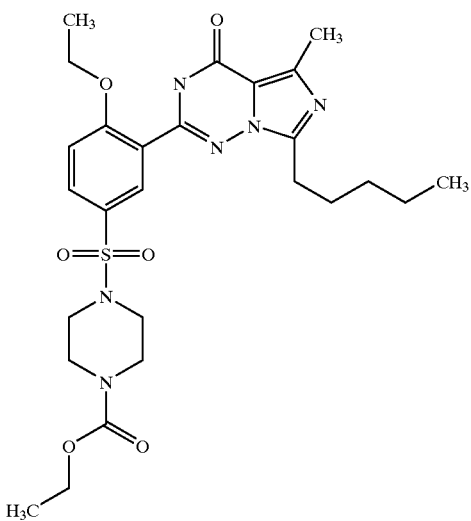 | 560.6774 | 83 | 561 |
| 357 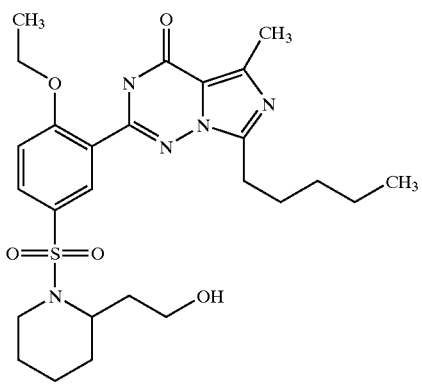 | 531.6793 | 84 | 532 |

TABLE 1-continued

| | | | | |
|---|---|---|---|---|
| 358 | (structure) | | 517.6522 | 85 | 518 |
| 359 | (structure) | | 489.598 | 85 | 490 |
| 360 | (structure) | | 517.6522 | 84 | 518 |
| 361 | (structure) | | 593.751 | 81 | 594 |

| | | | |
|---|---|---|---|
| 362 | 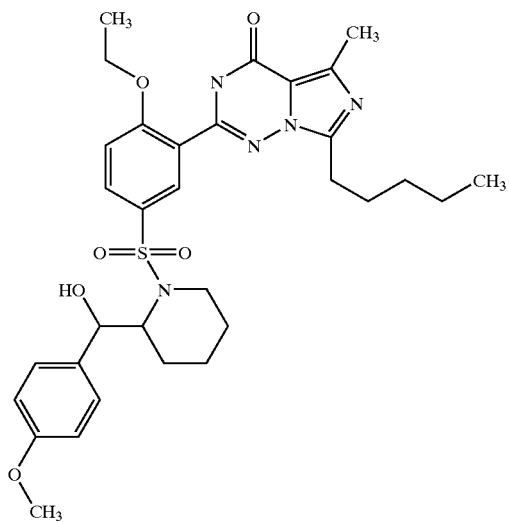 | 623,7775 50 | 624 |
| 363 | 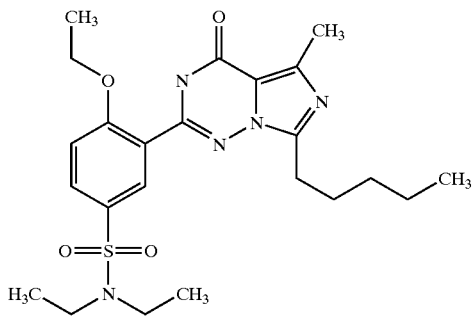 | 475,6146 90 | 476 |
| 364 | 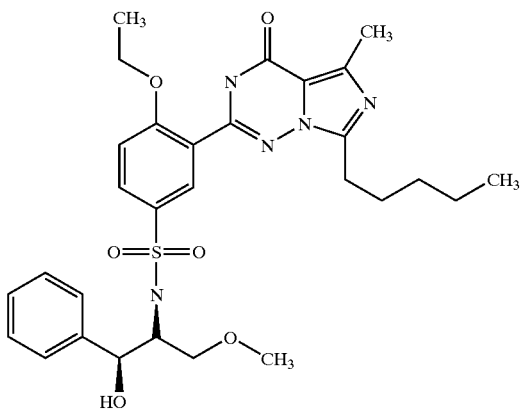 | 583,7121 76 | 584 |

| | | | |
|---|---|---|---|
| 365 | 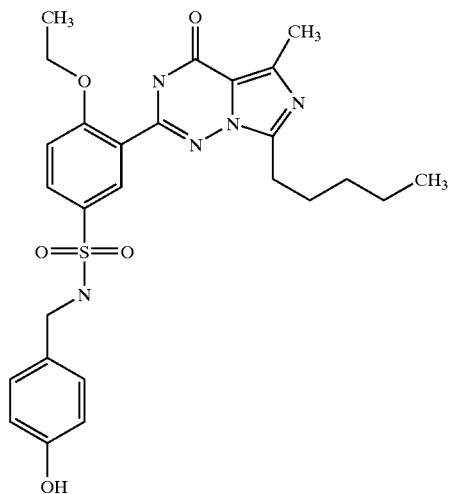 | 525,6315 69 | 526 |
| 366 | 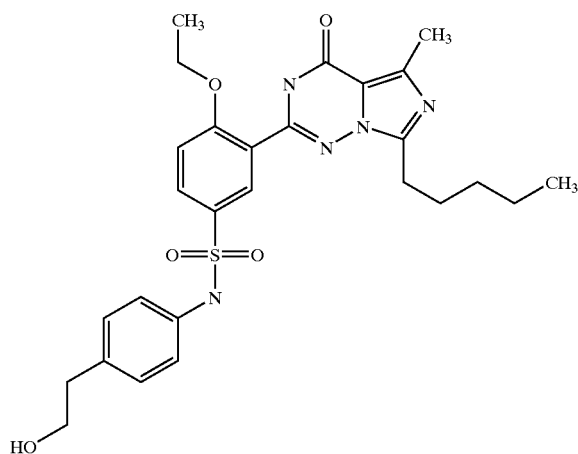 | 539,6586 71 | 540 |
| 367 | 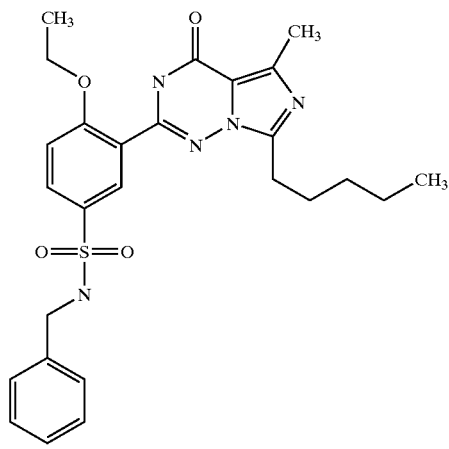 | 509,6321 56 | 510 |

TABLE 1-continued
| | | | |
|---|---|---|---|
| 368 | | 523,6592 86 | 524 |
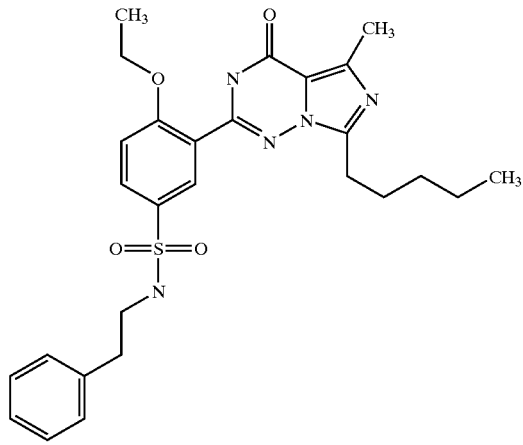
| | | | |
|---|---|---|---|
| 369 | | 583,7121 80 | 584 |
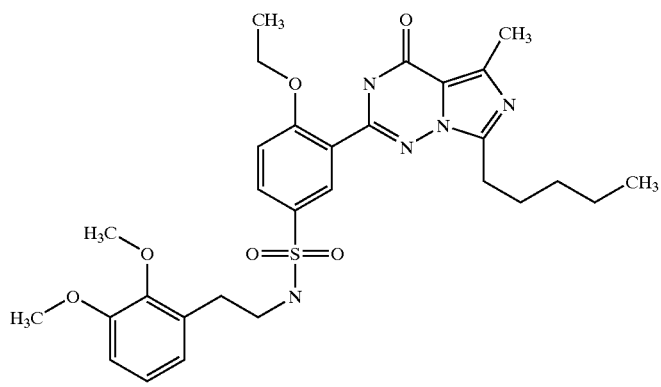
| | | | |
|---|---|---|---|
| 370 | | 525,6315 72 | 526 |
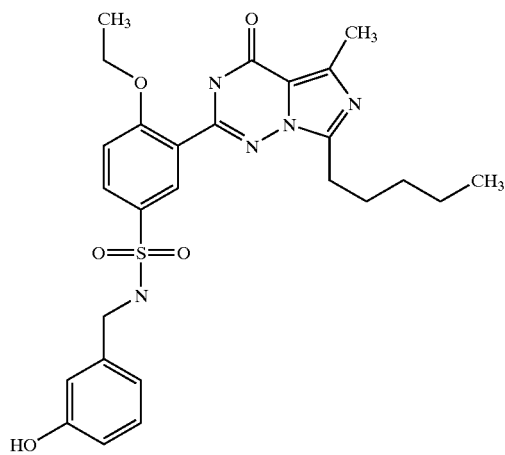

TABLE 1-continued

| | | | | |
|---|---|---|---|---|
| 371 | (structure) | 495,605 | 83 | 496 |
| 372 | (structure) | 560,0765 | 52 | 560 |
| 373 | (structure) | 511,6044 | 73 | 512 |
| 374 | (structure) | 537,6863 | 81 | 538 |

TABLE 1-continued
| | | | |
|---|---|---|---|
| 375 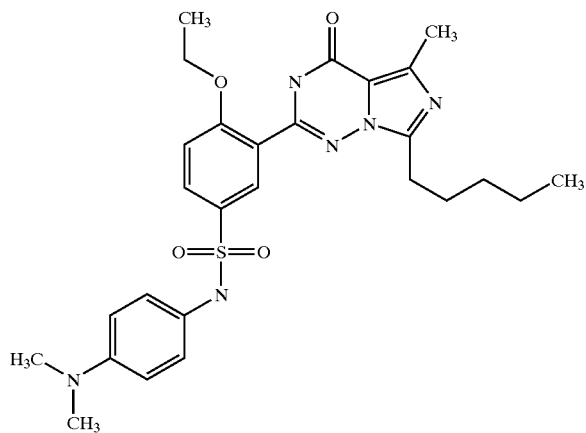 | 538,6738 | 74 | 539 |
| 376 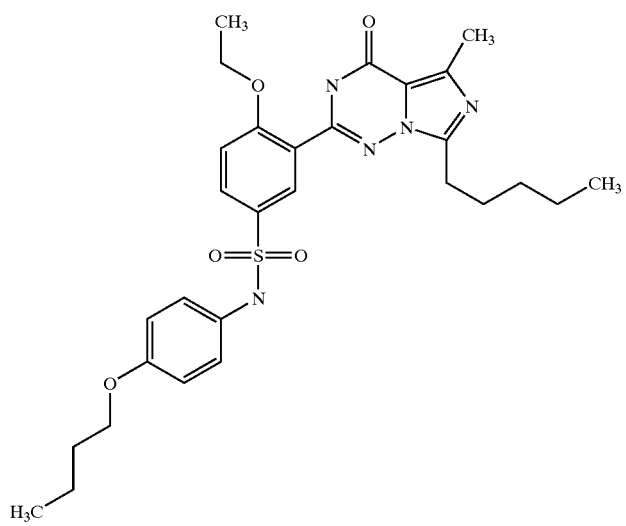 | 567,7127 | 74 | 568 |
| 377 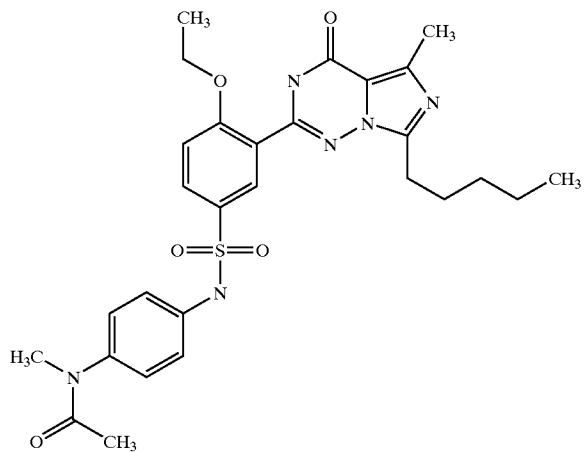 | 566,6844 | 88 | 567 |

TABLE 1-continued
| | | | |
|---|---|---|---|
| 378 | | 531,5858  82 | 532 |
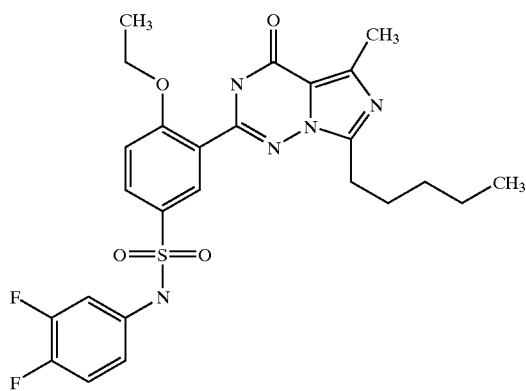
| | | | |
|---|---|---|---|
| 379 | | 537,6426  47 | 538 |
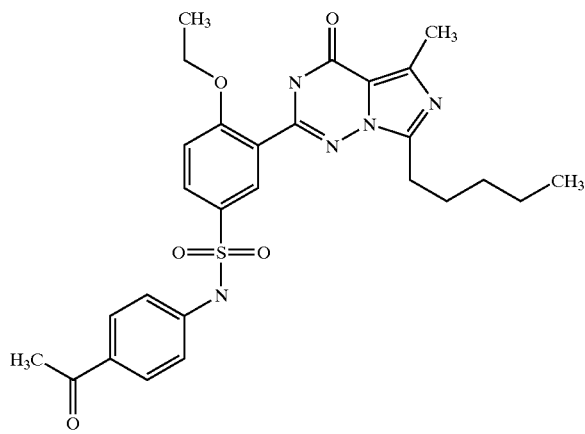
| | | | |
|---|---|---|---|
| 380 | | 513,5954  83 | 514 |
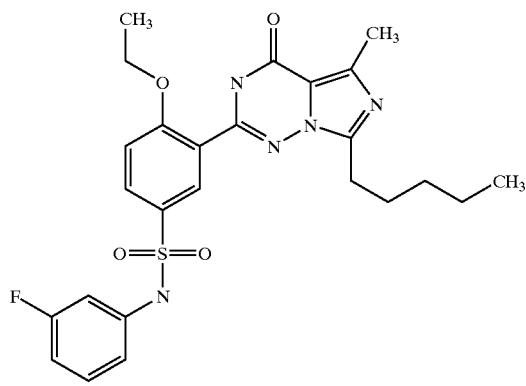

| | | | |
|---|---|---|---|
| 381 | 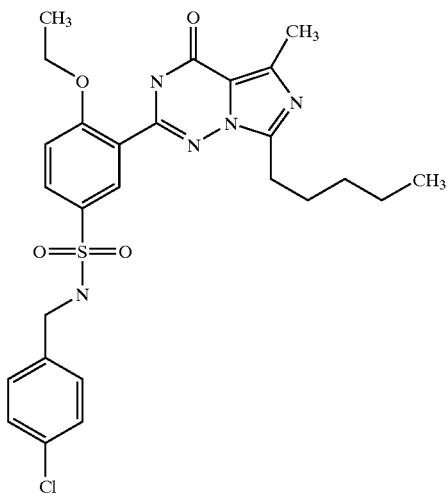 | 544,0771  82 | 545 |
| 382 | 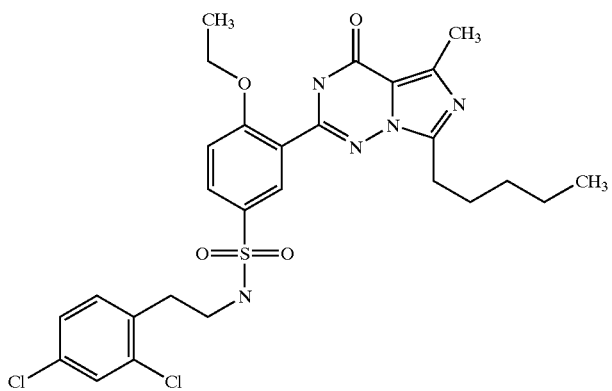 | 592,5492  72 | 593 |
| 383 | 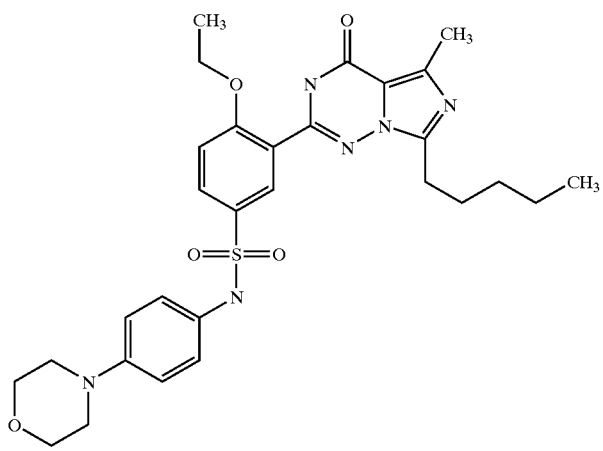 | 580,7115  70 | 581 |

TABLE 1-continued
| | | | | |
|---|---|---|---|---|
| 384 | 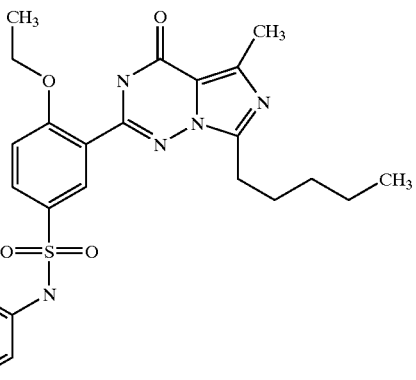 | 555,658 | 81 | 556 |
| 385 | 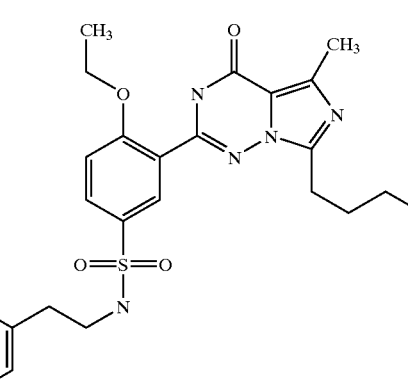 | 553,6857 | 80 | 554 |
| 386 | 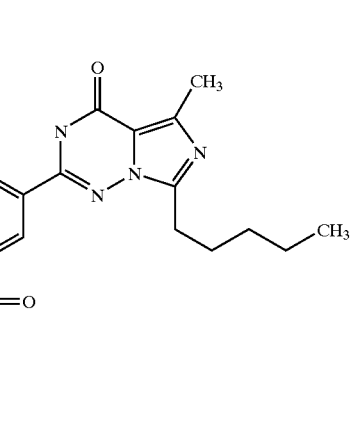 | 539,6586 | 75 | 540 |
| 387 | 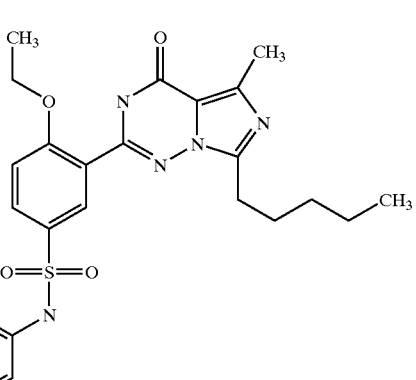 | 525,6315 | 86 | 526 |

TABLE 1-continued

| # | Structure | | | |
|---|---|---|---|---|
| 388 | (structure) | 530,05 | 80 | 531 |
| 389 | (structure) | 525,6315 | 86 | 526 |
| 390 | (structure) | 543,6219 | 76 | 544 |
| 391 | (structure) | 563,6034 | 81 | 564 |

TABLE 1-continued
| 392 | 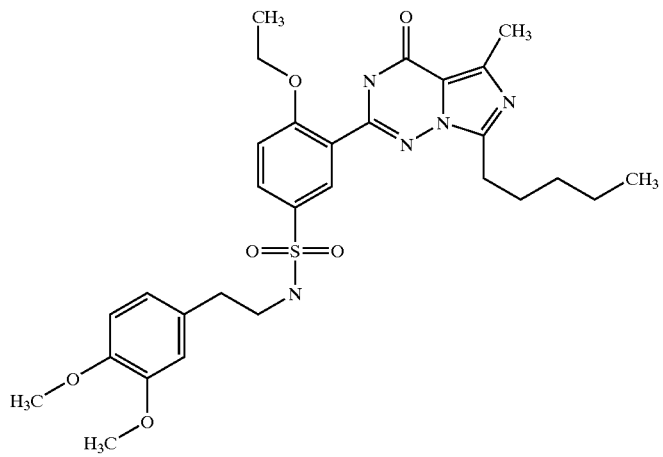 | 583,7121 | 79 | 584 |
| --- | --- | --- | --- | --- |
| 393 | 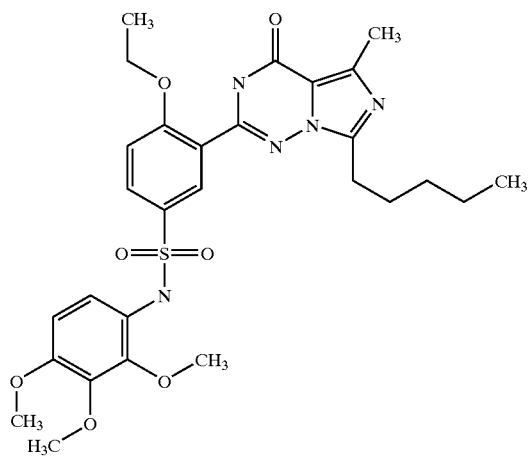 | 585,6845 | 84 | 586 |
| 394 | 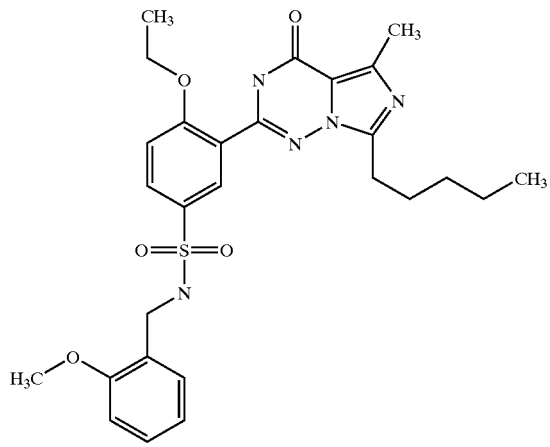 | 539,6586 | 80 | 540 |

TABLE 1-continued
| 395 | 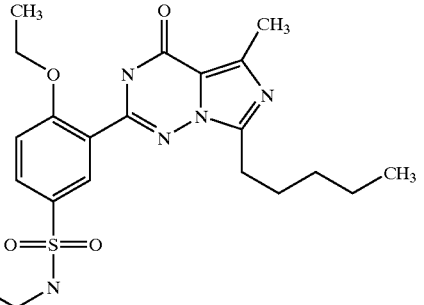 | 477,5869 | 87 | 478 |
| 396 | 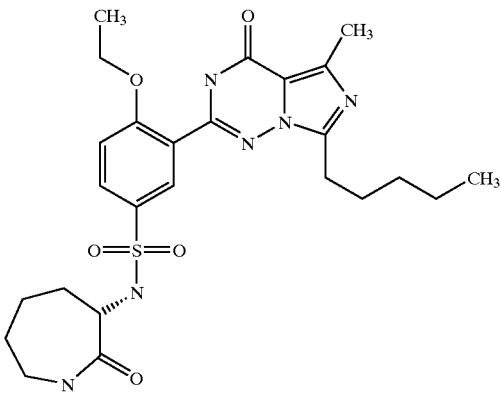 | 530,6509 | 91 | 531 |
| 397 | 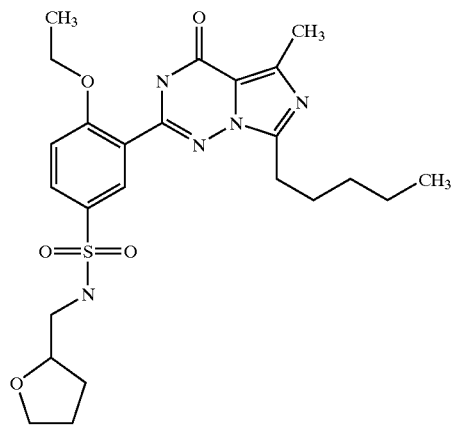 | 503,6251 | 87 | 504 |
| 398 | 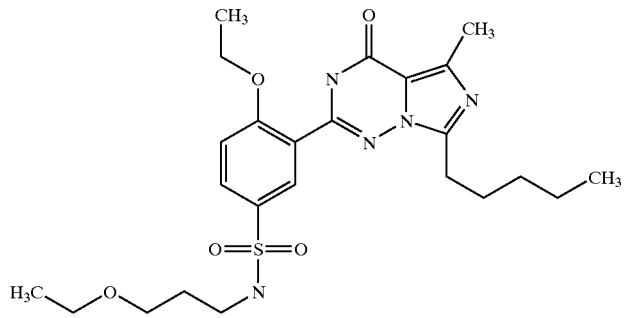 | 505,6411 | 90 | 506 |

TABLE 1-continued
| | | | | |
|---|---|---|---|---|
| 399 | 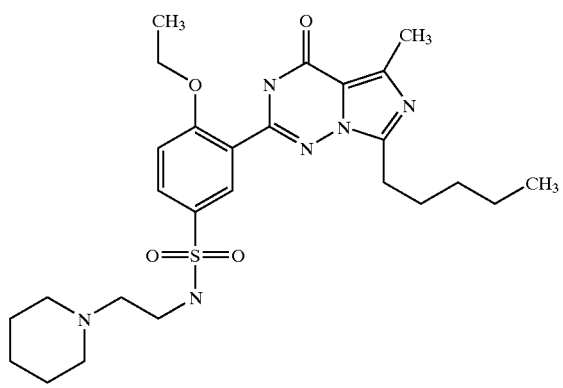 | 530,6946 | 51 | 531 |
| 400 | 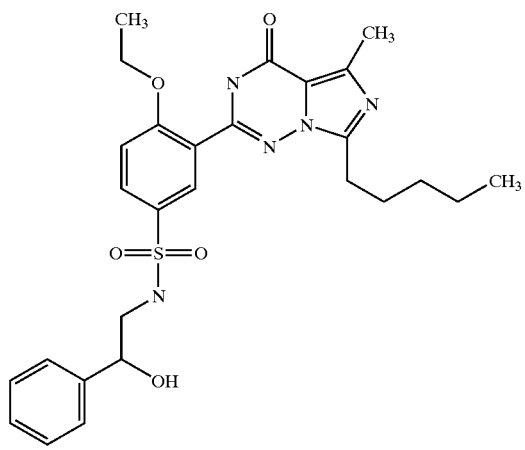 | 539,6586 | 74 | 540 |
| 401 | 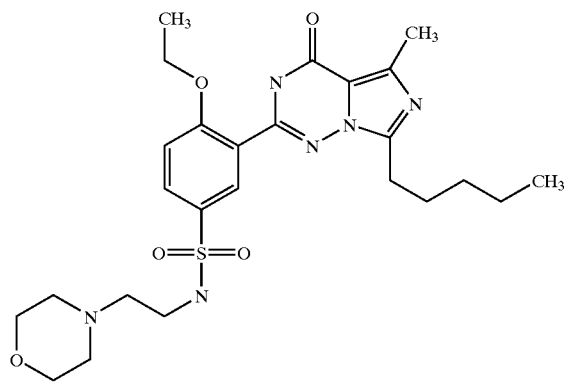 | 532,6669 | 70 | 533 |

TABLE 1-continued
| | | | |
|---|---|---|---|
| 402 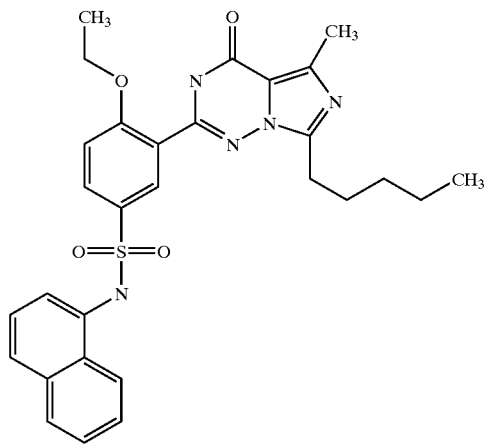 | 545,6655 | 79 | 546 |
| 403 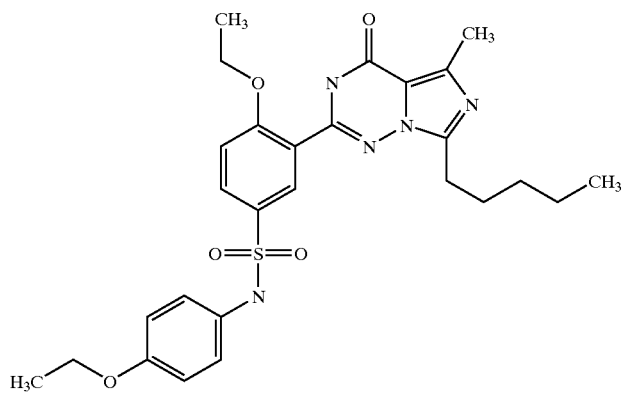 | 539,6586 | 85 | 540 |
| 404 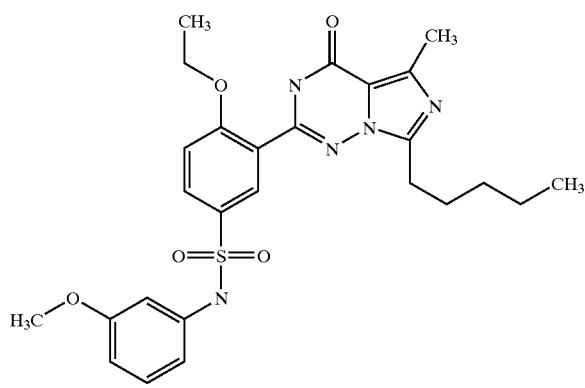 | 525,6315 | 81 | 526 |

TABLE 1-continued
| | | | |
|---|---|---|---|
| 405 | 564,495 | 90 | 565 |
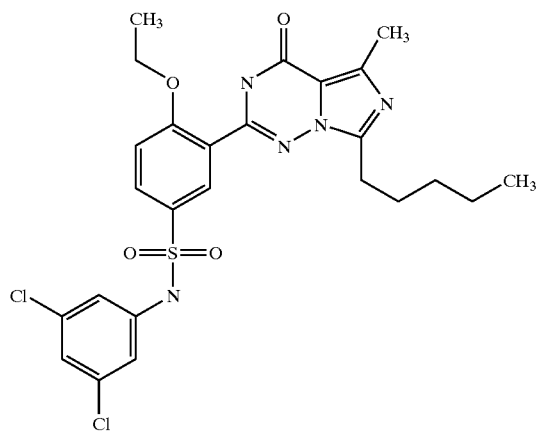
| | | | |
|---|---|---|---|
| 406 | 564,495 | 60 | 565 |
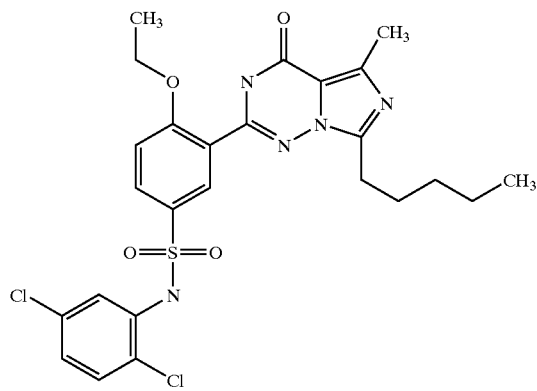
| | | | |
|---|---|---|---|
| 407 | 611,7663 | 84 | 612 |
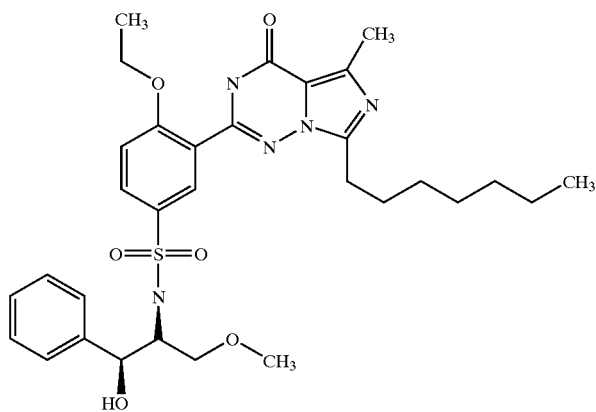

TABLE 1-continued
| | | | |
|---|---|---|---|
| 408 | | 553,6857  79 | 554 |
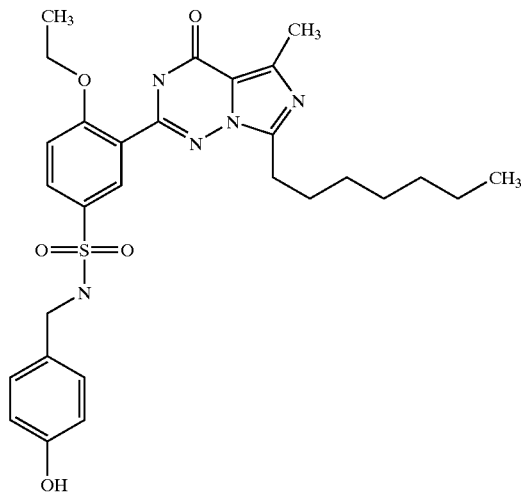
| | | | |
|---|---|---|---|
| 409 | | 567,7127  75 | 568 |
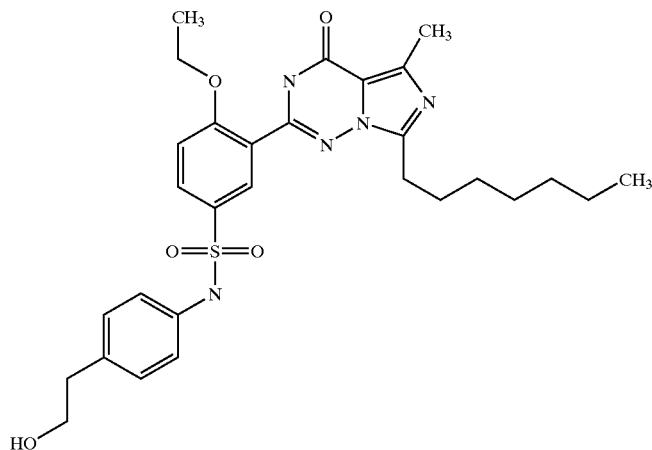
| | | | |
|---|---|---|---|
| 410 | | 537,6863  80 | 538 |
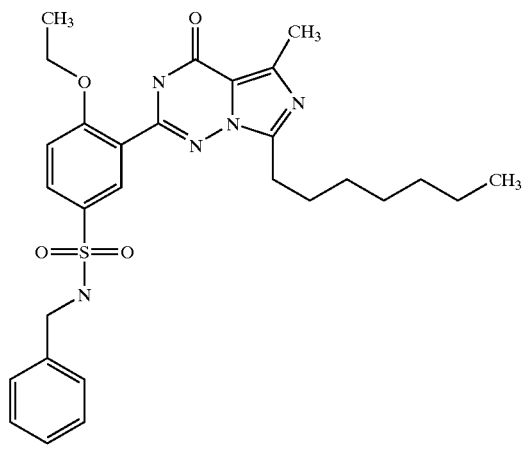

| | | | |
|---|---|---|---|
| 411 | 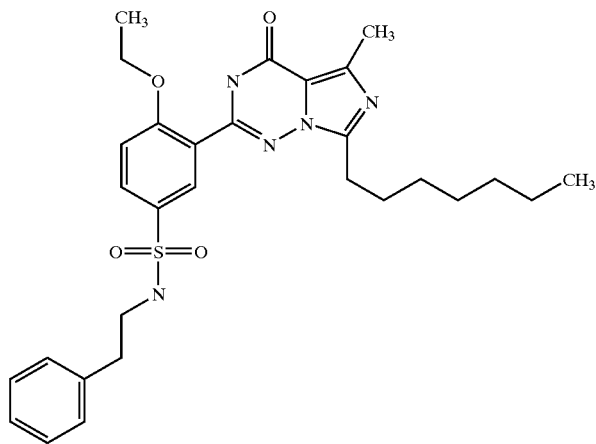 | 551,7133  86 | 552 |
| 412 | 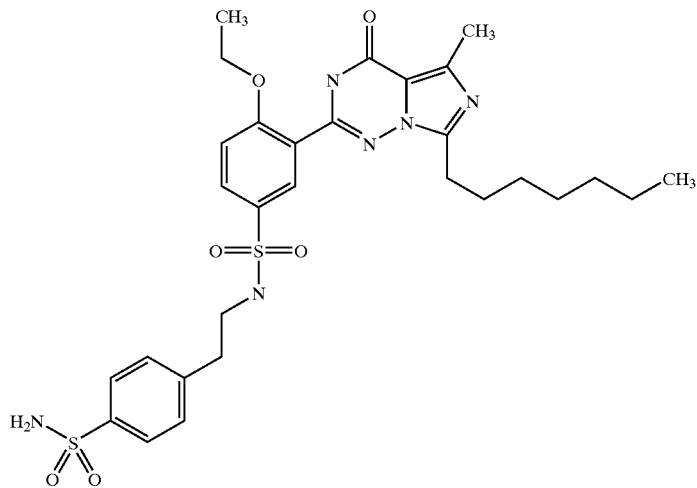 | 630,7908  37 | 631 |
| 413 | 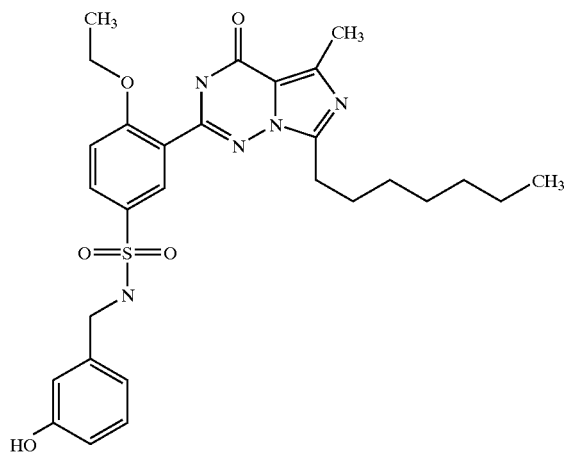 | 553,6857  66 | 554 |

TABLE 1-continued

| | | | | |
|---|---|---|---|---|
| 414 | (structure) | 523,6592 | 82 | 524 |
| 415 | (structure) | 588,1307 | 31 | 588 |
| 416 | (structure) | 539,6586 | 77 | 540 |
| 417 | (structure) | 565,7404 | 80 | 566 |

TABLE 1-continued
| 418 | 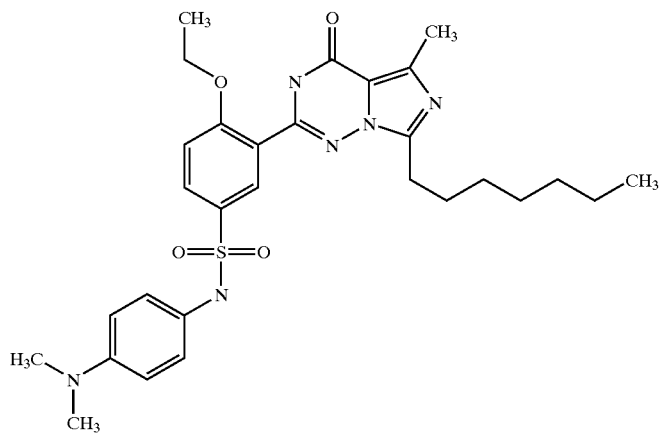 | 566,728 | 68 | 567 |
| 419 | 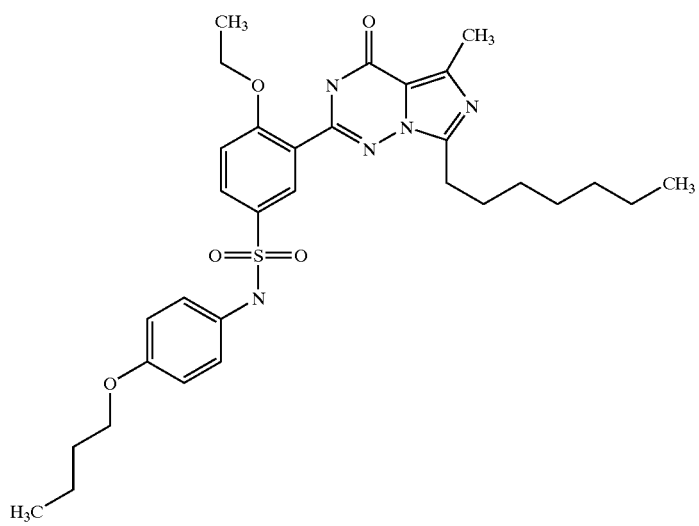 | 595,7669 | 84 | 596 |
| 420 | 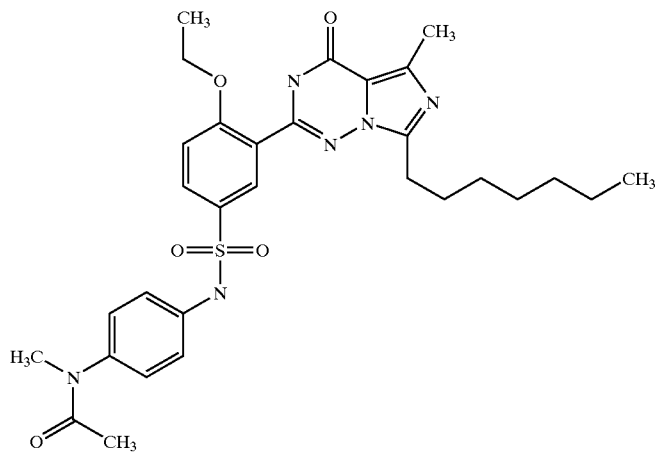 | 594,7386 | 77 | 595 |

TABLE 1-continued
| | | | |
|---|---|---|---|
| 421 | 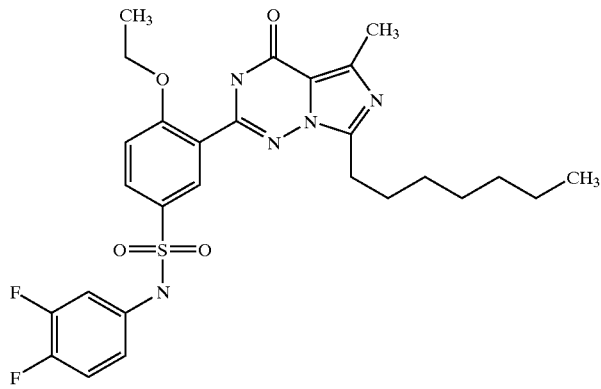 | 559,64 81 | 560 |
| 422 | 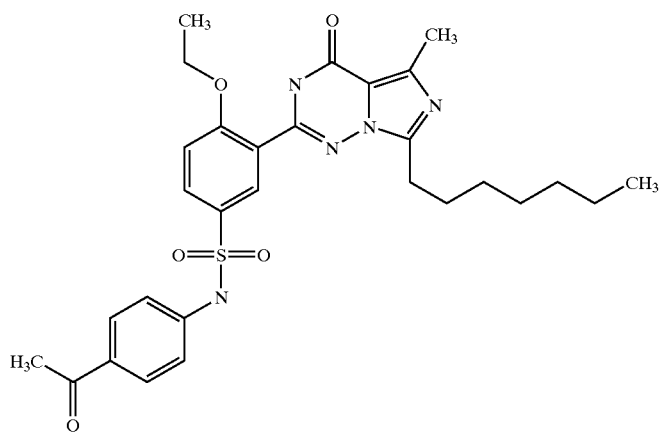 | 565,6968 42 | 566 |
| 423 | 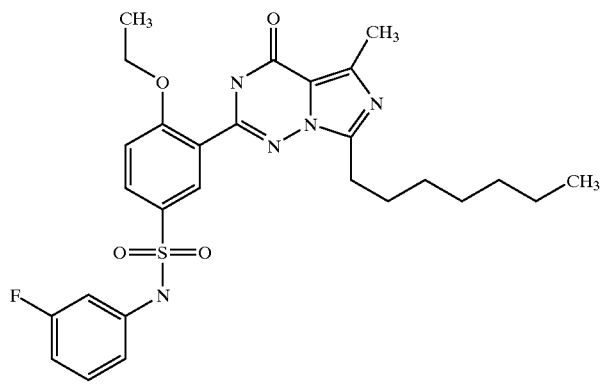 | 541,6496 82 | 542 |

TABLE 1-continued
| | | | |
|---|---|---|---|
| 424 | 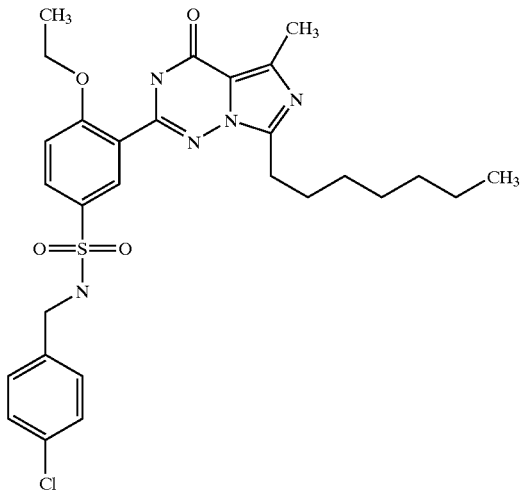 | 572,1313  85 | 572 |
| 425 | 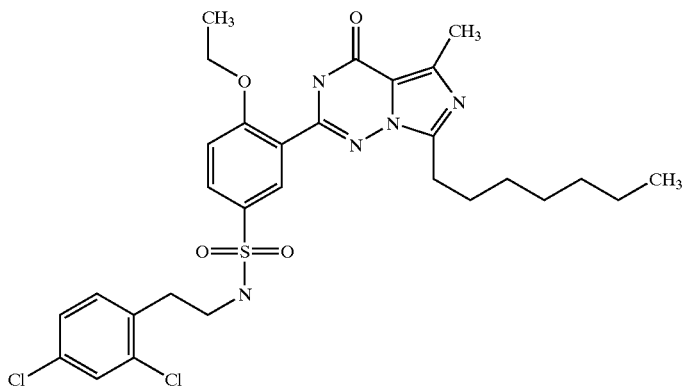 | 620,6034  80 | 620 |
| 426 | 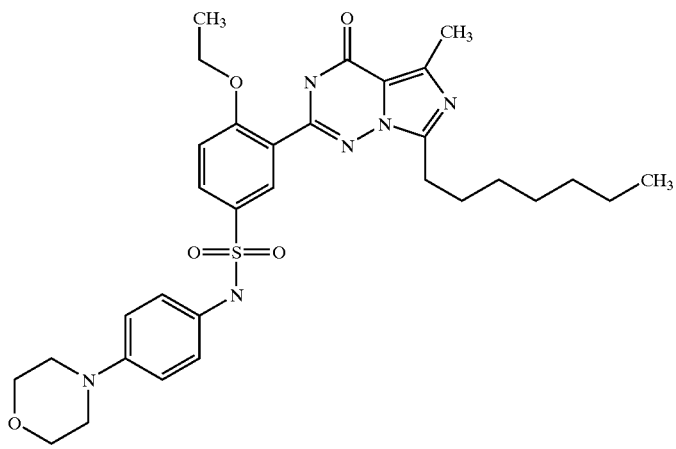 | 608,7657  84 | 609 |

TABLE 1-continued
| | | | | |
|---|---|---|---|---|
| 427 | 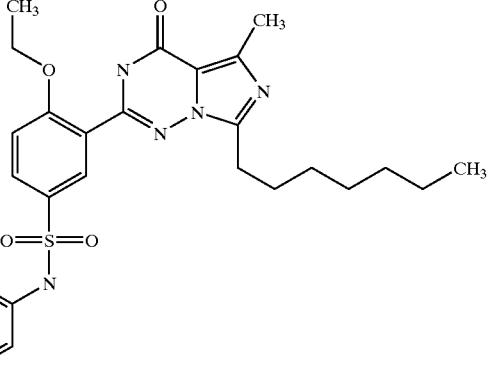 | 583,7121 | 82 | 584 |
| 428 | 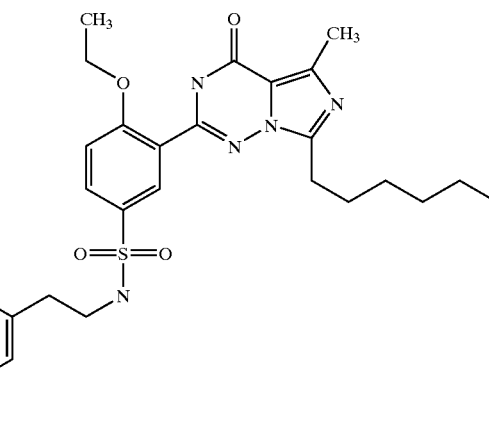 | 581,7398 | 77 | 582 |
| 429 | 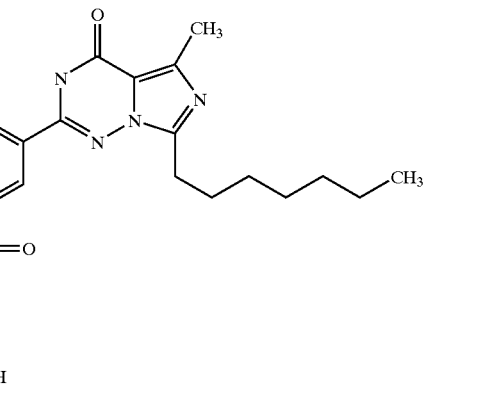 | 567,7127 | 80 | 568 |
| 430 | 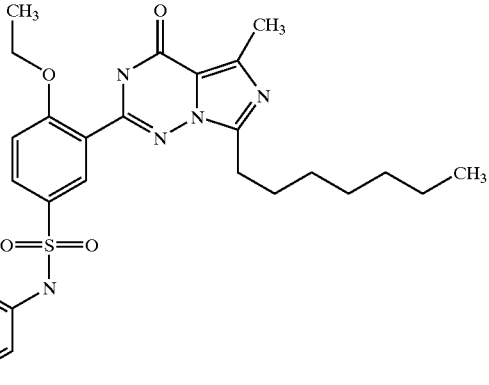 | 553,6857 | 82 | 554 |

TABLE 1-continued

| | | | | |
|---|---|---|---|---|
| 431 | (structure) | 558,1042 | 80 | 558 |
| 432 | (structure) | 553,6857 | 85 | 554 |
| 433 | (structure) | 571,6761 | 79 | 572 |
| 434 | (structure) | 591,6575 | 83 | 592 |

TABLE 1-continued
| | | | | |
|---|---|---|---|---|
| 435 | 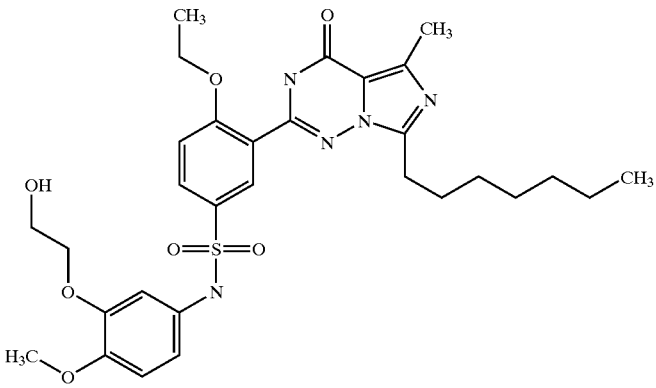 | 613,7386 | 77 | 614 |
| 436 | 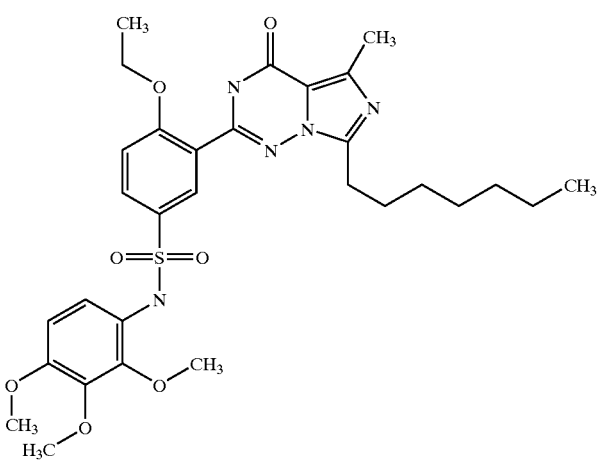 | 613,7386 | 82 | 614 |
| 437 | 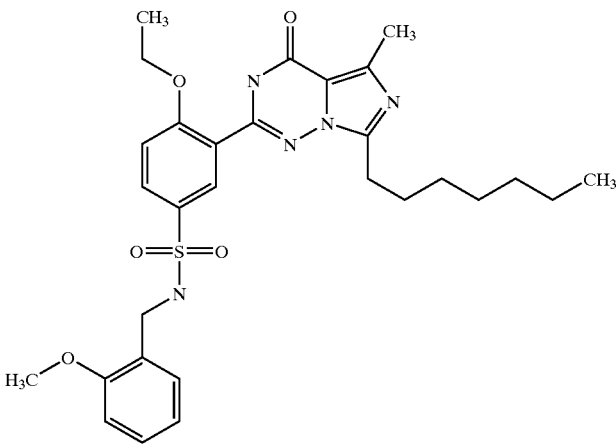 | 567,7127 | 84 | 568 |
| 438 | 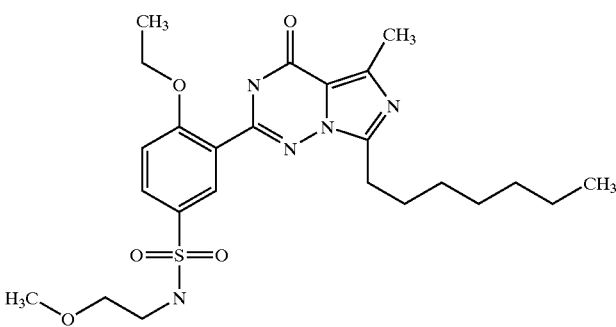 | 505,6411 | 85 | 506 |

TABLE 1-continued
| | | | | |
|---|---|---|---|---|
| 439 | 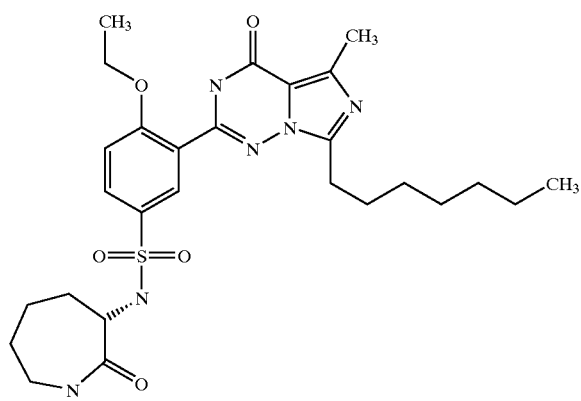 | 558,7051 | 90 | 559 |
| 440 | 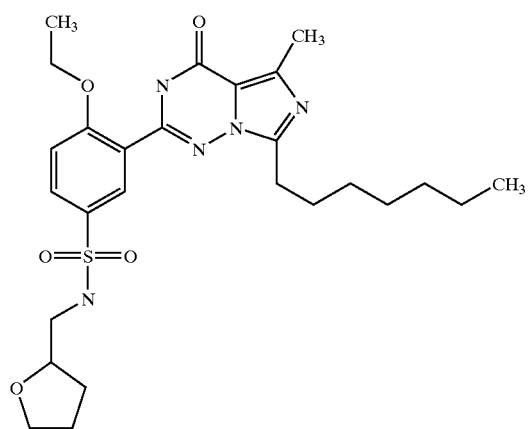 | 531,6793 | 87 | 532 |
| 441 | 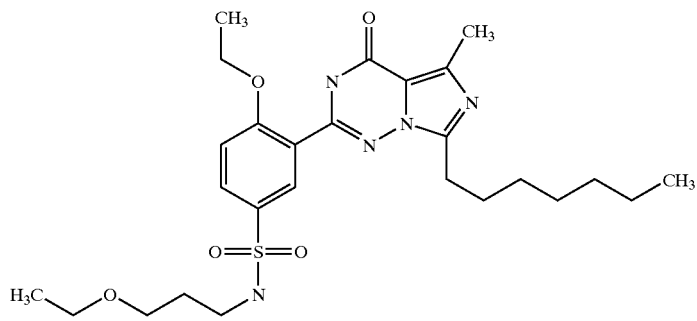 | 533,6952 | 90 | 534 |
| 442 | 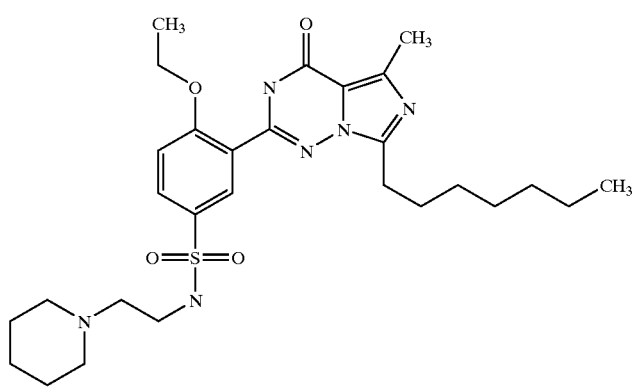 | 558,7487 | 75 | 559 |

| | | | |
|---|---|---|---|
| 443 | 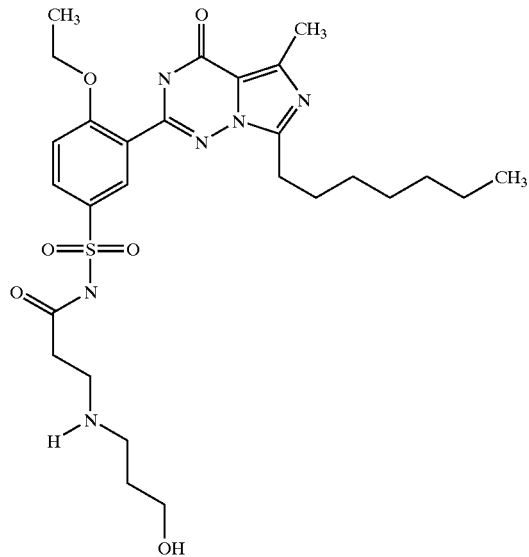 | 576,7205 66 | 577 |
| 444 | 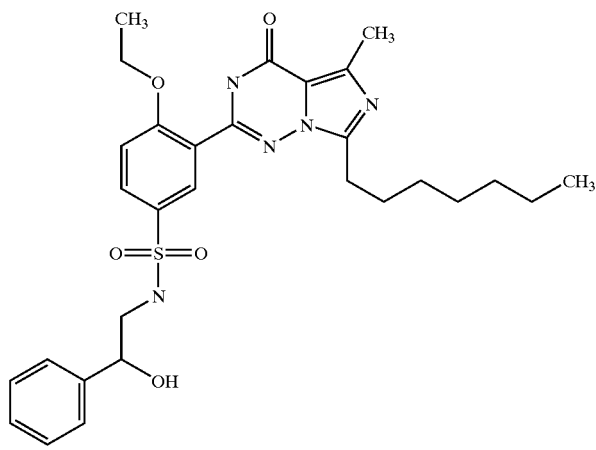 | 567,7127 77 | 568 |
| 445 | 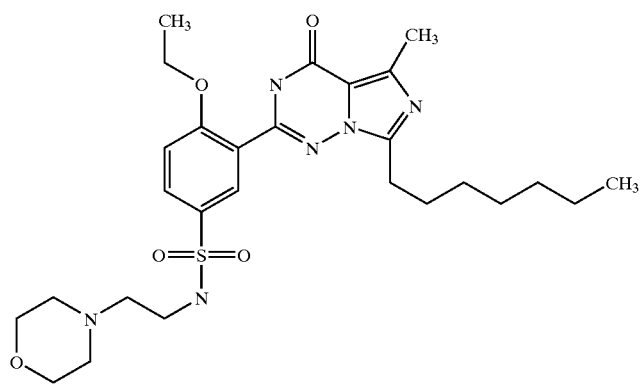 | 560,7211 79 | 561 |

TABLE 1-continued
| | | | |
|---|---|---|---|
| 446 | | 573,7197 76 | 574 |
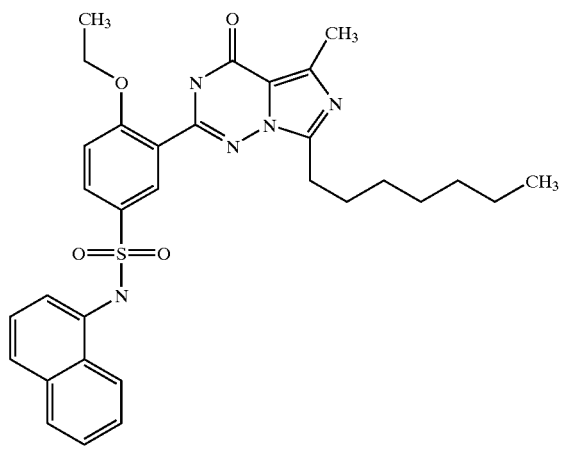
| | | | |
|---|---|---|---|
| 447 | | 567,7127 80 | 568 |
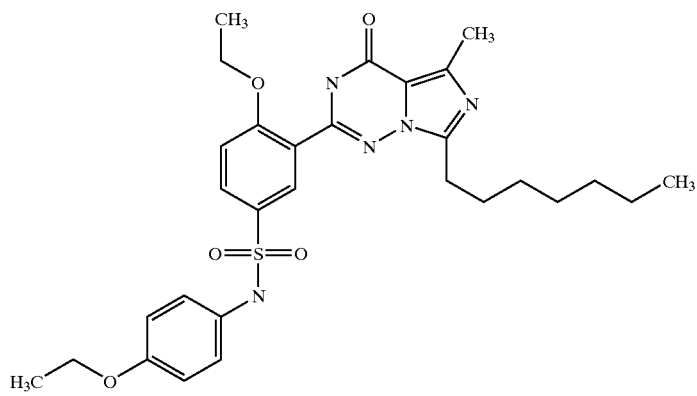
| | | | |
|---|---|---|---|
| 448 | | 553,6857 83 | 554 |
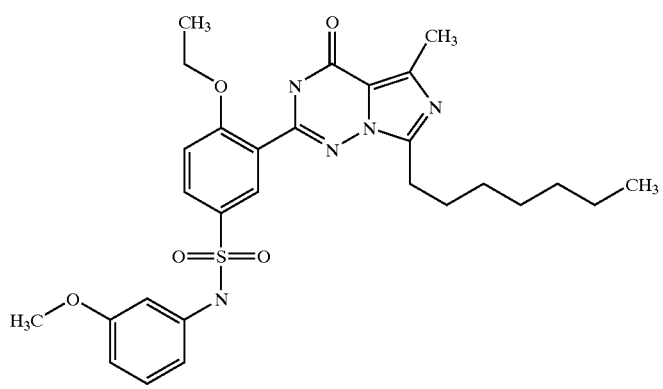

TABLE 1-continued
| | | | |
|---|---|---|---|
| 449 | | 592,5492  30 | 592 |
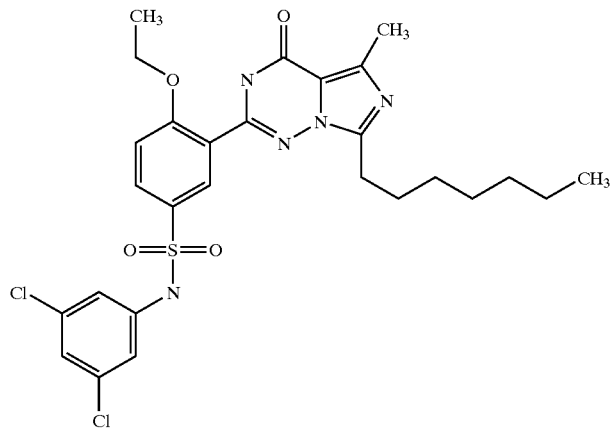
| | | | |
|---|---|---|---|
| 450 | | 592,5492  43 | 592 |
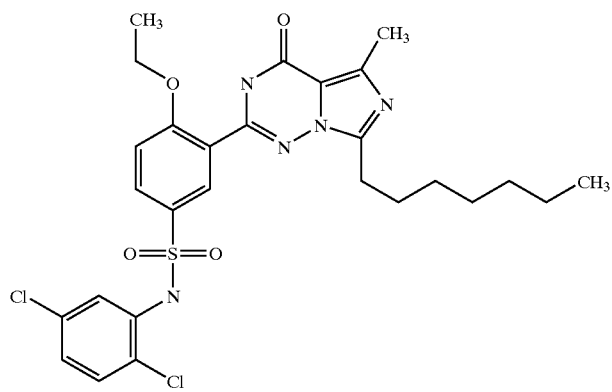
| | | | |
|---|---|---|---|
| 451 | | 609,750  78 | 610 |
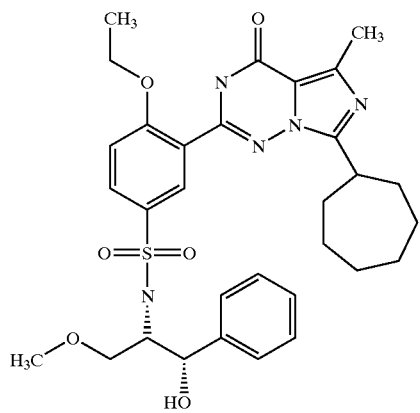

TABLE 1-continued
| | | | |
|---|---|---|---|
| 452 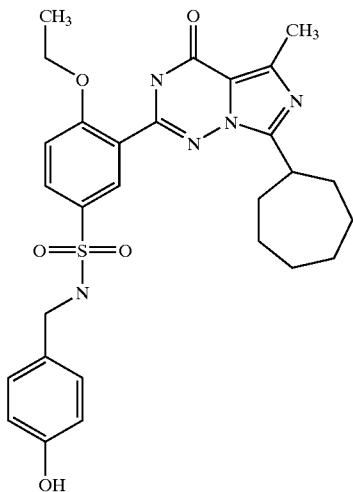 | 551,670 | 74 | 552 |
| 453 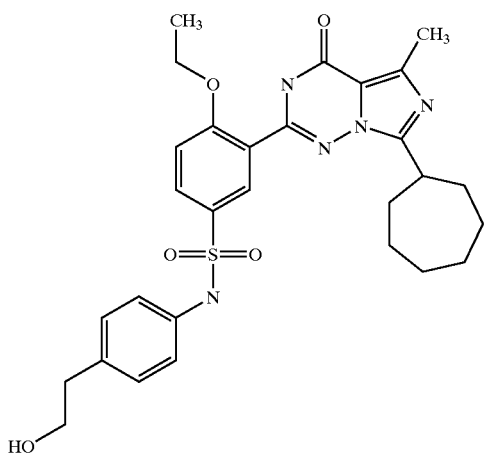 | 565,697 | 65 | 566 |
| 454 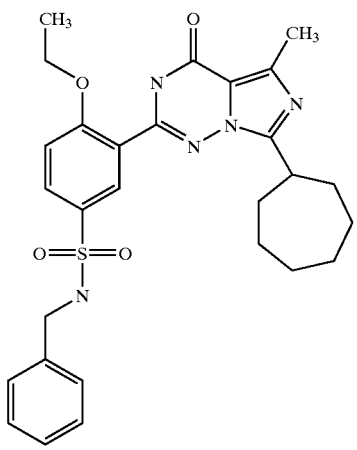 | 535,670 | 80 | 536 |

| | | | |
|---|---|---|---|
| 455 | 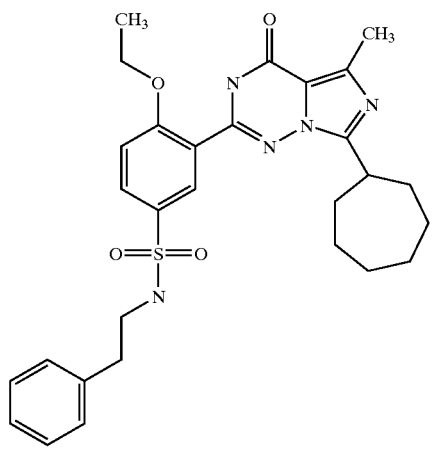 | 549,697 79 | 550 |
| 456 | 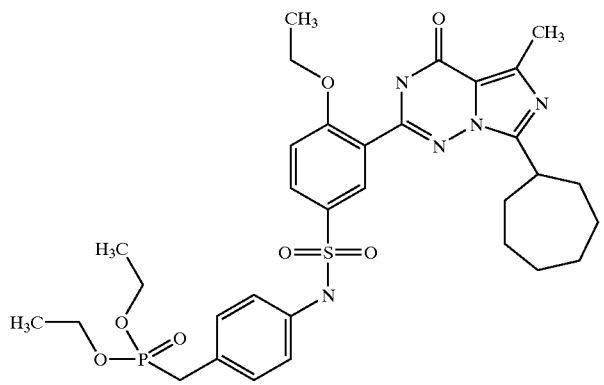 | 671,759 83 | 672 |
| 457 | 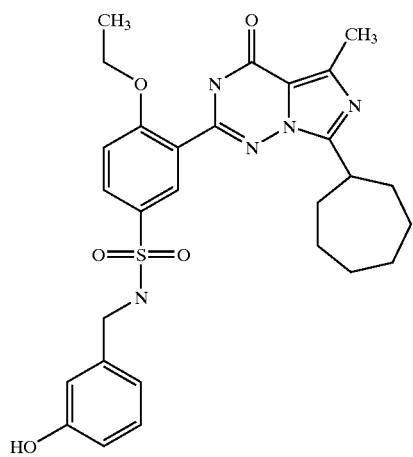 | 551,670 69 | 552 |

TABLE 1-continued
| | | | | | |
|---|---|---|---|---|---|
| 458 | 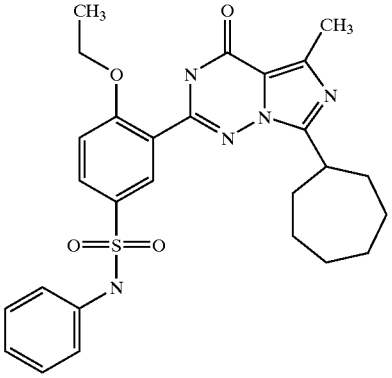 | | 521,643 | 80 | 522 |
| 459 | 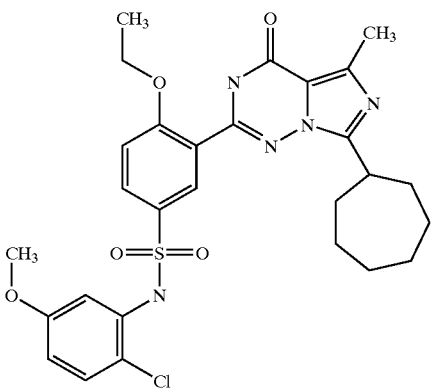 | | 586,115 | 34 | 586 |
| 460 | 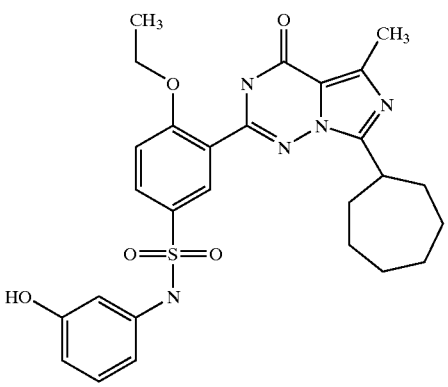 | | 537,643 | 76 | 538 |
| 461 | 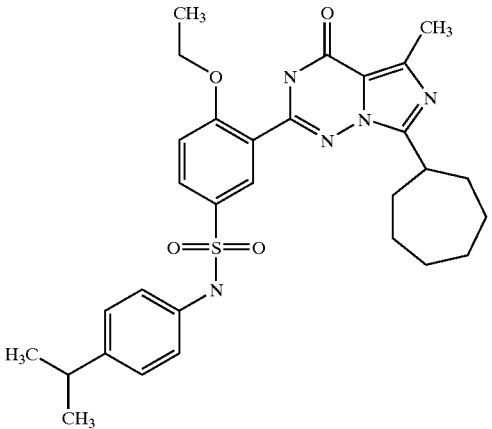 | | 563,724 | 67 | 564 |

TABLE 1-continued
| | | | |
|---|---|---|---|
| 462 | | 564,712 73 | 565 |
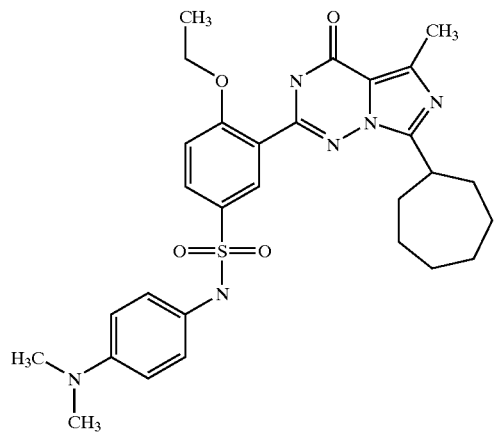
| | | | |
|---|---|---|---|
| 463 | | 593,751 79 | 594 |
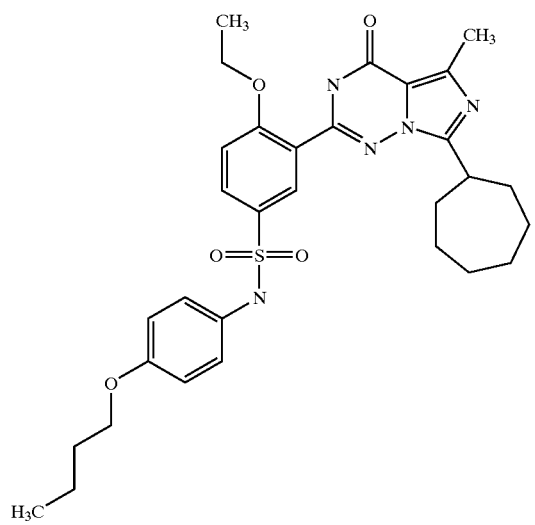
| | | | |
|---|---|---|---|
| 464 | | 592,723 72 | 593 |
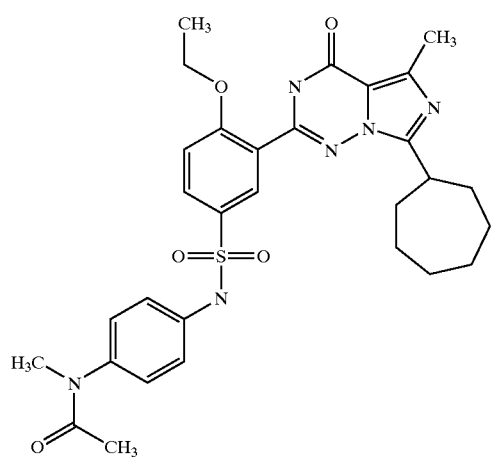

TABLE 1-continued
| | | | |
|---|---|---|---|
| 465 | 557,624 | 78 | 558 |
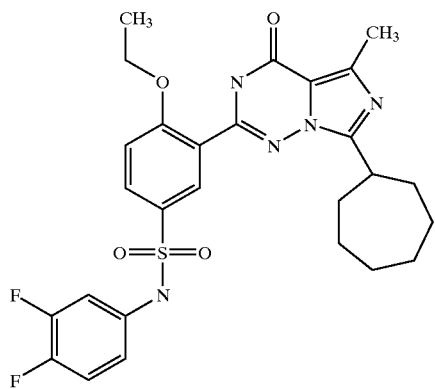
| | | | |
|---|---|---|---|
| 466 | 563,681 | 44 | 564 |
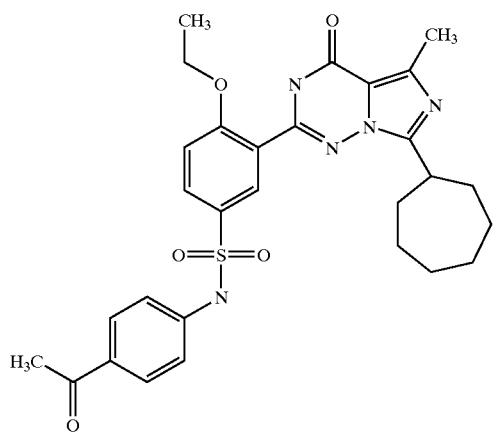
| | | | |
|---|---|---|---|
| 467 | 539,634 | 67 | 540 |
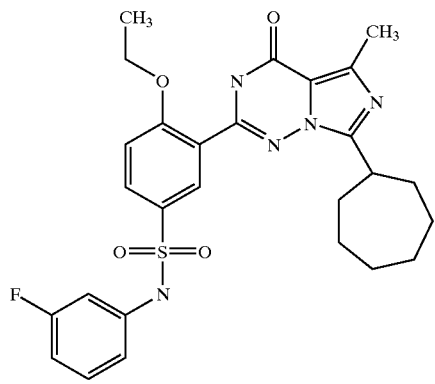

TABLE 1-continued
| | | | |
|---|---|---|---|
| 468 | 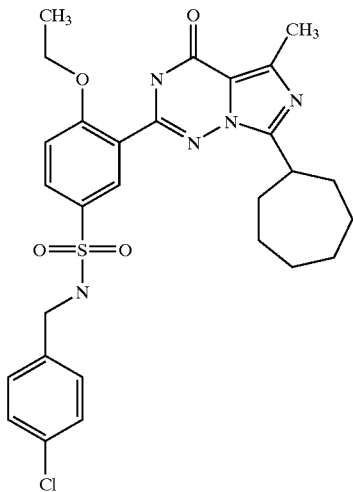 | 570,115 75 | 570 |
| 469 | 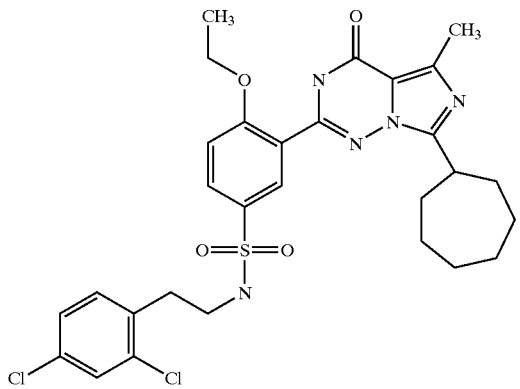 | 618,587 65 | 618 |
| 470 | 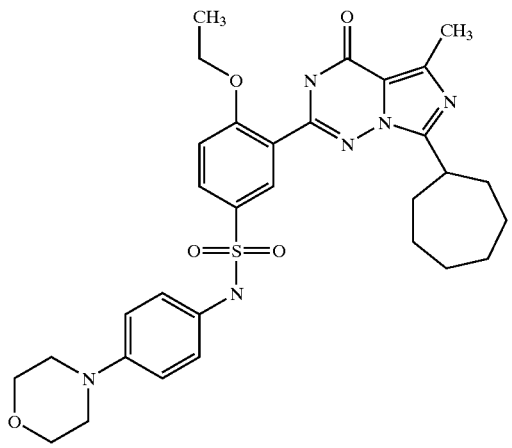 | 606,750 69 | 607 |

TABLE 1-continued
| | | | | |
|---|---|---|---|---|
| 471 | 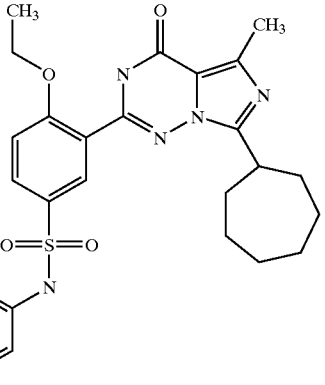 | 581,696 | 80 | 582 |
| 472 | 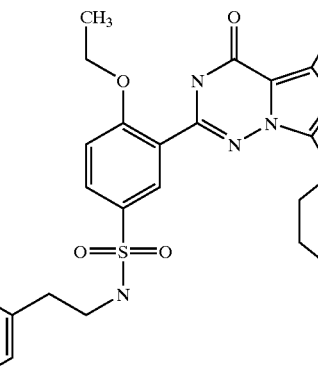 | 579,724 | 76 | 580 |
| 473 | 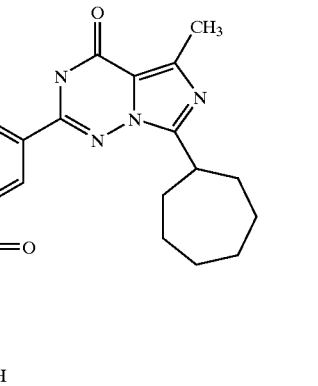 | 565,697 | 72 | 566 |
| 474 | 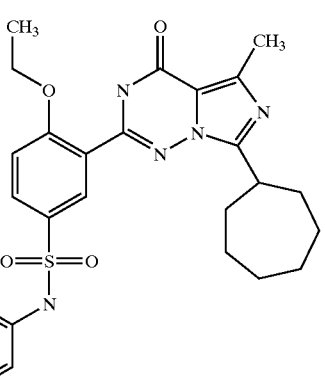 | 551,670 | 78 | 552 |

TABLE 1-continued

| # | Structure | | | |
|---|---|---|---|---|
| 475 | (4-chlorophenyl sulfonamide derivative) | 556,088 | 67 | 556 |
| 476 | (2-methoxyphenyl sulfonamide derivative) | 551,670 | 79 | 552 |
| 477 | (3-fluoro-4-methoxyphenyl sulfonamide derivative) | 569,660 | 77 | 570 |
| 478 | (4-trifluoromethylphenyl sulfonamide derivative) | 589,642 | 62 | 590 |

TABLE 1-continued
| | | | | |
|---|---|---|---|---|
| 479 | 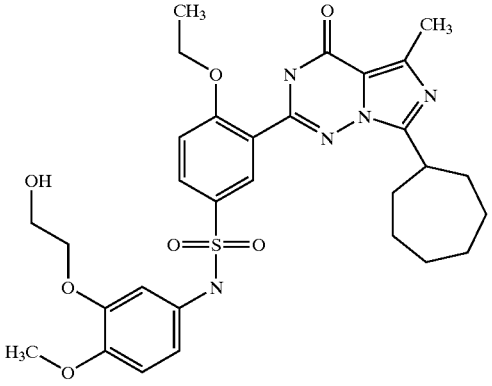 | 611,723 | 66 | 612 |
| 480 | 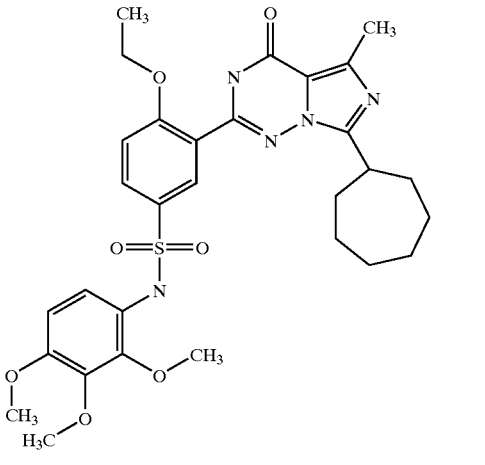 | 611,723 | 86 | 612 |
| 481 | 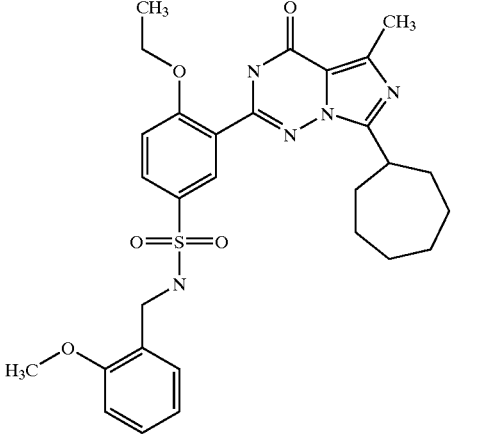 | 565,697 | 80 | 566 |
| 482 | 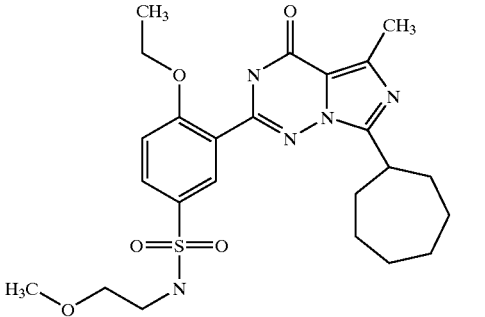 | 503,625 | 85 | 504 |

| | | | |
|---|---|---|---|
| 483 | | 556,689 88 | 557 |
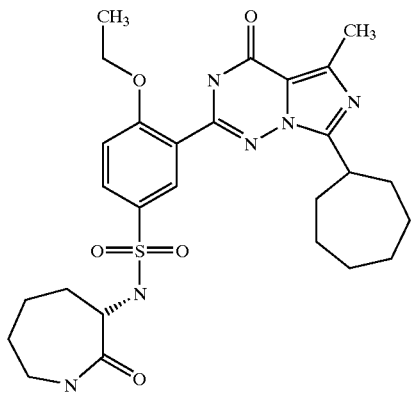
| | | | |
|---|---|---|---|
| 484 | | 529,663 81 | 530 |
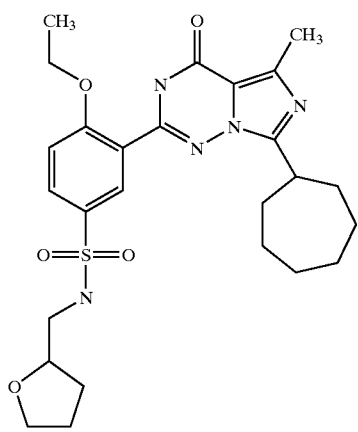
| | | | |
|---|---|---|---|
| 485 | | 531,679 86 | 532 |
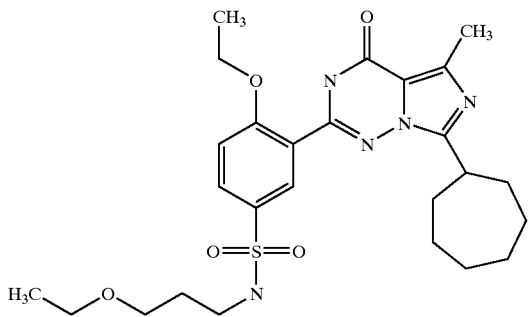

TABLE 1-continued
| 486 | 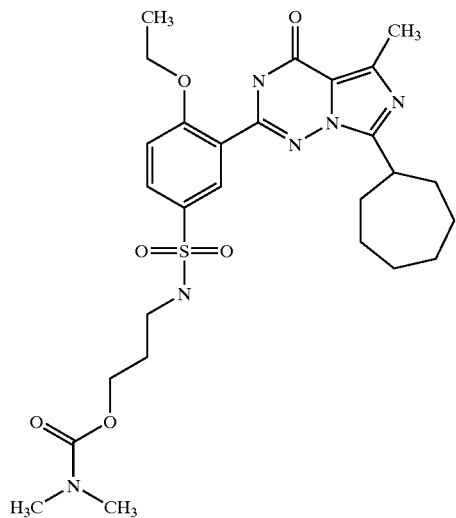 | 574,705 | 33 | 575 |
| 487 | 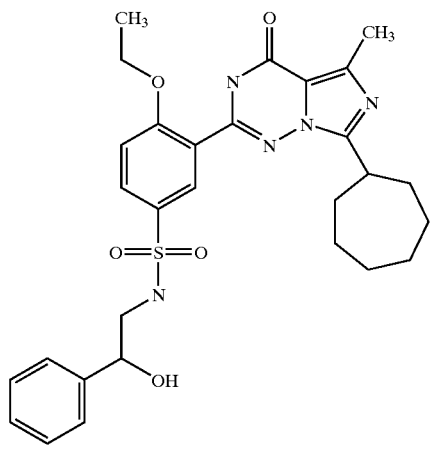 | 565,697 | 61 | 566 |
| 488 | 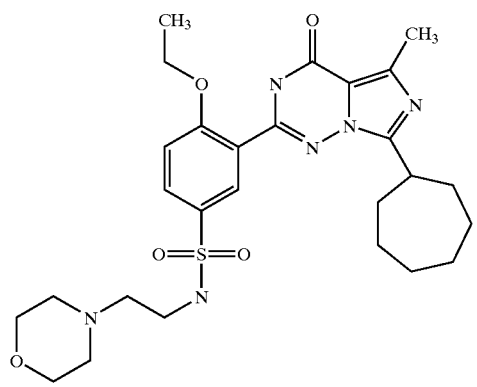 | 558,705 | 47 | 559 |

TABLE 1-continued
| | | | |
|---|---|---|---|
| 489 | 571,704 | 59 | 572 |
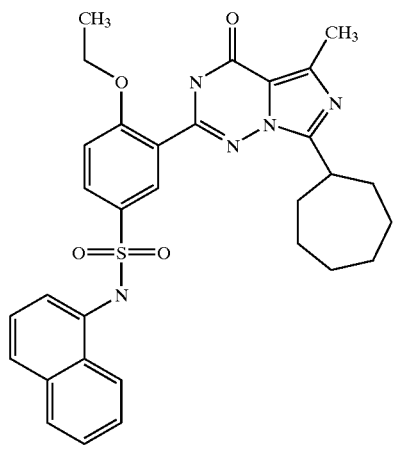
| | | | |
|---|---|---|---|
| 490 | 565,697 | 70 | 566 |
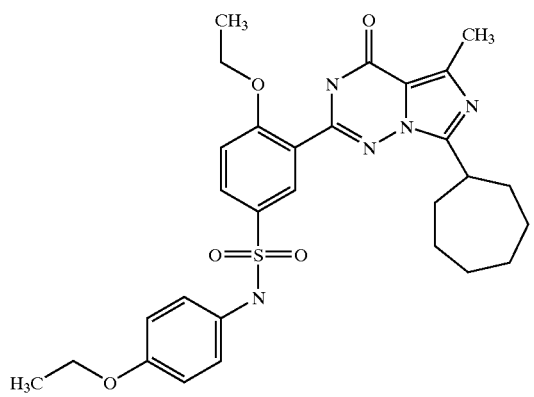
| | | | |
|---|---|---|---|
| 491 | 551,670 | 65 | 552 |
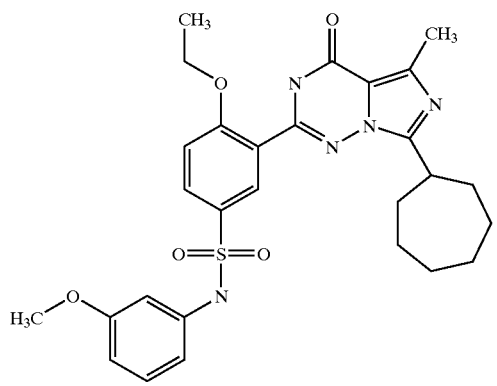

TABLE 1-continued
| | | | | |
|---|---|---|---|---|
| 492 | 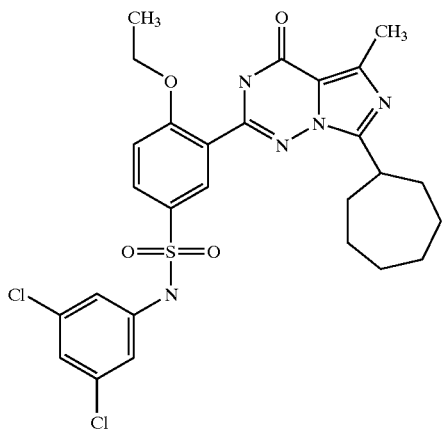 | 590,533 | 46 | 590 |
| 493 | 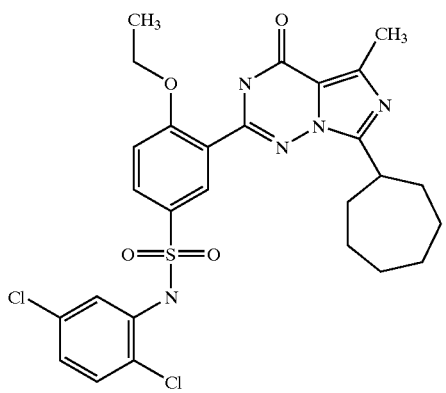 | 590,533 | 83 | 590 |
| 494 | 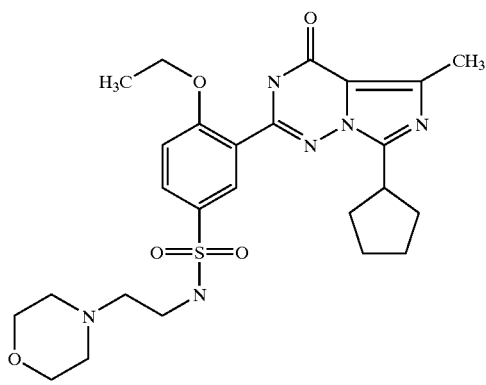 | 530,65 | 82 | 531 |

TABLE 1-continued
| | | | |
|---|---|---|---|
| 495 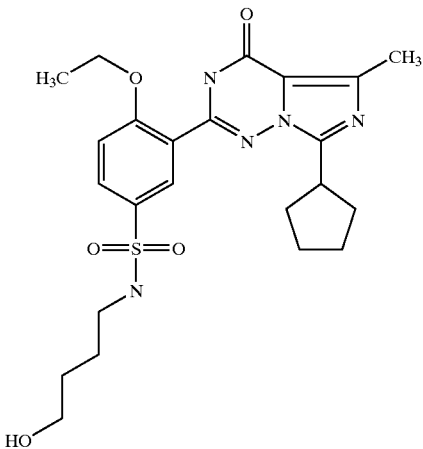 | 489,60 | 49 | 490 |
| 496 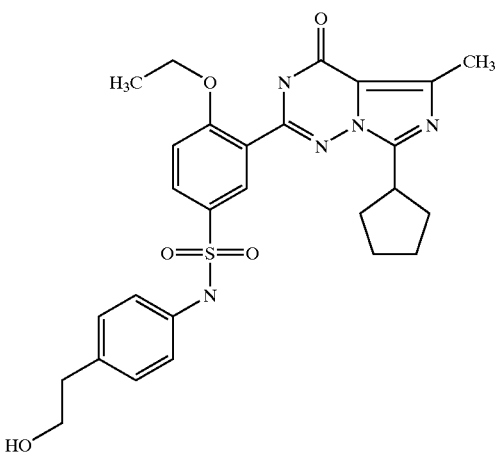 | 537,64 | 63 | 538 |
| 497 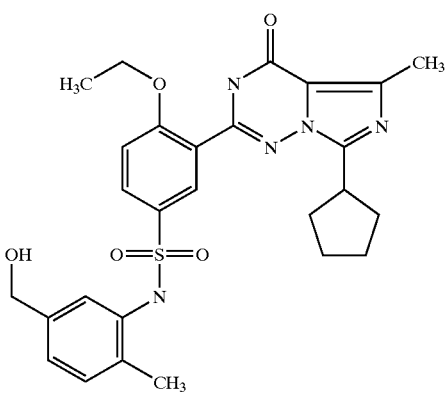 | 537,64 | 44 | 538 |

TABLE 1-continued
| | | | | |
|---|---|---|---|---|
| 498 | 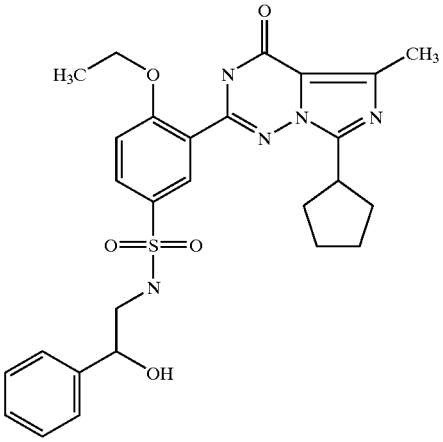 | 537,64 | 72 | 538 |
| 499 | 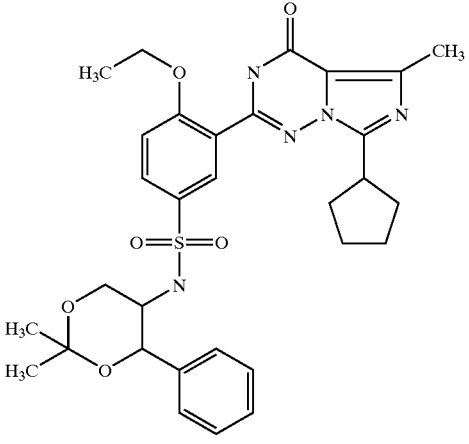 | 607,73 | 50 | 608 |
| 500 | 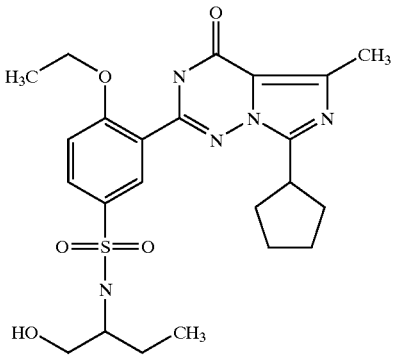 | 489,60 | 64 | 490 |
| 501 | 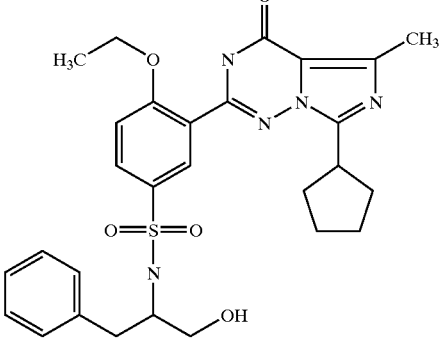 | 551,67 | 70 | 552 |

TABLE 1-continued
| | | | | |
|---|---|---|---|---|
| 502 | 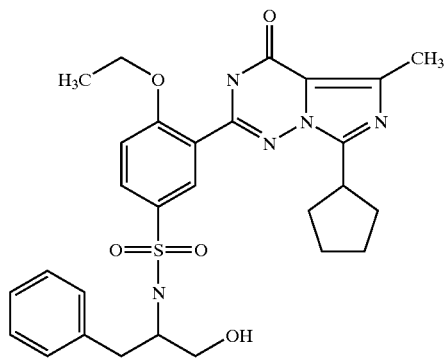 | 551,67 | 77 | 552 |
| 503 | 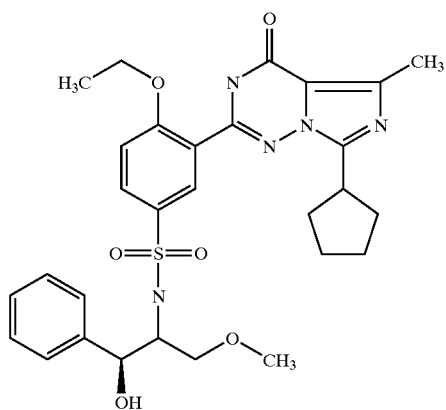 | 581,70 | 85 | 582 |
| 504 | 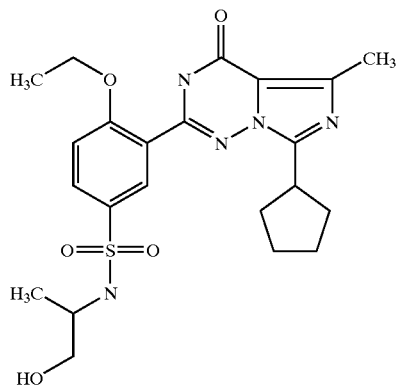 | 475,57 | 45 | 476 |
| 505 | 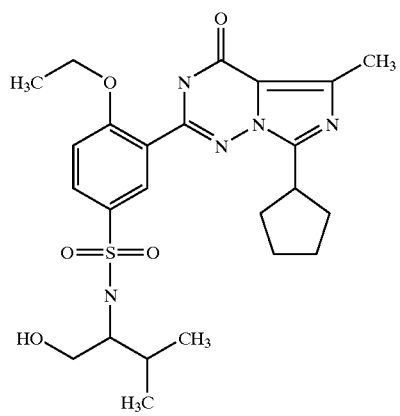 | 503,63 | 74 | 504 |

TABLE 1-continued
| | | | | |
|---|---|---|---|---|
| 506 | 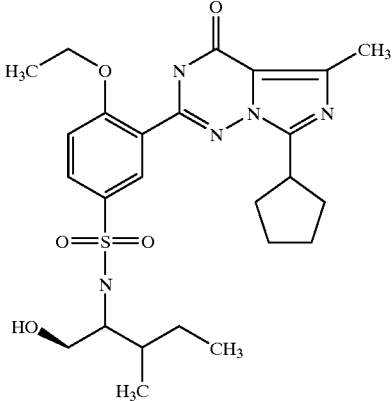 | 517,65 | 76 | 518 |
| 507 | 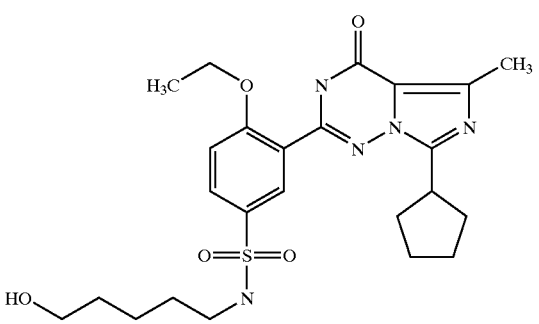 | 503,63 | 59 | 504 |
| 508 | 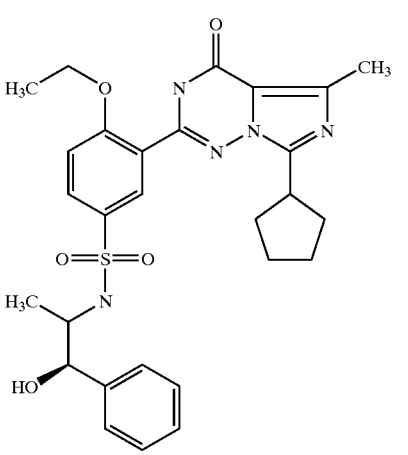 | 551,67 | 74 | 552 |
| 509 | 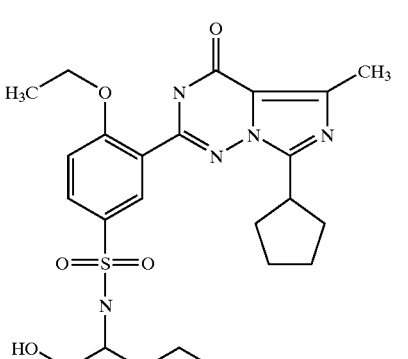 | 503,63 | 70 | 504 |

TABLE 1-continued

| # | Structure | | | |
|---|---|---|---|---|
| 510 | (structure) | 551.67 | 73 | 552 |
| 511 | (structure) | 489.60 | 57 | 490 |
| 512 | (structure) | 489.60 | 44 | 490 |
| 513 | (structure) | 475.57 | 42 | 476 |

TABLE 1-continued
| | | | | |
|---|---|---|---|---|
| 514 | 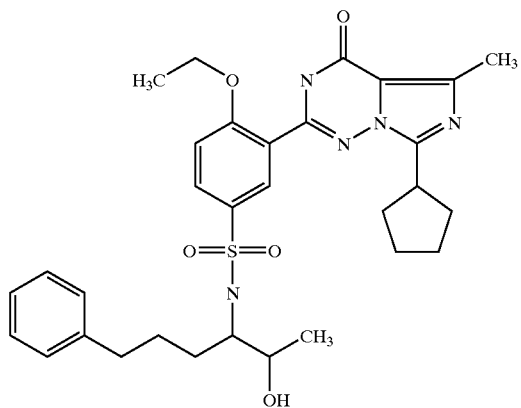 | 593,75 | 68 | 594 |
| 515 | 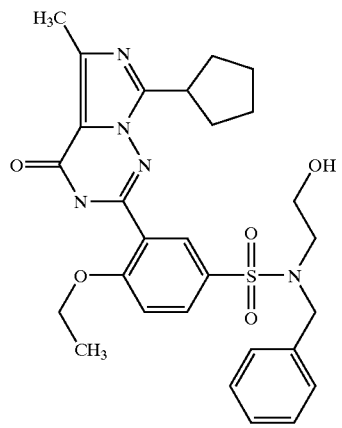 | 551,67 | 77 | 552 |
| 516 | 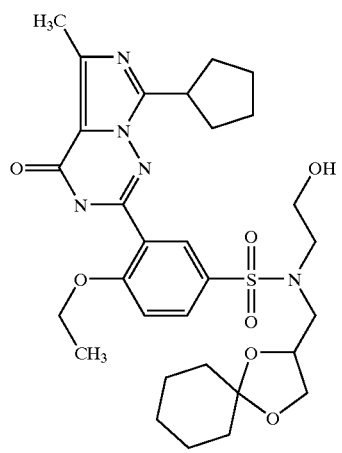 | 615,75 | 78 | 616 |

TABLE 1-continued

| | | | | |
|---|---|---|---|---|
| 517 | [structure] | 503,63 | 52 | 504 |
| 518 | [structure] | 529,66 | 59 | 530 |
| 519 | [structure] | 515,64 | 50 | 516 |
| 520 | [structure] | 584,74 | 42 | 585 |

TABLE 1-continued
| | | | |
|---|---|---|---|
| 521 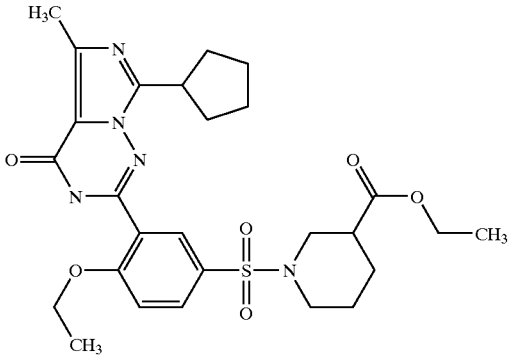 | 557,67 | 82 | 558 |
| 522 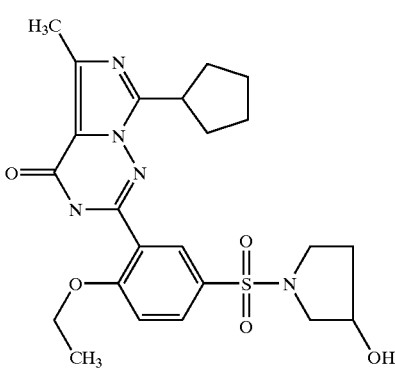 | 487,58 | 30 | 488 |
| 523 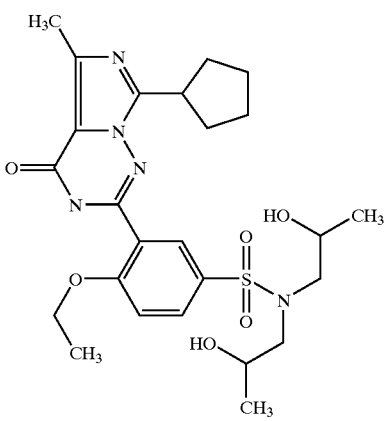 | 533,65 | 60 | 534 |
| 524 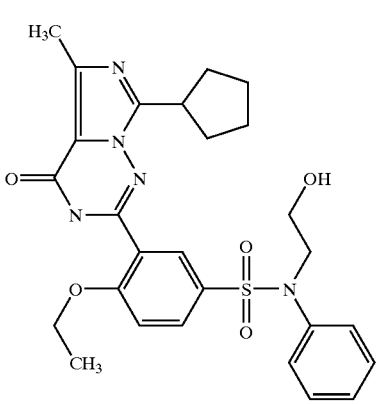 | 537,64 | 81 | 538 |

TABLE 1-continued
| | | | |
|---|---|---|---|
| 525 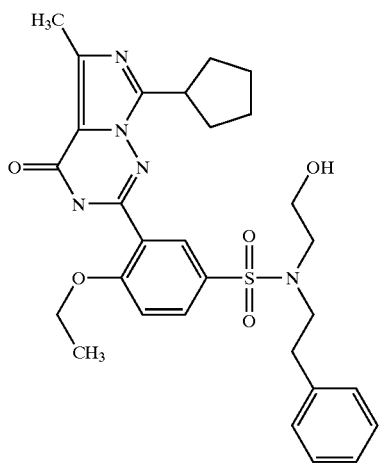 | 565,70 | 82 | 566 |
| 526 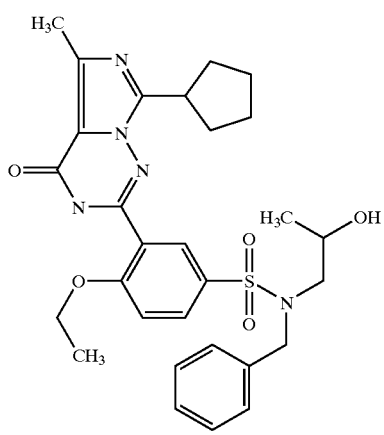 | 565,70 | 56 | 566 |
| 527 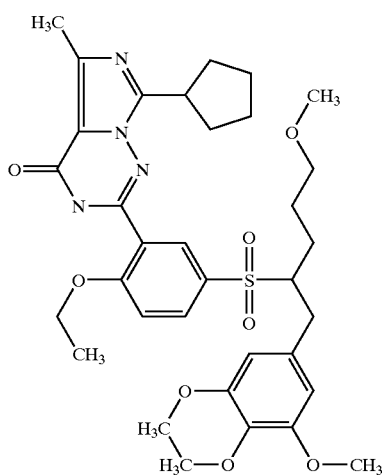 | 669,80 | 82 | 670 |

TABLE 1-continued
| | | | | |
|---|---|---|---|---|
| 528 | 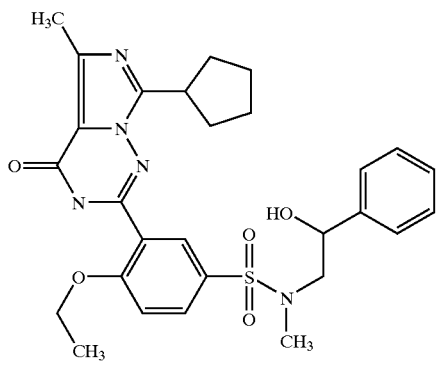 | 551,67 | 77 | 552 |
| 529 | 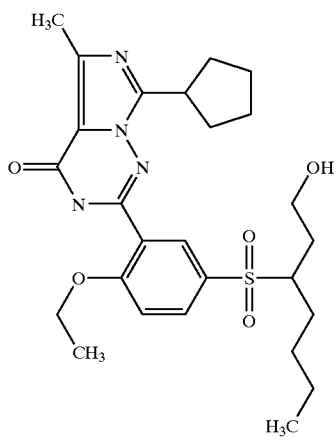 | 517,65 | 91 | 518 |
| 530 | 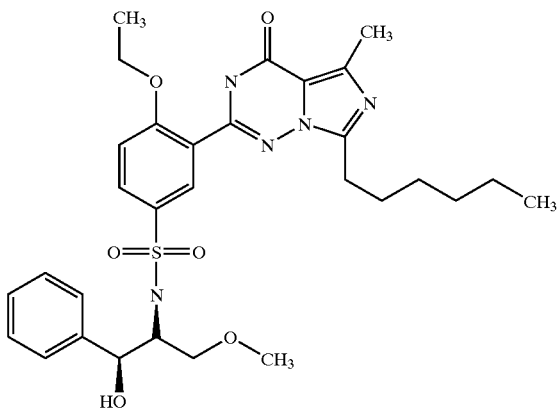 | 597,7392 | 84 | 598 |

TABLE 1-continued
| 531 | | 539,6586 | 74 | 540 |
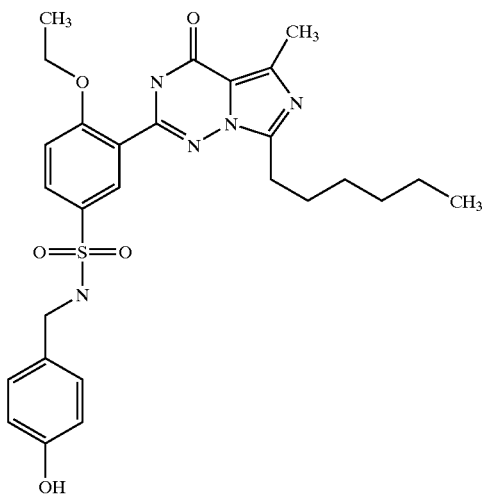
| 532 | | 553,6857 | 77 | 554 |
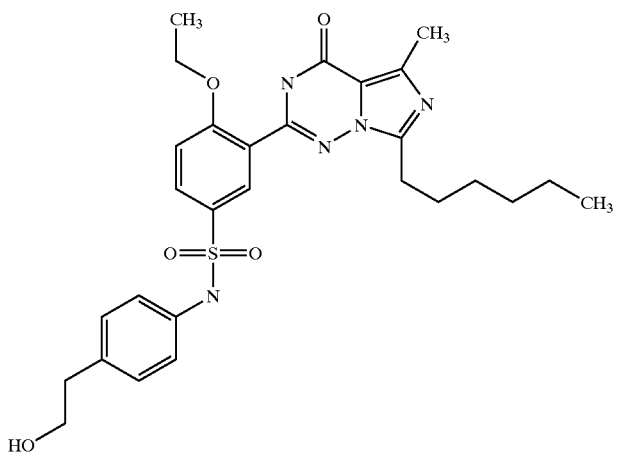
| 533 | | 523,6592 | 93 | 524 |
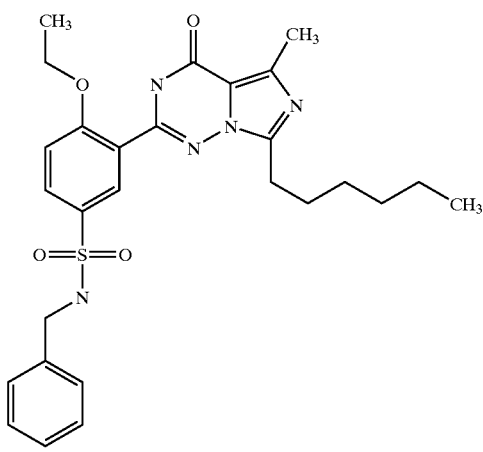

TABLE 1-continued
| | | | | |
|---|---|---|---|---|
| 534 | | 537,6863 | 94 | 538 |
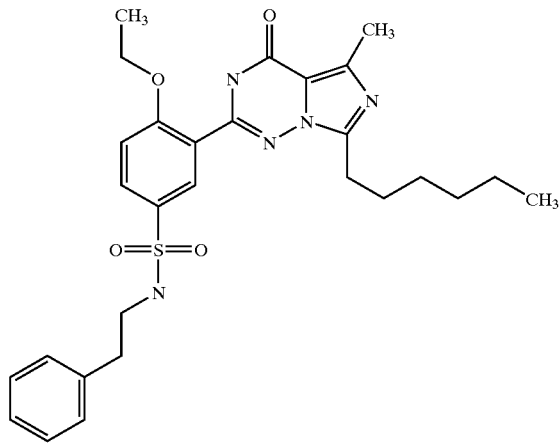
| | | | | |
|---|---|---|---|---|
| 535 | | 659,74 | 89 | 660 |
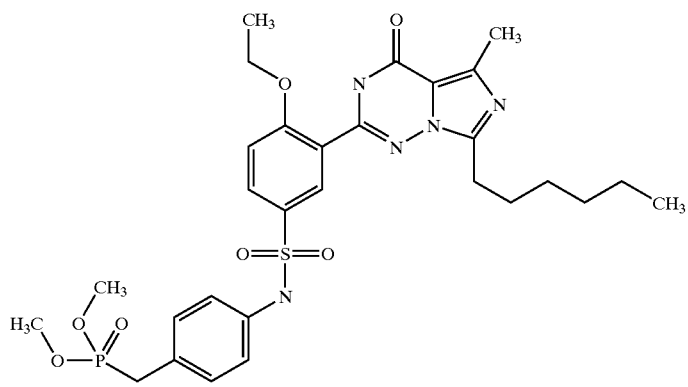
| | | | | |
|---|---|---|---|---|
| 536 | | 616,7637 | 80 | 617 |
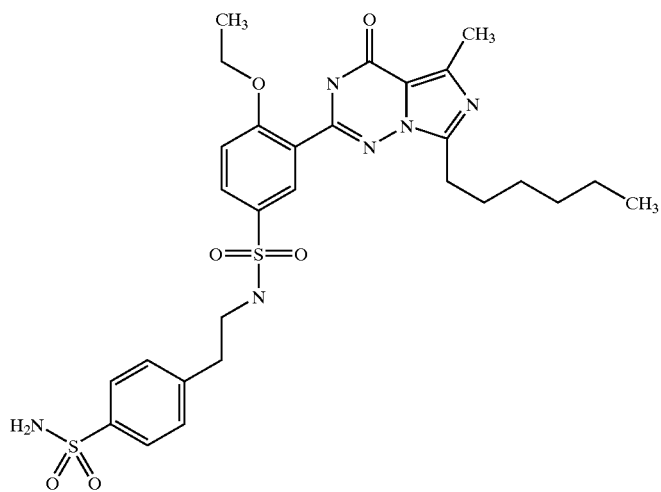

TABLE 1-continued
| | | | | |
|---|---|---|---|---|
| 537 | 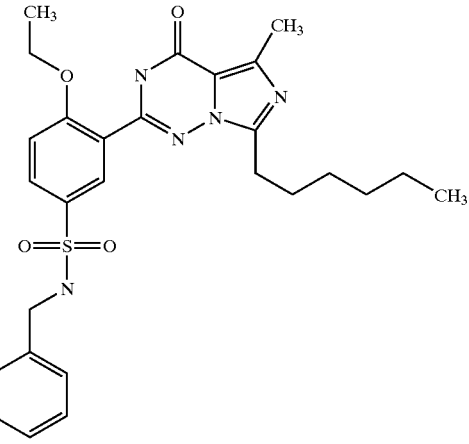 | 539,6586 | 73 | 540 |
| 538 | 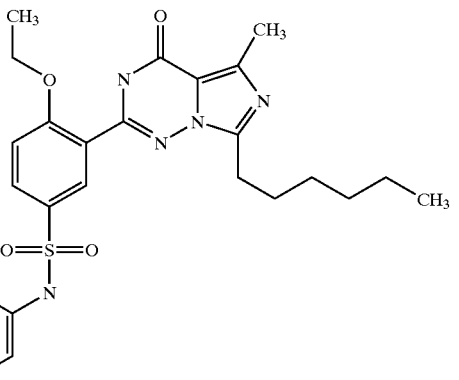 | 509,6321 | 92 | 510 |
| 539 | 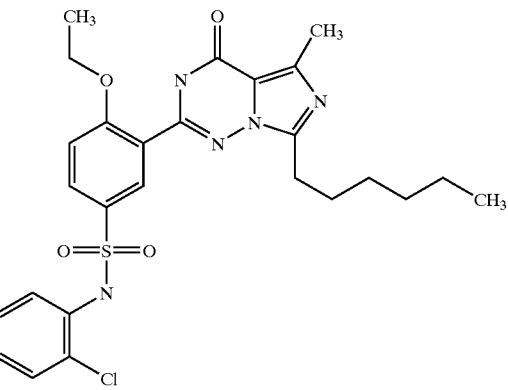 | 574,1036 | 48 | 574 |
| 540 | 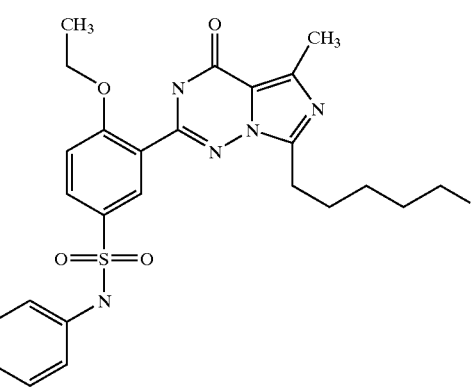 | 525,6315 | 75 | 526 |

TABLE 1-continued
| | | | |
|---|---|---|---|
| 541 | 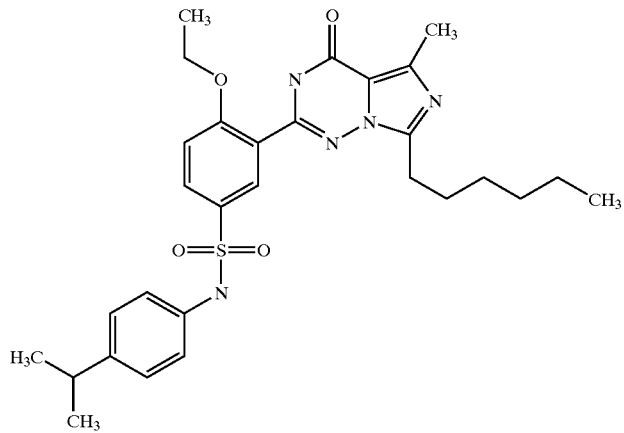 | 551,7133 84 | 552 |
| 542 | 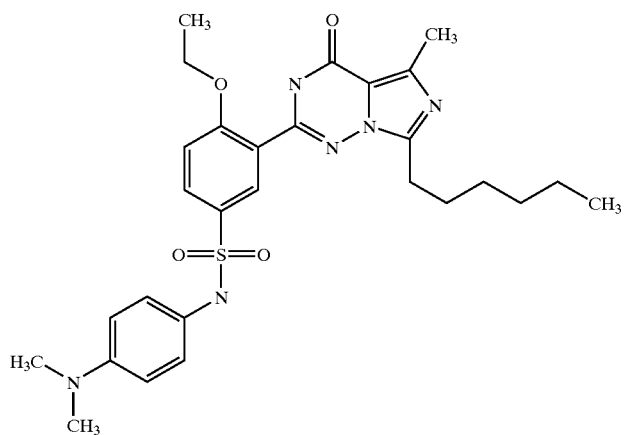 | 552,7009 75 | 553 |
| 543 | 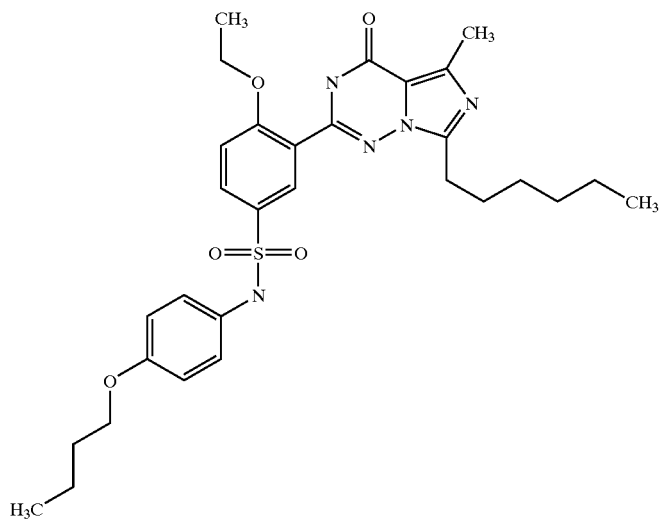 | 581,7398 83 | 582 |

TABLE 1-continued
| 544 | 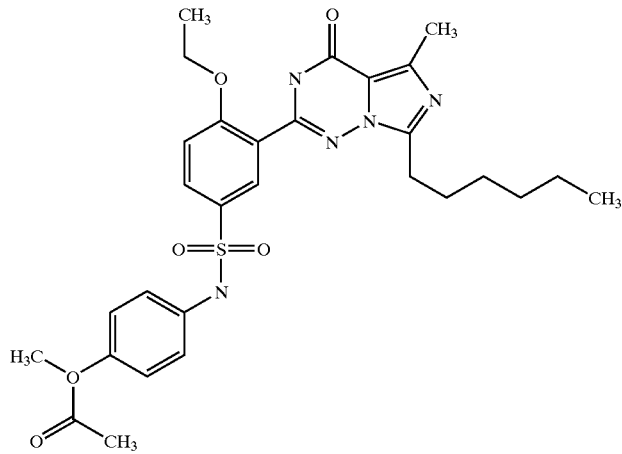 | 580,7115 | 80 | 581 |
| 545 | 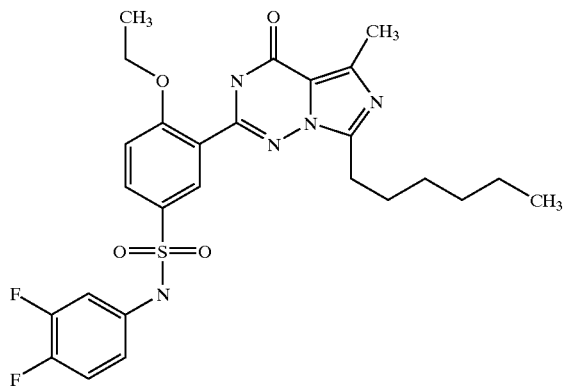 | 545,6129 | 91 | 546 |
| 546 | 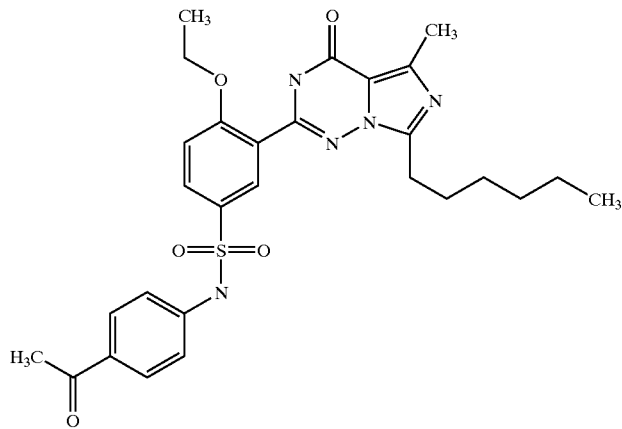 | 551,6697 | 54 | 552 |

| | | | |
|---|---|---|---|
| 547 | 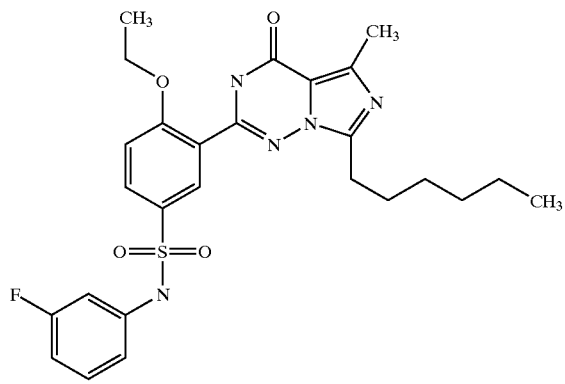 | 527,6225 89 | 528 |
| 548 | 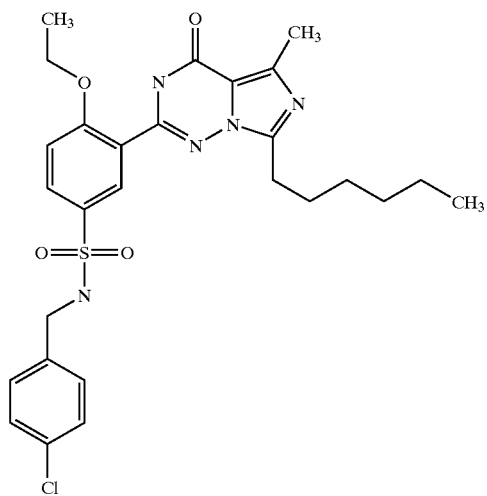 | 558,1042 83 | 558 |
| 549 | 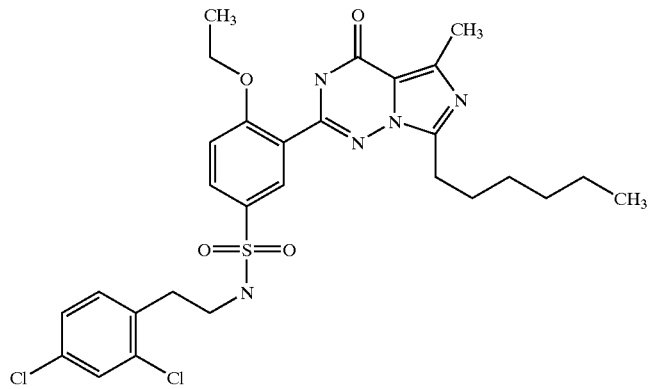 | 606,5763 55 | 606 |

TABLE 1-continued
| 550 | 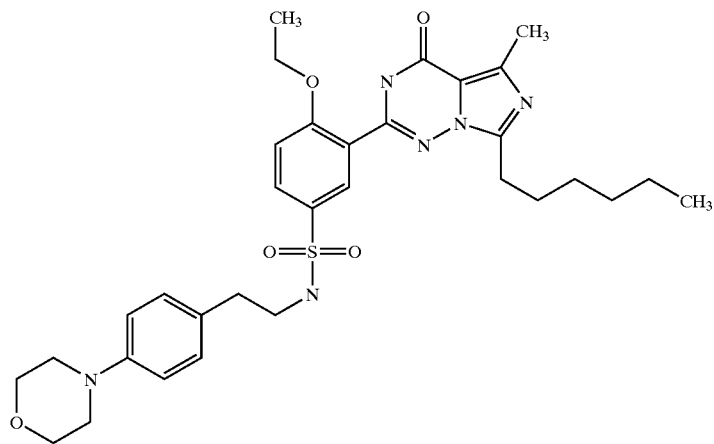 | 594,7386 | 83 | 595 |
| 551 | 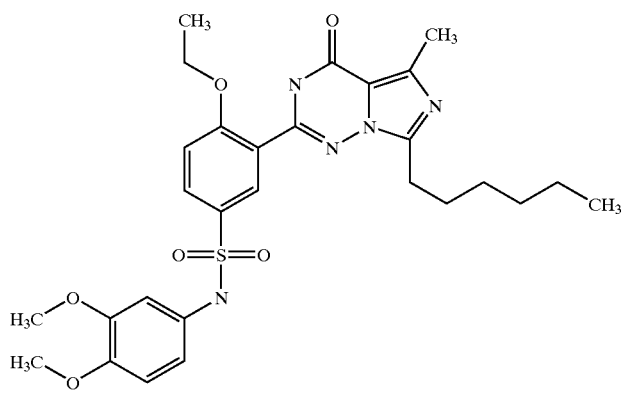 | 569,6851 | 87 | 570 |
| 552 | 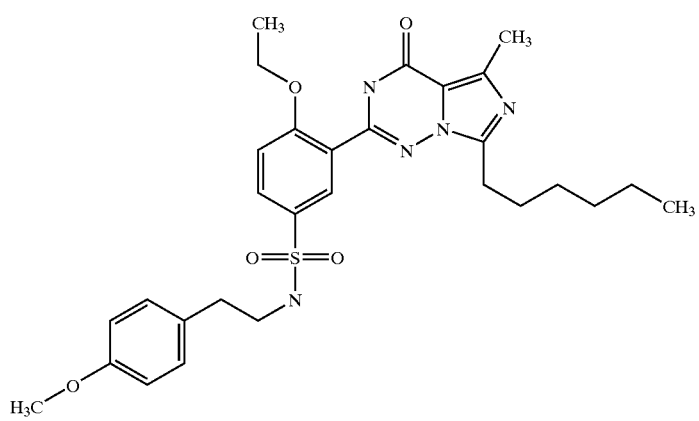 | 567,7127 | 79 | 568 |

TABLE 1-continued
| | | | | |
|---|---|---|---|---|
| 553 | 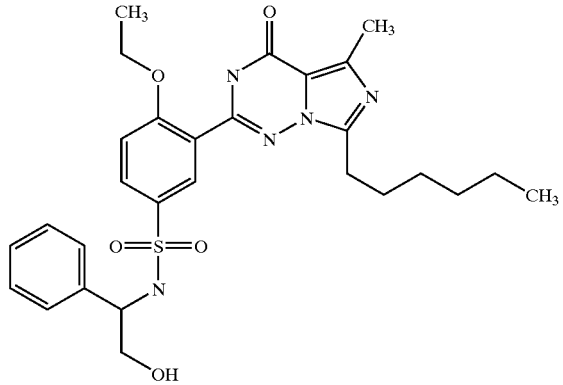 | 553,6857 | 88 | 554 |
| 554 | 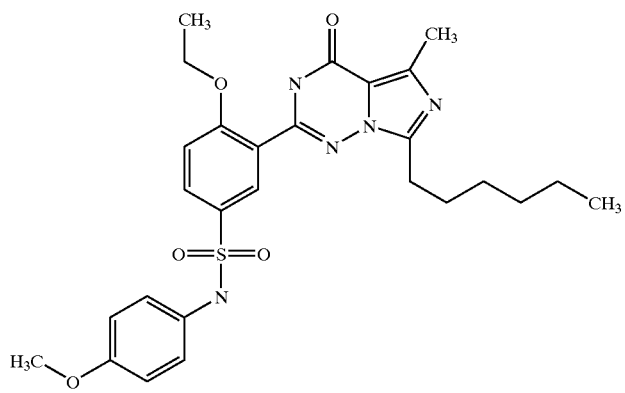 | 539,6586 | 88 | 540 |
| 555 | 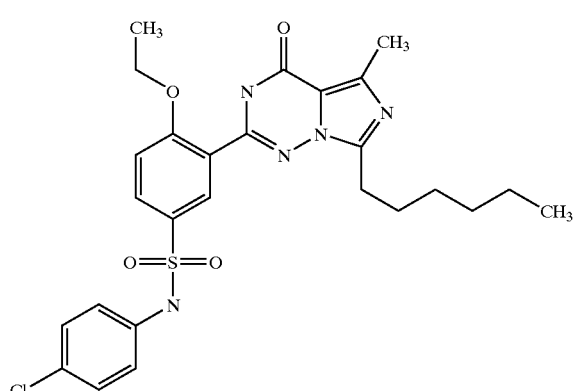 | 544,0771 | 83 | 544 |
| 556 | 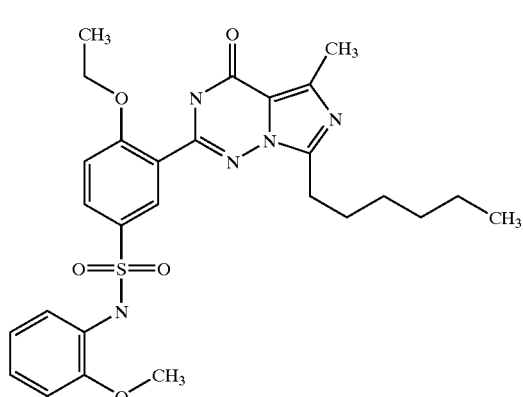 | 539,6586 | 93 | 540 |

TABLE 1-continued
| 557 | | 557,649 | 88 | 558 |
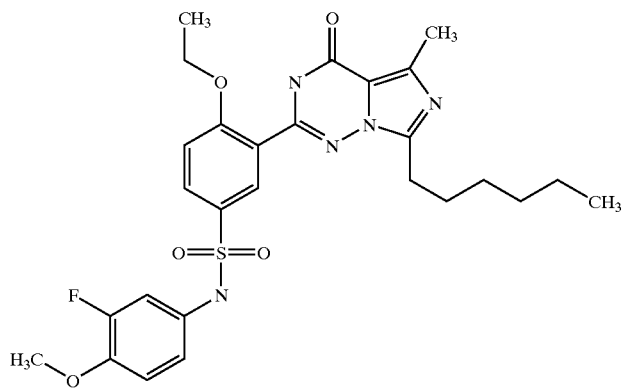
| 558 | | 577,6305 | 77 | 578 |
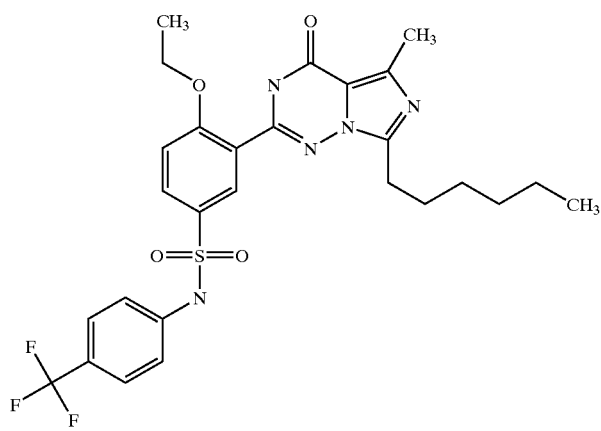
| 559 | | 599,7115 | 81 | 600 |
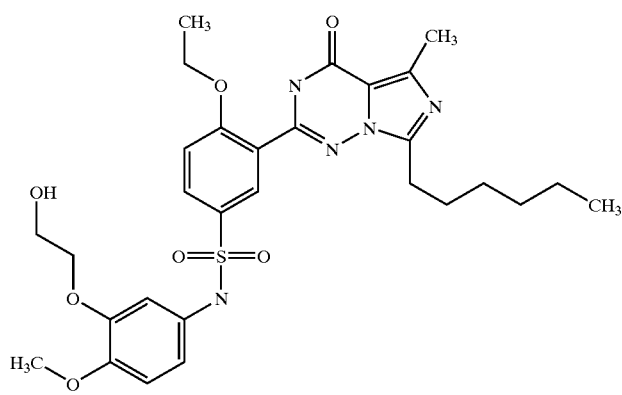

TABLE 1-continued
| | | | | |
|---|---|---|---|---|
| 560 | 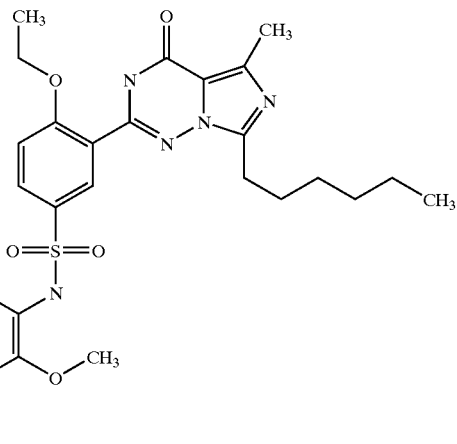 | 599,7115 | 88 | 600 |
| 561 | 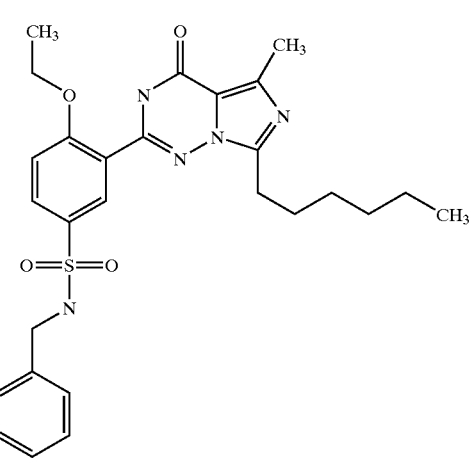 | 553,6857 | 89 | 554 |
| 562 | 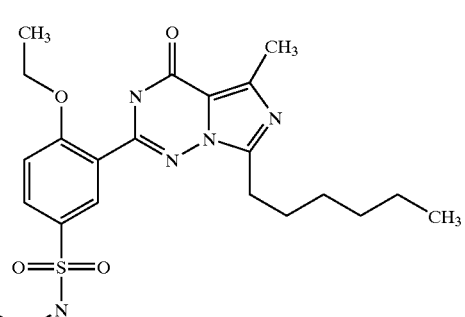 | 491,614 | 92 | 492 |
| 563 | 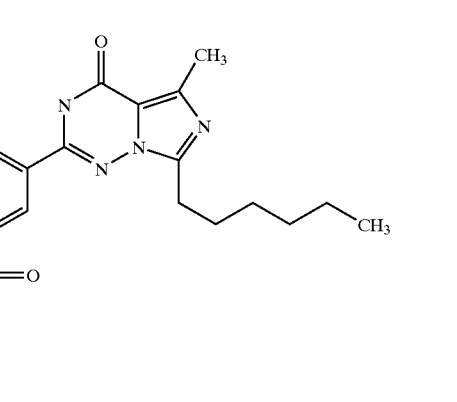 | 517,6086 | 83 | 518 |

TABLE 1-continued
| | | | |
|---|---|---|---|
| 564 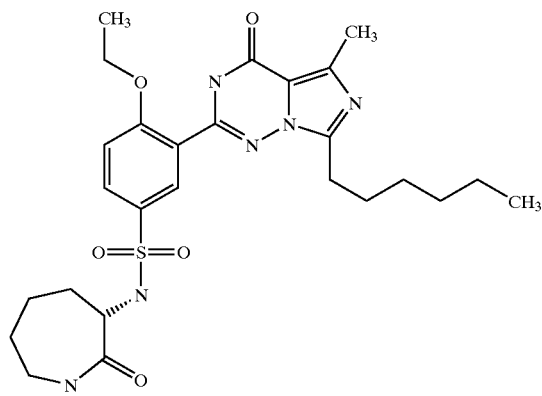 | | 544,678  94 | 545 |
| 565 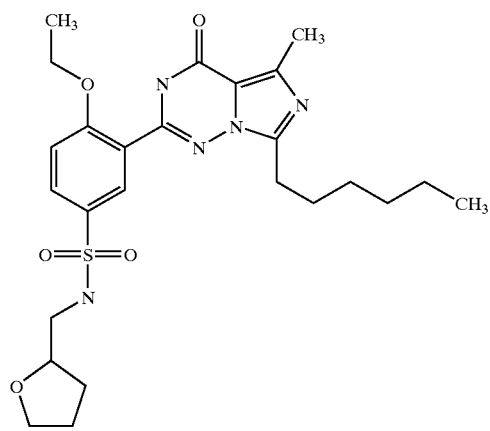 | | 517,6522  94 | 518 |
| 566 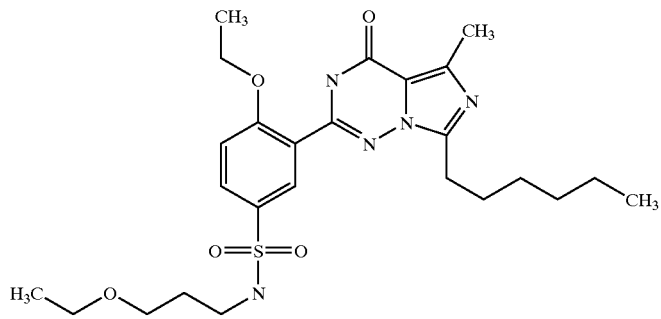 | | 519,6681  95 | 520 |

TABLE 1-continued
| 567 | | 562,6934 | 74 | 563 |
|---|---|---|---|---|
| 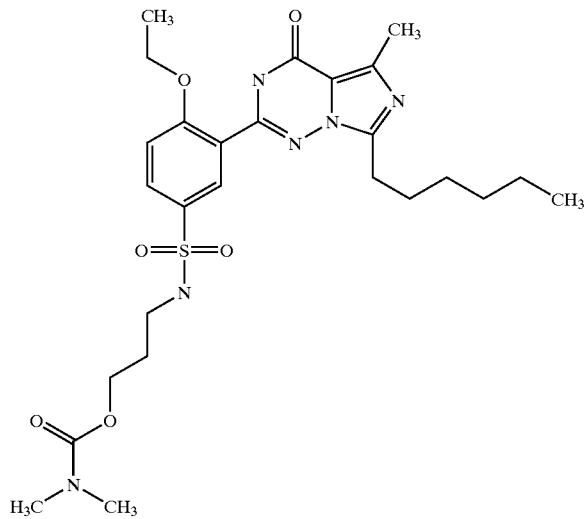 | | | | |
| 568 | | 553,6857 | 80 | 554 |
| 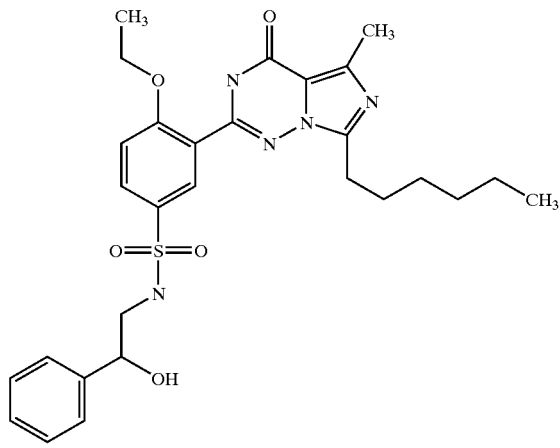 | | | | |
| 569 | | 546,694 | 87 | 547 |
| 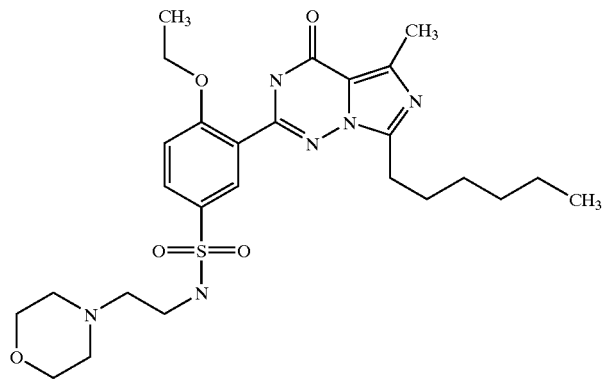 | | | | |

TABLE 1-continued
| | | | |
|---|---|---|---|
| 570 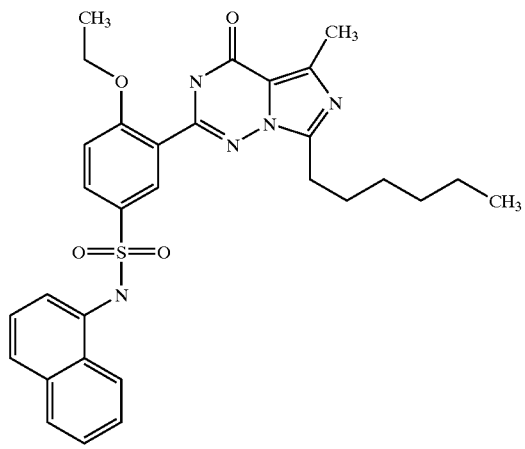 | 559,6926 | 73 | 560 |
| 571 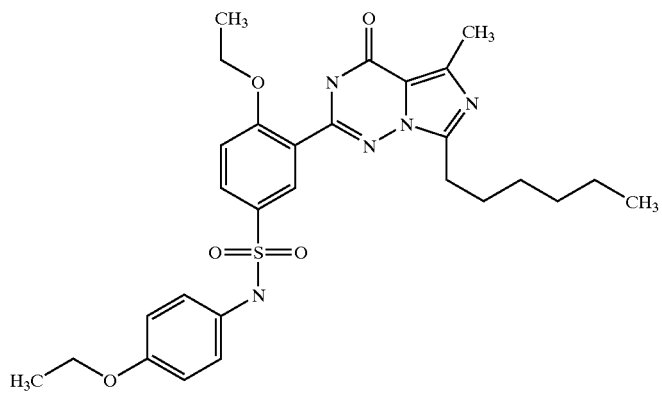 | 553,6857 | 86 | 554 |
| 572 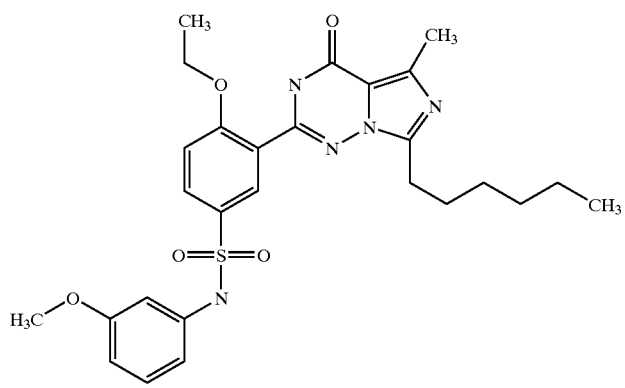 | 539,6586 | 90 | 540 |

TABLE 1-continued

| | | | |
|---|---|---|---|
| 573 | [structure] | 578,5221 87 | 578 |
| 574 | [structure] | 578,5221 92 | 578 |
| 575 | [structure] | 501,6528 50 | 502 |
| 576 | [structure] | 643,80875 76 | 644 |

TABLE 1-continued
| | | | | |
|---|---|---|---|---|
| 577 | 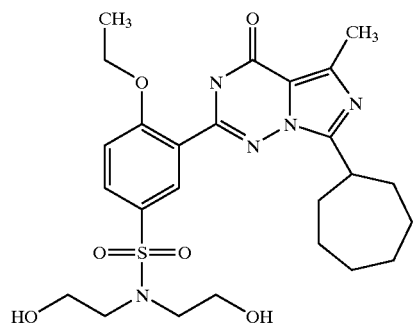 | 533,6516 | 75 | 534 |
| 578 | 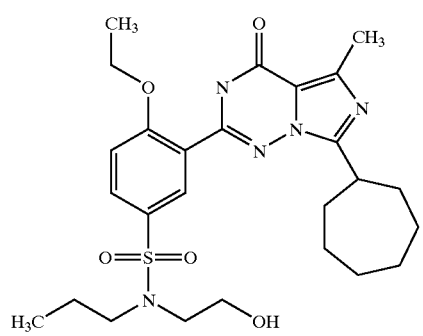 | 531,67929 | 88 | 532 |
| 579 | 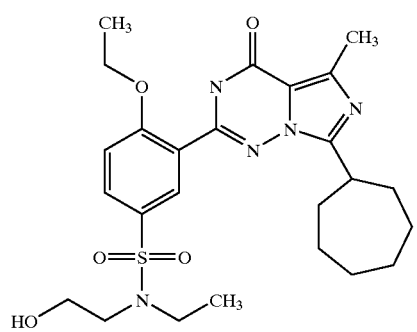 | 517,6522 | 87 | 518 |
| 580 | 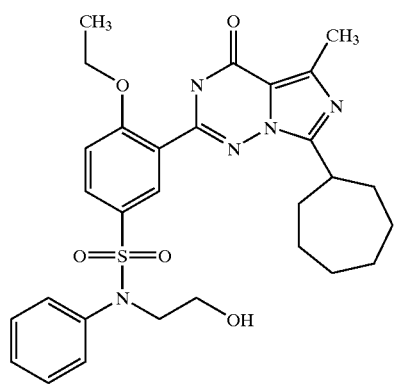 | 565,6968 | 84 | 566 |

TABLE 1-continued
| | | | | |
|---|---|---|---|---|
| 581 | 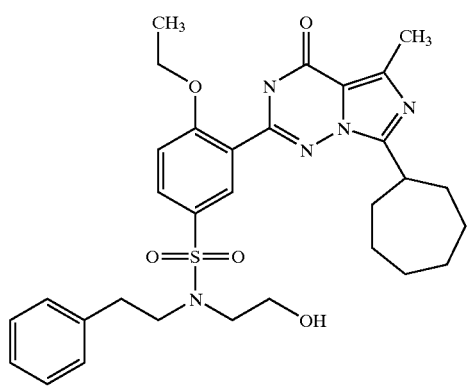 | 593,75098 | 88 | 594 |
| 582 | 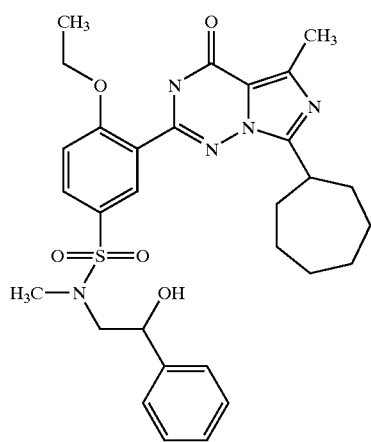 | 579,72389 | 74 | 580 |
| 583 | 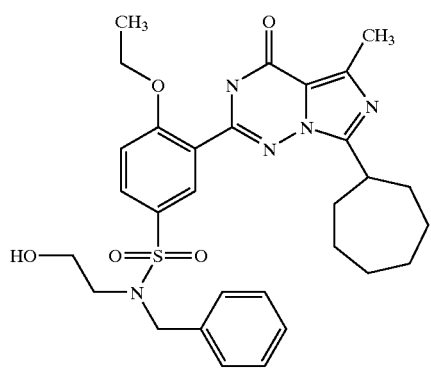 | 579,72389 | 65 | 580 |
| 584 | 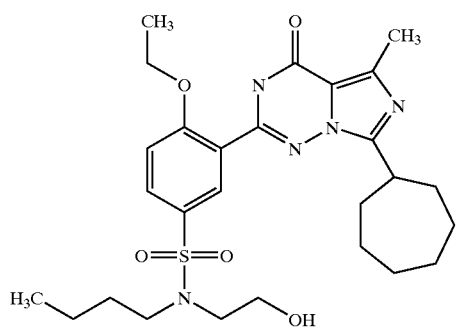 | 545,70638 | 85 | 546 |

TABLE 1-continued
| 585 | 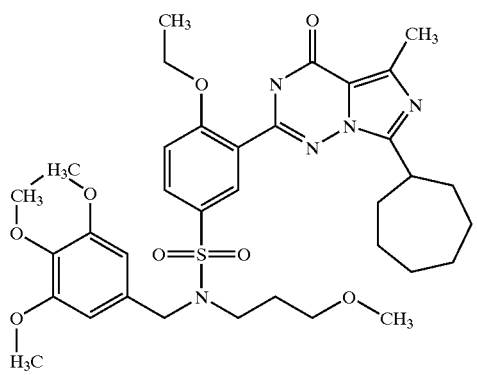 | 697,85754 | 68 | 698 |
| --- | --- | --- | --- | --- |
| 586 | 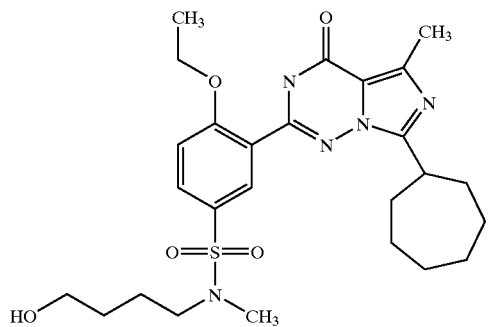 | 531,67929 | 52 | 532 |
| 587 | 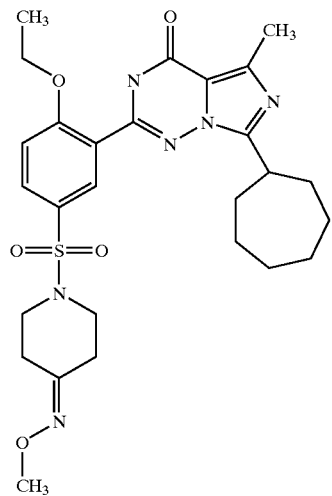 | 556,68917 | 88 | 557 |

| | | | |
|---|---|---|---|
| 588 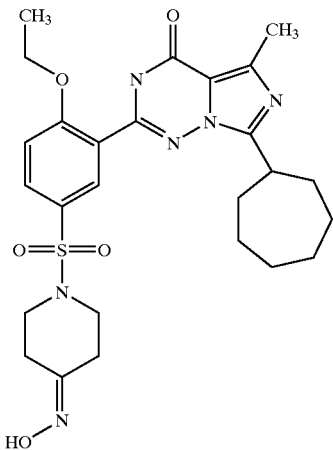 | | 542,66208 78 | 543 |
| 589 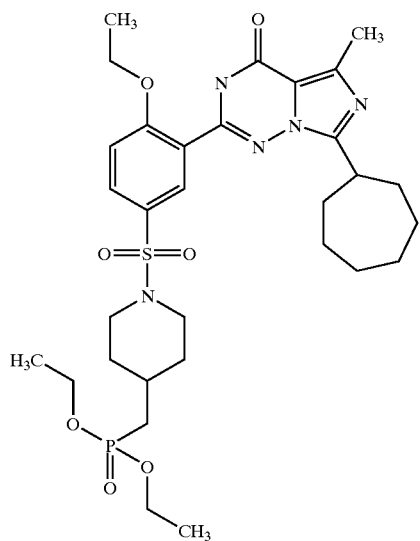 | | 663,77937 92 | 664 |
| 590 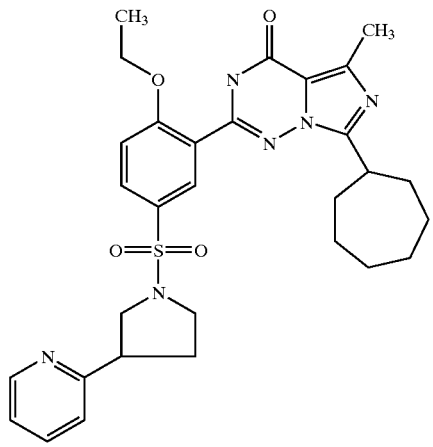 | | 576,72322 85 | 577 |

TABLE 1-continued
| | | | |
|---|---|---|---|
| 591 | 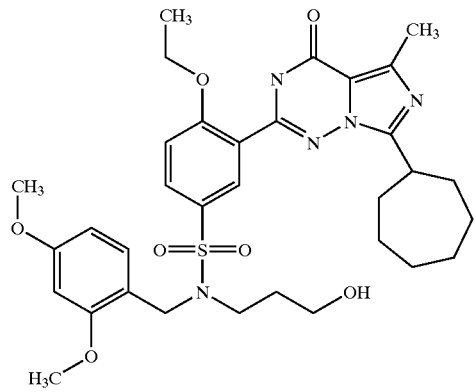 | 653,80396 77 | 654 |
| 592 | 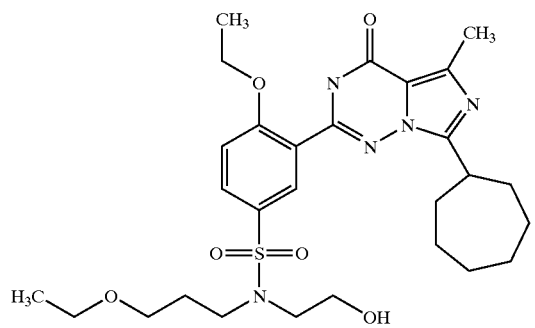 | 575,73287 91 | 576 |
| 593 | 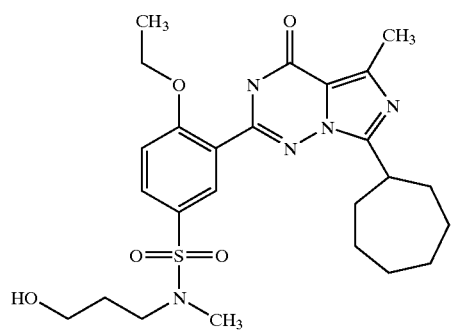 | 517,6522 86 | 518 |
| 94 | 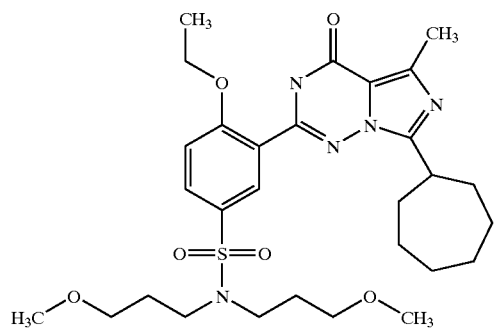 | 589,75996 90 | 590 |

TABLE 1-continued
| | | | | |
|---|---|---|---|---|
| 595 | 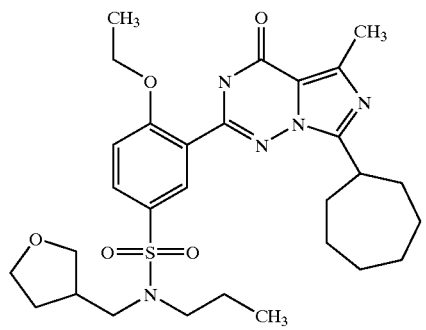 | 571,74462 | 71 | 572 |
| 596 | 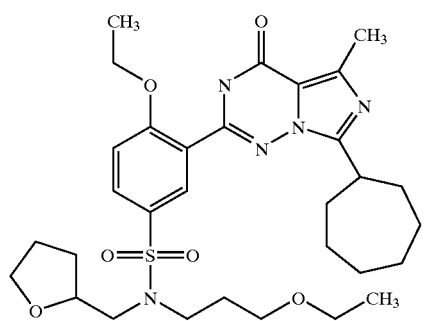 | 615,7982 | 92 | 616 |
| 597 | 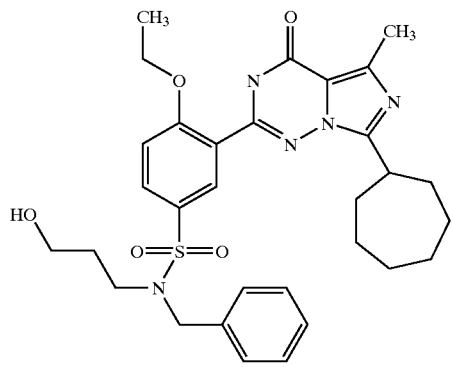 | 593,75098 | 78 | 594 |
| 598 | 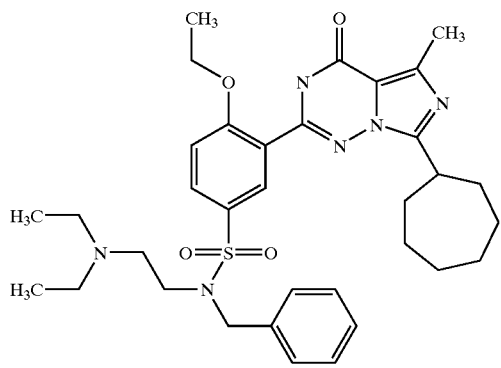 | 634,84752 | 76 | 635 |

TABLE 1-continued
| 599 | | 630,81287 | 81 | 631 |
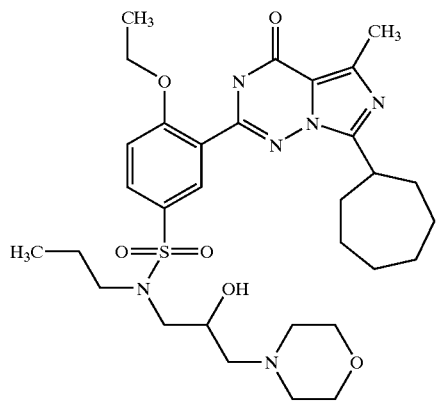
| 600 | | 582,77104 | 82 | 583 |
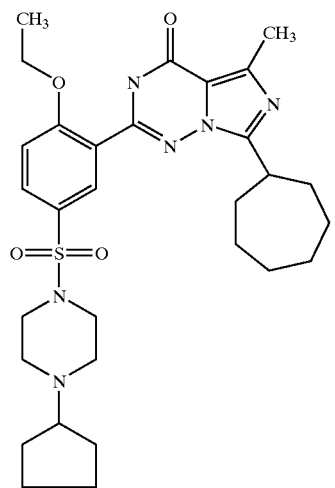
| 601 | | 570,75989 | 34 | 571 |
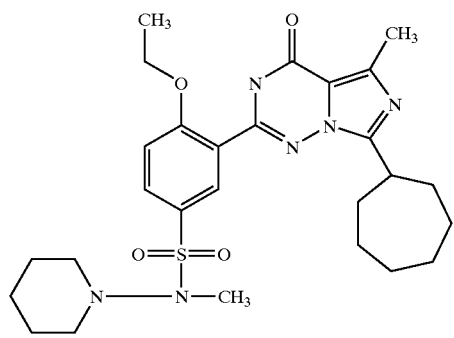

TABLE 1-continued
| | | | |
|---|---|---|---|
| 602 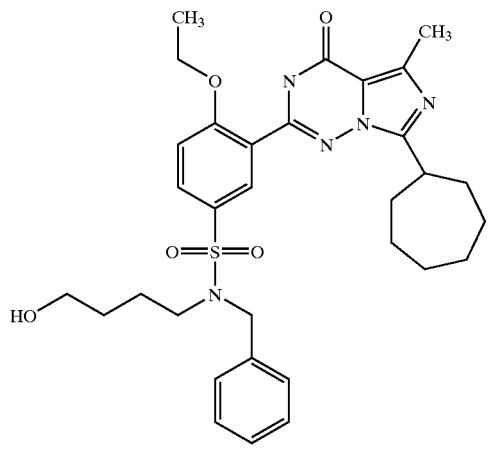 | | 607, 77807 82 | 608 |
| 603 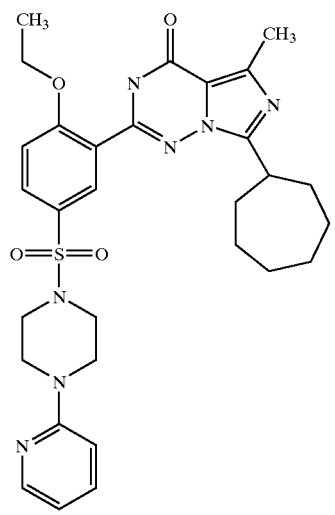 | | 591, 73789 73 | 592 |
| 604 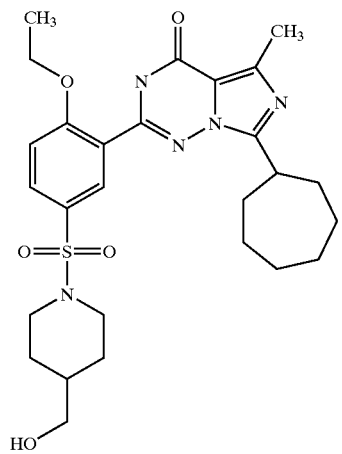 | | 543, 69044 79 | 544 |

TABLE 1-continued
| | | | |
|---|---|---|---|
| 605 | | 598,72681 68 | 599 |
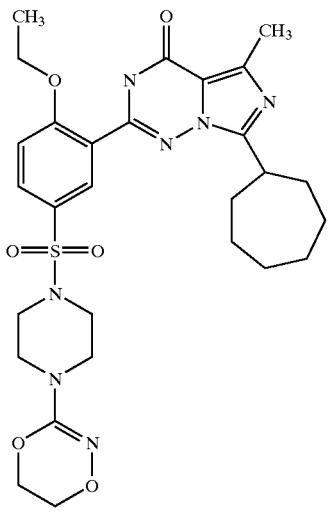
| | | | |
|---|---|---|---|
| 606 | | 592,72547 42 | 593 |
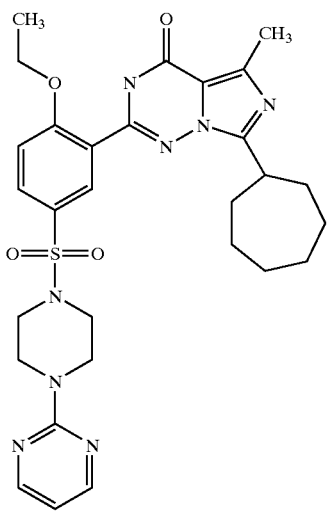
| | | | |
|---|---|---|---|
| 607 | | 529,66335 76 | 530 |
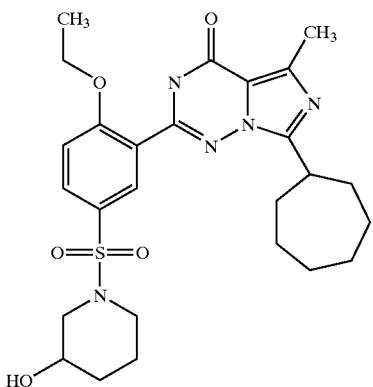

TABLE 1-continued
| | | | | |
|---|---|---|---|---|
| 608 | 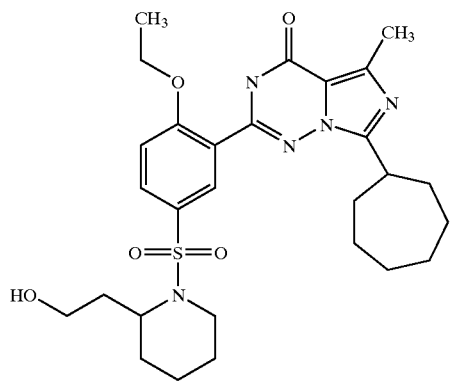 | 557,71753 | 88 | 558 |
| 609 | 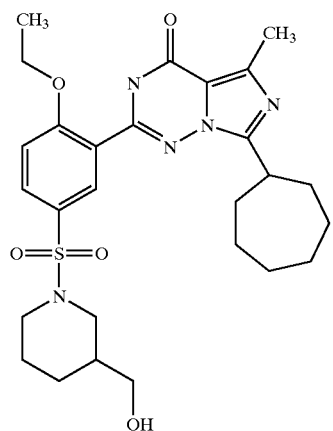 | 543,69044 | 83 | 544 |
| 610 | 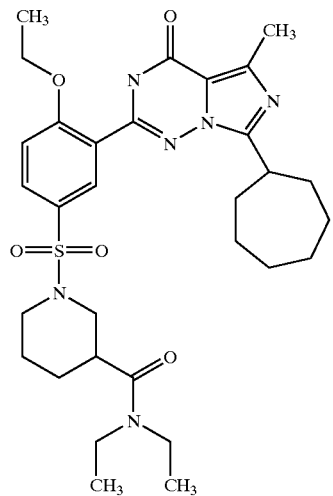 | 612,79753 | 64 | 613 |

TABLE 1-continued
| 611 | 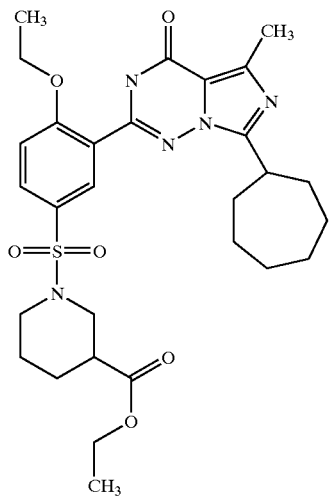 | 585,72808 | 88 | 586 |
| 612 | 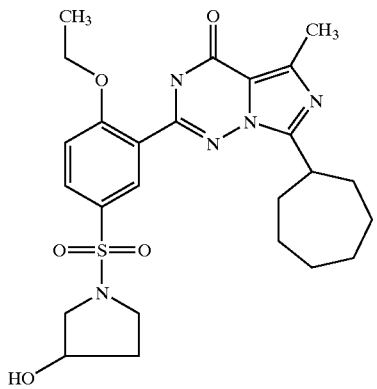 | 515,63626 | 81 | 516 |
| 613 | 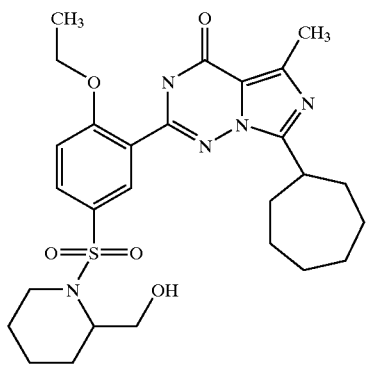 | 543,69044 | 78 | 544 |

TABLE 1-continued
| | | | | |
|---|---|---|---|---|
| 614 | 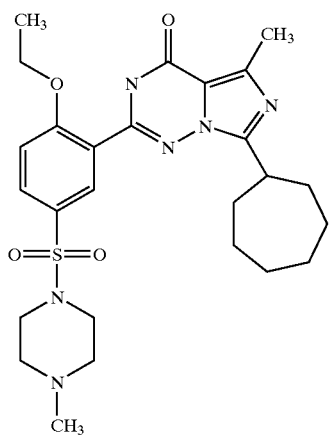 | 528,67862 | 30 | 529 |
| 615 | 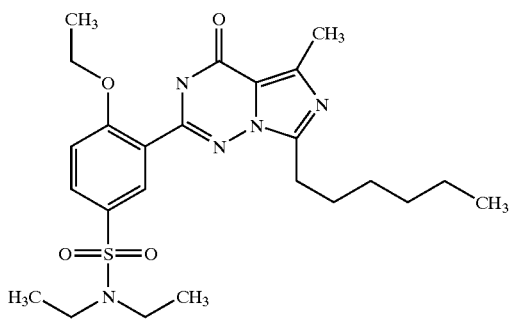 | 489,64 | 84 | 490 |
| 616 | 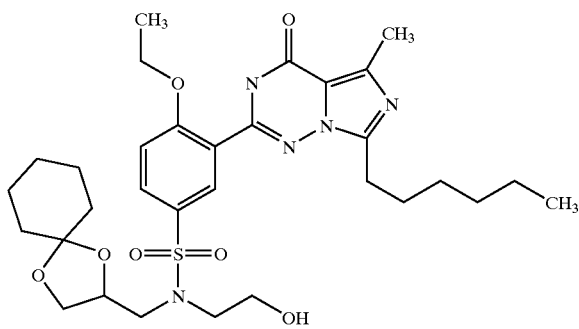 | 631,80 | 88 | 632 |
| 617 | 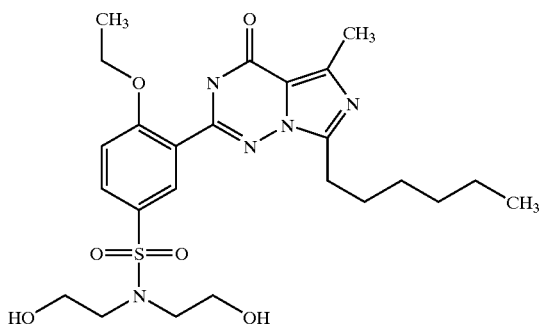 | 521,64 | 87 | 522 |

TABLE 1-continued

| | | | | |
|---|---|---|---|---|
| 618 | [structure] | 519,67 | 89 | 520 |
| 619 | [structure] | 505,64 | 94 | 506 |
| 620 | [structure] | 553,69 | 90 | 554 |
| 621 | [structure] | 581,74 | 85 | 582 |

TABLE 1-continued
| | | | | |
|---|---|---|---|---|
| 622 | 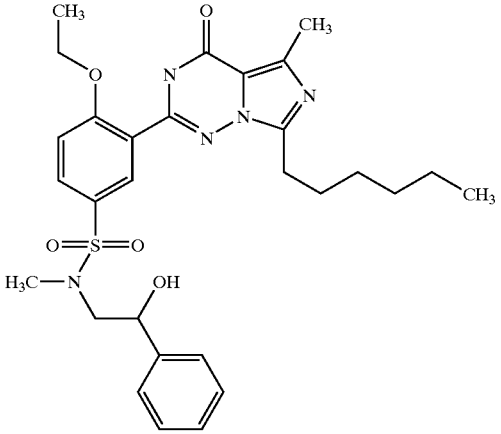 | 567,71 | 85 | 568 |
| 623 | 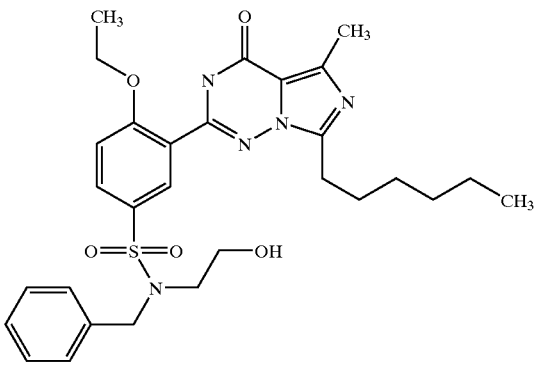 | 576,71 | 86 | 568 |
| 624 | 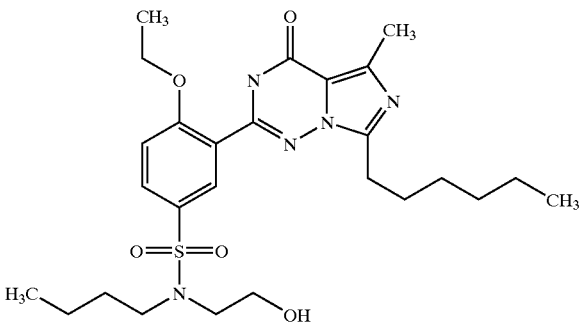 | 533,70 | 85 | 534 |
| 625 | 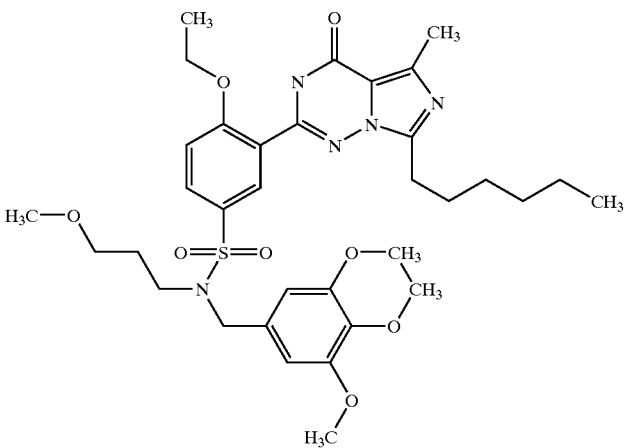 | 685,85 | 84 | 686 |

| | | | |
|---|---|---|---|
| 626 | | 519,67  83 | 520 |
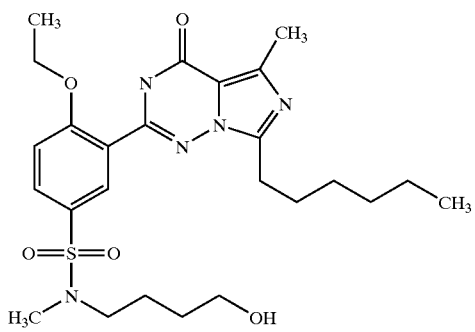
| | | | |
|---|---|---|---|
| 627 | | 544,68  92 | 545 |
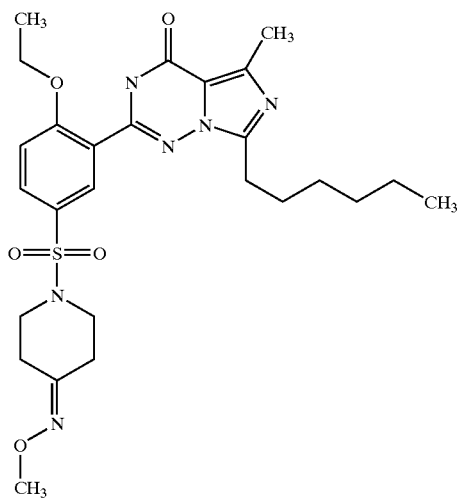
| | | | |
|---|---|---|---|
| 628 | | 530,65  82 | 531 |
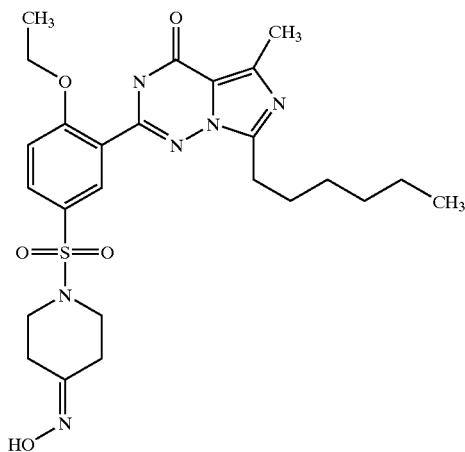

TABLE 1-continued
| | | | |
|---|---|---|---|
| 629 | 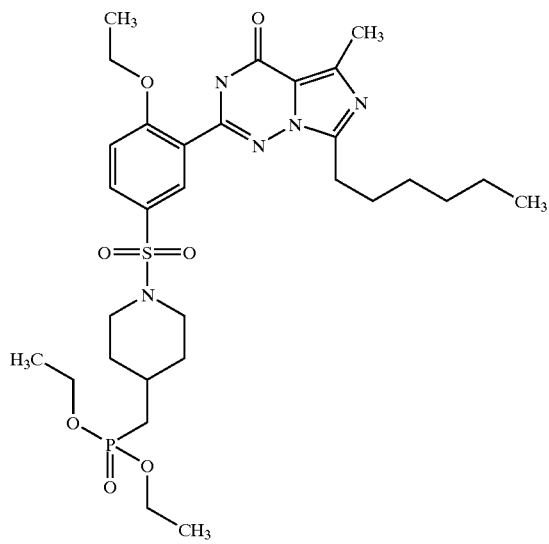 | 651,77 | 89 | 652 |
| 630 | 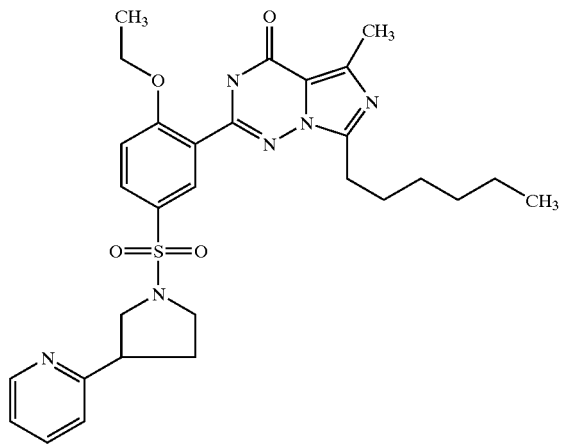 | 564,71 | 87 | 565 |
| 631 | 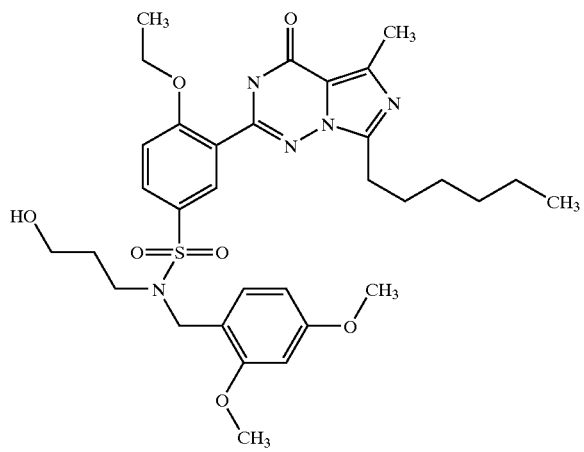 | 641,79 | 87 | 642 |

| | | | |
|---|---|---|---|
| 632 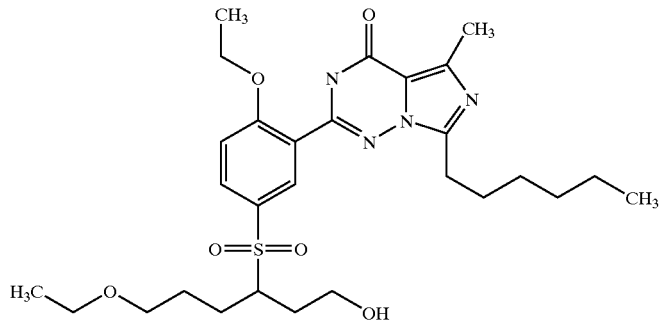 | 563,72 | 85 | 564 |
| 633 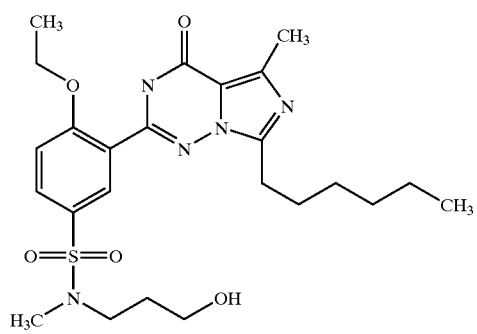 | 505,64 | 88 | 506 |
| 634 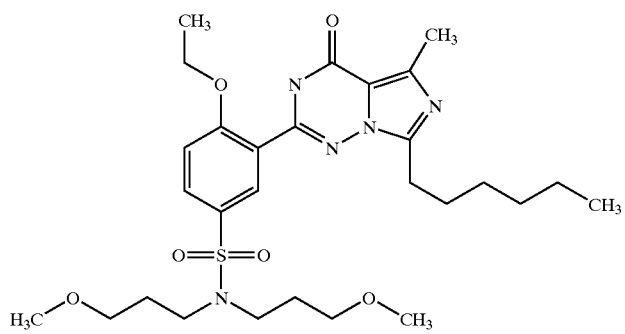 | 577,75 | 96 | 578 |
| 635 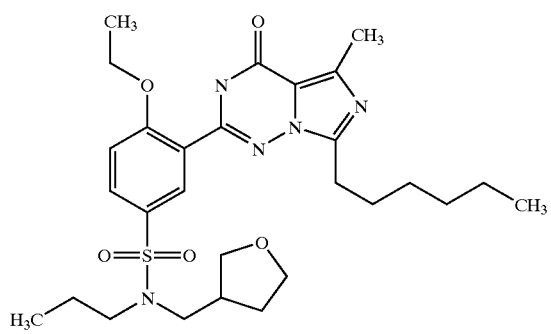 | 559,73 | 79 | 560 |

TABLE 1-continued

| | | | | |
|---|---|---|---|---|
| 636 | (structure) | 603,79 | 88 | 604 |
| 637 | (structure) | 581,74 | 83 | 582 |
| 638 | (structure) | 622,84 | 90 | 623 |
| 639 | (structure) | 618,80 | 85 | 619 |

TABLE 1-continued
| | | | | |
|---|---|---|---|---|
| 640 | | 570,76 | 60 | 571 |
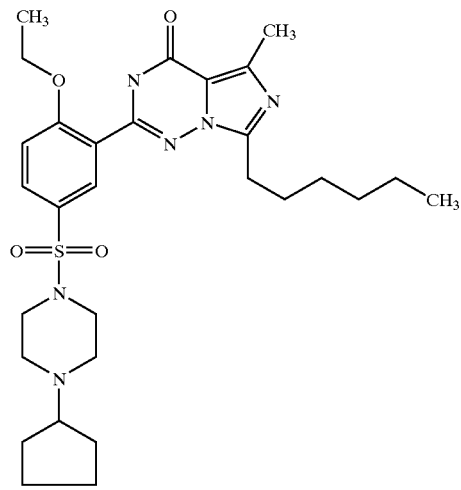
| | | | | |
|---|---|---|---|---|
| 641 | | 558,75 | 40 | 559 |
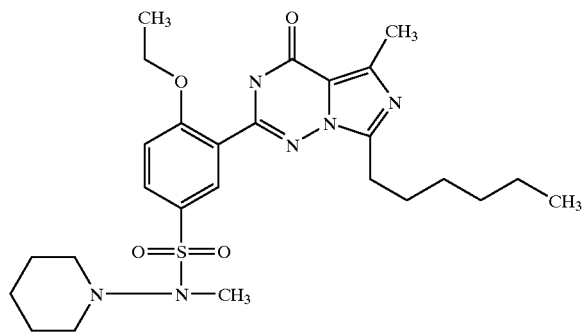
| | | | | |
|---|---|---|---|---|
| 642 | | 595,77 | 90 | 596 |
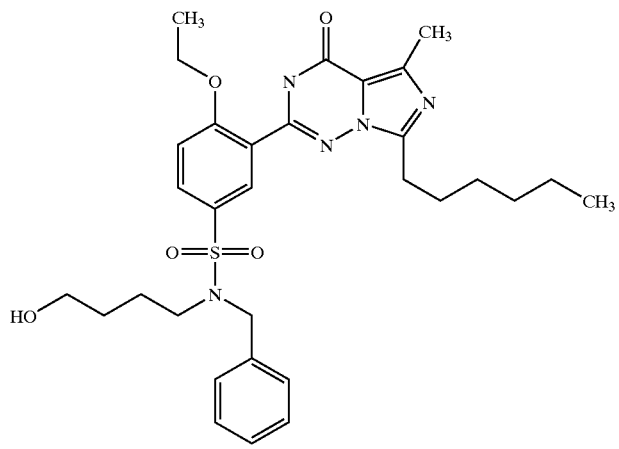

TABLE 1-continued
| 643 | 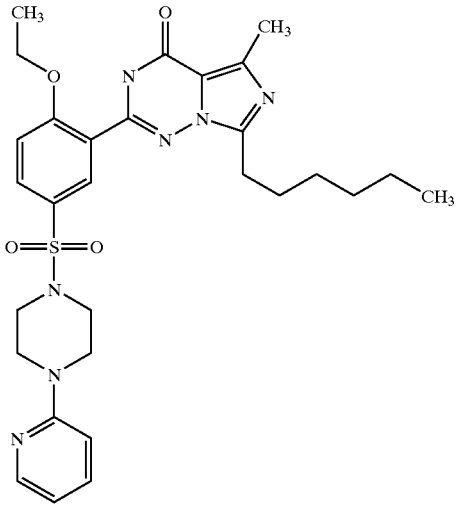 | 579,73 | 87 | 580 |
| 644 | 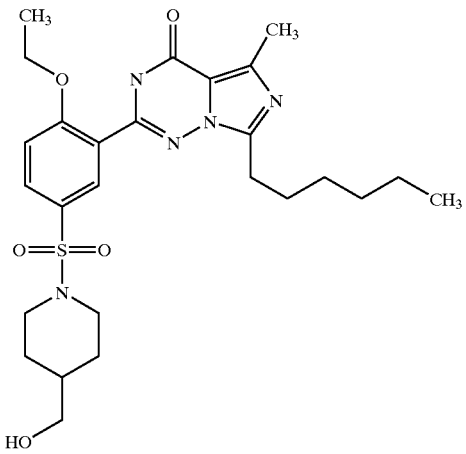 | 531,68 | 91 | 532 |
| 645 | 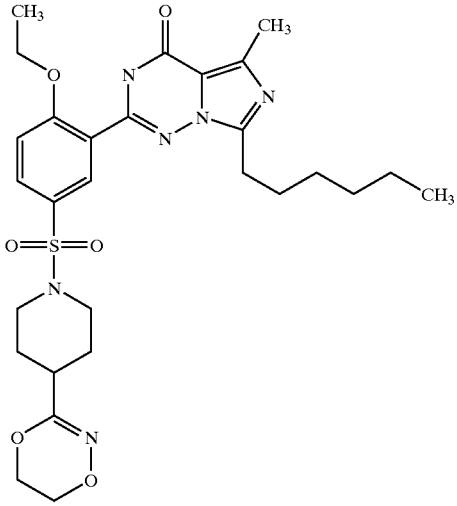 | 586,72 | 69 | 587 |

TABLE 1-continued
| | | | |
|---|---|---|---|
| 646 | 580,71 | 78 | 581 |
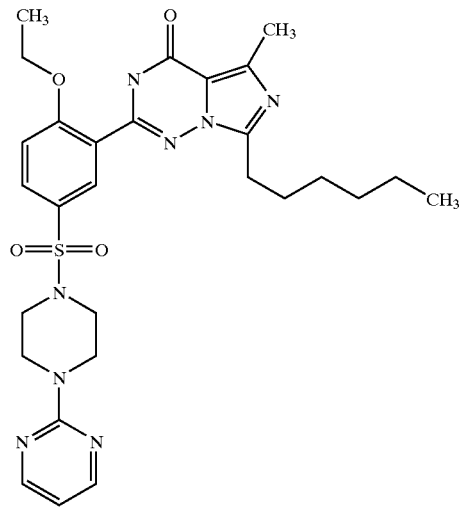
| | | | |
|---|---|---|---|
| 647 | 517,65 | 86 | 518 |
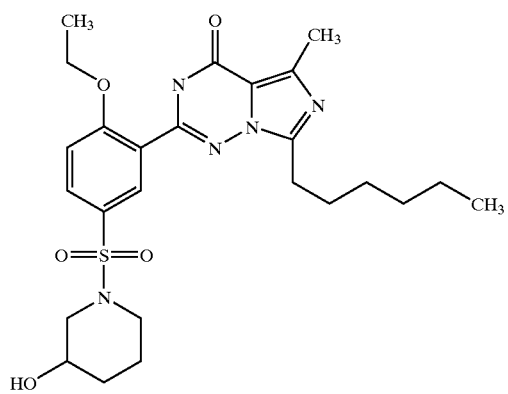
| | | | |
|---|---|---|---|
| 648 | 545,71 | 82 | 546 |
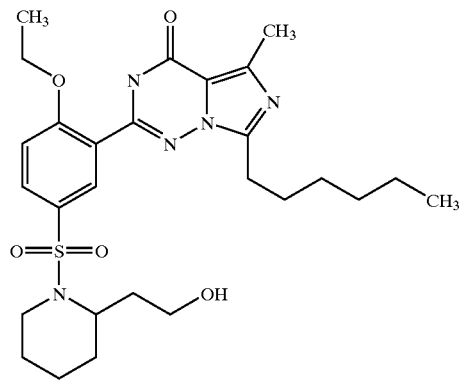

TABLE 1-continued
| | | | | |
|---|---|---|---|---|
| 649 | 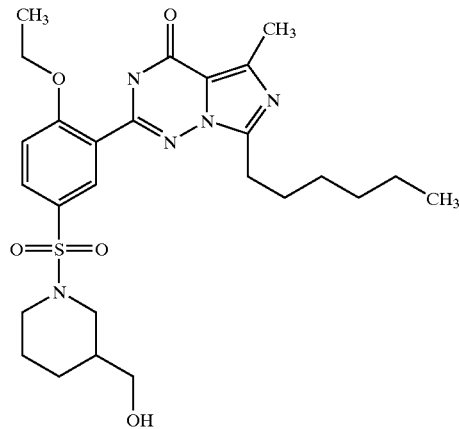 | 531,68 | 86 | 532 |
| 650 | 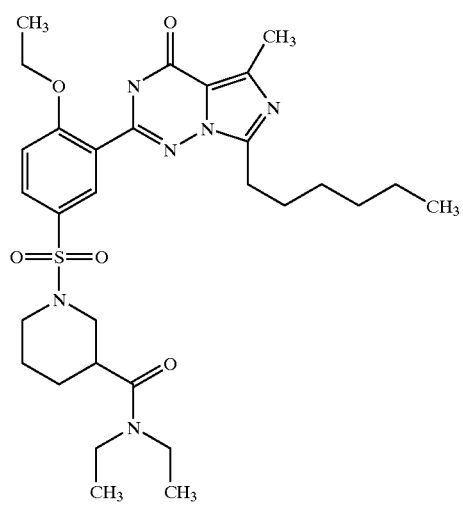 | 600,79 | 57 | 601 |
| 651 | 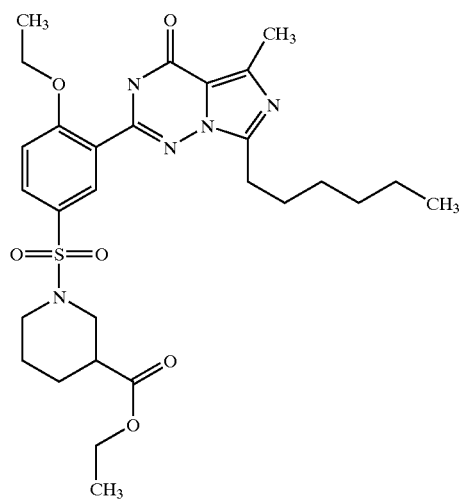 | 573,72 | 82 | 574 |

TABLE 1-continued

| | | | | |
|---|---|---|---|---|
| 652 | 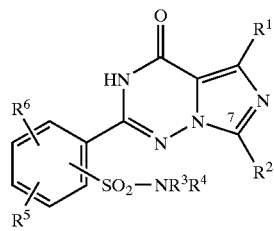 | 503,63 | 83 | 504 |
| 653 | | 531,68 | 83 | 532 |

What is claimed is:
1. A method of promoting anti-aggregatory, anti-thrombic, anti-prolific, anti-vasospastic, vasodilative, natriuretic and/or diuretic effects in a mammal, comprising administering a therapeutically effective amount of a compound of formula I

(I)

in which
R$^1$ represents straight-chain or branched alkyl having up to 4 carbon atoms,
R$^2$ represent straight-chain alkyl having at least 5 carbon atoms or branched alkyl having at least 3 carbon atoms, or
represents cycloalkyl having 3 to 10 carbon atoms,
R$^3$ and R$^4$ are identical or different and represent hydrogen, or
represent straight-chain or branched alkenyl having up to 8 carbon atoms, or
represent a straight-chain or branched alkyl chain having up to 10 carbon atoms which is optionally interrupted by an oxygen atom and which is optionally mono- to trisubstituted by identical or different substituents from the group consisting of trifluoromethyl, trifluoromethoxy, hydroxyl, halogen carboxyl, benzyloxycarbonyl, straight-chain or branched alkoxy, alkoxycarbonyl and alkylthio having in each case up to 6 carbon atoms and/or by radicals of the formulae —SO$_3$H, —(A)$_a$—NR$^7$R$^8$, —O—CO—NR$^7$R$^{8'}$, —S(O)$_b$—R$^9$, HN=SO—R$^{9'}$, —P(O)(OR$^{10}$)(OR$^{11}$),

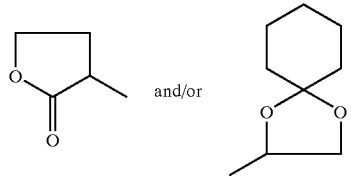

in which
a and b are identical or different and represent a number 0 or 1,
A represents a radical CO or SO$_2$,
R$^7$, R$^{7'}$, R$^8$ and R$^{8'}$ are identical or different and represent hydrogen, or
represent cycloalkyl having 3 to 8 carbon atoms, aryl having 6 to 10 carbon atoms, a 5- to 6-membered unsaturated, partially unsaturated or saturated, optionally benzo-fused heterocycle having up to 3 heteroatoms from the group consisting of S, N and/or O, where the ring systems listed above are optionally mono- to trisubstituted by identical or different substituents from the group consisting of hydroxyl, nitro, trifluoromethyl, trifluoromethoxy, carboxyl, halogen, straight-chain or branched alkoxy and alkoxycarbonyl having in each case up to 6 carbon atoms or by a group of the formula $—(SO_2)_c—NR^{12}R^{13}$,
in which
c represents a number 0 or 1,
$R^{12}$ and $R^{13}$ are identical or different and represent hydrogen or straight-chain or branched alkyl having up to 5 carbon atoms,
or
$R^7$, $R^{7'}$, $R^8$ and $R^{8'}$ represent straight-chain or branched alkoxy having up to 6 carbon atoms, or represent straight-chain or branched alkyl having up to 8 carbon atoms which is optionally mono- or polysubstituted by identical or different substituents from the group consisting of hydroxyl, halogen, aryl having from 6 to 10 carbon atoms, straight-chain or branched alkoxy and alkoxycarbonyl having in each case up to 6 carbon atoms or by a group of the formula $—(CO)_d—NR^{14}R^{15}$,
in which
$R^{14}$ and $R^{15}$ are identical or different and represent hydrogen or straight-chain or branched alkyl having up to 4 carbon atoms, and
d represents a number 0 or 1,
or
$R^7$ and $R^8$ and/or $R^{7'}$ and $R^{8'}$ together with the nitrogen atom form a 5- to 7-membered saturated heterocycle which may optionally contain a further heteroatom from the group consisting of S and O or a radical of the formula $—NR^{16}$,
in which
$R^{16}$ represents hydrogen, aryl having 6 to 10 carbon atoms, or straight-chain or branched alkyl having up to 6 carbon atoms, which is optionally substituted by hydroxyl,
$R^9$ and $R^{9'}$ are identical or different and represent aryl having 6 to 10 carbon atoms or benzyl, or represent straight-chain or branched allyl having up to 4 carbon atoms,
$R^{10}$ and $R^{11}$ are identical or different and represent hydrogen or straight-chain or branched alkyl having up to 4 carbon atoms,
and/or the alkyl chain listed above under $R^3/R^4$ is optionally substituted by cycloalkyl having 3 to 8 carbon atoms, aryl having 6 to 10 carbon atoms or by a 5- to 7-membered partially unsaturated, saturated or unsaturated, optionally benzo-fused heterocycle which may contain up to 4 ring heteroatoms from the group consisting of S, N; O or a radical of the formula $—NR^{17}$, where the alkyl chain may optionally also be attached via a ring nitrogen atom,
in which
$R^{17}$ represents hydrogen, hydroxyl, formyl, trifluoromethyl, straight-chain or branched acyl or alkoxy having in each case up to 4 carbon atoms,
or represents straight-chain or branched alkyl having up to 6 carbon atoms which is optionally mono- to polysubstituted by identical or different substituents from the group consisting of hydroxyl and straight-chain or branched alkoxy having up to 6 carbon atoms,
and where aryl and the heterocycle are optionally mono- to trisubstituted by identical or different substituents from the group consisting of nitro, halogen, —SO$_3$H, straight chain or branched monohydroxy-substituted alkyl, alkylthio or alkoxy having in each case up to 6 carbon atoms, hydroxyl, trifluoromethyl, trifluoromethoxy and/or by a radical of the formula $—(SO_2)_e—R^{18}R^{19}$,
in which
e represents a number 0 or 1,
$R^{18}$ and $R^{19}$ are identical or different and represent hydrogen, phenyl, benzyl or straight-chain or branched alkyl or acyl having in each case up to 6 carbon atoms,
and/or
$R^3$ or $R^4$ represent radicals of the formulae $—NR^{20}R^{21}$ or $—(O)—E—NR^{22}R^{23}$,
in which
$R^{20}$ and $R^{21}$ have the meaning of $R^{18}$ and $R^{19}$ given above and are identical to or different from this meaning, or
together with the nitrogen atom form a 5- or 6-membered saturated heterocycle having a further ring heterocycle from the group consisting of S and O or a radical $—NR^{24}$,
in which
$R^{24}$ has the meaning of $R^{16}$ given above and is identical to or different from this meaning,
E is a straight-chain alkylene group having up to 5 carbon atoms,
$R^{22}$ and $R^{23}$ have the meaning of $R^{18}$ and $R^{19}$ given above and are identical to or different from this meaning,
and/or
$R^3$ or $R^4$ represent radicals of the formulae

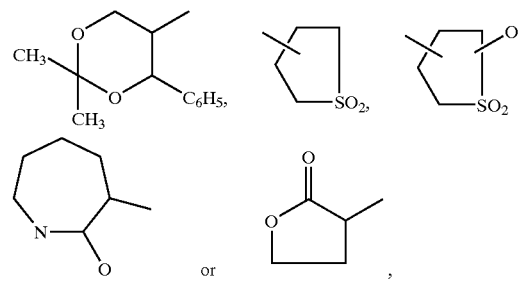

or represent cycloalkyl having 3 to 8 carbon atoms, aryl having 6 to 10 carbon atoms or represent a 5- to 7-membered partially unsaturated, saturated and unsaturated, optionally benzo-fused heterocycle which may contain up to 4 heteroatoms from the group consisting of S, N; O or a radical of the formula $—NR^{25}$ which may optionally also be attached via a ring nitrogen atom,
in which
$R^{25}$ has the meaning of $R^{16}$ given above and is identical to or different from this meaning, or
represents carboxyl, formyl or straight-chain or branched acyl having up to 5 carbon atoms,
and where cycloalkyl, aryl and/or the heterocycle are optionally mono- to trisubstituted by identical or different substituents from the group consisting of halogen, trifluoromethyl, trifluoromethoxy, carboxyl, straight-chain or branched acyl or alkoxycarbonyl having in each case up to 6 carbon atoms, nitro and/or by groups of the formulae —SO$_3$H, $—OR^{26}$, $(SO_2)_fNR^{27}R^{28}$, $—P(O)(OR^{29}(OR^{30})$, in which $R^{26}$ represents a radical of the formula

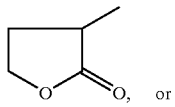, or represents cycloalkyl having 3 to 7 carbon atoms, or hydrogen or straight-chain or branched alkyl having up to 5 carbon atoms which is optionally substituted by cycloalkyl having 3 to 7 carbon atoms, straight-chain or branched alkoxy or alkoxycarbonyl having in each case up to 6 carbon atoms, hydroxyl, carboxyl or phenyl, which for its part may be mono- to trisubstituted by identical or different substituents from the group consisting of straight-chain or branched alkoxy having up to 4 carbon atoms, hydroxyl and halogen, f is a number 0 or 1, $R^{27}$ and $R^{28}$ have the meaning of $R^{18}$ and $R^{19}$ given above and are identical to or different from this meaning or represent a radical of the formula —CO—NH$_2$, $R^{29}$ and $R^{30}$ have the meaning of $R^{10}$ and $R^{11}$ given above and are identical to or different from this meaning, and/or cycloalkyl, aryl and/or the heterocycle are optionally substituted by straight-chain or branched alkyl having up to 6 carbon atoms which is optionally substituted by hydroxyl, carboxyl, by a 5- to 7-membered heterocycle having up to 3 heteroatoms from the group consisting of S, N and/or O or by groups of the formulae —SO$_2$—R$^{31}$, P(O)(OR$^{32}$)(OR$^{33}$) or —NR$^{34}$R$^{35}$, in which $R^{31}$ is hydrogen or has the meaning of $R^9$ given above and is identical to or different from this meaning, $R^{32}$ and $R^{33}$ have the meaning of $R^{10}$ and $R^{11}$ given above and are identical to or different from this meaning, $R^{34}$ and $R^{35}$ are identical or different and represent hydrogen or straight-chain or branched alkyl having up to 6 carbon atoms which is optionally substituted by hydroxyl or straight-chain or branched alkoxy having up to 4 carbon atoms, or $R^{34}$ and $R^{35}$ together with the nitrogen atom form a 5- to 6-membered saturated heterocycle which may contain a further heteroatom from the group consisting of S and O or a radical of the formula —NR$^{36}$, in which $R^{36}$ has the meaning of $R^{16}$ given above and is identical to or different from this meaning, or $R^3$ and $R^4$ together with the nitrogen atom form a 5- to 7-membered unsaturated or saturated or partially unsaturated, optionally benzo-fused heterocycle which may optionally contain up to 3 heteroatoms from the group consisting of S, N, O or a radical of the formula —NR$^{37}$ in which $R^{37}$ represents hydrogen, hydroxyl, formyl, trifluoromethyl, straight-chain or branched acyl, alkoxy or alkoxycarbonyl having in each case up to 4 carbon atoms, or represents cycloalkyl having 3 to 8 carbon atoms, or represents straight-chain or branched alkyl having up to 6 carbon atoms which is optionally mono- to trisubstituted by identical or different substituets from the group consisting of hydroxyl, trifluoromethyl, pyridyl, carboxyl, straight-chain or branched alkoxy and alkoxycarbonyl having in each case up to 6 carbon atoms, or $R^{37}$ represents a radical of the formula —(CO)$_g$—G, in which g represents a number 0 or 1, G represents aryl having 6 to 10 carbon atoms or a 5- to 6-membered aromatic heterocycle having up to 4 heteroatoms from the group consisting of S, N and/or O, where the ring systems listed above are optionally mono- to trisubstituted by identical or different substituents from the group consisting of halogen, straight-chain or branched alkoxy, alkyl or alkylthio having in each case up to 6 carbon atoms, hydroxyl and trifluoromethyl, and the heterocycle mentioned under $R^3$ and $R^4$, formed via the nitrogen, is optionally mono- to trisubstituted, optionally also geminally, by identical or different substituents from the group consisting of hydroxyl, formyl, carboxyl, straight-chain or branched acyl and alkoxycarbonyl having in each case up to 6 carbon atoms and groups of the formulae —P(O)(OR$^{38}$)(OR$^{39}$) and —(CO)$_g$)—NR$^{40}$R$^{41}$, in which $R^{38}$ and $R^{39}$ have the meaning of $R^{10}$ and $R^{11}$ given above and are identical to or different from this meaning, g represents a number 0 or 1, and $R^{40}$ and $R^{41}$ are identical or different and have the meaning of $R^{18}$ and $R^{19}$ given above, and/or the heterocycle mentioned under $R^3$ and $R^4$, formed via the nitrogen, is optionally substituted by straight-chain or branched alkyl having up to 6 carbon atoms which is optionally mono- to trisubstituted by identical or different substituents from the group consisting of hydroxyl, halogen, carboxyl, cycloalkyl or cycloalkyloxy having in each case 3 to 8 carbon atoms, straight-chain or branched alkoxy and alkoxycarbonyl having in each case up to 6 carbon atoms or by a radical of the formula —SO$_3$H, —NR$^{42}$R$^{43}$ or P(O)OR$^{44}$OR$^{45}$, in which $R^{42}$ and $R^{43}$ are identical or different and represent hydrogen, phenyl, carboxyl, benzyl or straight-chain or branched alkyl or alkoxy having in each case up to 6 carbon atoms, $R^{44}$ and $R^{45}$ are identical or different and have the meaning of $R^{10}$ and $R^{11}$ given above, and/or the alkyl is optionally substituted by benzyloxy or aryl having 6 to 10 carbon atoms, which for its part may be mono- to trisubstituted by identical or different substituents from the group consisting of halogen, hydroxyl, straight-chain or branched alkoxy or alkylthio having in each case up to 6 carbon atoms, or by a group of the formula —NR$^{42'}$R$^{43'}$, in which $R^{42'}$ and $R^{43'}$ have the meaning of $R^{42}$ and $R^{43}$ given above and are identical to or different from this meaning, and/or the heterocycle mentioned under $R^3$ and $R^4$, formed via a nitrogen atom, is optionally substituted by aryl having 6 to 10 carbon atoms or by a 5- to 7-membered saturated, partially unsaturated or unsaturated heterocycle having up to 3 ring heteroatoms from the group consisting of S, N and/or O, optionally also attached via an N function, where the ring systems for their part may be substituted by halogen, hydroxyl or by straight-chain or branched alkyl, alkylthio or alkoxy having in each case up to 6 carbon atoms, or $R^3$ and $R^4$ together with the nitrogen atom form radicals of the formulae

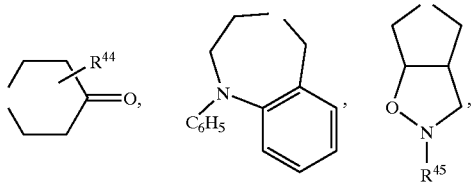

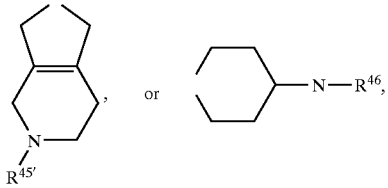

in which
$R^{44}$ represents hydrogen or straight-chain or branched alkyl or alkoxycarbonyl having in each case up to 6 carbon atoms,
$R^{45}$ and $R^{45'}$ are identical or different and represent hydrogen or straight-chain or branched alkyl having up to 3 carbon atoms,
$R^{46}$ represents hydroxyl or straight-chain or branched alkoxy having up to 6 carbon atoms,
$R^5$ and $R^6$ are identical or different and represent hydrogen, straight-chain or branched alkyl having up to 6 carbon atoms, hydroxy or represents straight-chain or branched alkoxy having up to 6 carbon atoms,
or stereoisomers thereof.

* * * * *